US 11,066,397 B2
United States Patent
Lin et al.

(10) Patent No.: US 11,066,397 B2
(45) Date of Patent: Jul. 20, 2021

(54) PROTEASOME INHIBITORS AND USES THEREOF

(71) Applicant: CORNELL UNIVERSITY, Ithaca, NY (US)

(72) Inventors: Gang Lin, Forest Hills, NY (US); Carl Nathan, Larchmont, NY (US); Pradeep K. Singh, New York, NY (US); Lei Shi, Edison, NJ (US); Laura Kirkman, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/768,628

(22) PCT Filed: Oct. 17, 2016

(86) PCT No.: PCT/US2016/057346
§ 371 (c)(1),
(2) Date: Apr. 16, 2018

(87) PCT Pub. No.: WO2017/066763
PCT Pub. Date: Apr. 20, 2017

(65) Prior Publication Data
US 2018/0282317 A1 Oct. 4, 2018

Related U.S. Application Data

(60) Provisional application No. 62/242,139, filed on Oct. 15, 2015.

(51) Int. Cl.
| C07D 413/12 | (2006.01) |
| C07D 237/22 | (2006.01) |
| C07D 261/18 | (2006.01) |
| C07D 213/81 | (2006.01) |
| C07D 231/12 | (2006.01) |
| C07D 233/70 | (2006.01) |
| C07D 209/42 | (2006.01) |
| C07D 215/48 | (2006.01) |
| A61P 33/06 | (2006.01) |
| A61K 39/39 | (2006.01) |
| C07C 237/22 | (2006.01) |

(52) U.S. Cl.
CPC ......... *C07D 413/12* (2013.01); *A61K 39/39* (2013.01); *A61P 33/06* (2018.01); *C07C 237/22* (2013.01); *C07D 209/42* (2013.01); *C07D 213/81* (2013.01); *C07D 215/48* (2013.01); *C07D 231/12* (2013.01); *C07D 233/70* (2013.01); *C07D 261/18* (2013.01); *Y02A 50/30* (2018.01)

(58) Field of Classification Search
CPC ...... C07D 413/12; C07C 237/22; A61P 33/06
See application file for complete search history.

(56) References Cited

U.S. PATENT DOCUMENTS

| 5,763,604 | A | 6/1998 | Ackermann et al. |
| 8,048,911 | B2 | 11/2011 | Ogata |
| 8,367,668 | B2 | 2/2013 | Stieber et al. |
| 9,988,421 | B2 | 6/2018 | Lin et al. |
| 2005/0171146 | A1 | 8/2005 | Weber et al. |
| 2006/0241056 | A1 | 10/2006 | Orlowski et al. |
| 2007/0010515 | A1 | 1/2007 | Masuda et al. |
| 2007/0244153 | A1 | 10/2007 | Kakimoto et al. |
| 2009/0227601 | A1 | 9/2009 | Zhu et al. |
| 2010/0249197 | A1 | 9/2010 | Watkins et al. |
| 2010/0249400 | A1 | 9/2010 | Shiina |
| 2013/0053303 | A1 | 2/2013 | Shenk et al. |
| 2013/0072422 | A1 | 3/2013 | Shenk et al. |
| 2014/0315786 | A1 | 10/2014 | Jirousek et al. |
| 2018/0221431 | A1 | 8/2018 | Lin et al. |

FOREIGN PATENT DOCUMENTS

| CN | 1984880 A | 6/2007 |
| CN | 101506224 A | 8/2009 |
| CN | 102807601 A | 12/2012 |

(Continued)

OTHER PUBLICATIONS

Pubchem. CID 17857389.04 Dec. 2007, pp. 1-13[online], [retrieved on Feb. 27, 2017] Retrieved from the Internet <URL: https://pubchem.ncbi.nlm.nih.gov/compound/17857389; p. 4, formula.
PCT International Search Report and Written Opinion corresponding to PCT/US2016/057346, dated Mar. 23, 2017.
International Preliminary Report on Patentability for Application No. PCT/US2016/057346 (dated Apr. 17, 2018).
Extended European Search Report and Opinion for European Application No. 16856412.8 dated Mar. 22, 2019.
Solomon et al., "Synthesis and Antimalarial Activity of Novel Side Chain Modified Antimalarial Agents Derived From 4-Aminoquinoline," Medicinal Chemistry, 4:446-456 (2008).

(Continued)

*Primary Examiner* — Kamal A Saeed
(74) *Attorney, Agent, or Firm* — Troutman Pepper Hamilton Sanders LLP

(57) ABSTRACT

The compounds of the present invention are represented by the following compounds having Formula (I) where the substituents R, $R^1$-$R^5$, k, m, n, and q are as defined herein. These compounds are used in the treatment of cancer, immunologic disorders, autoimmune disorders, neurodegenerative disorders, or inflammatory disorders, infectious disease, or for providing immunosuppression for transplanted organs or tissues.

(I)

49 Claims, 7 Drawing Sheets

(56) References Cited

FOREIGN PATENT DOCUMENTS

| | | | |
|---|---|---|---|
| JP | 02006298785 A | * | 11/2006 |
| JP | 2008-512476 A | | 4/2008 |
| JP | 2014-91731 A | | 5/2014 |
| JP | 2014-167005 A | | 9/2014 |
| WO | 98/29387 A1 | | 7/1998 |
| WO | 2006/009134 A1 | | 1/2006 |
| WO | 2006/029210 A2 | | 3/2006 |
| WO | 2006/065826 A2 | | 6/2006 |
| WO | 2006/099261 A2 | | 9/2006 |
| WO | 2007/083394 A1 | | 7/2007 |
| WO | 2007149512 A2 | | 12/2007 |
| WO | 2009/051581 A1 | | 4/2009 |
| WO | 2010/036357 A1 | | 4/2010 |
| WO | 2011/123502 A1 | | 10/2011 |
| WO | 2012/065891 A1 | | 5/2012 |
| WO | 2013/005045 A1 | | 1/2013 |
| WO | 2013/092979 A1 | | 6/2013 |
| WO | 2014/095773 A1 | | 6/2014 |
| WO | 2015/076359 A1 | | 5/2015 |
| WO | 2015/106200 A2 | | 7/2015 |
| WO | 2019/075252 A1 | | 4/2019 |

OTHER PUBLICATIONS

Lin et al., "N,C-Capped Dipeptides With Selectivity for Mycobacterial Proteasome Over Human Proteasomes: Role of S3 and S1 Binding Pockets," Journal of the American Chemical Society, 135:9968-9971 (2013).

Blackburn et al., "Characterization of a New Series of Non-Covalent Proteasome Inhibitors With Exquisite Potency and Selectivity for the 20S β5-Subunit," Biochemical Journal, 430:461-476 (2010).

International Search Report and Written Opinion for corresponding Application No. PCT/US2015/044876 (dated Nov. 13, 2015).

Pubchem. SID 132358420.24 Jan. 2012, pp. 1-6 [online], [retrieved on Oct. 1, 2015] Retrieved from the Internet <URL: http://pubchem.ncbi.nih.gov/substance/132358420>; p. 3, formula.

Pubchem. SID 132071324.24 Jan. 2012, pp. 1-6 [online], [retrieved on Oct. 1, 2015]. Retrieved from the Internet <URL: http://pubchem.ncbi.nih.gov/substance/132071324>; p. 3, formula.

Pubchem. SID 146191084. 19 Oct. 2012, pp. 1-6 [online]. [retrieved on Oct. 1, 2015]. Retrieved from the Internet <URL: http://pubchem.ncbi.nih.gov/substance/146191084>; p. 3, formula.

Pubchem. SID 144773390. 18 Oct. 2012, pp. 1-6 [online], [retrieved on Oct. 1, 2015]. Retrieved from the Internet <URL: http://pubchem.ncbi.nih.gov/substance/144773390>; p. 3, formula.

Allen et al., "Analysis of the Cytosolic Proteome in a Cell Culture Model of Familial Amyotrophic Lateral Sclerosis Reveals Alterations to the Proteasome, Antioxidant Defenses, and Nitric Oxide Synthetic Pathways," J. Biol. Chem. 278:6371-6383 (2003).

Basler et al., "Prevention of Experimental Colitis by a Selective Inhibitor of the Immunoproteasome," J. Immunol. 185:634-641 (2010).

Basler et al., "Inhibition of the Immunoproteasome Ameliorates Experimental Autoimmune Encephalomyelitis," EMBO Mol. Med. 6:226-238 (2014).

Baumeister et al., "The Proteasome: Paradigm of a Self-Compartmentalizing Protease," Cell 92:367-380 (1998).

Bedford et al., "Ubiquitin-Like Protein Conjugation and the Ubiquitin-Proteasome System as Drug Targets," Nat. Rev. Drug Discov. 10:29-46 (2011).

Bontscho et al., "Myeloperoxidase-Specific Plasma Cell Depletion by Bortezomib Protects From Anti-Neutrophil Cytoplasmic Autoantibodies-Induced Glomerulonephritis," J. Am. Soc. Nephrol. 22:336-348 (2011).

Brun, "Proteasome Inhibition as a Novel Therapy in Treating Rheumatoid Arthritis," Med. Hypotheses 71:65-72 (2008).

Egerer et al., "Tissue-Specific Up-Regulation of the Proteasome Subunit beta5i (LMP7) in Sjogren's Syndrome," Arthritis Rheum. 54:1501-1508 (2006).

El-Hashim et al., "Effect of Inhibition of the Ubiquitin-Proteasome-System and IkappaB Kinase on Airway Inflammation and Hyperresponsiveness in a Murine Model of Asthma," Int. J. Immunopathol. Pharmacol. 24:33-42 (2011).

Elliott et al., "Proteasome Inhibition: A Novel Mechanism to Combat Asthma," J. Allergy Clin. Immunol. 104:294-300 (1999).

Goldberg, "Functions of the Proteasome: From Protein Degradation and Immune Surveillance to Cancer Therapy," Biochem. Soc. Trans. 35:12-17 (2007).

Guillaume et al., "Two Abundant Proteasome Subtypes That Uniquely Process Some Antigens Presented by HLA Class I Molecules," Proc. Natl. Acad. Sci. U.S.A. 107:18599-18604 (2010).

Henry et al., "Proteolytic Activity and Expression of the 20S Proteasome are Increased in Psoriasis Lesional Skin," Br. J. Dermatol. 165:311-320 (2011).

Hirai, et al., "Bortezomib Suppresses Function and Survival of Plasmacytoid Dendritic Cells by Targeting Intracellular Trafficking of Toll-Like Receptors and Endoplasmic Reticulum Homeostasis," Blood 117:500-509 (2011).

Huber et al, "Immuno- and Constitutive Proteasome Crystal Structures Reveal Differences in Substrate and Inhibitor Specificity," Cell 148:727-738 (2012).

Huber et al., "Inhibitors for the Immuno- and Constitutive Proteasome: Current and Future Trends in Drug Development," Angew Chem. Int. Ed Engl. 51:8708-8720 (2012).

Ichikawa et al., "Novel Proteasome Inhibitors Have a Beneficial Effect of Novel Proteasome Inhibitors in Murine Lupus via the Dual Inhibition of Type I Interferon and Autoantibody-Secreting Cells," HHS Public Access Author Manuscript, Available in PMC Sep. 28, 2015, 19 pages, Published in final edited form as: Arthritis Rheum. 64(2):493-503 (2012).

Inoue et al., "The Effect of Proteasome Inhibitor MG132 on Experimental Inflammatory Bowel Disease," Clin. Exp. Immunol. 156:172-82 (2009).

Kincaid et al., "Mice Completely Lacking Immunoproteasomes Display Major Alternatives in Antigen Presentation," HHS Public Access Author Manuscript, Available in PMC Aug. 1, 2012, 18 pages, Published in final edited form as: Nat. Immunol. 13(2):129-135 (2012).

Lang et al., "The Early Marginal Zone B Cell-Initiated T-Independent Type 2 Response Resists the Proteasome Inhibitor Bortezomib," J. Immunol. 185:5637-5647 (2010).

Liang et al., "Proteasome Inhibition in Transplantation-Focusing on the Experience with Bortezomib," Curr. Pharm. Design 19:3299-3304 (2013).

Meng et al., "Epoxomicin, a Potent and Selective Proteasome Inhibitor, Exhibits in Vivo Antiinflammatory Activity," P. Natl. Acad. Sci. U.S.A. 96:10403-10408 (1999).

Minagar et al., "Plasma Ubiquitin-Proteasome System Profile in Patients With Multiple Sclerosis: Correlation With Clinical Features, Neuroimaging, and Treatment With Interferon-Beta-1 b," Neurol. Res. 34:611-618 (2012).

Muchamuel et al., "A Selective Inhibitor of the Immunoproteasome Subunit LMP7 Blocks Cytokine Production and Attenuates Progression of Experimental Arthritis," Nat. Med. 15:781-787 (2009).

Neubert et al., "The Proteasome Inhibitor Bortezomib Depletes Plasma Cells and Protects Mice With Lupus-Like Disease From Nephritis," Nat. Med. 14:748-755 (2008).

Niewerth et al., "Anti-Leukemic Activity and Mechanisms Underlying Resistance to the Novel Immunoproteasome Inhibitor PR-924," Biochem. Pharmacol. 89:43-51 (2014).

Padrissa-Altes et al., "The use of a Reversible Proteasome Inhibitor in a Model of Reduced-Size Orthotopic Liver Transplantation in Rats," Exp. Mol. Pathol. 93:99-110 (2012).

Perkins, "Integrating Cell-Signalling Pathways With NF-[kappa]B and IKK Function," Nat. Rev. Mol. Cell. Biol. 8:49-62 (2007).

Roccaro et al., "Selective Inhibition of Chymotrypsin-Like Activity of the Immunoproteasome and Constitutive Proteasome in Waldenstrom Macroglobulinemia," Blood 115:4051-4060 (2010).

Rock et al., "Proteases in MHC Class I Presentation and Cross-Presentation," NIH Public Access Author Manuscript, Available in PMC May 13, 2011, 16 pages, Published in final edited form as: J. Immunol. 184 (1):9-15 (2010).

(56) References Cited

OTHER PUBLICATIONS

Rock et al., "Inhibitors of the Proteasome Block the Degradation of Most Cell Proteins and the Generation of Peptides Presented on MHC Class I Molecules," Cell 78:761-771 (1994).
Rock et al., "Protein Degradation and the Generation of MHC Class I-Presented Peptides," Adv. Immunol 80:1-70 (2002).
Schmidt et al., "Targeting the Proteasome: Partial Inhibition of the Proteasome by Bortezomib or Deletion of the Immunosubunit LMP7 Attenuates Experimental Colitis," Gut 59:896-906 (2010).
Singh et al., "PR-924, a Selective Inhibitor of the Immunoproteasome Subunit LMP-7, Blocks Multiple Myeloma Cell Growth Both in Vitro and in Vivo," NIH Public Access Author Manuscript, Available in PMC Jan. 1, 2012, 15 pages, Published in final edited form as: Br. J. Haematol. 152(2):155-163 (2011).
Sureshkumar et al., "Proteasome Inhibition With Bortezomib: an Effective Therapy for Severe Antibody Mediated Rejection After Renal Transplantation," Clin. Nephrol. 77: 246-253 (2012).
Van der Heijden et al., "The Proteasome Inhibitor Bortezomib Inhibits the Release of NFkappaB-Inducible Cytokines and Induces Apoptosis of Activated T Cells From Rheumatoid Arthritis Patients," Clin. Exp. Rheumatol. 27:92-98 (2009).
Verbrugge et al., "Inactivating PSMB5 Mutations and P-glycoprotein (Multidrug Resistance-Associated Protein/ATP-Binding Cassette B1) Mediate Resistance to Proteasome Inhibitors: ex Vivo Efficacy of (Immuno)Proteasome Inhibitors in Mononuclear Blood Cells From Patients With Rheumatoid Arthritis," J. Pharmacol. Exp. Ther. 341:174-182 (2012).
Zhang et al., "In Vitro and in Vivo Therapeutic Efficacy of Carfilzomib in Mantle Cell Lymphoma: Targeting the Immunoproteasome," Mol. Cancer Ther. 12:2494-2504 (2013).
Lei et al., "Structural Features and Binding Free Energies for Non-Covalent Inhibitors Interacting with Immunoproteasome by Molecular Modeling and Dynamics Simulations," Theor. Chem. Acc. 131:1-11 (2012).
Singh et al., "Recent Trends in Targeted Anticancer Prodrug and Conjugate Design," NIH Public Access Author Manuscript, Available in PMC Jan. 5, 2010, 53 pages, Published in final edited form as: Curr. Med. Chem. 15 (18):1802-1826 (2008).
Office Action for U.S. Appl. No. 15/768,628 (dated Oct. 11, 2019).
Restriction Requirement for U.S. Appl. No. 15/110,000 (dated Mar. 6, 2017).
Office Action for U.S. Appl. No. 15/110,000 (dated Jun. 5, 2017).
Zollner et al., "Proteasome Inhibition Reduces Superantigen-Mediated T Cell Activation and the Severity of Psoriasis in a SCID-hu Model," J. Clin. Invest. 109:671-679 (2002).
DFHBI IT Datasheet (Lucerna).
International Preliminary Report on Patentability for Application No. PCT/US2015/044876 (dated Feb. 21, 2017).
Supplementary European Search Report dated Mar. 27, 2018 for EP Application Serial No. 15834073.7.
Fuchise et al., "Atlantic Cod Trypsin-Catalyzed Peptide Synthesis with Inverse Substrates as Acyl Donor Components," Chem. Pharm. Bull. 58(4):484-487 (2010).
Notice of Reasons for Rejection for Japanese Patent Application No. 2017-509632 (dated Jun. 5, 2019).
Coumar et al., "3-[2-((2S)-2-Cyano-pyrrolidin-1-yl)-2-oxo-ethylamino]-3-methyl-butyramide Analogues as Selective DPP-IV Inhibitors for the Treatment of Type-II Diabetes," Bioorg. Med. Chem. Lett. 17(5):1274-1279 (2007).
Office Action for U.S. Appl. No. 15/504,951 (dated Sep. 10, 2020).
Beaumont et al. "Design of Ester Prodrugs to Enhance Oral Absorption of Poorly Permeable Compounds: Challenges to the Discovery Scientist" Curr. Drug Metab. 4:461-485 (2003).
Vippagunta et al. "Crystalline Solids" Advanced Drug Delivery Reviews 48:3-26 (2001).
Hook et al. "The Proteolytic Stability of 'Designed' [beta]-Peptides Containing [alpha]-Peptide-Bond Mimics and of Mixed [alpha,beta]-Peptides: Application to Construction of MHC-Binding Peptides" Chemistry & Biodiversity 2:591-632(2005).

U.S. Reissue U.S. Appl. No. 16/893,086, first named inventor Gang Lin, filed Jun. 4, 2020.
Drey et al., "Synthesis of β-Amino-Acid Peptides by Aminolysis of Substituted Di-hydro-1,3-oxazinones and Amino-Protected β-Lactams," Perkin Transactions 1, J. Chem. Soc. 17:2001-2006 (1973).
Liotta et al., "Antibody-Catalyzed Rearrangement of a Peptide Bond: Mechanistic and Kinetic Investigations," J. Am. Chem. Soc. 117(17):4729-4741 (1995).
Examination Report for Indian Patent Application No. 201747005687 (dated Aug. 29, 2019).
Singh et al., "Immunoproteasome β5i-Selective Dipeptidomimetic Inhibitors," ChemMedChem 11:1-6 (2016).
El-Naggar et al., "Synthesis and Biological Activity of Some New 4-(Aminoacyl)Aminopyridines and 2-(Aminoacyl)Aminopyrimidine Derivatives," Polish J. Chem. 56:1279-1285 (1982).
Yamazaki et al., "Two New Tryptamine Derivatives, Leptoclinidamide and (-)-Leptoclinidamine B, from an Indonesian Ascidian Leptoclinides dubius," Marine Drugs 10(12):349-357 (2012).
Examination report for Europe Patent Application No. 15834073.7 (dated Mar. 25, 2020).
Database Registry Database accession No. 1299989-71-1.
Database Registry Database accession No. 1276335-00-2.
Database Registry Database accession No. 1060993-03-4.
El-Naggar et al., "Database CA [Online]: 'Synthesis and Biological Activity of Some New 4-(Aminoacyl) Aminopyridines and 2-(Aminoacyl)Aminopyrimidine Derivatives,'" Polish Journal of Chemistry, 56:1279-1285 (1982).
Translation of the Office Action for Chinese Patent Application No. 201580056519.4 (dated Jun. 29, 2020).
CAS Registry No. 3641-55-2, Entered STN: Nov. 16, 1984.
CAS Registry No. 294889-15-9, Entered STN: Oct. 12, 2000.
CAS Registry No. 51219-75-1, Entered STN: Nov. 16, 1984.
CAS Registry No. 51219-69-3, Entered STN: Nov. 16, 1984.
CAS Registry No. 59973-55-6, Entered STN: Nov. 16, 1984.
Duke et al., "Synthesis and Biological Evaluation of Sparsomycin Analogues," J. Med. Chem. 26:1556-1561 (1983).
Baud et al., "Defining the Mechanism of Action and Enzymatic Selectivity of Psammaplin A against Its Epigenetic Targets," J. Med. Chem. 55:1731-1750 (2012).
CAS Registry No. 839730-13-1, Entered STN: Mar. 1, 2005.
CAS Registry No. 839730-22-2, Entered STN: Mar. 1, 2005.
CAS Registry No. 839730-21-1, Entered STN: Mar. 1, 2005.
CAS Registry No. 866779-17-1, Entered STN: Nov. 4, 2005.
CAS Registry No. 1461869-28-2, Entered STN: Oct. 21, 2013.
CAS Registry No. 50633-04-0, Entered STN: Nov. 16, 1984.
CAS Registry No. 87639-77-8, Entered STN: Nov. 16, 1984.
CAS Registry No. 120655-16-5, Entered STN: May 12, 1989.
Supplementary European Search Report for European Patent Application No. 15735399.6 (dated Jun. 29, 2017).
Lei et al., "Structural Features and Binding Free Energies for Non-Covalent Inhibitors Interacting with Immunoproteasome by Molecular Modeling and Dynamics Simulations," Theor. Chem. Am. 131:1-11 (2012).
Siebler et al., "Molecular Mutil-Wavelength Optical Anion Sensors," Eur. J. Inorg. Chem. 523-527 (2010).
Ahlford et al., "Fine-Tuning Catalytic Activity and Selectivity-[Rh(Amino Acid Thioamide)] Complexes for Efficient Ketone Reduction," Tetrahedron Lett. 50:6321-6324 (2009).
Blackburn et al. "Optimization of a Series of Dipeptides with a P3 Beta-Neopentyl Asparagine Residue as Non-covalent Inhibitors of the Chymotrypsin-Like Activity of the Human 20S Proteasome," Med. Chem. Commun. 3:710-719 (2012).
International Preliminary Report on Patentability and Written Opinion for PCT/US2015/011022 (dated Jul. 21, 2016).
International Search Report and Written Opinion for corresponding Application No. PCT/US2015/011022 (dated Jun. 24, 2015).
PUBCHEM: Compound Summary for CID 269632 (Mar. 26, 2005).
Office Action for European Patent Application No. 15735399.6 (dated Jun. 11, 2018).
Office Action in Chinese Patent Application No. 201680065296.2 (dated Dec. 4, 2019).
Pubchem CID 91250924, https://pubchem.ncbi.nlm.nih.gov/compound/91250924, Retrieved Nov. 24, 2019.

(56) References Cited

OTHER PUBLICATIONS

International Search Report and Written Opinion for corresponding Application No. PCT/2018/055482 (dated Feb. 8, 2019).
Pubchem CID 64894495, Oct. 23, 2012 (Accession date Nov. 29, 2018).
Pubchem CID 129847054, Sep. 13, 2017 (Accession date Jan. 18, 2019).
Restriction Requirement for U.S. Appl. No. 15/504,951 (dated Jun. 8, 2018).
Office Action for U.S. Appl. No. 15/504,951 (dated Jun. 11, 2019).
Office Action for U.S. Appl. No. 15/504,951 (dated Oct. 12, 2018).
Ettmayer et al., "Lessons Learned from Marketed and Investigational Prodrugs," J. Med. Chem. 47:2393-2404 (2004).
Han, Hyo-Kyung "Targeted Prodrug Design to Optimize Drug Delivery," AAPS Pharmsci 2:1-11 (2000).
Muller, Christa "Prodrug Approaches for Enhancing the Bioavailability of Drugs with Low Solubility," Chemistry & Biodiversity 6:2071-2083 (2009).
Singh et al., "Recent Trends in Targeted Anticancer Prodrug and Conjugate Design," NIH Public Access Author Manuscript, Available in PMC Jan. 5, 2010, 53 pages, Published in final edited form as: Curr. Med. Chem. 15 r18):1802-1826 (2008).
Testa, Bernard "Prodrug Research: Futile or Failure?" Biochemical Pharmacology 68:2097-2106 (2004).
Office Action for U.S. Appl. No. 15/768,628 (dated May 1, 2020).
Office Action in Chinese Patent Application No. 201680065296.2 (dated Sep. 28, 2020).
Office Action in European Application No. 16856412.8 (dated Sep. 16, 2020).
Notice of Reasons for Rejection for Japanese Patent Application No. 2018-519271 (dated Oct. 22, 2020).
Korshin et al., "Aminoamidines. 7.* 2-(Arylaminomethyl)imidazolines and Their Acylated Derivatives," Izvestiya Akademii Nauk, Seriya Khimicheskaya 3:472-479 (1994) with English translation as Korshin et al., "Aminoamidines. 7.* 2-(Arylaminomethyl)imidazolines and Their Acylated Derivatives," Russ. Chem. Bull. 43(3):431-438 (1994).
Grudzinski et al., "Studia nad Procesami Uwodornienia Aminonitryli. IX. Otrzymywanie N,N'-Dwuacylo-Trojmetylenodwuamin o Niejednakowych Resztach Kwasowych w Czateczce [Studies on the Hydrogenation of Aminonitriles. IX. Synthesis of N,N'-Diacyltrimethylenediamines Containing Different Acyl Residues]," Acta Poloniae Pharmaceutica 22(6):485-490 (1965) (Article in Polish, English Title and Summary at pp. 489-490).
Restriction Requirement for U.S. Appl. No. 16/755,427 (dated Dec. 21, 2020).
Office Action for U.S. Appl. No. 15/504,951 (dated Mar. 26, 2021).
Office Action in Chinese Patent Application No. 201680065296.2 (dated Apr. 30, 2021).
Office Action for Chinese Patent Application No. 201580056519.4 (dated May 7, 2021).
Examination Report for Indian Patent Application No. 202048025018 (dated Jun. 3, 2021).

\* cited by examiner

PROTEASOME INHIBITORS AND USES THEREOF

This application is a national stage application under 35 U.S.C. § 371 of PCT Application No. PCT/US2016/057346, filed Oct. 17, 2016, which claims the priority benefit of U.S. Provisional Patent Application Ser. No. 62/242,139, filed Oct. 15, 2015, which are hereby incorporated by reference in their entirety.

This invention was made with government support under Grant No. AI123794 awarded by the National Institutes of Health. The government has certain rights in the invention.

FIELD OF USE

The present invention relates to proteasome inhibitors and uses thereof.

BACKGROUND OF THE INVENTION

Proteasomes are highly conserved self-compartmentalizing proteases found in three kingdoms of life. A proteasome is a large, ATP-dependent, multi-subunit, barrel-shaped N-terminal nucleophile hydrolase present in the cytosol and nucleus of eukaryotic cells and is responsible for the degradation of the majority of cellular proteins (Baumeister et al., "The Proteasome: Paradigm of a Self-Compartmentalizing Protease," *Cell* 92(3):367-380 (1998); Goldberg A L., "Functions of the Proteasome: from Protein Degradation and Immune Surveillance to Cancer Therapy," *Biochem. Soc. Trans.* 35(Pt 1): 12-17 (2007)). Through regulated degradation, a proteasome regulates protein homeostasis, the cell cycle, signal transduction, protein trafficking, immune responses, etc, which are important cellular functions. Degradation product oligopeptides are reservoirs of antigenic peptides for MHC class I antigen presentation.

Proteasome inhibition interrupts many cellular pathways, particularly, the NF-kB activation pathway, the induction of unfolded protein response, and ER stress, while strongly inducing apoptosis. For this reason, highly specific proteasome inhibitors have been approved for the treatment of hematological cancer. Proteasome inhibitors can also markedly limit the overall supply of peptides for MHC class I molecules and thus block antigen presentation (Rock et al., "Protein Degradation and the Generation of MHC Class I-Presented Peptides," *Adv. Immunol.* 80:1-70 (2002)). As a result, proteasome inhibitors reduce immune response via multiple routes.

*Plasmodium falciparum*: (*P. falciparum*), the most deadly of the human malarias, accounts for nearly 0.5 million deaths a year, primarily in children (Zhang et al., "Transcriptome Analysis Reveals Unique Metabolic Features in the *Cryptosporidium Parvum* Oocysts Associated with Environmental Survival and Stresses," *BMC Genomics* 13:647 (2012)). The most important current therapies are combinations of artemisinins (ART). The emergence of ART resistant parasites (Ariey et al., "A Molecular Marker of Artemisinin-Resistant *Plasmodium Falciparum* Malaria," *Nature* 505 (7481):50-55 (2014); Straimer et al., "K13-Propeller Mutations Confer Artemisinin Resistance in *Plasmodium Falciparum* Clinical Isolates," *Science* 347(6220):428-431 (2015); Dogovski et al., "Targeting the Cell Stress Response of *Plasmodium Falciparum* to Overcome Artemisinin Resistance," *PLoS Biol.* 13(4):e1002132 (2015); Mbengue et al., "A Molecular Mechanism of Artemisinin Resistance in *Plasmodium Falciparum* Malaria," *Nature* 520(7549):683-687 (2015)) highlights the need for new antimalarials with novel targets (Wells T N et al., "*Malaria* Medicines: a Glass Half Full?" *Nat. Rev. DrugDiscov.* 14(6):424-442 (2015)). Upregulation of the ubiquitin proteasome system (UPS) is important for survival of artemisinin-resistant parasites and emphasizes the importance of the UPS in parasite survival and its importance as a drug target moving forward (Dogovski et al., "Targeting the Cell Stress Response of *Plasmodium Falciparum* to Overcome Artemisinin Resistance," *PLoS Biol.* 13(4):e1002132 (2015); Mok et al., "Drug Resistance. Population Transcriptomics of Human *Malaria* Parasites Reveals the Mechanism of Artemisinin Resistance," *Science* 347(6220):431-435(2015)).

Proteasome inhibitors are known to kill *malaria* parasites in vitro and are efficacious against multiple parasite stages; peptide epoxyketone inhibitors, a peptide vinyl sulfone inhibitor and a cyclic peptide inhibitor, have potent antimalarial activities (Dogovski et al., "Targeting the Cell Stress Response of *Plasmodium Falciparum* to Overcome Artemisinin Resistance," *PLoS Biol.* 13(4):e1002132 (2015); Featherstone C. "Proteasome Inhibitors in Development for *Malaria*," *Mol. Med. Today* 3(9):367 (1997); Gantt et al., "Proteasome Inhibitors Block Development of *Plasmodium* Spp," *Antimicrob. Agents Chemother.* 42(10):2731-2738 (1948); Aminake et al., "The Proteasome of *Malaria* Parasites: A Multi-Stage Drug Target for Chemotherapeutic Intervention?" *Int. J. Parasitol. Drugs Drug Resist.* 2:1-10 (2012); Li et al., "Validation of the Proteasome as a Therapeutic Target in *Plasmodium* Using an Epoxyketone Inhibitor with Parasite-Specific Toxicity," *Chem. Biol.* 19(12): 1535-1545 (2012); Tschan et al., "Broad-Spectrum Antimalarial Activity of Peptido Sulfonyl Fluorides, a New Class of Proteasome Inhibitors," *Antimicrob. Agents Chemother.* 57(8):3576-8354 (2013); Li et al., "Assessing Subunit Dependency of the *Plasmodium* Proteasome Using Small Molecule Inhibitors and Active Site Probes," *ACS Chem. Biol.* 9(8):1869-1876 (2014); Li et al., "Structure- and Function-Based Design of *Plasmodium*-Selective Proteasome Inhibitors," *Nature* 530(7589):233-236 (2016)). Bortezomib (BTZ) and MLN-273 were effective against *plasmodium* in blood and liver stages (Lindenthal et al., "The Proteasome Inhibitor MLN-273 Blocks Exoerythrocytic and Erythrocytic Development of *Plasmodium* Parasites," *Parasitology* 131(Pt 1):37-44 (2005); Reynolds et al., "Antimalarial Activity of the Anticancer and Proteasome Inhibitor Bortezomib and its Analog ZL3B," *BMC. Clin. Pharmacol.* 7:13 (2007)); MG-132 against blood stage and gametocytes (Lindenthal et al., "The Proteasome Inhibitor MLN-273 Blocks Exoerythrocytic and Erythrocytic Development of *Plasmodium* Parasites," *Parasitology* 131(Pt 1):37-44 (2005); Prudhomme et al., "Marine *Actinomycetes*: a New Source of Compounds Against the Human *Malaria* Parasite," *PLoS One* 3(6):e2335 (2008)); epoxomicin against blood and liver stages and gametocytes (Aminake et al., "Thiostrepton and Derivatives Exhibit Antimalarial And Gametocytocidal Activity by Dually Targeting Parasite Proteasome and Apicoplast," *Antimicrob. Agents Chemother.* 55(4):1338-1348 (2011); Czesny et al., "The Proteasome Inhibitor Epoxomicin Has Potent *Plasmodium Falciparum* Gametocytocidal Activity," *Antimicrob. Agents Chemother.* 53(10):4080-4085 (2009); Kreidenweiss et al., "Comprehensive Study of Proteasome Inhibitors Against *Plasmodium Falciparum* Laboratory Strains and Field Isolates From Gabon," *Malar. J.* 7:187 (2008); Li et al., "Validation of the Proteasome as a Therapeutic Target in *Plasmodium* Using an Epoxyketone Inhibitor With Parasite-Specific Toxicity," *Chem. Biol.* 19(12):1535-1545 (2012)). These inhibitors are in general not species selective. They are cytotoxic to host cells and unsuitable for treating *malaria*. There is an urgent need to develop *Plasmodium* spp. proteasome (Pf20S) selective inhibitors that target parasite proteasomes over human host proteasomes.

Degradation of the majority of cytosolic proteins is a highly regulated, ATP-dependent cellular activity executed by the ubiquitin-proteasome system (UPS) (Goldberg, A. L. "Functions of the Proteasome: From Protein Degradation and Immune Surveillance to Cancer Therapy," *Biochem. Soc. Trans.*, 35:12-17 (2007)). The UPS plays essential roles in diverse cellular activities, including cell cycle control, signal transduction, protein homeostasis, and immune surveillance. The 26S proteasome is composed of a hydrolytic 20S core and regulators, such as 19S or 11S. The 20S core that is constitutively expressed in most cells (c-20S) is a stack of 4 rings of 14 α and β subunits organized in $\alpha_{1-7}\beta_{1-7}\beta_{1-7}\alpha_{1-7}$ fashion, where 2 copies of each caspase-like β1, trypsin-like β2, and chymotrypsin-like β5 active subunits are located in the inner β rings (Baumeister, et al., "The Proteasome: Paradigm of a Self-Compartmentalizing Protease," *Cell* 92:367-380 (1998)). The chymotrypsin-like β5 active subunits of the 20S have been clinically validated as a target for the treatment of multiple myeloma and certain lymphomas. Bortezomib (BTZ) and carfilzomib (CFZ) are FDA-approved drugs that represent two classes of covalent proteasome inhibitors: reversible peptide boronates and irreversible peptide epoxyketones, respectively (Borissenko et al., "20S Proteasome and its Inhibitors: Crystallographic Knowledge for Drug Development," *Chem. Rev.* 107:687-717 (2007); Parlati et al., *Haematol-Hematol. J.* 94:148-149 (2009)). Several other classes of proteasome inhibitors have been identified and optimized, such as β-lactones and peptide sulfonyl fluorides (Huber et al., "Inhibitors for the Immuno- and Constitutive Proteasome: Current and Future Trends in Drug Development," *Angew. Chem. Int. Ed. Engl.* 51(35):8708-8720 (2012)); however, the reactive warheads of these classes pose a great challenge to overcome for developing a drug candidate.

Researchers have been focusing on developing noncovalent proteasome inhibitors for various isoforms of proteasomes, such as *Mycobacterium tuberculosis* proteasome (Bryk et al., "Selective Killing of Nonreplicating Mycobacteria," *Cell Host Microbe* 3:137-145 (2008); Hu et al., "Structure of the *Mycobacterium Tuberculosis* Proteasome and Mechanism of Inhibition by a Peptidyl Boronate," *Mol. Microbiol.* 59:1417-1428 (2006); Li et al., "Structural Basis for the Assembly and Gate Closure Mechanisms of the *Mycobacterium Tuberculosis* 20S Proteasome," *Embo J.* 29:2037-2047 (2010); Lin et al., "N,C-Capped Dipeptides With Selectivity for Mycobacterial Proteasome Over Human Proteasomes: Role of S3 and S1 Binding Pockets," *J Am Chem Soc.* 135:9968-9971 (2013); Lin et al., "*Mycobacterium Tuberculosis* prcBA Genes Encode a Gated Proteasome With Broad Oligopeptide Specificity," *Mol. Microbiol.* 59:1405-1416 (2006); Lin et al., "Fellutamide B is a Potent Inhibitor of the *Mycobacterium Tuberculosis* Proteasome," *Arch. Biochem. Biophys.* 501:214-220 (2010); Lin et al., "Inhibitors Selective for Mycobacterial Versus Human Proteasomes," *Nature* 461(7264):621-626 (2009); Lin et al., "Distinct Specificities of *Mycobacterium Tuberculosis* and Mammalian Proteasomes for N-Acetyl Tripeptide Substrates," *J. Biol. Chem.* 283:34423-31 (2008)) and human immunoproteasome (i-20S) (Fan et al., "Oxathiazolones Selectively Inhibit the Human Immunoproteasome over the Constitutive Proteasome," *ACS Med. Chem. Lett.* 5:405-410 (2014)). I-20S is expressed in cells of the immune system and other cells exposed to cytokines that are elevated during immune responses, where the active subunits β1c, β2c and β5c in c-20S are replaced by β1i, β2i and β5i, respectively (Tanaka K "Role of Proteasomes Modified by Interferon-γ in Antigen Processing," *J. Leukoc. Biol.* 56:571-575 (1994); Heink et al., "IFN-γ-Induced Immune Adaptation of the Proteasome System is an Accelerated and Transient Response," *Proc. Natl. Acad. Sci. U.S.A.* 102:9241-9246 (2005); Kim et al., "A draft map of the human proteome," *Nature* 509:575-581 (2014)). The i-20S serves diverse functions in the immune system, including the provision of oligopeptides for antigen presentation, T-cell differentiation and proliferation (Palombella et al., "Role of the Proteasome and NF-kB in Streptococcal Cell Wall-Induced Polyarthritis," *Proc. Natl. Acad. Sci. U.S.A.* 95:15671-15676 (1998); Kalim et al., "Immunoproteasome Subunit LMP7 Deficiency and Inhibition Suppresses Th1 and Th17 but Enhances Regulatory T Cell Differentiation," *J. Immunol.* 189:4182-4193 (2012)). Antibody-secreting plasma cells are highly sensitive to proteasome inhibition and BTZ, which inhibits both c-20S and i-20S, has been used in renal transplant recipients to prevent antibody-mediated graft rejection (Aull et al., *Clin Transpl* 495-498 (2009); Raghavan et al., "Bortezomib in Kidney Transplantation," *J. Transplant.* 2010: 698594 (2010); Al-Homsi et al., "Effect of Novel Proteasome and Immunoproteasome Inhibitors on Dendritic Cell Maturation, Function, and Expression of IKb and NfKb," *Transpl. Immunol.* 29:1-6 (2013); Pai et al., "Treatment of Chronic Graft-Versus-Host Disease with Bortezomib," *Blood* 124:1677-1688 (2014)). BTZ was also reported to be efficacious in patients with refractory systemic lupus erythematosus (Alexander et al., "The Proteasome Inhibitior Bortezomib Depletes Plasma Cells and Ameliorates Clinical Manifestations of Refractory Systemic Lupus Erythematosus," *Ann Rheum Dis* 74:1474-1478 (2015)). However, BTZ's substantial mechanism-based toxicity requires use of much reduced doses in the treatment of non-malignant conditions.

The present invention is directed to overcoming these and other deficiencies in the art.

SUMMARY OF THE INVENTION

One aspect of the present invention relates to a compound of Formula (I):

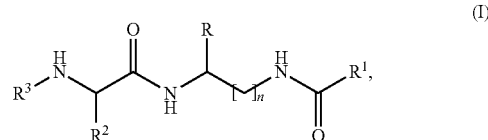

wherein
R is H or $C_{1-6}$ alkyl
$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —NO$_2$, —CF$_3$, —OC$_{1-6}$ alkyl, aryl, heteroaryl, non-aromatic heterocycle, and non-aromatic heterocycle substituted with =O;

$R^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —$(CH_2)_m C(O)NHR^4$, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —$SO_pR^5$, —$C(O)R^5$, —$C(O)(CH_2)_kAr$, —$SO_2Ar$, —$SO_2C_{3-8}$ cycloalkyl, —$C(O)(CH_2)_kHet$, —$C(O)C_{1-6}$ alkyl, and —$C(O)OC_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;

$R^4$ is selected from the group consisting of H, $C_{1-6}$ alkyl, and $C_{3-8}$ cycloalkyl, wherein $C_{3-8}$ cycloalkyl can be optionally substituted with —$CF_3$;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

k is 0 or 2;
m is 1 or 2;
n is 1, 2, or 3; and
p is 1 or 2;

or an oxide thereof, a pharmaceutically acceptable salt thereof, a solvate thereof, or a prodrug thereof.

A second aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (I):

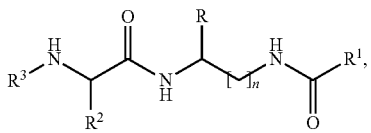

(I)

wherein
R is H or $C_{1-6}$ alkyl;
$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —$NO_2$, —$CF_3$, —$OC_{1-6}$ alkyl, aryl, heteroaryl, non-aromatic heterocycle, and non-aromatic heterocycle substituted with =O;

$R^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —$(CH_2)_m C(O)NHR^4$, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —$SO_pR^5$, —$C(O)R^5$, —$C(O)(CH_2)_kAr$, —$SO_2Ar$, —$SO_2C_{3-8}$ cycloalkyl, —$C(O)(CH_2)_kHet$, —$C(O)C_{1-6}$ alkyl, and —$C(O)OC_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;

$R^4$ is selected from the group consisting of H, $C_{1-6}$ alkyl, and $C_{3-8}$ cycloalkyl, wherein $C_{3-8}$ cycloalkyl can be optionally substituted with —$CF_3$;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

k is 0 or 2;
m is 1 or 2;
n is 1, 2, or 3; and
p is 1 or 2;

or an oxide thereof, a pharmaceutically acceptable salt thereof, a solvate thereof, or a prodrug thereof.

A third aspect of the present invention relates to a method of inhibiting chymotryptic β5i in a cell or a tissue. This method includes providing a compound of Formula (I):

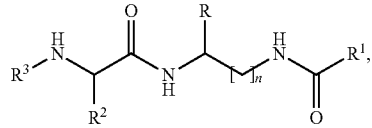

(I)

wherein
R is H or $C_{1-6}$ alkyl;
$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —NO$_2$, —CF$_3$, —OC$_{1-6}$ alkyl, aryl, heteroaryl, non-aromatic heterocycle, and non-aromatic heterocycle substituted with =O;

R$^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —(CH$_2$)$_m$C(O)NHR$^4$, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

R$^3$ is selected from the group consisting of H, —SO$_p$R$^5$, —C(O)R$^5$, —C(O)(CH$_2$)$_k$Ar, —SO$_2$Ar, —SO$_2$C$_{3-8}$ cycloalkyl, —C(O)(CH$_2$)$_k$Het, —C(O)C$_{1-6}$ alkyl, and —C(O)OC$_{1-6}$ alkyl, wherein aryl (Ar) and heteroaryl (Het) can be optionally substituted from 1 to 3 times with a substituent selected independently at each occurrence thereof from halogen or C$_{1-6}$ alkyl;

R$^4$ is selected from the group consisting of H, C$_{1-6}$ alkyl, and C$_{3-8}$ cycloalkyl, wherein C$_{3-8}$ cycloalkyl can be optionally substituted with —CF$_3$;

R$^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;
m is 1 or 2;
n is 1, 2, or 3;
p is 1 or 2; and
contacting a cell or tissue with the compound under conditions effective to inhibit chymotryptic β5i.

A fourth aspect of the present invention relates to a method of treating infectious disease in a subject. This method includes administering to the subject in need thereof a compound of the Formula (I):

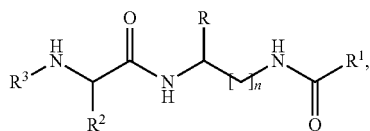

(I)

wherein
R is H or C$_{1-6}$ alkyl;
R$^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —NO$_2$, —CF$_3$, —OC$_{1-6}$ alkyl, aryl, heteroaryl, non-aromatic heterocycle, and non-aromatic heterocycle substituted with =O;

R$^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —(CH$_2$)$_m$C(O)NHR$^4$, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

R$^3$ is selected from the group consisting of H, —SO$_p$R$^5$, —C(O)R$^5$, —C(O)(CH$_2$)$_k$Ar, —SO$_2$Ar, —SO$_2$C$_{3-8}$ cycloalkyl, —C(O)(CH$_2$)$_k$Het, —C(O)C$_{1-6}$ alkyl, and —C(O)OC$_{1-6}$ alkyl, wherein aryl (Ar) and heteroaryl (Het) can be optionally substituted from 1 to 3 times with a substituent selected independently at each occurrence thereof from halogen or C$_{1-6}$ alkyl;

R$^4$ is selected from the group consisting of H, C$_{1-6}$ alkyl, and C$_{3-8}$ cycloalkyl, wherein C$_{3-8}$ cycloalkyl can be optionally substituted with —CF$_3$;

R$^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;
m is 1 or 2;
n is 1, 2, or 3; and
p is 1 or 2;
or an oxide thereof, a pharmaceutically acceptable salt thereof, a solvate thereof, or a prodrug thereof.

The present application describes that asparagine-ethylenediamine (AsnDEA) can serve as a versatile scaffold for proteasome inhibitors. Kinetic studies of representative compounds showed a noncompetitive modality of inhibition. Structure-activity relationship studies guided the development of potent, non-covalent, reversible, cell-permeable inhibitors with high selectivity for human immunoproteasomes over constitutive proteasomes. A selective AsnDEA immunoproteasome inhibitor is selectively cytotoxic against tumor cell lines of multiple myeloma and lymphoma over a liver carcinoma cell line, illustrating the potential of such compounds against multiple myeloma or other hematological cancers.

BRIEF DESCRIPTION OF DRAWINGS

In FIG. 2A, Karpas 1106P cells were treated with PKS21221 or HepG2 for 2 hours at the concentrations indicated prior to incubation with substrate (Ac-ANW)₂R110 for β5i, suc-LLVY-luciferin for β5 in Karpas cells, and suc-LLVY-luciferin for β5c in HepG2 cells, respectively. IC50s were determined to be 0.154 μM and 0.149 μM. FIG. 2B is a graph showing cytotoxicity of PKS21221 against multiple myeloma cell lines MM1.S and RPMI8226, Karpas and HepG2. Values of IC50 of intracellular proteasome inhibition by PKS21221 and EC50s of cytotoxicity by PKS21221 were listed in Table 3 supra. Data were average of three independent experiments.

DETAILED DESCRIPTION OF INVENTION

Figure 1A:
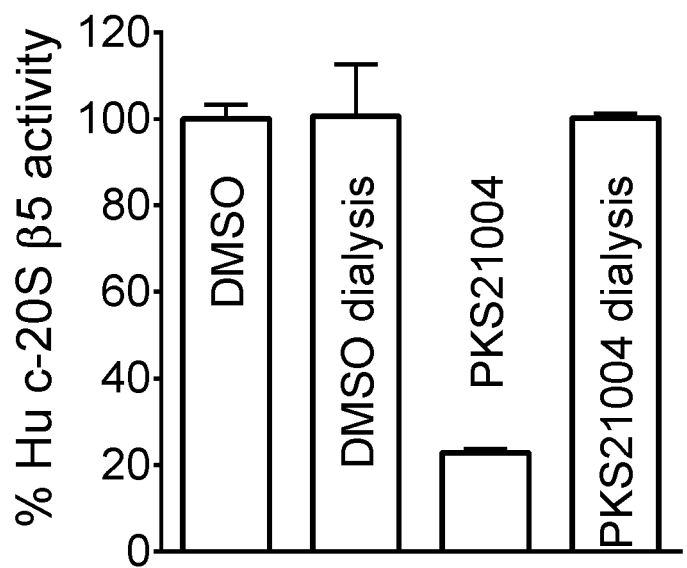
FIGS. 1A-1E are graphs showing inhibition modality of PKS21004 against human proteasomes. Washout of c-20S from the preincubated c-20S and PKS21104 to recover the β5c activity (FIG. 1A). Substrate titration of hu i-20S (FIG. 1B) and c-20S (FIG. 1D) steady state velocities in the presence of PKS21004 at the concentrations indicated next to each curve. Data as in (FIG. 1B) were plotted double reciprocal in (FIG. 1C), and (FIG. 1D) in (FIG. 1E). Values of Ki and α for PKS21004 were determined by fitting to an equation for noncompetitive inhibitors: 0.077 μM, 0.28 for i-20S, and 0.55 μM, 0.98, respectively.
Figure 1B:
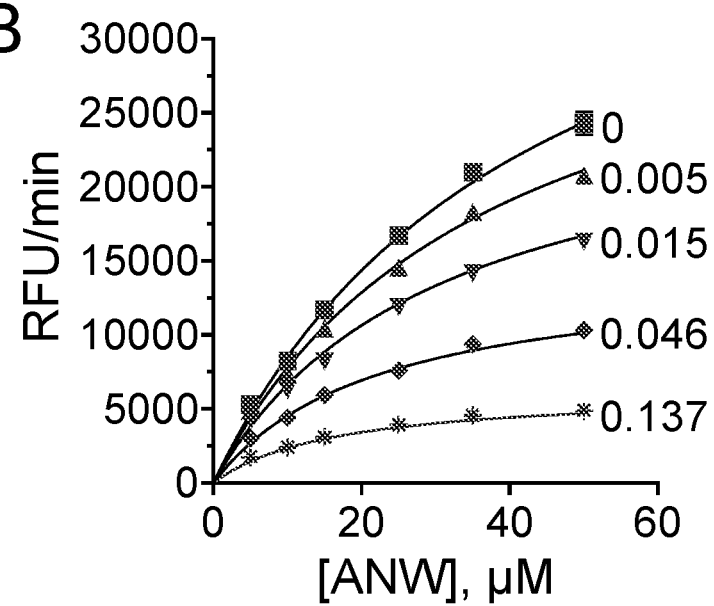
Figure 1C:
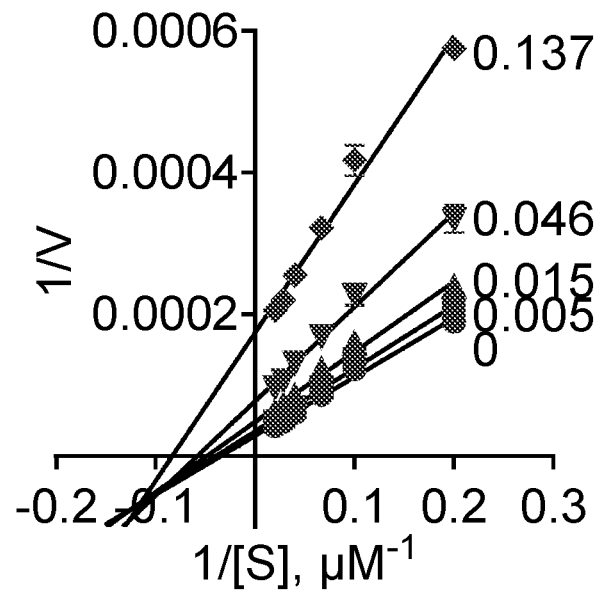
Figure 1D:
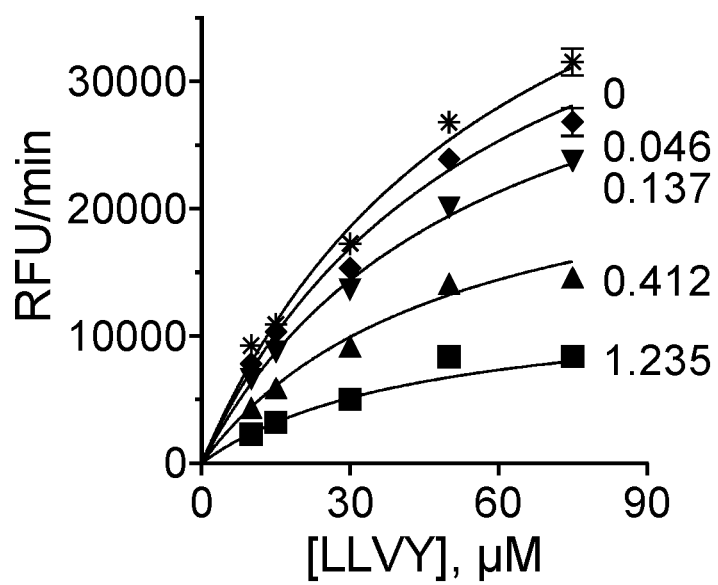
Figure 1E:
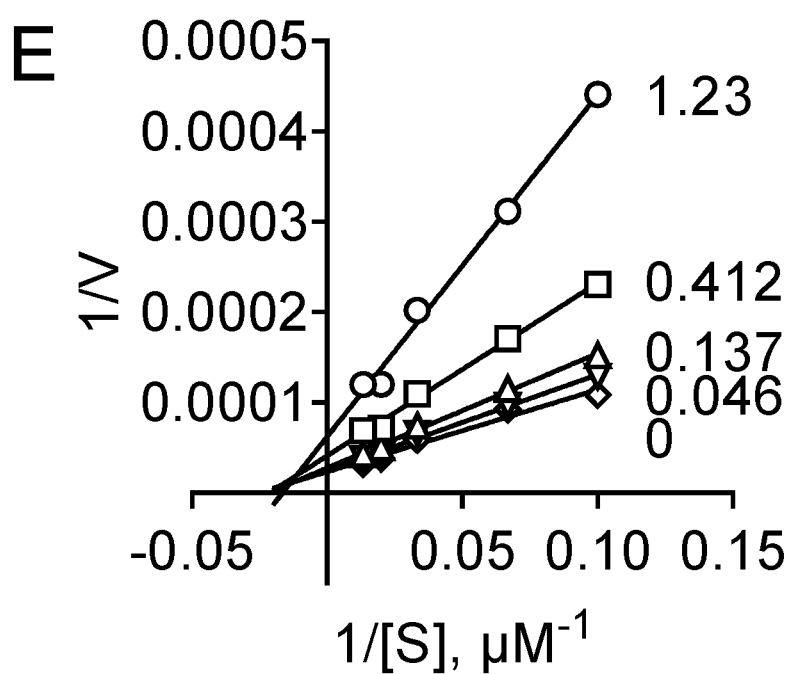

One aspect of the present invention relates to a compound of Formula (I):

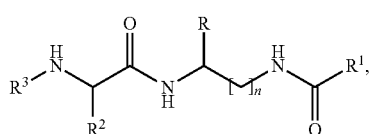

wherein
R is H or $C_{1-6}$ alkyl
$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —NO₂, —CF₃, —OC$_{1-6}$ alkyl, aryl, heteroaryl, non-aromatic heterocycle, and non-aromatic heterocycle substituted with =O;

$R^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —(CH₂)$_m$C(O)NHR⁴, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO₂, —CF₃, —OC$_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —SO$_p$R⁵, —C(O)R⁵, —C(O)(CH₂)$_k$Ar, —SO₂Ar, —SO₂C$_{3-8}$ cycloalkyl, —C(O)(CH₂)$_k$Het, —C(O)C$_{1-6}$ alkyl, and —C(O)OC$_{1-6}$ alkyl, wherein aryl (Ar) and heteroaryl (Het) can be optionally substituted from 1 to 3 times with a substituent selected independently at each occurrence thereof from halogen or C$_{1-6}$ alkyl;

$R^4$ is selected from the group consisting of H, C$_{1-6}$ alkyl, and C$_{3-8}$ cycloalkyl, wherein C$_{3-8}$ cycloalkyl can be optionally substituted with —CF₃;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO₂, —CF₃, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;
m is 1 or 2;
n is 1, 2, or 3; and
p is 1 or 2;
or an oxide thereof, a pharmaceutically acceptable salt thereof, a solvate thereof, or a prodrug thereof.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Particular alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. The term "alkenyl" may also refer to a hydrocarbon chain having 2 to 6 carbons containing at least one double bond and at least one triple bond.

The term "cycloalkyl" means a non-aromatic mono- or multicyclic ring system of about 3 to about 8 carbon atoms, preferably of about 5 to about 7 carbon atoms. Exemplary monocyclic cycloalkyls include cyclopentyl, cyclohexyl, cycloheptyl, and the like.

The term "aryl" means an aromatic monocyclic or multicyclic ring system of 6 to about 14 carbon atoms, preferably of 6 to about 10 carbon atoms. Representative aryl groups include phenyl and naphthyl.

As used herein, "biphenyl" or "bi-phenyl" refers to a phenyl group substituted by another phenyl group.

The term "heteroaryl" or "Het" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "biheteroaryl" or "bi-heteroaryl" refers to a heteroaryl group substituted by another heteroaryl group.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

As used herein, "biheterocyclyl" or "bi-heterocyclyl" refers to a heterocyclyl group substituted by another heterocyclyl or heterocycle group.

The term "non-aromatic heterocycle" means a non-aromatic monocyclic system containing 3 to 10 atoms, preferably 4 to about 7 carbon atoms, in which one or more of the atoms in the ring system is/are element(s) other than carbon, for example, nitrogen, oxygen, or sulfur. Representative non-aromatic heterocycle groups include pyrrolidinyl, 2-oxopyrrolidinyl, piperidinyl, 2-oxopiperidinyl, azepanyl, 2-oxoazepanyl, 2-oxooxazolidinyl, morpholino, 3-oxomorpholino, thiomorpholino, 1,1-dioxothiomorpholino, piperazinyl, tetrohydro-2H-oxazinyl, and the like.

The term "monocyclic" used herein indicates a molecular structure having one ring.

The term "bicyclic" used herein indicates a molecular structure having two ring.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, Protective Groups in Organic Synthesis, John Wiley & Sons, New York (1991), which is hereby incorporated by reference in its entirety.

The term "halo" or "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; a "stable compound" or "stable structure" is meant to be a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "method of treating" means amelioration or relief from the symptoms and/or effects associated with the disorders described herein. As used herein, reference to "treatment" of a patient is intended to include prophylaxis.

The term "compounds of the invention", and equivalent expressions, are meant to embrace compounds of general Formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic, and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like (see, for example, Berge et al., "Pharmaceutical Salts," *J. Pharm. Sci.,* 66:1-9 (1977) and Remington's Pharmaceutical Sciences, 17th ed., Mack Publishing Company, Easton, Pa., 1985, p. 1418, which are hereby incorporated by reference in their entirety). Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); Methods in Enzymology, K. Widder et al, Ed., Academic Press, 42, p. 309-396 (1985); A Textbook of Drug Design and Development, Krogsgaard-Larsen and H. Bundgaard, ed., Chapter 5; "Design and Applications of Prodrugs" p. 113-1[91] (1991); Advanced Drug Delivery Reviews, H. Bundgard, 8, p. 1-38 (1992); *J. Pharm. Sci.,* 77:285 (1988); Nakeya et al, *Chem. Pharm. Bull.,* 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amounts" is meant to describe an amount of compound of the present invention effective in inhibiting the proteasome or immunoproteasome and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history; the particular compound used, as well as the carrier in which it is formulated and the route of administration selected for it; and, the nature and severity of the condition being treated.

The term "pharmaceutical composition" means a composition comprising a compound of Formula (I) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

Compounds of Formula (I) can be produced according to known methods. For example, compounds of Formula (I) can be prepared according to Scheme 1 outlined below.

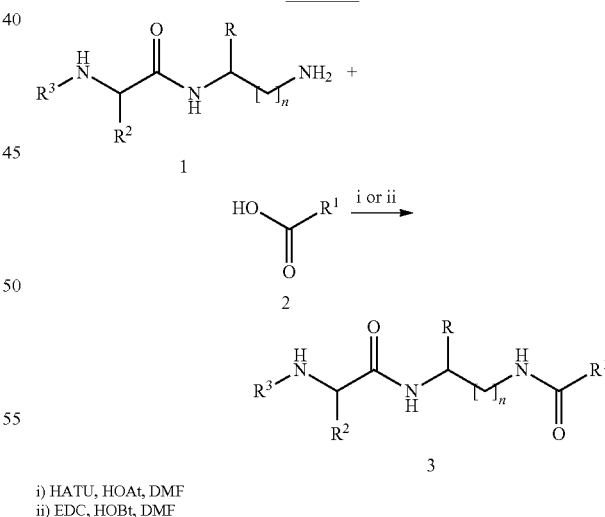

Scheme 1 i) HATU, HOAt, DMF
ii) EDC, HOBt, DMF

Coupling of the amine (1) with the carboxylic acid (2) leads to formation of the compound (3). The coupling reaction can be carried out in a variety of solvents, for example in methylene chloride ($CH_2Cl_2$), tetrahydrofuran (THFE), dimethylformamide (DMF), or other such solvents or in the mixture of such solvents. During the coupling process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like.

Amine (1) can be prepared according to the general scheme outlined below (Scheme 2).

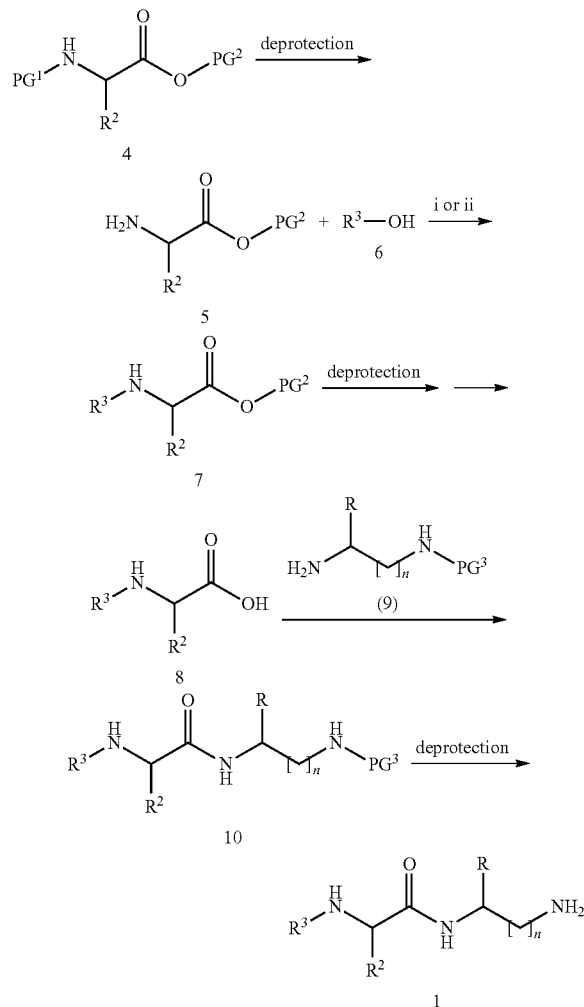

i) HATU, HOAt, DMF
ii) EDC, HOBt, DMF
$PG^1$, $PG^2$, and $PG^3$ are protecting group Amine (5) can be prepared by deprotection of compound (4). Coupling of the amine (5) with the carboxylic acid (6) leads to formation of the compound (7). The coupling reactions are conducted in solvents such as methylene chloride ($CH_2Cl_2$), tetrahydrofuran (THF), dimethylformamide (DMF), or other such solvents. During the coupling process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Following the deprotection reaction, compound (8) is coupled with amine (9) to form compound (10). Amine (1) can be prepared by deprotection of compound (10).

In one embodiment, compound has the Formula (Ia):

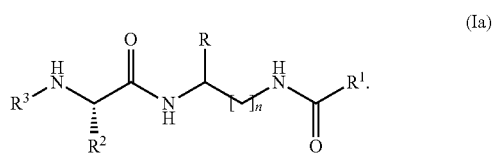

In another embodiment, compound has the Formula (Ib):

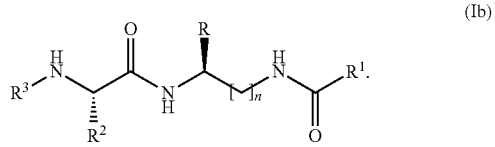

In yet another embodiment, compound has the Formula (Ic):

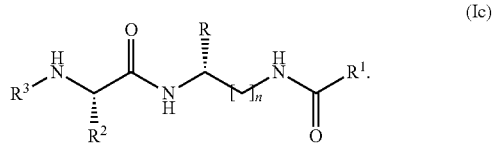

Another embodiment relates to the compound of Formula (I) where alkyl is $C_{1-6}$ alkyl.

Yet another embodiment relates to the compound of Formula (I) where alkenyl is $C_{2-6}$ alkenyl.

Another embodiment relates to the compound of Formula (I) where $R^1$ is selected from the group consisting of

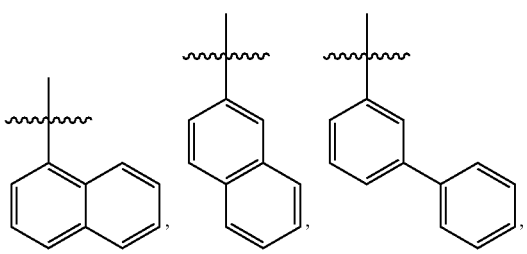

-continued

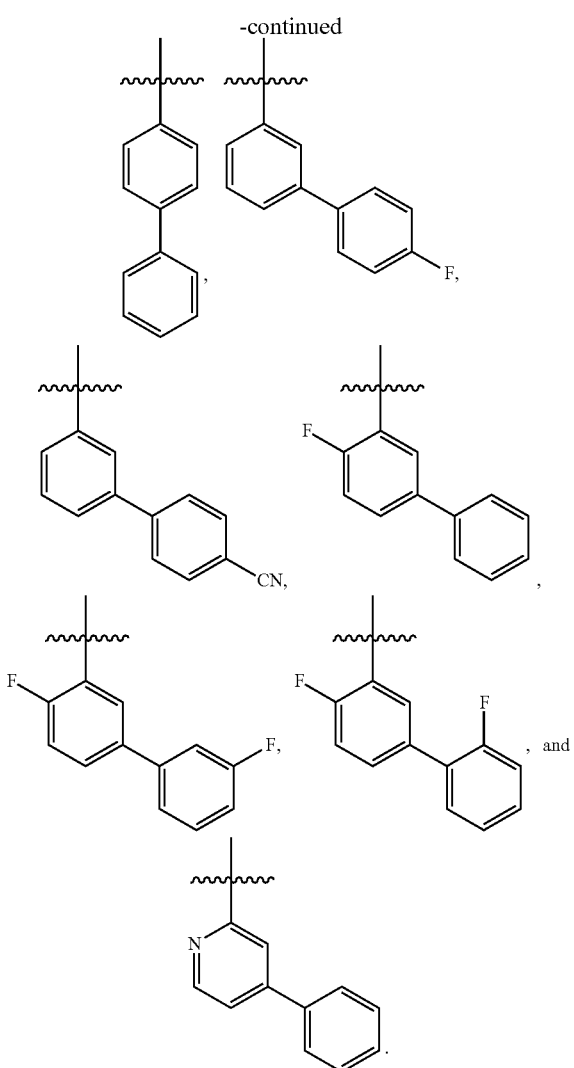

Yet another embodiment relates to the compound of Formula (I) where $R^2$ is selected from the group consisting of H, CH$_3$,

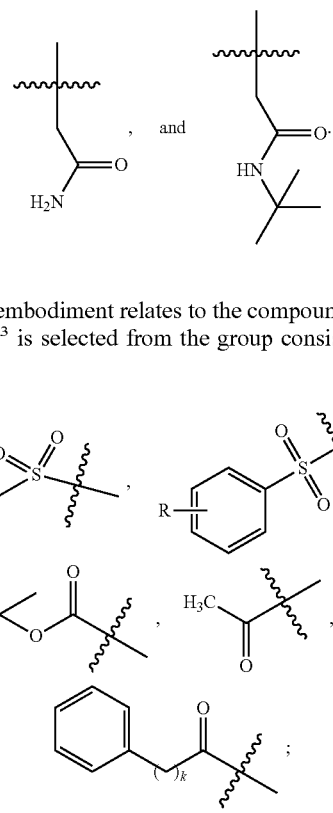

Another embodiment relates to the compound of Formula (I) where $R^3$ is selected from the group consisting of H, and R is C$_{1-6}$ alkyl.

Another embodiment relates to the compound of Formula (I) where the compound has a structure selected from the group consisting of:

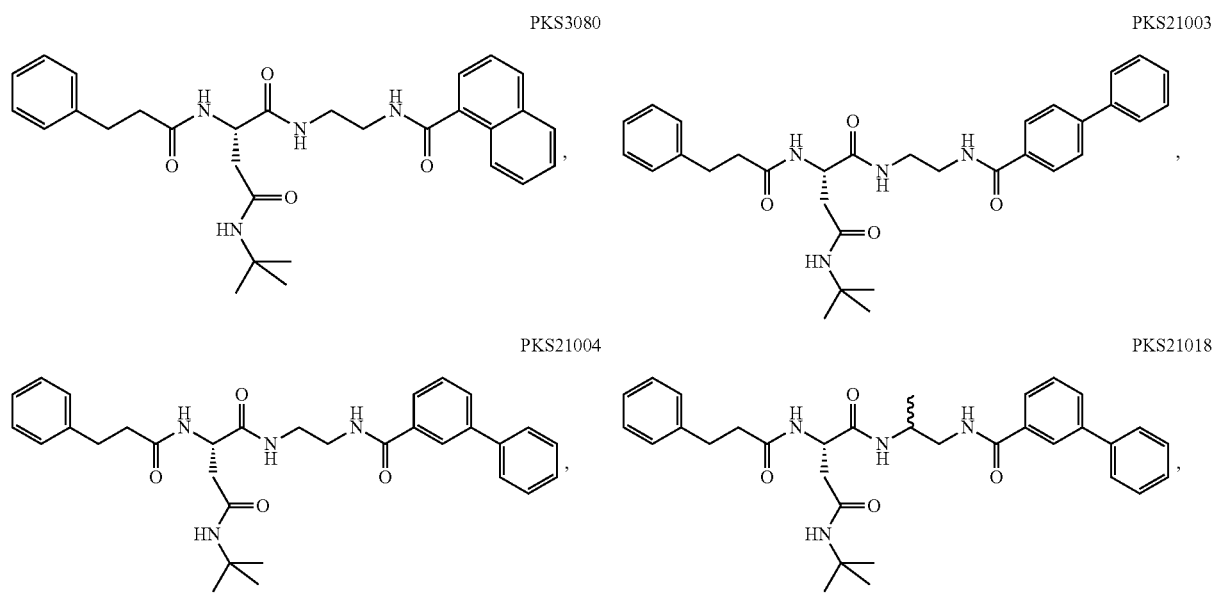

-continued
PKS21019
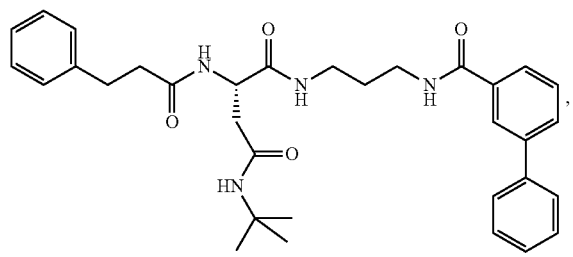
PKS21025
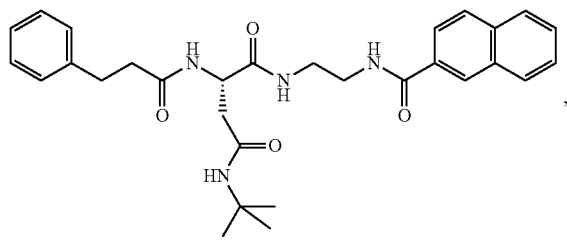
PKS21026
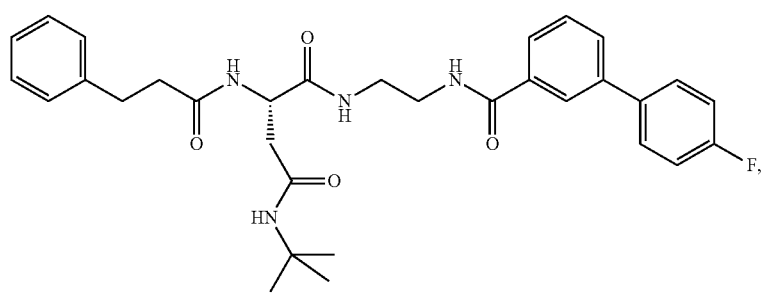
PKS21028
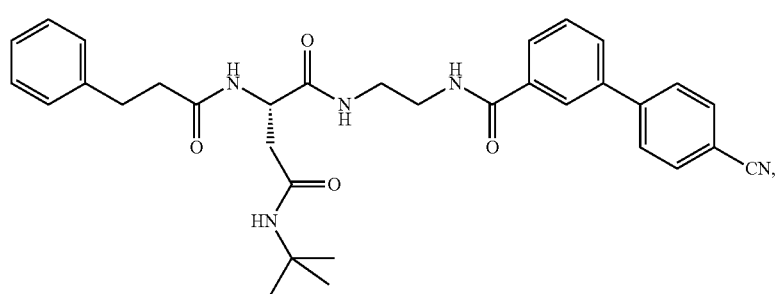
PKS21030
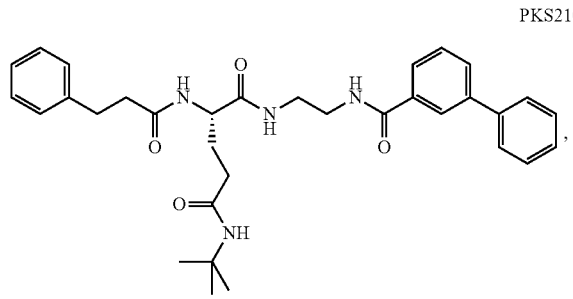
PKS21186
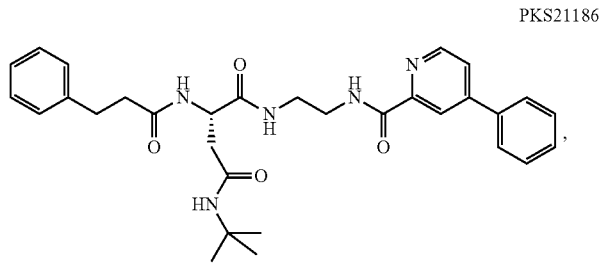
PKS21187
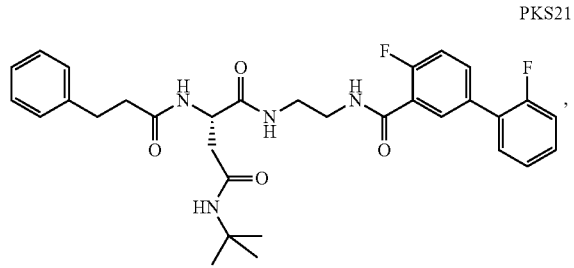
PKS21195
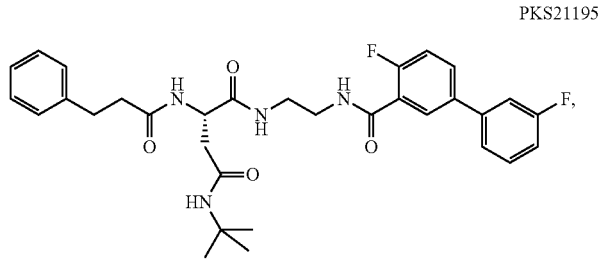

-continued
PKS21196
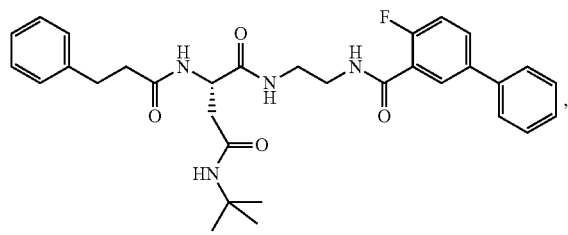
PKS21208
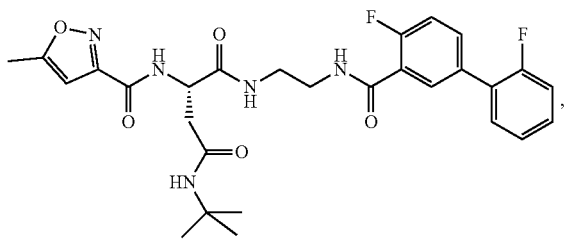
PKS21221
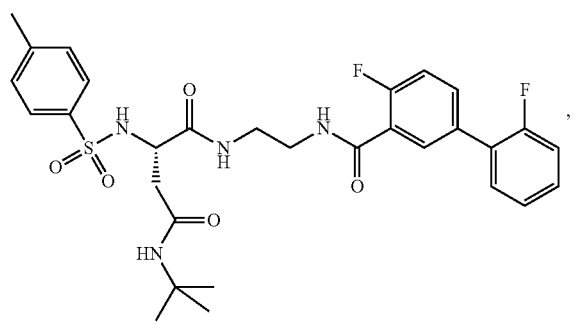
PKS21224
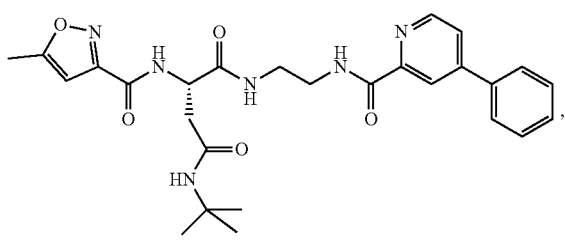
PKS21225
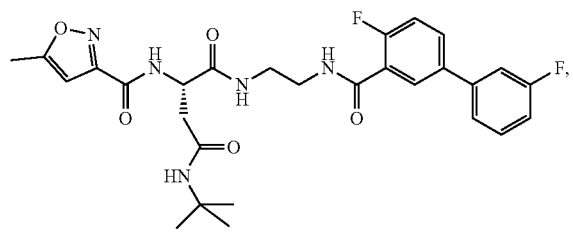
PKS21228
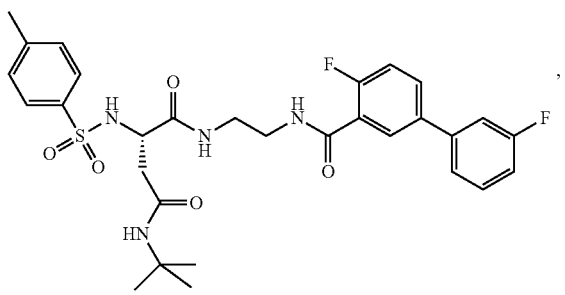
PKS21229
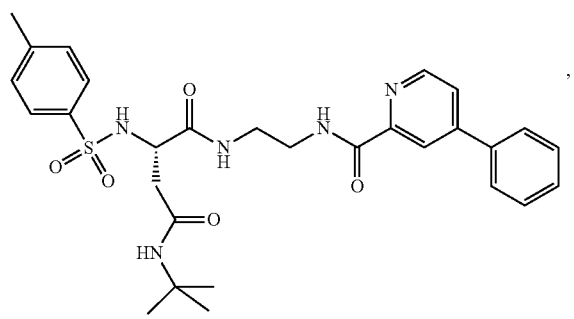
PKS21250
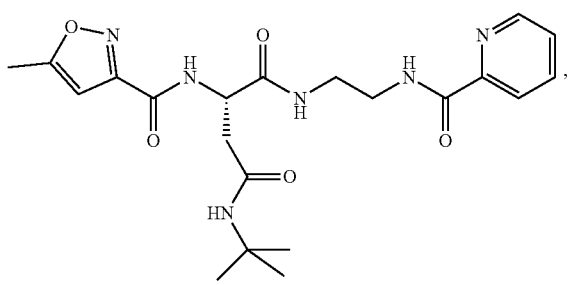
PKS21251
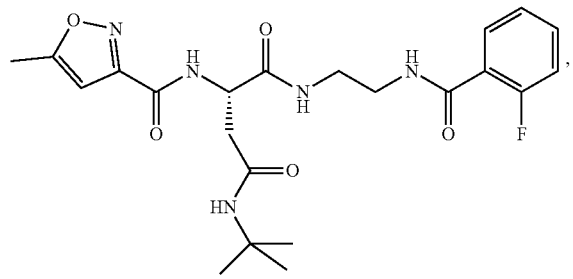
PKS21254
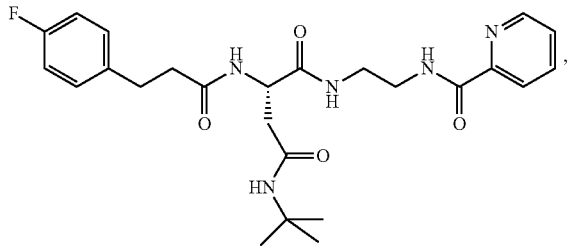

-continued
PKS21255
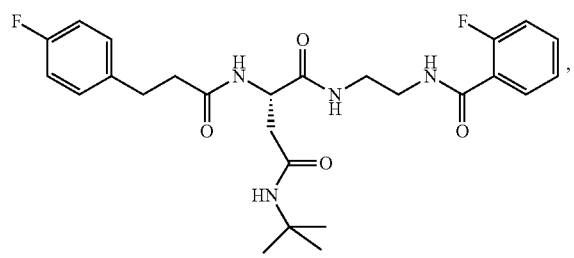
PKS21258
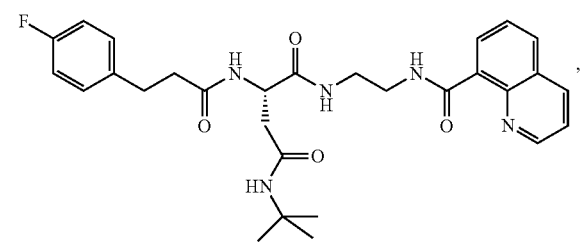
PKS21259
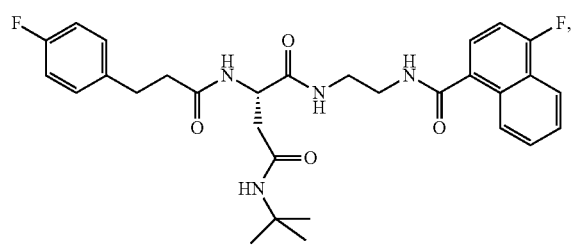
PKS21276
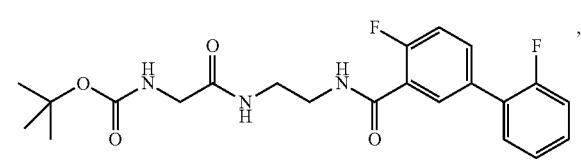
PKS21277
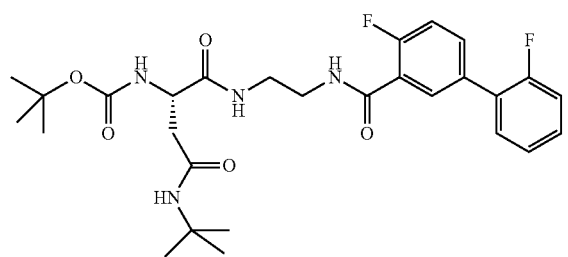
PKS21280
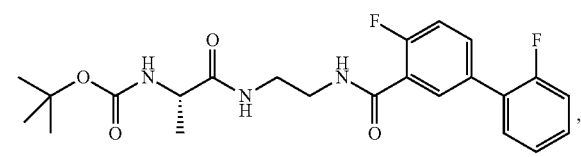
PKS21281
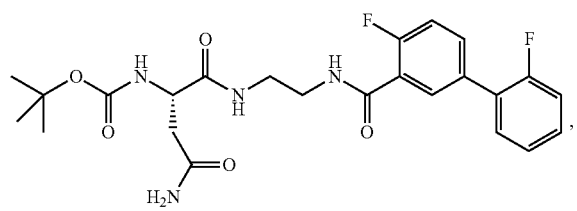
PKS21278
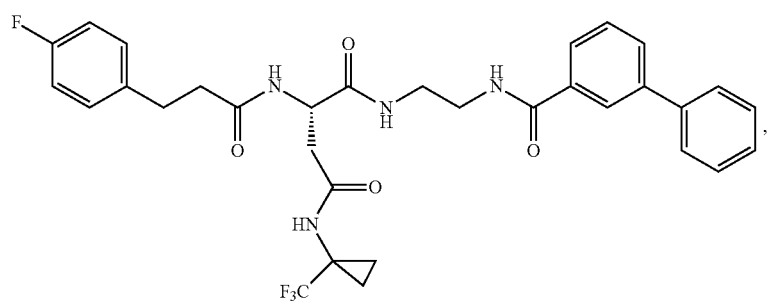
PKS21279
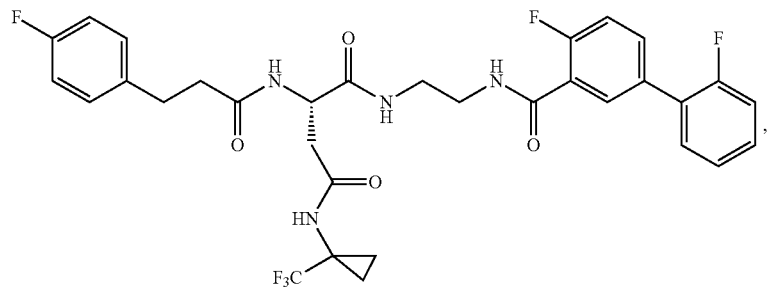

-continued
PKS21282
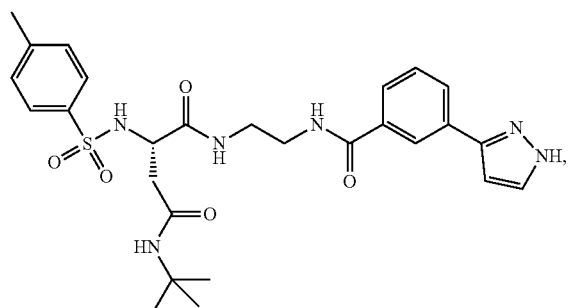
PKS21284
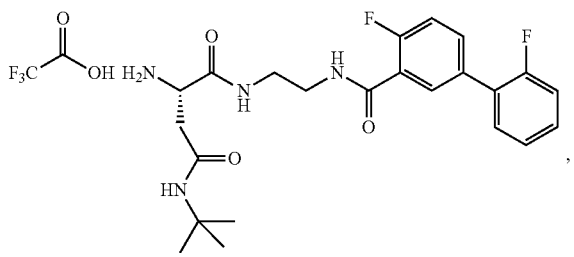
PKS21287
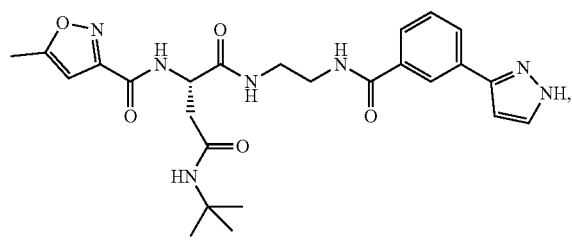
PKS21288
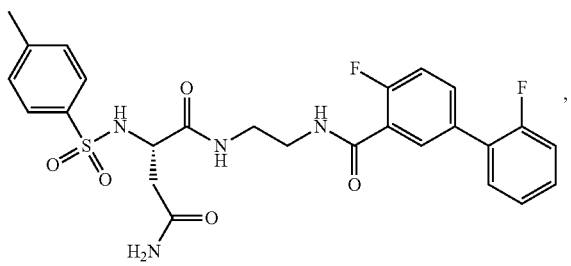
PKS21289
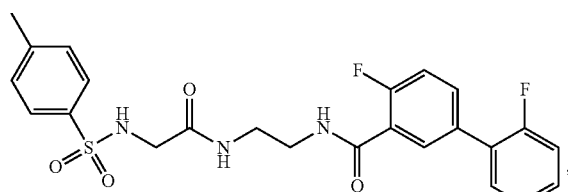
PKS21290
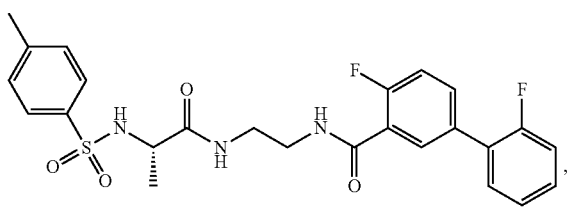
PKS21291
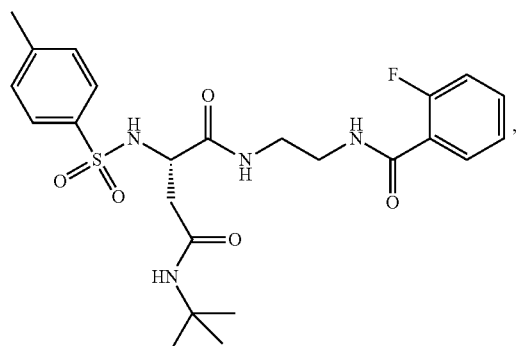
PKS21292
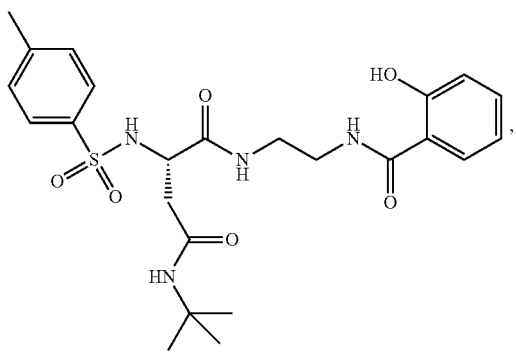
PKS21293
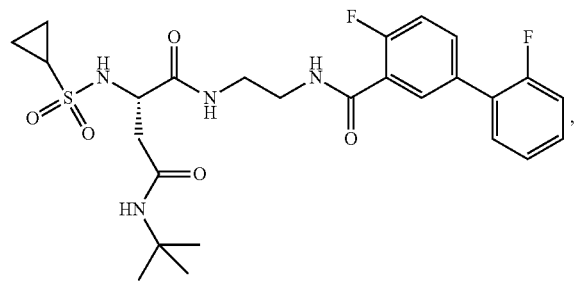
PKS21294
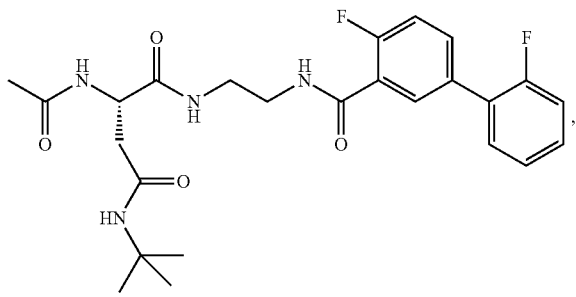

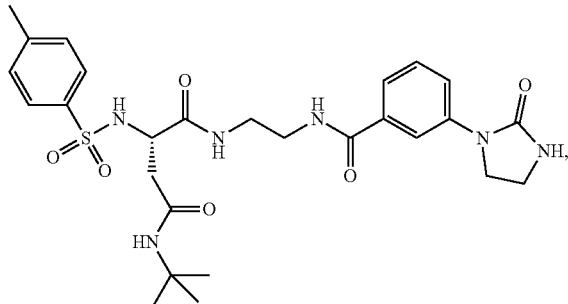

PKS21295

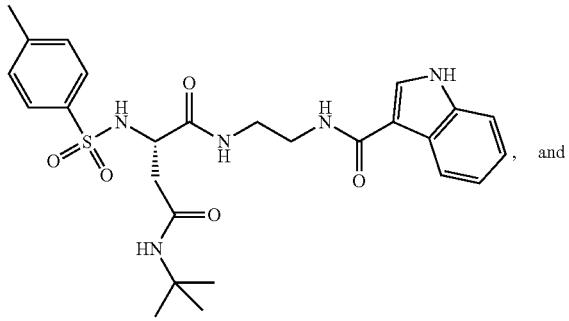

PKS21315, and

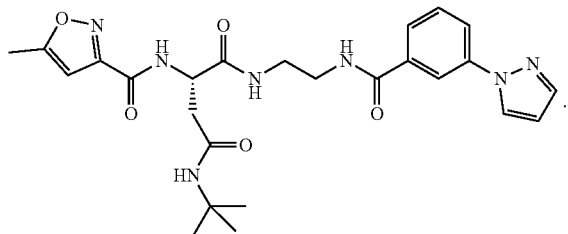

TDI4258

A second aspect of the present invention relates to a method of treating cancer, immunologic disorders, autoimmune disorders, neurodegenerative disorders, or inflammatory disorders in a subject or for providing immunosuppression for transplanted organs or tissues in a subject. This method includes administering to the subject in need thereof a compound of the Formula (I):

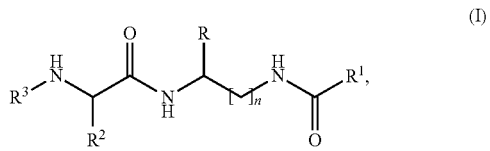

wherein

R is H or $C_{1-6}$ alkyl;

$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —$NO_2$, —$CF_3$, —$OC_{1-6}$ alkyl, aryl, heteroaryl, non-aromatic heterocycle, and non-aromatic heterocycle substituted with =O;

$R^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —$(CH_2)_mC(O)NHR^4$, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —$SO_pR^5$, —$C(O)R^5$, —$C(O)(CH_2)_kAr$, —$SO_2Ar$, —$SO_2C_{3-8}$ cycloalkyl, —$C(O)(CH_2)_kHet$, —$C(O)C_{1-6}$ alkyl, and —$C(O)OC_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;

$R^4$ is selected from the group consisting of H, $C_{1-6}$ alkyl, and $C_{3-8}$ cycloalkyl, wherein $C_{3-8}$ cycloalkyl can be optionally substituted with —$CF_3$;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

k is 0 or 2;

m is 1 or 2;

n is 1, 2, or 3; and p is 1 or 2;

or an oxide thereof, a pharmaceutically acceptable salt thereof, a solvate thereof, or a prodrug thereof.

The different forms of Formula (I) discussed above are all applicable to this embodiment of the present invention.

In one embodiment, an autoimmune disorder is treated. The autoimmune disorder is selected from the group consisting of arthritis, colitis, multiple sclerosis, lupus, systemic sclerosis, and sjögren syndrome.

In another embodiment, immunosuppression is provided for transplanted organs or tissues. The immunosuppression is used to prevent transplant rejection and graft-verse-host disease.

In another embodiment, an inflammatory disorder is treated. The inflammatory disorder is Crohn's disease or ulcerative colitis.

In yet another embodiment, cancer is treated. The cancer is selected from the group consisting of multiple myeloma, lymphoma, and other hematological cancers.

While it may be possible for compounds of Formula (I) to be administered as raw chemicals, it will often be preferable to present them as a part of a pharmaceutical composition. Accordingly, another aspect of the present invention is a pharmaceutical composition containing a therapeutically effective amount of the compound of Formula (I), or a pharmaceutically acceptable salt or solvate thereof, and a pharmaceutically acceptable carrier. The carrier must be "acceptable" in the sense of being compatible with the other ingredients of the formulation and not deleterious to the recipient thereof.

In practicing this method of the present invention, agents suitable for treating a subject can be administered using any method standard in the art. The agents, in their appropriate delivery form, can be administered orally, intradermally, intramuscularly, intraperitoneally, intravenously, subcutaneously, or intranasally. The compositions of the present invention may be administered alone or with suitable pharmaceutical carriers, and can be in solid or liquid form, such as tablets, capsules, powders, solutions, suspensions, or emulsions.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. (Abuchowski and Davis, "Soluble Polymer-Enzyme Adducts," In: *Enzymes as Drugs*, Hocenberg and Roberts, eds., Wiley-Interscience, New York, N.Y., pp. 367-383 (1981), which are hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucrulose, or saccharin. When the dosage unit form is a capsule, it may contain, in addition to the above types of materials, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agents of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The agents of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Effective doses of the compositions of the present invention, for the treatment of cancer or pathogen infection vary depending upon many different factors, including type and stage of cancer or the type of pathogen infection, means of administration, target site, physiological state of the patient, other medications or therapies administered, and physical state of the patient relative to other medical complications. Treatment dosages need to be titrated to optimize safety and efficacy.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.1 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

A third aspect of the present invention relates to a method of inhibiting chymotryptic β5i in a cell or a tissue. This method includes providing a compound of Formula (I):

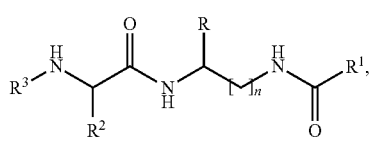

(I)

wherein
R is H or $C_{1-6}$ alkyl;
$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —NO₂, —CF₃, —OC$_{1-6}$ alkyl, aryl, heteroaryl, non-aromatic heterocycle, and non-aromatic heterocycle substituted with =O;

$R^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —(CH₂)$_m$C(O)NHR⁴, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO₂, —CF₃, —OC$_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —SO$_p$R⁵, —C(O)R⁵, —C(O)(CH₂)$_k$Ar, —SO₂Ar, —SO₂C$_{3-8}$ cycloalkyl, —C(O)(CH₂)$_k$Het, —C(O)C$_{1-6}$ alkyl, and —C(O)OC$_{1-6}$ alkyl, wherein aryl (Ar) and heteroaryl (Het) can be optionally substituted from 1 to 3 times with a substituent selected independently at each occurrence thereof from halogen or C$_1$-6 alkyl;

$R^4$ is selected from the group consisting of H, C$_{1-6}$ alkyl, and C$_{3-8}$ cycloalkyl, wherein C$_{3-8}$ cycloalkyl can be optionally substituted with —CF₃;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO₂, —CF₃, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;
m is 1 or 2;
n is 1, 2, or 3;
p is 1 or 2; and contacting a cell or tissue with the compound under conditions effective to inhibit chymotryptic β5i.

The different forms of Formula (I) discussed above are all applicable to this embodiment of the present invention.

In one embodiment, the chymotryptic 35i is inhibited selectively over 35c.

In another embodiment, the chymotryptic 35c is inhibited selectively over 35i.

A fourth aspect of the present invention relates to a method of treating infectious disease in a subject. This method includes administering to the subject in need thereof a compound of the Formula (I):

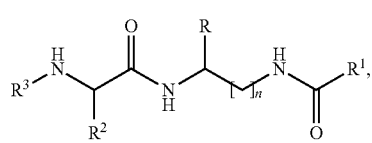

(I)

wherein

R is H or $C_{1-6}$ alkyl;

$R^1$ is selected from the group consisting of alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle, wherein alkyl, alkenyl, monocyclic and bicyclic aryl, biphenyl, monocyclic and bicyclic heteroaryl and bi-heteroaryl, monocyclic and bicyclic heterocyclyl and bi-heterocyclyl, and monocyclic and bicyclic non-aromatic heterocycle can be optionally substituted from 1 to 3 times with a substituent selected independently at each occurrence thereof from the group consisting of halogen, cyano, —OH, —$NO_2$, —$CF_3$, —$OC_{1-6}$ alkyl, aryl, heteroaryl, non-aromatic heterocycle, and non-aromatic heterocycle substituted with =O;

$R^2$ is independently selected at each occurrence thereof from the group consisting of H, alkyl, alkenyl, monocyclic and bicyclic aryl, monocyclic and bicyclic heteroaryl, monocyclic and bicyclic heterocyclyl, and —$(CH_2)_mC(O)NHR^4$, wherein alkyl, alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —$SO_pR^5$, —$C(O)R^5$, —$C(O)(CH_2)_kAr$, —$SO_2Ar$, —$SO_2C_{3-8}$ cycloalkyl, —$C(O)(CH_2)_kHet$, —$C(O)C_{1-6}$ alkyl, and —$C(O)OC_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;

$R^4$ is selected from the group consisting of H, $C_{1-6}$ alkyl, and $C_{3-8}$ cycloalkyl, wherein $C_{3-8}$ cycloalkyl can be optionally substituted with —$CF_3$;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —$NO_2$, —$CF_3$, —$OC_{1-6}$ alkyl, alkyl, alkenyl, monocyclic and bicyclic aryl, monocyclic and bicyclic heteroaryl, and monocyclic and bicyclic heterocyclyl;

k is 0 or 2;

m is 1 or 2;

n is 1, 2, or 3; and p is 1 or 2;

or an oxide thereof, a pharmaceutically acceptable salt thereof, a solvate thereof, or a prodrug thereof.

The different forms of Formula (I) discussed above are all applicable to this embodiment of the present invention.

Likewise, the modes of formulation and administration of the compounds of Formula (I) discussed above can be used in carrying out this aspect of the present invention.

In one embodiment, the infectious disease is caused by bacterial, viral, parasitic, and fungal infectious agents.

In one embodiment, the infectious disease is caused by a bacteria selected from the group consisting of *Escherichia coli, Salmonella, Shigella, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcusfaecalis, Proteus vulgaris, Proteus mirabilis, Helicobacter pylori, Treponema palladium, Borrelia burgdorferi, Borrelia recurrentis, Rickettsial pathogens, Nocardia,* and *Actinomycetes*.

In another embodiment, the infectious disease is caused by a fungal infectious agent selected from the group consisting of *Cryptococcus neoformans, Blastomyces dermatitidis, Histoplasma capsulatum, Coccidioides immitis, Paracoccicioides brasiliensis, Candida albicans, Aspergillusfumigautus, Phycomycetes (Rhizopus), Sporothrix schenckii, Chromomycosis,* and *Maduromycosis*.

In another embodiment, the infectious disease is caused by a viral infectious agent selected from the group consisting of human immunodeficiency virus, human T-cell lymphocytotrophic virus, hepatitis viruses, Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

In yet another embodiment, the infectious disease is caused by a parasitic infectious agent selected from the group consisting of *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii,* and *Necator americanis*.

In one embodiment, the infectious disease is *malaria*.

EXAMPLES

The following examples are provided to illustrate embodiments of the present invention but are by no means intended to limit its scope.

Example 1—Chemicals and Spectroscopy

Unless otherwise stated, all commercially available materials were purchased from Bachem, Aldrich, P3 BioSystems, or other vendors and were used as received. All non-aqueous reactions were performed under argon in oven-dried glassware. Routine monitoring of reactions was performed using Waters Acquity Ultra Performance Liquid Chromatography (UPLC). All HPLC purifications were done by Varian Prep-Star HPLC system or Waters Autopure (mass directed purification system) using Prep C18 5 µm OBD (19×150 mm) column. $^1$H- and $^{13}$C-NMR spectra were acquired on a Bruker DRX-500 spectrometer. Chemical shifts δ are expressed in parts per million, with the solvent resonance as an internal standard (chloroform-d, $^1$H: 7.26; $^{13}$C: 77.16 ppm; DMSO-d6, $^1$H: 2.50 ppm; $^{13}$C: 39.52 ppm). Hexafluorobenzene was used as internal standard for $^{19}$F NMR. NMR data are reported as following: chemical shift, multiplicity (s=singlet, d=doublet, t=triplet, q=quartet, m=multiplet, br=broad), coupling constant, and integration.

Example 2—General Procedure for HATU Mediated Amide Bond Formation

To a solution of carboxylic acid (1 equivalent), O-(7-Azabenzotriazole-1-yl)-N,N,N',N'-tetramethyluronium hexafluorophosphate (HATU, 1.2 equivalent), and 1-hydroxy-7-azabenzotriazole (HOAt; 0.6 M in DMF) in DMF, Hunig base (3-5 equiv) was added dropwise at 0° C. The mixture was stirred at 0° C. for 5 minutes and amine (1 equivalent) was added. The reaction mixture was stirred at 0° C. until complete consumption of starting material (monitored by LCMS). After completion of reaction, water was added to the reaction mixture and stirred for 30 minutes. The product was isolated by either filtration or ethyl acetate extraction.

Example 3—General Procedure for Boc-Deprotection

The solution of substrate in dichloromethane was cooled to 0° C. Trifluoroacetic acid (20% v/v with respect to dichloromethane) was added to the solution drop wise at 0° C. with constant stirring. The mixture was allowed to warm to room temperature slowly (over a period of 1 hour), and stirred until the completion of reaction (monitored by LCMS). Excess trifluoroacetic acid and dichloromethane were evaporated and crude was dried under vacuum.

Example 4—General Procedure for O-Debenzylation

Palladium on carbon (10%) was added carefully to a solution of substrate in methanol. Residual air from the flask was removed and flushed with hydrogen. The mixture was stirred at room temperature for 3-4 hours under hydrogen atmosphere using a hydrogen balloon. After completion of the reaction, the mixture was filtered through celite. Filtrate was evaporated and dried under vacuum to give product.

Example 5—General Procedure for N-sulfonamide Synthesis of Amines

Triethylamine (2.0-3.0 eq.) was added to a solution of substrate (amine, generally TFA salt) in dichloromethane at 0° C. The mixture was warmed to room temperature (25° C.) and sulfonyl chloride (1.5 eq.) was added in one portion. After completion of the reaction (2-3 hours), dichloromethane was evaporated and crude product was isolated by ethyl acetate extraction.

Example 6—Synthesis of PKS3070

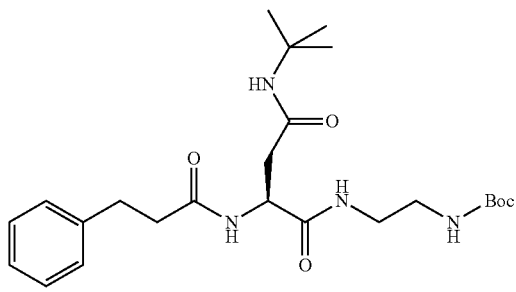 [SMILES: CC(C)(C)NC(=O)C[C@H](NC(=O)CCc1ccccc1)C(=O)NCCNC(=O)OC(C)(C)C]

The title compound was synthesized by following the general procedure of HATU mediated coupling of N-tert-butyl-N²-(1-oxo-3-phenylpropyl)-L-Aspargine (778 mg, 2.43 mmol) and N-Boc-ethylenediamine (428 mg, 2.67 mmol). After completion of the reaction, water was added. White precipitate formed, was filtered and dried in air to give product (955 mg, 85%) as a white solid. Product was used in next step without further purification. $^1$H NMR (500 MHz, Chloroform-d) δ 7.32-7.27 (m, 3H), 7.24-7.18 (m, 3H), 6.92 (br, 1H), 5.72 (br, 1H), 5.01 (br, 1H), 4.65-4.56 (m, 1H), 3.29-3.14 (m, 4H), 3.05-2.92 (m, 2H), 2.70 (dd, J=15.0, 3.7 Hz, 1H), 2.60 (t, J=7.6 Hz, 2H), 2.31 (dd, J=15.0, 6.1 Hz, 1H), 1.44 (s, 9H), 1.31 (s, 9H).

Example 7—Synthesis of PKS3072

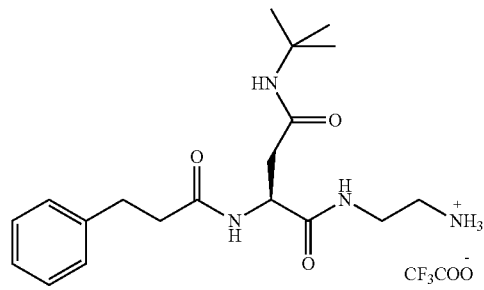

The title compound was synthesized by following the general procedure for Boc-deprotection of PKS3070 (953 mg, 2.06 mmol). After completion of the reaction, excess trifluoroacetic acid and dichloromethane were evaporated. Crude was dried and triturated with diethyl ether to give a white solid. Diethyl ether was decanted and white solid was dried under vacuum to give product (980 mg, quant.). Product was used in next step without further purification. $^1$H NMR (500 MHz, DMSO-d$_6$) δ 8.08 (d, J=7.9 Hz, 1H), 8.05 (t, J=5.6 Hz, 1H), 7.80 (br, 3H), 7.56 (s, 1H), 7.30-7.23 (m, 2H), 7.22-7.14 (m, 3H), 4.50-4.42 (m, 1H), 3.42-3.31 (m, 1H), 3.29-3.19 (m, 1H), 2.92-2.82 (m, 2H), 2.80 (t, J=7.9 Hz, 2H), 2.48-2.34 (m, 4H), 1.22 (s, 9H).

Example 8—Synthesis of PKS3080

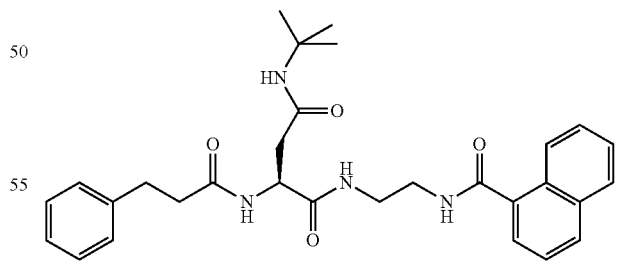

The title compound was synthesized by following the general procedure for HATU mediated coupling of 1-naphthoic acid (20.7 mg, 0.12 mmol) and PKS3072 (47.6 mg, 0.1 mmol). After completion of the reaction, the mixture was purified by HPLC to give product (30.2 mg, 58%) as a white solid. $^1$H NMR (500 MHz, DMSO-d$_6$) δ 8.47 (t, J=5.6 Hz, 1H), 8.25-8.18 (m, 1H), 8.03-7.92 (m, 4H), 7.66 (dd, J=7.1, 1.3 Hz, 1H), 7.60-7.48 (m, 3H), 7.38 (s, 1H), 7.28-7.22 (m, 2H), 7.19-7.12 (m, 3H), 4.57-4.46 (m, 1H), 3.45-3.37 (m, 2H), 3.32-3.21 (m, 2H), 2.77 (t, J=8.0 Hz, 2H), 2.46 (dd, J=14.6, 6.0 Hz, 1H), 2.43-2.37 (m, 2H), 2.32 (dd, J=14.6, 7.9 Hz, 1H), 1.19 (s, 9H). $^{13}$C NMR (126 MHz, DMSO-$d_6$) δ 171.3, 171.2, 168.9, 168.7, 141.3, 134.7, 133.1, 129.8, 129.7, 128.3, 128.1, 128.1, 126.7, 126.2, 125.8, 125.5, 125.3, 124.9, 50.2, 50.0, 38.9, 38.7, 38.7, 36.9, 30.9, 28.4. HRMS calc. for $C_{30}H_{36}N_4O_4Na$ [M+Na]$^+$: 539.2634. Found: 539.2637.

Example 9—Synthesis of PKS21003

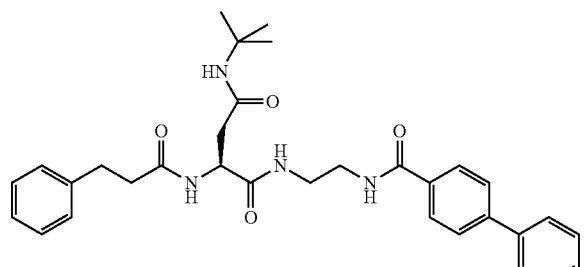

The title compound was synthesized by HATU mediated coupling of 4-phenylbenzoic acid (104.0 mg, 524.7 μmol) and PKS3072 (250.0 mg, 524.7 μmol). After completion of the reaction (1 hour), water was added. The white precipitate obtained was filtered, washed with water and dried in air to give 284.0 mg white solid. The white solid was triturated with ethyl acetate and isolated by centrifugation (4700 rpm, 10 min). Isolated white solid (235 mg, 82%) was pure product (by LCMS & NMR). $^1$H NMR (500 MHz, DMSO-$d_6$) δ 8.51-8.44 (m, 1H), 8.00 (d, J=7.9 Hz, 1H), 7.99-7.89 (m, 3H), 7.76-7.72 (m, 2H), 7.72-7.67 (m, 2H), 7.52-7.45 (m, 2H), 7.43-7.36 (m, 2H), 7.28-7.22 (m, 2H), 7.20-7.12 (m, 3H), 4.54-4.45 (m, 1H), 3.36-3.33 (m, 2H), 3.29-3.14 (m, 2-H), 2.78 (t, J=8.0 Hz, 2H), 2.48-2.38 (m, 3H), 2.32 (dd, J=15.0, 8.0 Hz, 1H), 1.21 (s, 9H); $^{13}$C NMR (126 MHz, DMSO-$d_6$) δ 171.3, 171.2, 168.9, 166.1, 142.7, 141.3, 139.2, 133.3, 129.0, 128.3, 128.1, 128.0, 127.9, 126.8, 126.4, 125.9, 50.2, 50.1, 38.9, 38.7, 38.6, 36.9, 31.0, 28.4. HRMS calc. for $C_{32}H_{38}N_4O_4Na$ [M+Na]$^+$: 565.2791. Found: 565.2786.

Example 10—Synthesis of PKS21004

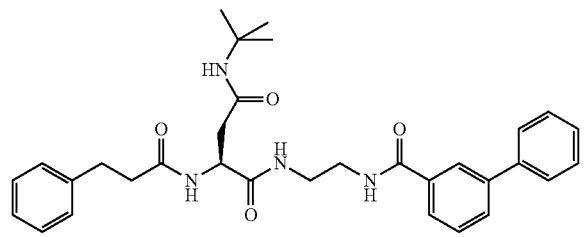

The title compound was synthesized by HATU mediated coupling of 3-phenylbenzoic acid (396.8 mg, 2.00 mol) and PKS3072 (867.2 mg, 1.82 mmol). After completion of the reaction (2 hours), water was added to the reaction mixture. An off white precipitate appeared. The precipitate was filtered and recrystallized from ethanol to give pure product as a white solid (905 mg, 92%). $^1$H NMR (500 MHz, DMSO-$d_6$) δ 8.57 (t, J=5.5 Hz, 1H), 8.13 (s, 1H), 8.01-7.93 (m, 2H), 7.87-7.79 (m, 2H), 7.76-7.70 (m, 2H), 7.54 (t, J=7.7 Hz, 1H), 7.51-7.46 (m, 2H), 7.43-7.35 (m, 2H), 7.28-7.22 (m, 2H), 7.19-7.13 (m, 3H), 4.54-4.46 (m, 1H), 3.38-3.15 (m, 4H), 2.77 (t, J=7.9 Hz, 2H), 2.48-2.36 (m, 3H), 2.32 (dd, J=14.7, 7.9 Hz, 1H), 1.20 (s, 9H); $^{13}$C NMR (126 MHz, DMSO-$d_6$) δ 171.3, 171.2, 168.9, 166.3, 141.3, 140.1, 139.6, 135.1, 129.3, 129.0, 129.0, 128.3, 128.1, 127.7, 126.8, 126.4, 125.8, 125.4, 50.2, 50.0, 38.9, 38.7, 38.6, 36.9, 30.9, 28.4. HRMS calc. for $C_{32}H_{38}N_4O_4Na$ [M+Na]$^+$: 565.2791. Found: 565.2774.

Example 11—Synthesis of PKS21025

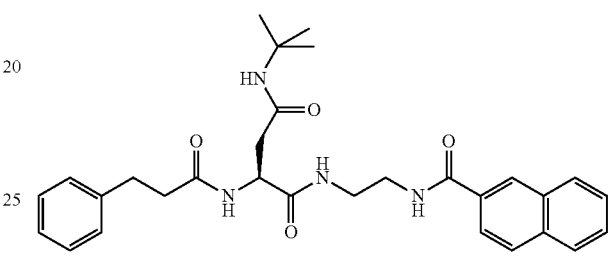

The title compound was synthesized by following the general procedure for HATU mediated coupling of 2-naphthoic acid (5.2 mg, 30 μmol) and PKS3072 (11.9 mg, 25 μmol). After completion of the reaction (1 hour), the mixture was purified by HPLC to give product (11.5 mg, 89%) as a white solid. $^1$H NMR (500 MHz, DMSO-$d_6$) δ 8.61 (t, J=5.6 Hz, 1H), 8.43 (s, 1H), 8.03-7.95 (m, 5H), 7.92 (d, J=8.6 Hz, 1H), 7.65-7.53 (m, 2H), 7.40 (s, 1H), 7.29-7.20 (m, 2H), 7.20-7.10 (m, 3H), 4.55-4.46 (m, 1H), 3.44-3.34 (m, 2H), 3.32-3.18 (m, 2H), 2.77 (t, J=8.0 Hz, 2H), 2.49-2.37 (m, 3H), 2.32 (dd, J=14.6, 7.9 Hz, 1H), 1.19 (s, 9H); $^{13}$C NMR (126 MHz, DMSO-$d_6$) δ 171.6, 171.6, 169.1, 166.9, 141.4, 134.3, 132.3, 131.9, 129.0, 128.5, 128.3, 128.0, 127.8, 127.8, 127.6, 126.9, 126.1, 124.3, 50.4, 50.3, 39.2, 38.9, 38.8, 37.1, 31.1, 28.6. HRMS calc. for $C_{30}H_{36}N_4O_4Na$ [M+Na]$^+$: 539.2634. Found: 539.2617.

Example 12—Synthesis of PKS21026

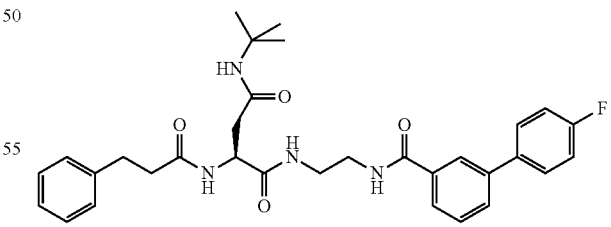

The title compound was synthesized by following the general procedure for HATU mediated coupling of 3-(4-fluorophenyl)benzoic acid (6.49 mg, 30 μmol) and PKS3072 (11.9 mg, 25 μmol). After completion of the reaction (1 hour), the mixture was purified by HPLC to give product (11.0 mg, 78%) as a white solid. $^1$H NMR (500 MHz, DMSO-$d_6$) δ 8.57 (t, J=5.6 Hz, 1H), 8.12-8.07 (m, 1H), 7.99 (d, J=8.0 Hz, 1H), 7.96 (t, J=5.7 Hz, 1H), 7.85-7.72 (m, 4H), 7.57-7.50 (m, 1H), 7.39 (s, 1H), 7.35-7.26 (m, 2H), 7.28-7.21 (m, 2H), 7.19-7.13 (m, 3H), 4.49 (td, J=7.9, 5.9 Hz, 1H), 3.37-3.14 (m, 4H), 2.76 (t, J=8.0 Hz, 2H), 2.49-2.35 (m, 3H), 2.32 (dd, J=14.6, 7.9 Hz, 1H), 1.19 (s, 9H); $^{13}$C NMR (126 MHz, DMSO-d$_6$) δ 171.5, 171.5, 169.0, 166.6, 162.2 (d, J=244.8 Hz), 141.3, 139.2, 136.1, 135.2, 129.4, 129.1, 129.0 (d, J=9.6 Hz), 128.4, 128.2, 126.5, 126.0, 125.4, 115.9 (d, J=21.5 Hz), 50.4, 50.2, 39.1, 38.8, 38.7, 37.0, 31.1, 28.5; $^{19}$F NMR (471 MHz, DMSO-d$_6$) δ −117.4 (m). HRMS calc. for C$_{32}$H$_{37}$FN$_4$O$_4$Na [M+Na]$^+$: 583.2697. Found: 583.2701.

Example 13—Synthesis of PKS21028

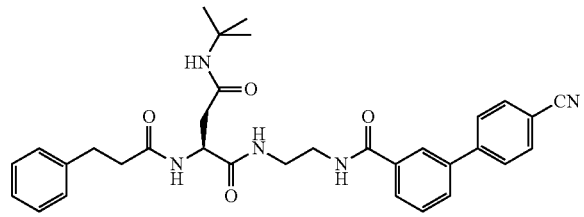

The title compound was synthesized by following the general procedure for HATU mediated coupling of 3-(4-cyanophenyl)benzoic acid (6.7 mg, 30 μmol) and PKS3072 (11.9 mg, 25 μmol). After completion of the reaction, the mixture was purified by HPLC to give product (11.0 mg, 78%) as a white solid. $^1$H NMR (500 MHz, DMSO-d$_6$) δ 8.61 (t, J=5.6 Hz, 1H), 8.19 (t, J=1.9 Hz, 1H), 8.01 (d, J=8.0 Hz, 1H), 7.99-7.93 (m, 5H), 7.91 (d, J=7.8 Hz, 2H), 7.59 (t, J=7.8 Hz, 1H), 7.39 (s, 1H), 7.28-7.21 (m, 2H), 7.19-7.13 (m, 3H), 4.54-4.46 (m, 1H), 3.45-3.15 (m, 4H), 2.76 (t, J=8.0 Hz, 2H), 2.45 (dd, J=14.5, 5.9 Hz, 1H), 2.42-2.38 (m, 2H), 2.32 (dd, J=14.5, 7.9 Hz, 1H), 1.19 (s, 9H); $^{13}$C NMR (126 MHz, DMSO-d$_6$) δ 171.3, 171.2, 168.9, 166.1, 144.0, 141.3, 138.2, 135.4, 132.9, 129.7, 129.2, 128.3, 128.1, 127.7, 127.7, 125.8, 125.7, 118.8, 110.4, 50.2, 50.0, 38.9, 38.7, 38.6, 36.9, 30.9, 28.4.

Example 14—Synthesis of PKS21186

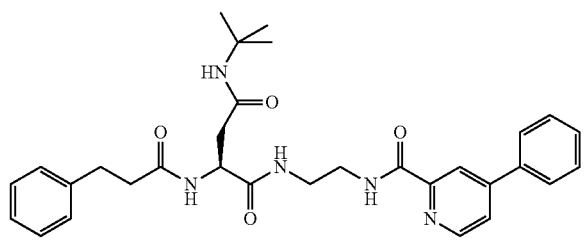 [SMILES: CC(C)(C)NC(=O)C[C@H](NC(=O)CCc1ccccc1)C(=O)NCCNC(=O)c1cccc(-c2ccccc2)c1]

The title compound was synthesized by following the general procedure for HATU mediated coupling of 4-phenylpicolinic acid (10.0 mg, 50 μmol) and PKS3072 (23.8 mg, 50 μmol). After completion of the reaction, the mixture was purified by HPLC to give product (21.5 mg, 79%) as a white solid. $^1$H NMR (500 MHz, DMSO-d$_6$) δ 8.96 (t, J=6.0 Hz, 1H), 8.69 (d, J=5.0 Hz, 1H), 8.28 (d, J=1.8 Hz, 1H), 7.97 (d, J=8.1 Hz, 1H), 7.95-7.90 (m, 2H), 7.83 (d, J=6.8 Hz, 2H), 7.58-7.48 (m, 3H), 7.34 (s, 1H), 7.27-7.21 (m, 2H), 7.19-7.13 (m, 3H), 4.54-4.44 (m, 1H), 3.43-3.38 (m, 2H), 3.28-3.18 (m, 2H), 2.77 (t, J=7.9 Hz, 2H), 2.46-2.35 (m, 3H), 2.29 (dd, J=14.6, 8.1 Hz, 1H), 1.20 (s, 9H); $^{13}$C NMR (126 MHz, DMSO-d$_6$) δ 171.2, 171.1, 168.8, 164.2, 150.8, 149.1, 148.6, 141.3, 136.7, 129.6, 129.3, 128.3, 128.1, 126.9, 125.8, 123.7, 119.0, 50.1, 50.0, 38.9, 38.7, 38.7, 36.9, 31.0, 28.4. HRMS calc. for C$_{31}$H$_{37}$N$_5$O$_4$Na [M+Na]$^+$: 566.2743. Found: 566.2736.

Example 15—Synthesis of PKS21187

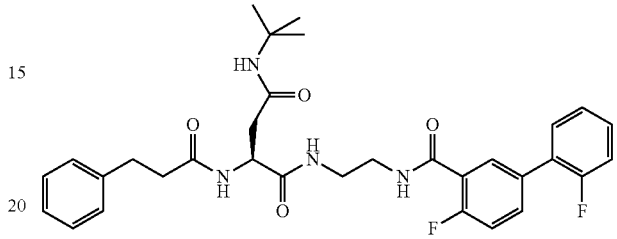

The title compound was synthesized by following the general procedure for HATU mediated coupling of 2-fluoro-5-(2-fluorophenyl)benzoic acid (11.7 mg, 50 μmol) and PKS3072 (23.8 mg, 50 μmol). After completion of the reaction, the mixture was purified by HPLC to give product (24.8 mg, 86%) as a white solid. $^1$H NMR (500 MHz, DMSO-d$_6$) δ 8.38 (t, J=4.6 Hz, 1H), 7.96 (d, J=8.0 Hz, 1H), 7.92 (t, J=5.7 Hz, 1H), 7.82-7.78 (m, 1H), 7.71-7.66 (m, 1H), 7.58-7.53 (m, 1H), 7.47-7.41 (m, 1H), 7.41-7.28 (m, 4H), 7.27-7.22 (m, 2H), 7.19-7.13 (m, 3H), 4.53-4.42 (m, 1H), 3.38-3.29 (m, 2H), 3.29-3.23 (m, 1H), 3.22-3.15 (m, 1H), 2.76 (t, J=7.9 Hz, 2H), 2.46-2.36 (m, 3H), 2.30 (dd, J=14.6, 7.9 Hz, 1H), 1.18 (s, 9H); $^{13}$C NMR (126 MHz, DMSO-d$_6$) δ 171.3, 171.2, 168.8, 163.6, 159.0 (d, J=247.4 Hz), 158.8 (d, J=251.0 Hz), 141.3, 132.8-132.6 (m), 131.4-131.1 (m), 130.8, 130.3, 130.0 (d, J=7.9 Hz), 128.2, 128.1, 126.7, 125.8, 125.0 (d, J=2.9 Hz), 124.2 (d, J=14.5 Hz), 116.5 (d, J=22.1 Hz), 116.1 (d, J=23.1 Hz), 50.1, 50.0, 39.0, 38.6, 38.5, 36.9, 30.9, 28.4; $^{19}$F NMR (471 MHz, DMSO-d$_6$) δ −117.8 (m), −120.8 (m). HRMS calc. for C$_{32}$H$_{36}$F$_2$N$_4$O$_4$Na [M+Na]$^+$: 601.2602. Found: 601.2601.

Example 16—Synthesis of PKS21195

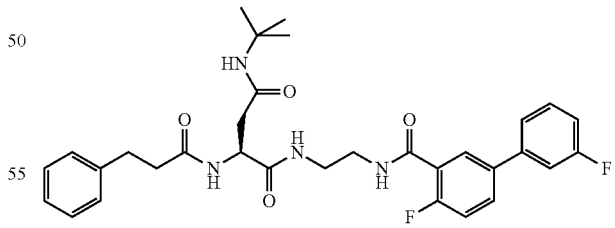

The title compound was synthesized by following the general procedure for HATU mediated coupling of 2-fluoro-5-(3-fluorophenyl)benzoic acid (14.3 mg, 61 μmol) and PKS3072 (29.0 mg, 61 μmol). After completion of the reaction, the mixture was purified by HPLC to give product (28.5 mg, 81%) as a white solid. $^1$H NMR (500 MHz, DMSO-d$_6$) δ 8.41 (t, J=5.6 Hz, 1H), 8.00 (d, J=8.0 Hz, 1H), 7.97-7.89 (m, 2H), 7.88-7.79 (m, 1H), 7.59-7.53 (m, 2H), 7.53-7.46 (m, 1H), 7.41-7.32 (m, 2H), 7.27-7.18 (m, 3H), 7.17-7.12 (m, 3H), 4.54-4.44 (m, 1H), 3.40-3.15 (m, 4H), 2.76 (t, J=8.0 Hz, 2H), 2.45 (dd, J=14.5, 6.0 Hz, 1H), 2.42-2.36 (m, 2H), 2.32 (dd, J=14.5, 7.9 Hz, 1H), 1.18 (s, 9H); 13C NMR (126 MHz, DMSO-$d_6$) δ 171.3, 171.2, 168.8, 163.7, 162.7 (d, J=243.3 Hz), 159.1 (d, J=250.7 Hz), 141.3, 141.0 (d, J=7.7 Hz), 135.0, 130.9 (d, J=8.0 Hz), 130.5 (d, J=8.9 Hz), 128.3, 128.2, 128.1, 125.8, 124.5 (d, J=14.5 Hz), 122.8, 116.8 (d, J=21.9 Hz), 114.4 (d, J=21.6 Hz), 113.4, 50.2, 50.0, 38.9, 38.6, 38.6, 36.9, 30.9, 28.4; $^{19}$F NMR (471 MHz, DMSO-$d_6$) δ −114.7 (m), −117.9 (m). HRMS calc. for $C_{32}H_{36}F_2N_4O_4Na$ [M+Na]$^+$: 601.2602. Found: 601.2600.

Example 17—Synthesis of PKS21196

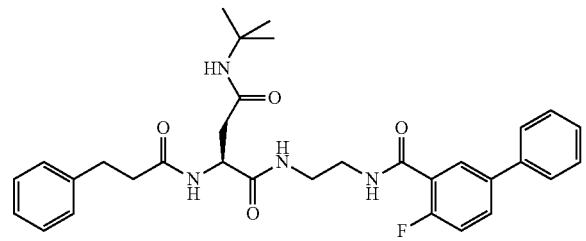 [SMILES: CC(C)(C)NC(=O)C[C@H](NC(=O)CCc1ccccc1)C(=O)NCCNC(=O)c1cc(-c2ccccc2)ccc1F]

The title compound was synthesized by following the general procedure for HATU mediated coupling of 2-fluoro-5-phenyl-benzoic acid (13.2 mg, 61 μmol) and PKS3072 (29.0 mg, 61 μmol). After completion of the reaction, the mixture was purified by HPLC to give product (30.0 mg, 88%) as a white solid. $^1$H NMR (500 MHz, DMSO-$d_6$) δ 8.40 (t, J=5.6 Hz, 1H), 8.00 (d, J=8.0 Hz, 1H), 7.94 (t, J=5.7 Hz, 1H), 7.90 (dd, J=6.9, 2.4 Hz, 1H), 7.82-7.77 (m, 1H), 7.69 (d, J=7.6 Hz, 2H), 7.49-7.44 (m, 2H), 7.40-7.33 (m, 3H), 7.27-7.21 (m, 2H), 7.18-7.13 (m, 3H), 4.54-4.45 (m, 1H), 3.39-3.15 (m, 4H), 2.76 (t, J=8.0 Hz, 2H), 2.45 (dd, J=14.5, 5.9 Hz, 1H), 2.42-2.37 (m, 2H), 2.32 (dd, J=14.5, 7.9 Hz, 1H), 1.18 (s, 9H); $^{13}$C NMR (126 MHz, DMSO-$d_6$) δ 171.3, 171.2, 168.8, 163.8, 158.8 (d, J=250.7 Hz), 141.3, 138.5, 136.4, 130.3 (d, J=8.9 Hz), 129.0, 128.3, 128.1 (d, J=3.1 Hz), 128.1, 127.7, 126.7, 125.8, 124.4 (d, J=14.5 Hz), 116.7 (d, J=23.0 Hz), 50.2, 50.0, 38.9, 38.6, 38.6, 36.9, 30.9, 28.4; $^{19}$F NMR (471 MHz, DMSO-$d_6$) δ −119.2 (m). HRMS calc. for $C_{32}H_{37}FN_4O_4Na$ [M+Na]$^+$: 583.2697. Found: 583.2697.

Example 18—Synthesis of PKS3086

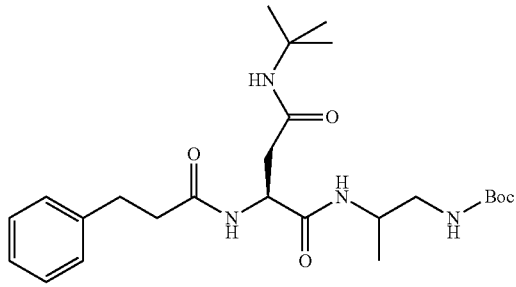 [SMILES: CC(CNC(=O)OC(C)(C)C)NC(=O)[C@H](CC(=O)NC(C)(C)C)NC(=O)CCc1ccccc1]

The title compound was synthesized by following the general procedure of HATU mediated coupling of N-tert-butyl-N$^2$-(1-oxo-3-phenylpropyl)-L-Aspargine (32.0 mg, 0.1 mmol) and tert-Butyl (2-aminopropyl)carbamate (17.4 mg, 0.1 mmol). After completion of the reaction, water was added. The white precipitate formed, was filtered and dried in air to give product (44.9 mg, 94%) as a white solid. Product was used in next step without further purification. $^1$H NMR (500 MHz, DMSO-$d_6$; A mixture of diastereomers) δ 7.91 (d, J=8.0 Hz, 1H), 7.56 (d, J=8.1 Hz, 1H), 7.37 (s, 1H), 7.30-7.23 (m, 2H), 7.22-7.13 (m, 3H), 6.70 (t, J=6.0 Hz, 1H), 4.50-4.41 (m, 1H), 3.81-3.70 (m, 1H), 2.94 (t, J=6.1 Hz, 2H), 2.79 (t, J=7.9 Hz, 2H), 2.45-2.34 (m, 3H), 2.30 (dd, J=14.7, 7.5 Hz, 1H), 1.37 (s, 9H), 1.22 (s, 9H), 0.96 (d, J=6.7 Hz, 3H).

Example 19—Synthesis of PKS21006

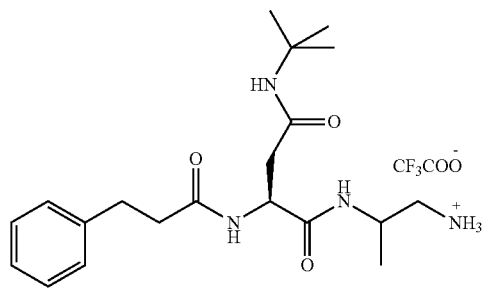

The title compound was synthesized by following the general procedure for Boc-deprotection of PKS3086 (40.0 mg, 84 μmol). Isolated crude was dried under vacuum and triturated with diethyl ether to give a white solid. The diethylether was decanted and white solid was dried under vacuum to give product (40 mg, 97%) as a white solid. Product was used in next step without further purification. $^1$H NMR (500 MHz, DMSO-$d_6$; A mixture of diastereomers) δ 8.11 (d, J=7.2 Hz, 1H), 7.86 (d, J=8.4 Hz, 1H), 7.55 (s, 1H), 7.30-7.24 (m, 2H), 7.22-7.15 (m, 3H), 4.46-4.32 (m, 1H), 4.09-3.93 (m, 1H), 2.87 (dd, J=13.4, 5.1 Hz, 1H), 2.84-2.72 (m, 3H), 2.47-2.39 (m, 4H), 1.23 (s, 9H), 1.11-1.03 (m, 3H).

Example 20—Synthesis of PKS21018

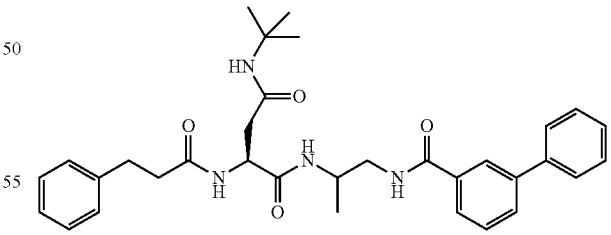

The title compound was synthesized by following the general procedure for HATU mediated coupling of 3-phenyl-benzoic acid (4.8 mg, 24 μmol) and PKS21006 (9.8 mg, 20 μmol). After completion of the reaction, the mixture was purified by HPLC to give product (6.2 mg, 56%) as a white solid. $^1$H NMR (500 MHz, DMSO-$d_6$; A mixture of diastereomers) δ 8.51 (t, J=5.9 Hz, 1H), 8.12 (t, J=1.9 Hz, 1H), 7.94 (d, J=7.8 Hz, 1H), 7.86-7.79 (m, 2H), 7.77 (d, J=7.9 Hz, 1H), 7.74-7.69 (m, 2H), 7.53 (t, J=7.7 Hz, 1H), 7.51-7.44

(m, 2H), 7.43-7.34 (m, 2H), 7.27-7.21 (m, 2H), 7.19-7.12 (m, 3H), 4.52-4.44 (m, 1H), 4.00-3.91 (m, 1H), 3.44-3.36 (m, 1H), 3.30-3.24 (m, 1H), 2.75 (t, J=8.0 Hz, 2H), 2.46-2.35 (m, 3H), 2.32 (dd, J=14.7, 7.6 Hz, 1H), 1.20 (s, 9H), 1.06 (d, J=6.6 Hz, 3H); $^{13}$C NMR (126 MHz, DMSO-$d_6$) δ 171.2, 170.6, 168.8, 166.6, 141.2, 140.2, 139.6, 135.1, 129.3, 129.0, 129.0, 128.9, 128.9, 128.2, 128.1, 127.7, 126.8, 126.4, 125.8, 125.4, 50.3, 50.0, 45.1, 43.9, 38.6, 36.8, 30.9, 28.4, 17.7. HRMS calc. for $C_{33}H_{40}N_4O_4Na$ [M+Na]$^+$: 579.2947. Found: 579.2958.

Example 21—Synthesis of PKS3087

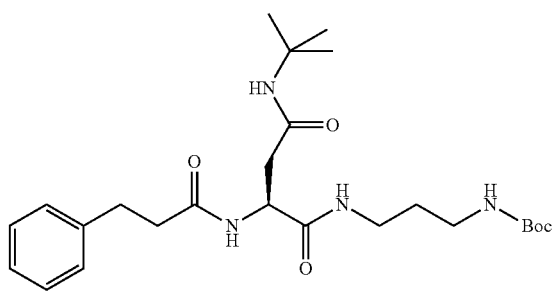 [SMILES: CC(C)(C)NC(=O)C[C@H](NC(=O)CCc1ccccc1)C(=O)NCCCNC(=O)OC(C)(C)C]

The title compound was synthesized by following the general procedure of HATU mediated coupling of N-tert-butyl-$N^2$-(1-oxo-3-phenylpropyl)-L-Aspargine (32.0 mg, 0.1 mmol) and tert-Butyl N-(3-aminopropyl)carbamate (17.4 mg, 0.1 mmol). After completion of the reaction, water was added. The white precipitate formed, was filtered and dried in air to give product (44.3 mg, 93%) as a white solid. Product was used in next step without further purification. $^1$H NMR (500 MHz, DMSO-$d_6$) δ 7.99-7.94 (m, 1H), 7.69 (t, J=5.9 Hz, 1H), 7.34 (s, 1H), 7.29-7.23 (m, 2H), 7.21-7.14 (m, 3H), 6.74 (t, J=5.9 Hz, 1H), 4.52-4.42 (m, 1H), 3.03-2.98 (m, 2H), 2.92-2.86 (m, 2H), 2.82-2.77 (m, 2H), 2.46-2.36 (m, 3H), 2.28 (dd, J=14.6, 8.0 Hz, 1H), 1.50-1.41 (m, 2H), 1.37 (s, 9H), 1.21 (s, 9H).

Example 22—Synthesis of PKS21007

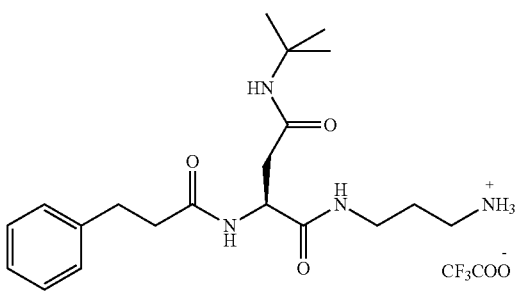

The title compound was synthesized by following the general procedure for Boc-deprotection of PKS3087 (44.3 mg, 93 μmol). After completion of the reaction (3 hours), excess trifluoroacetic acid and dichloromethane were evaporated. Crude was dried under vacuum and triturated with diethyl ether to give a white solid. The diethylether was decanted and the white solid was dried under vacuum to give product (41.0 mg, 90%) as a white solid. Product was used in next step without further purification. $^1$H NMR (500 MHz, DMSO-$d_6$) δ 8.04 (d, J=7.8 Hz, 1H), 7.91 (t, J=6.0 Hz, 1H), 7.73 (br, 3H), 7.41 (s, 1H), 7.33-7.22 (m, 2H), 7.23-7.11 (m, 3H), 4.52-4.40 (m, 1H), 3.15-3.02 (m, 2H), 2.84-2.68 (m, 4H), 2.46-2.37 (m, 3H), 2.32 (dd, J=14.7, 8.0 Hz, 1H), 1.72-1.59 (m, 2H), 1.22 (s, 9H).

Example 23—Synthesis of PKS21019

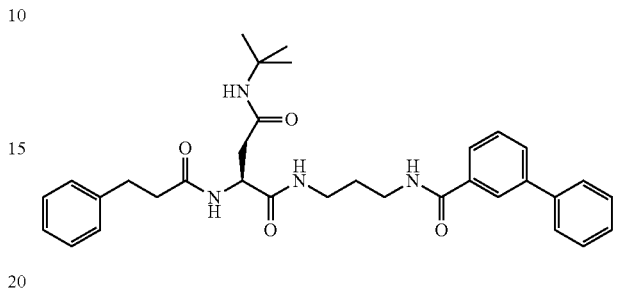

The title compound was synthesized by following the general procedure for HATU mediated coupling of 3-phenyl-benzoic acid (4.8 mg, 24 μmol) and PKS21007 (9.8 mg, mol). After completion of the reaction, the mixture was purified by HPLC to give product (11.1 mg, 72%) as a white solid. $^1$H NMR (500 MHz, DMSO-$d_6$) δ 8.57 (t, J=5.8 Hz, 1H), 8.11 (t, J=1.9 Hz, 1H), 8.00 (d, J=8.0 Hz, 1H), 7.86-7.78 (m, 3H), 7.75-7.69 (m, 2H), 7.58-7.53 (m, 1H), 7.53-7.47 (m, 2H), 7.43-7.38 (m, 1H), 7.35 (s, 1H), 7.27-7.21 (m, 2H), 7.21-7.12 (m, 3H), 4.50 (td, J=8.0, 5.8 Hz, 1H), 3.31-3.26 (m, 2H), 3.15-3.08 (m, 2H), 2.84-2.77 (m, 2H), 2.47-2.38 (m, 3H), 2.31 (dd, J=14.6, 8.0 Hz, 1H), 1.67-1.61 (m, 2H), 1.21 (s, 9H); $^{13}$C NMR (126 MHz, DMSO-$d_6$) δ 171.2, 171.0, 168.8, 166.1, 141.3, 140.2, 139.6, 135.2, 129.3, 129.0, 129.0, 128.3, 128.1, 127.7, 126.8, 126.3, 125.8, 125.3, 50.2, 50.0, 38.6, 36.9, 36.6, 36.3, 31.0, 29.1, 28.4. HRMS calc. for $C_{33}H_{40}N_4O_4Na$ [M+Na]$^+$: 579.2947. Found: 579.2953.

Example 24—Synthesis of PKS21017

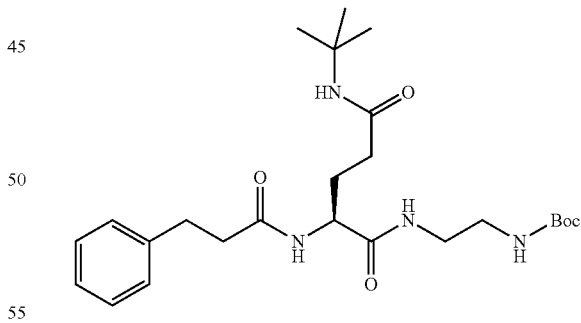

The title compound was synthesized by following the general procedure of HATU mediated coupling of N-tert-butyl-$N^2$-(1-oxo-3-phenylpropyl)-L-Glutamine (100.3 mg, 0.30 mmol) and N-boc-ethylenediamine (53.95 mg, 0.33 mmol). After completion of the reaction, water was added. The white precipitate formed, was filtered and dried in air to give product (105.0 mg, 73%) as a white solid. Product was used in the next step without further purification. $^1$H NMR (500 MHz, DMSO-$d_6$) δ 7.95 (d, J=8.0 Hz, 1H), 7.85 (t, J=5.4 Hz, 1H), 7.33 (s, 1H), 7.30-7.23 (m, 2H), 7.23-7.14 (m, 3H), 6.77 (t, J=5.0 Hz, 1H), 4.18-4.09 (m, 1H), 3.13-

3.00 (m, 2H), 3.00-2.93 (m, 2H), 2.80 (t, J=7.9 Hz, 2H), 2.48-2.40 (m, 2H), 1.97 (t, J=8.0 Hz, 2H), 1.80 (dt, J=13.9, 7.8, 7.2 Hz, 1H), 1.71-1.58 (m, 1H), 1.37 (s, 9H), 1.23 (s, 9H).

Example 25—Synthesis of PKS21021

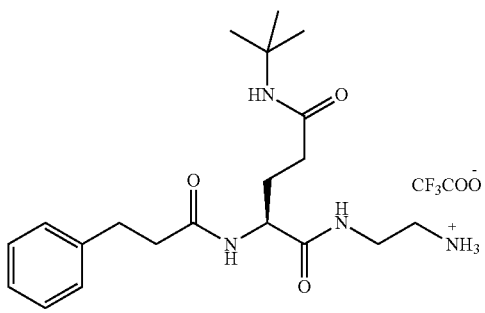

The title compound was synthesized by following the general procedure for Boc-deprotection of PKS21017 (98.0 mg, 0.206 mmol). After completion of the reaction (3 hours), excess trifluoroacetic acid and dichloromethane were evaporated. Crude was dried under vacuum and triturated with diethyl ether to give a white solid. The diethylether was decanted and white solid was dried under vacuum to give product (100.0 mg, 99%) as a white solid. Product was used in next step without further purification. $^1$H NMR (500 MHz, DMSO-$d_6$) δ 8.09-8.01 (m, 2H), 7.76 (s, 3H), 7.37 (s, 1H), 7.30-7.24 (m, 2H), 7.22-7.14 (m, 3H), 4.16-4.08 (m, 1H), 3.32-3.25 (m, 2H), 2.89-2.77 (m, 4H), 2.48-2.38 (m, 2H), 2.01 (t, J=7.9 Hz, 2H), 1.90-1.79 (m, 1H), 1.73-1.62 (m, 1H), 1.23 (s, 9H).

Example 26—Synthesis of PKS21030

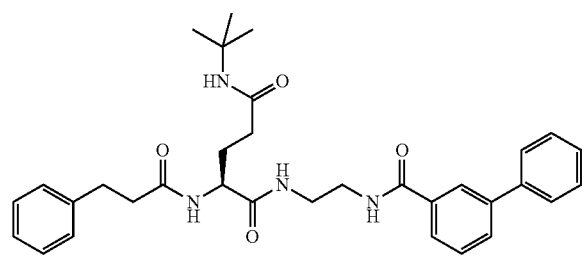 [SMILES: CC(C)(C)NC(=O)CC[C@H](NC(=O)CCc1ccccc1)C(=O)NCCNC(=O)c1cccc(-c2ccccc2)c1]

The title compound was synthesized by following the general procedure for HATU mediated coupling of 3-phenyl-benzoic acid (7.1 mg, 36 μmol) and PKS21021 (11.3 mg, 30.0 μmol). After completion of the reaction, the mixture was purified by HPLC to give product (10.0 mg, 60%) as a white solid. $^1$H NMR (500 MHz, DMSO-$d_6$) δ 8.61 (t, J=5.5 Hz, 1H), 8.13 (t, J=1.8 Hz, 1H), 8.05-7.98 (m, 2H), 7.86-7.79 (m, 2H), 7.76-7.70 (m, 2H), 7.54 (t, J=7.7 Hz, 1H), 7.52-7.45 (m, 2H), 7.42-7.37 (m, 2H), 7.34 (s, 1H), 7.29-7.22 (m, 2H), 7.20-7.12 (m, 3H), 4.16 (td, J=8.2, 5.6 Hz, 1H), 3.44-3.19 (m, 4H), 2.78 (t, J=7.9 Hz, 2H), 2.47-2.40 (m, 2H), 1.99 (t, J=8.0 Hz, 2H), 1.89-1.78 (m, 1H), 1.74-1.63 (m, 1H), 1.21 (s, 9H); $^{13}$C NMR (126 MHz, DMSO-$d_6$) δ 171.7, 171.4, 171.1, 166.4, 141.3, 140.2, 139.6, 135.1, 129.3, 129.0, 129.0, 128.2, 128.1, 127.8, 126.8, 126.4, 125.8, 125.4, 52.5, 49.8, 39.1, 38.5, 36.8, 32.5, 31.0, 28.5, 28.1.

Example 27—Synthesis of PKS21176

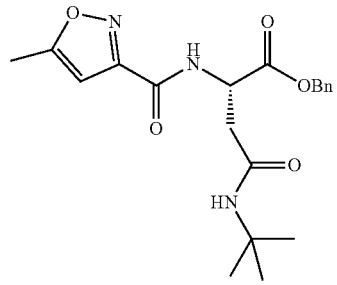 [SMILES: Cc1cc(C(=O)N[C@@H](CC(=O)NC(C)(C)C)C(=O)OCc2ccccc2)no1]

The title compound was synthesized by following the general procedure for HATU mediated coupling of 5-methylisoxazole-3-carboxylic acid (139.8 mg, 1.10 mmol) and N-tert-butyl-L-Aspargine benzyl ester (TFA salt; 431.0 mg, 1.10 mmol). After completion of the reaction, water was added. The white precipitate formed, was filtered, washed with water and dried in air to give product (395 mg, 93%) as a white solid. Product was pure (by NMR) and used in next step without further purification. $^1$H NMR (500 MHz, Chloroform-d) δ 8.00 (d, J=8.3 Hz, 1H), 7.37-7.26 (m, 5H), 6.40 (d, J=1.1 Hz, 1H), 5.30 (br, 1H), 5.25 (d, J=12.4 Hz, 1H), 5.19 (d, J=12.4 Hz, 1H), 4.97 (dt, J=8.7, 4.5 Hz, 1H), 2.89 (dd, J=15.6, 4.6 Hz, 1H), 2.71 (dd, J=15.6, 4.5 Hz, 1H), 2.47 (s, 3H), 1.28 (s, 9H).

Example 28—Synthesis of PKS21178

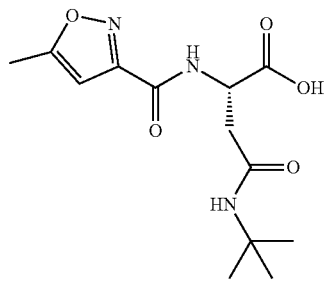 [SMILES: Cc1cc(C(=O)N[C@@H](CC(=O)NC(C)(C)C)C(=O)O)no1]

The title compound was synthesized by following the general procedure for 0-debenzylation of PKS21176 (195.0 mg, 0.503 mmol). After completion of the reaction, the mixture was filtered through celite. Filtrate was evaporated and dried to give product (146 mg, 98%) as a colorless gum. Product was used in next step without further purification. $^1$H NMR (500 MHz, Chloroform-d) δ 8.04 (d, J=6.5 Hz, 1H), 6.46 (s, 1H), 6.37 (s, 1H), 4.83-4.75 (m, 1H), 2.93 (dd, J=15.6, 3.6 Hz, 1H), 2.78 (dd, J=15.6, 8.1 Hz, 1H), 2.45 (s, 3H), 1.32 (s, 9H).

Example 29—Synthesis of PKS21184

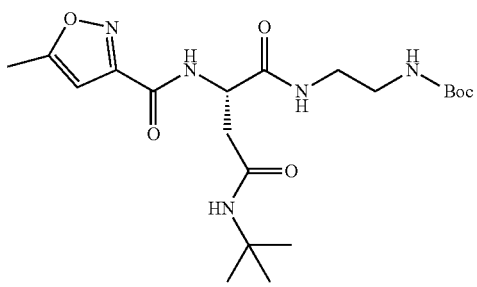 [SMILES: Cc1cc(C(=O)N[C@@H](CC(=O)NC(C)(C)C)C(=O)NCCNC(=O)OC(C)(C)C)no1]

The title compound was synthesized by following the general procedure of HATU mediated coupling of PKS21178 (145.0 mg, 0.488 mmol) and tert-butyl N-(2-aminoethyl)carbamate (78.1 mg, 0.488 mmol). After completion of the reaction, water was added. Mixture was extracted with ethyl acetate twice. Combined organic layer was washed with aq. NaHCO$_3$, water, 1N HCl, saturated brine, dried over anhydrous sodium sulfate and evaporated to give product (210.0 mg, 98%) as an off-white solid. Product was used in next step without further purification. $^1$H NMR (500 MHz, Chloroform-d) δ 8.32 (d, J=7.7 Hz, 1H), 7.44 (br, 1H), 6.41 (s, 1H), 6.05-5.82 (m, 1H), 5.13 (br, 1H), 4.90-4.80 (m, 1H), 3.41-3.29 (m, 2H), 3.28-3.18 (m, 2H), 2.86-2.76 (m, 1H), 2.65-2.56 (m, 1H), 2.46 (s, 3H), 1.39 (s, 9H), 1.32 (s, 9H).

Example 30—Synthesis of PKS21185

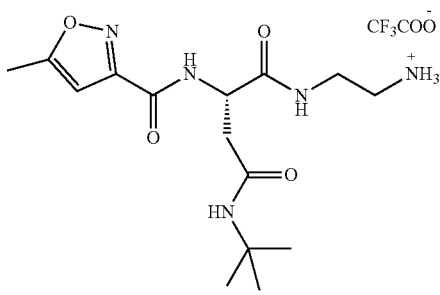 [SMILES: Cc1cc(C(=O)N[C@@H](CC(=O)NC(C)(C)C)C(=O)NCCN)no1 ; "CF3COO"]

The title compound was synthesized by following the general procedure for Boc-deprotection of PKS21184 (210.0 mg, 0.478 mmol). Isolated crude was dried under vacuum and triturated with diethyl ether to give a white solid. The diethylether was decanted and white solid was dried under vacuum to give product (197.0 mg, 91%) as a white solid. Product was used in the next step without further purification. $^1$H NMR (500 MHz, DMSO-d6) δ 8.54 (d, J=8.1 Hz, 1H), 8.25-8.16 (m, 1H), 7.78 (br, 3H), 7.60 (s, 1H), 6.56 (d, J=1.0 Hz, 1H), 4.73-4.62 (m, 1H), 3.35-3.23 (m, 2H), 2.89-2.81 (m, 2H), 2.59 (dd, J=13.3, 5.9 Hz, 1H), 2.55 (dd, J=13.3, 4.8 Hz, 1H), 2.47 (s, 3H), 1.20 (s, 9H).

Example 31—Synthesis of PKS21208

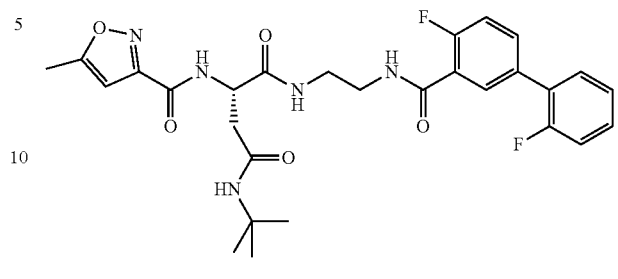

The title compound was synthesized by following the general procedure for HATU mediated coupling of 2-fluoro-5-(2-fluorophenyl)benzoic acid (11.7 mg, 50 μmol) and PKS21185 (22.7 mg, 50 μmol). After completion of the reaction, the mixture was purified by preparative LCMS to give product (21.0 mg, 76%) as a white solid. $^1$H NMR (500 MHz, DMSO-d$_6$) δ 8.52 (d, J=8.0 Hz, 1H), 8.38 (d, J=5.9 Hz, 1H), 8.16 (t, J=5.6 Hz, 1H), 7.78 (d, J=6.7 Hz, 1H), 7.72-7.67 (m, 1H), 7.60-7.54 (m, 1H), 7.49 (s, 1H), 7.47-7.42 (m, 1H), 7.42-7.36 (m, 1H), 7.36-7.28 (m, 2H), 6.49 (s, 1H), 4.69-4.61 (m, 1H), 3.43-3.15 (m, 4H), 2.56 (dd, J=14.4, 8.2 Hz, 1H), 2.52-2.46 (m, 1H), 2.44 (s, 3H), 1.17 (s, 9H); $^{13}$C NMR (126 MHz, DMSO-d$_6$) δ 171.2, 170.4, 168.9, 163.5, 159.0 (d, J=247.1 Hz), 158.8 (d, J=251.1 Hz), 158.6, 158.3, 132.8-132.5 (m), 131.3, 130.8 (d, J=3.3 Hz), 130.4, 130.0 (d, J=7.4 Hz), 126.6 (d, J=12.7 Hz), 125.0 (d, J=2.7 Hz), 124.1 (d, J=14.6 Hz), 116.5 (d, J=23.0 Hz), 116.1 (d, J=21.8 Hz), 101.3, 50.5, 50.1, 39.0, 38.5, 38.1, 28.3, 11.8; $^{19}$F NMR (471 MHz, DMSO-d$_6$) −117.8 (m), −120.8 (m). HRMS calc. for C$_{28}$H$_{31}$F$_2$N$_5$O$_5$Na [M+Na]$^+$: 578.2191. Found: 578.2177.

Example 32—Synthesis of PKS21224

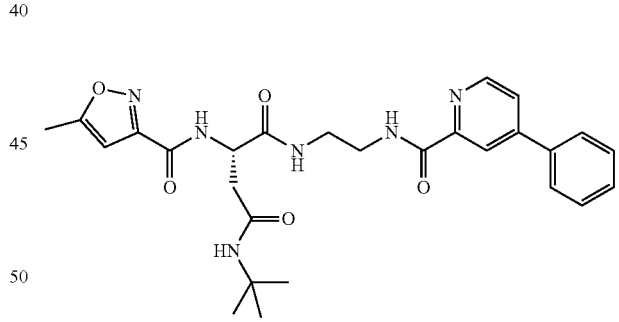

The title compound was synthesized by following the general procedure for HATU mediated coupling of 4-phenylpyridine-2-carboxylic acid (10.0 mg, 50 μmol) and PKS21185 (22.7 mg, 50 μmol). After completion of the reaction, the mixture was purified by preparative LCMS to give product (18.2 mg, 70%) as a white solid. $^1$H NMR (500 MHz, DMSO-d$_6$) δ 8.95 (t, J=6.0 Hz, 1H), 8.68 (d, J=5.0 Hz, 1H), 8.53 (d, J=8.0 Hz, 1H), 8.25 (s, 1H), 8.18 (t, J=5.6 Hz, 1H), 7.94-7.90 (m, 1H), 7.84 (d, J=7.3 Hz, 2H), 7.59-7.46 (m, 4H), 6.51 (s, 1H), 4.70-4.62 (m, 1H), 3.49-3.19 (m, 4H), 2.55 (dd, J=14.5, 8.3 Hz, 1H), 2.50-2.45 (m, 1H), 2.43 (s, 3H), 1.17 (s, 9H); $^{13}$C NMR (126 MHz, DMSO-d$_6$) δ 171.1, 170.4, 168.9, 164.2, 158.6, 158.2, 150.7, 149.1, 148.6, 136.7, 129.6, 129.3, 126.9, 123.7, 119.0, 101.3, 50.4, 50.1, 38.9, 38.7, 38.1, 28.3, 11.8. HRMS calc. for $C_{27}H_{32}N_6O_5Na$ [M+Na]$^+$: 543.2332. Found: 543.2315.

Example 33—Synthesis of PKS21225

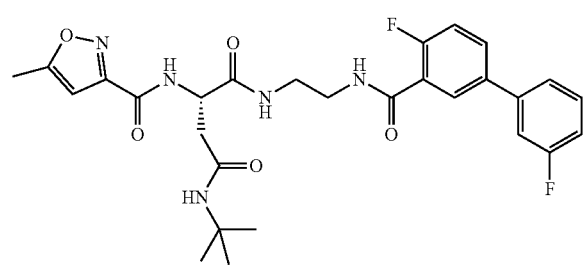 [SMILES: Cc1cc(C(=O)N[C@@H](CC(=O)NC(C)(C)C)C(=O)NCCNC(=O)c2cc(-c3cccc(F)c3)ccc2F)no1]

The title compound was synthesized by following the general procedure for HATU mediated coupling of 2-fluoro-5-(3-fluorophenyl)benzoic acid (11.7 mg, 50 µmol) and PKS21185 (22.7 mg, 50 µmol). After completion of the reaction, the mixture was purified by preparative LCMS to give product (24.4 mg, 88%) as a white solid. $^1$H NMR (500 MHz, DMSO-d$_6$) δ 8.53 (d, J=8.0 Hz, 1H), 8.41 (t, J=5.6 Hz, 1H), 8.18 (t, J=5.6 Hz, 1H), 7.93-7.89 (m, 1H), 7.87-7.82 (m, 1H), 7.59-7.47 (m, 4H), 7.42-7.31 (m, 1H), 7.24-7.18 (m, 1H), 6.49 (s, 1H), 4.71-4.62 (m, 1H), 3.42-3.17 (m, 4H), 2.57 (dd, J=14.4, 8.2 Hz, 1H), 2.53-2.46 (m, 1H), 2.44 (s, 3H), 1.17 (s, 9H). HRMS calc. for $C_{28}H_{31}F_2N_5O_5Na$ [M+Na]$^+$: 578.2191. Found: 578.2183.

Example 34—Synthesis of PKS21250

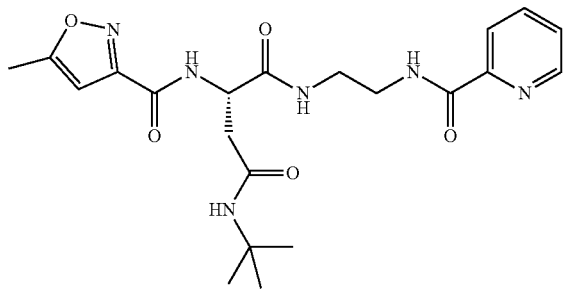 [SMILES: Cc1cc(C(=O)N[C@@H](CC(=O)NC(C)(C)C)C(=O)NCCNC(=O)c2ccccn2)no1]

The title compound was synthesized by following the general procedure for HATU mediated coupling of picolinic acid (6.2 mg, 50 µmol) and PKS21185 (22.7 mg, 50 mol). After completion of the reaction, the mixture was purified by preparative LCMS to give product (20.4 mg, 92%) as a white solid. $^1$H NMR (500 MHz, DMSO-d$_6$) δ 8.88 (t, J=6.0 Hz, 1H), 8.62 (d, J=4.7 Hz, 1H), 8.52 (d, J=8.0 Hz, 1H), 8.21-8.11 (m, 1H), 8.04-7.93 (m, 2H), 7.59 (dd, J=7.0, 4.6 Hz, 1H), 7.49 (s, 1H), 6.52 (s, 1H), 4.70-4.59 (m, 1H), 3.43-3.29 (m, 2H), 3.29-3.16 (m, 2H), 2.54 (dd, J=14.3, 8.3 Hz, 1H), 2.49-2.43 (m, 4H), 1.17 (s, 9H); $^{13}$C NMR (126 MHz, DMSO-d$_6$) δ 171.2, 170.4, 168.9, 164.2, 158.6, 158.2, 149.9, 148.3, 137.7, 126.4, 121.89, 101.3, 50.4, 50.1, 38.9, 38.6, 38.1, 28.3, 11.8. HRMS calc. for $C_{21}H_{28}N_6O_5Na$ [M+Na]$^+$: 467.2019. Found: 467.2003.

Example 35—Synthesis of PKS21251

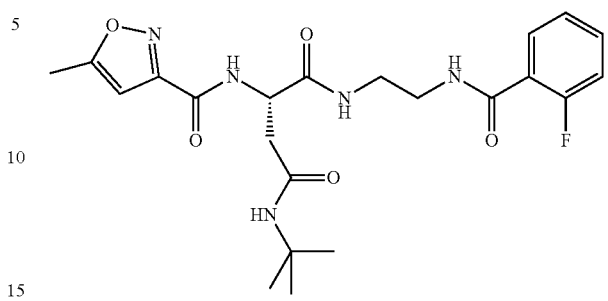

The title compound was synthesized by following the general procedure for HATU mediated coupling of 2-fluorobenzoic acid (7.0 mg, 50 µmol) and PKS21185 (22.7 mg, 50 µmol). After completion of the reaction, the mixture was purified by preparative LCMS to give product (19.8 mg, 86%) as a white solid. $^1$H NMR (500 MHz, DMSO-d$_6$) δ 8.53 (d, J=7.9 Hz, 1H), 8.26 (t, J=5.8 Hz, 1H), 8.14 (t, J=5.7 Hz, 1H), 7.66-7.59 (m, 1H), 7.56-7.46 (m, 2H), 7.30-7.21 (m, 2H), 6.52 (s, 1H), 4.70-4.60 (m, 1H), 3.39-3.14 (m, 4H), 2.56 (dd, J=14.5, 8.1 Hz, 1H), 2.49-2.44 (m, 4H), 1.18 (s, 9H); $^{13}$C NMR (126 MHz, DMSO-d$_6$) δ 171.2, 170.4, 168.9, 163.8, 159.1 (d, J=250.8 Hz), 158.6, 158.3, 132.4 (d, J=7.8 Hz), 130.2, 124.4, 123.9 (d, J=14.4 Hz), 116.0 (d, J=23.4 Hz), 101.3, 50.4, 50.1, 38.9, 38.5, 38.1, 28.3, 11.8; $^{19}$F NMR (471 MHz, DMSO-d$_6$) δ −116.5 (m). HRMS calc. for $C_{22}H_{28}FN_5O_5Na$ [M+Na]$^+$: 484.1972. Found: 484.1969.

Example 36—Synthesis of PKS21212

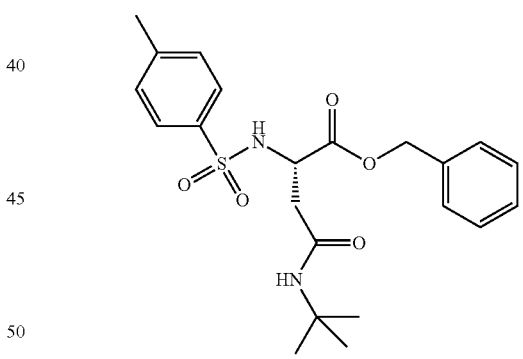

N-tert-butyl-N$^2$-Boc-L-Aspargine benzyl ester (1.60 g, 4.23 mmol) was dissolved in water: tetrahydrofuran (1:1, 20 mL) mixture and 5 mL of HCl (12 N) was added. The mixture was stirred at room temperature for 4 hours. Tetrahydrofuran was evaporated and the resulting solution was diluted with 10 mL water and basified with pinch-wise addition of solid sodium bicarbonate (approx. 12 g). 4-Toluenesulfonyl chloride (1.61 g, 8.46 mmol) and 50 mL ethyl acetate were added. The biphasic mixture was vigorously stirred at room temperature for 2 hours. The layers were separated and aqueous layer was washed with ethyl acetate. Combined ethyl acetate layer was evaporated and purified by combi-flash to give product (1.37 g, 75%) as a white solid. $^1$H NMR (500 MHz, Chloroform-d) δ 7.75-7.68 (m, 2H), 7.35-7.28 (m, 3H), 7.22 (d, J=7.9 Hz, 5H), 5.90 (d, J=7.8 Hz, 1H), 5.31 (s, 1H), 5.04 (d, J=12.2 Hz, 1H), 5.00 (d, J=12.2 Hz, 1H), 4.10 (dt, J=8.3, 4.3 Hz, 1H), 2.80 (dd, J=15.3, 4.1 Hz, 1H), 2.62 (dd, J=15.3, 4.6 Hz, 1H), 2.39 (s, 3H), 1.29 (s, 9H).

Example 37—Synthesis of PKS21241

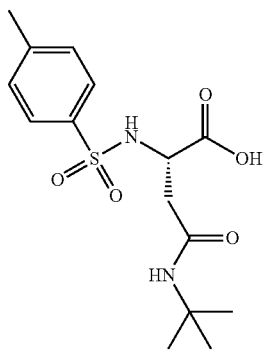 [SMILES: Cc1ccc(S(=O)(=O)N[C@@H](CC(=O)NC(C)(C)C)C(=O)O)cc1]

The title compound was synthesized by following the general procedure for O-debenzylation of PKS21212 (1.37 g, 3.17 mmol) in tetrahydrofuran (15.00 mL). After completion of the reaction, the mixture was filtered through celite. Filtrate was evaporated and dried to give product (1.06 g, 98%) as a white solid. $^1$H NMR (500 MHz, DMSO-$d_6$) δ 12.55 (s, 1H), 7.86 (d, J=8.7 Hz, 1H), 7.66 (d, J=7.8 Hz, 2H), 7.41 (s, 1H), 7.33 (d, J=7.8 Hz, 2H), 4.09-4.02 (m, 1H), 2.42 (dd, J=15.1, 6.8 Hz, 1H), 2.36 (s, 3H), 2.24 (dd, J=15.1, 6.5 Hz, 1H), 1.17 (s, 9H).

Example 38—Synthesis of PKS21177

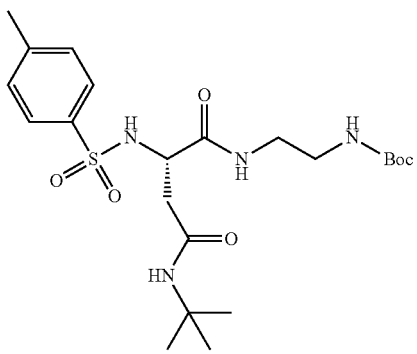 [SMILES: Cc1ccc(S(=O)(=O)N[C@@H](CC(=O)NC(C)(C)C)C(=O)NCCNC(=O)OC(C)(C)C)cc1]

The title compound was synthesized by following the general procedure of HATU mediated coupling of Ts-Asp(CONHtBu)-OH (342.4 mg, 1.00 mmol) and N-Boc-ethylenediamine (176.2 mg, 1.10 mmol). After completion of the reaction, water was added and mixture was stirred for 30 minutes at room temperature. The white precipitate formed, was filtered, washed with water and dried in air to give product (441.0 mg, 91%) as a white solid. Product was used in next step without further purification. $^1$H NMR (500 MHz, Chloroform-d) δ 7.76 (d, J=8.4 Hz, 2H), 7.34-7.30 (m, 3H), 6.71 (br, 1H), 5.51 (br, 1H), 4.98 (br, 1H), 3.93-3.84 (m, 1H), 3.34-3.26 (m, 2H), 3.23-3.15 (m, 2H), 2.67 (dd, J=15.1, 4.2 Hz, 1H), 2.43 (s, 3H), 2.16-2.04 (m, 1H), 1.45 (s, 9H), 1.27 (s, 9H).

Example 39—Synthesis of PKS21183

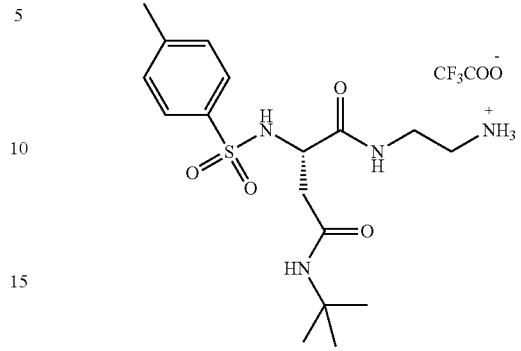

The title compound was synthesized by following the general procedure for Boc-deprotection of PKS21177 (431.0 mg, 0.889 mmol). After completion of the reaction (3 hours), excess trifluoroacetic acid and dichloromethane were evaporated. Crude was dried under vacuum and triturated with diethyl ether to give a white solid. The diethylether was decanted and a white solid was dried under vacuum to give product (440.0 mg, 99%) as a white solid. Product was used in next step without further purification. $^1$H NMR (500 MHz, DMSO-$d_6$) δ 8.07 (t, J=5.9 Hz, 1H), 7.88 (d, J=8.4 Hz, 1H), 7.69 (s, 3H), 7.66 (d, J=8.0 Hz, 2H), 7.57 (s, 1H), 7.34 (d, J=8.0 Hz, 2H), 3.96-3.87 (m, 1H), 3.21-3.11 (m, 1H), 3.10-3.00 (m, 1H), 2.80-2.64 (m, 2H), 2.37 (s, 3H), 2.34 (dd, J=14.8, 7.9 Hz, 1H), 2.27 (dd, J=14.8, 6.1 Hz, 1H), 1.18 (s, 9H).

Example 40—Synthesis of PKS21221

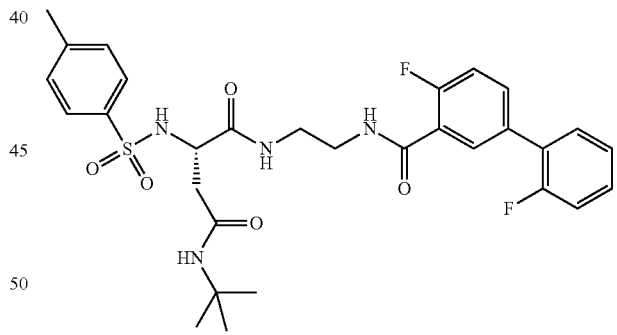

The title compound was synthesized by following the general procedure for HATU mediated coupling of 2-fluoro-5-(2-fluorophenyl)benzoic acid (11.7 mg, 50 µmol) and PKS21183 (24.9 mg, 50 µmol). After completion of the reaction, the mixture was purified by preparative LCMS to give product (25.0 mg, 83%) as a white solid. $^1$H NMR (500 MHz, DMSO-$d_6$) δ 8.27 (t, J=5.7 Hz, 1H), 7.95 (t, J=5.8 Hz, 1H), 7.80-7.74 (m, 2H), 7.72-7.67 (m, 1H), 7.64 (d, J=7.5 Hz, 2H), 7.59-7.53 (m, 1H), 7.48-7.28 (m, 7H), 4.02-3.91 (m, 1H), 3.24-3.11 (m, 2H), 3.09-2.93 (m, 2H), 2.35 (s, 3H), 2.31 (dd, J=14.7, 7.0 Hz, 1H), 2.20 (dd, J=14.7, 6.9 Hz, 1H), 1.14 (s, 9H); $^{13}$C NMR (126 MHz, DMSO-$d_6$) δ 170.1, 168.1, 163.4, 159.0 (d, J=247.2 Hz), 158.8 (d, J=251.2 Hz), 142.5, 138.1, 132.8-132.6 (m), 131.3 (d, J=2.5 Hz), 130.8, 130.3, 130.0 (d, J=7.5 Hz), 129.2, 126.6, 126.6, 125.0 (d, J=2.8 Hz), 124.1 (d, J=14.7 Hz), 116.5 (d, J=23.5 Hz), 116.2 (d, J=23.1 Hz), 53.7, 50.1, 39.4, 38.8, 38.2, 28.3, 20.9; $^{19}$F NMR (471 MHz, DMSO-d$_6$) δ −117.8 (m), −120.9 (m). HRMS calc. for C$_3$OH$_{34}$F$_2$N$_4$O$_5$SNa [M+Na]$^+$: 623.2116. Found: 623.2107.

Example 41—Synthesis of PKS21228

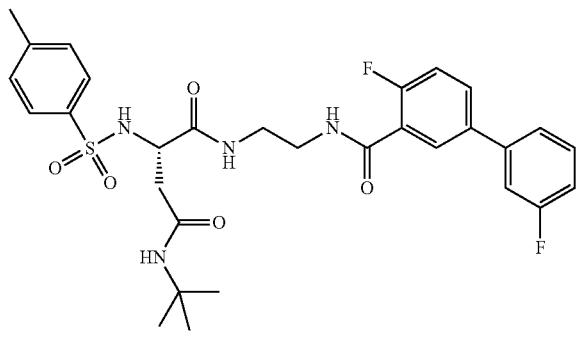 [SMILES: Cc1ccc(S(=O)(=O)N[C@@H](CC(=O)NC(C)(C)C)C(=O)NCCNC(=O)c2cc(-c3cccc(F)c3)ccc2F)cc1]

The title compound was synthesized by following the general procedure for HATU mediated coupling of 2-fluoro-5-(3-fluorophenyl)benzoic acid (11.7 mg, 50 μmol) and PKS21183 (24.9 mg, 50 μmol). After completion of the reaction, the mixture was purified by preparative LCMS to give product (24.5 mg, 82%) as a white solid. $^1$H NMR (500 MHz, DMSO-d$_6$) δ 8.31 (t, J=5.7 Hz, 1H), 7.98 (t, J=5.9 Hz, 1H), 7.91 (dd, J=6.7, 2.3 Hz, 1H), 7.87-7.82 (m, 1H), 7.78 (br, 1H), 7.65 (d, J=7.4 Hz, 2H), 7.59-7.46 (m, 3H), 7.41-7.35 (m, 2H), 7.31 (d, J=7.9 Hz, 2H), 7.25-7.18 (m, 1H), 4.02-3.92 (m, 1H), 3.26-3.12 (m, 2H), 3.11-2.93 (m, 2H), 2.35 (s, 3H), 2.34-2.29 (m, 1H), 2.20 (dd, J=14.7, 6.8 Hz, 1H), 1.14 (s, 9H); $^{13}$C NMR (126 MHz, DMSO-d$_6$) δ 170.2, 168.1, 163.5, 162.7 (d, J=243.9 Hz), 159.1 (d, J=252.7 Hz), 142.5, 140.9 (d, J=7.3 Hz), 138.1, 135.0, 130.9 (d, J=8.9 Hz), 130.6 (d, J=8.9 Hz), 129.2, 128.3, 126.6, 124.5 (d, J=14.5 Hz), 122.8, 116.8 (d, J=21.8 Hz), 114.4 (d, J=20.2 Hz), 113.5 (d, J=21.9 Hz), 53.7, 50.1, 39.3, 38.7, 38.3, 28.3, 20.9; $^{19}$F NMR (471 MHz, DMSO-d$_6$) δ −114.9 (m), −118.2 (m). HRMS calc. for C$_{30}$H$_{34}$F$_2$N$_4$O$_5$SNa [M+Na]$^+$: 623.2116. Found: 623.2117.

Example 42—Synthesis of PKS21229

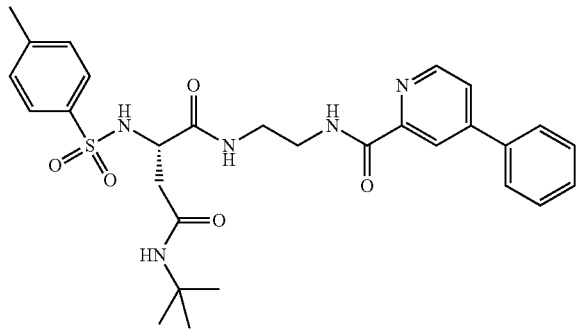 [SMILES: Cc1ccc(S(=O)(=O)N[C@@H](CC(=O)NC(C)(C)C)C(=O)NCCNC(=O)c2cc(-c3ccccc3)ccn2)cc1]

The title compound was synthesized by following the general procedure for HATU mediated coupling of 4-phenylpyridine-2-carboxylic acid (10.0 mg, 50 μmol) and PKS21183 (24.9 mg, 50 μmol). After completion of the reaction, the mixture was purified by preparative LCMS to give product (16.0 mg, 57%) as a white solid. $^1$H NMR (500 MHz, DMSO-d$_6$) δ 8.91 (t, J=6.0 Hz, 1H), 8.73 (d, J=5.0 Hz, 1H), 8.31 (s, 1H), 8.03 (t, J=5.7 Hz, 1H), 7.96 (dd, J=4.9, 2.3 Hz, 1H), 7.88 (d, J=7.4 Hz, 2H), 7.79 (br, 1H), 7.67 (d, J=7.8 Hz, 2H), 7.62-7.50 (m, 3H), 7.38 (s, 1H), 7.30 (d, J=7.8 Hz, 2H), 4.06-3.95 (m, 1H), 3.34-3.22 (m, 2H), 3.14-2.99 (m, 2H), 2.35 (s, 3H), 2.34-2.30 (m, 1H), 2.22 (dd, J=14.6, 7.1 Hz, 1H), 1.18 (s, 9H); $^{13}$C NMR (126 MHz, DMSO-d$_6$) δ 170.1, 168.0, 164.0, 150.8, 149.1, 148.6, 142.4, 138.1, 136.7, 129.7, 129.4, 129.2, 126.9, 126.6, 123.7, 119.0, 53.7, 50.1, 39.5, 38.6, 38.4, 28.4, 20.9. HRMS calc. for C$_{29}$H$_{35}$N$_5$O$_5$SNa [M+Na]$^+$: 588.2257. Found: 588.2238.

Example 43—Synthesis of PKS21282

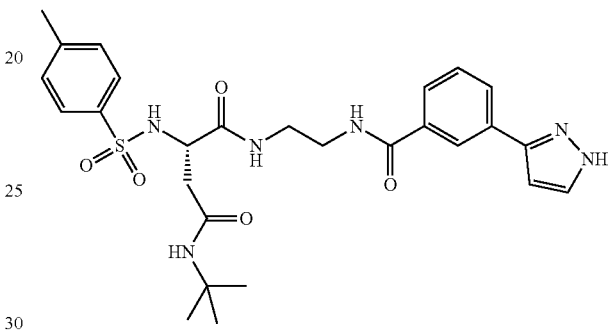

The title compound was synthesized by following the general procedure for HATU mediated coupling of 3-(1H-pyrazol-3-yl)benzoic acid (6.2 mg, 33 μmol) and PKS21183 (15.0 mg, 30 μmol). After completion of the reaction, the mixture was purified by preparative LCMS to give product (10.6 mg, 64%) as a white solid. $^1$H NMR (500 MHz, DMSO-d$_6$) δ 8.40 (t, J=5.6 Hz, 1H), 8.27-8.22 (m, 1H), 8.00 (t, J=5.7 Hz, 1H), 7.95 (dt, J=7.7, 1.4 Hz, 1H), 7.79 (d, J=8.8 Hz, 1H), 7.77-7.75 (m, 1H), 7.74 (dt, J=7.7, 1.4 Hz, 1H), 7.65 (d, J=8.0 Hz, 2H), 7.49 (t, J=7.7 Hz, 1H), 7.40 (s, 1H), 7.29 (d, J=8.0 Hz, 2H), 6.76 (d, J=2.2 Hz, 1H), 4.04-3.96 (m, 1H), 3.23-3.15 (m, 2H), 3.11-2.95 (m, 2H), 2.34 (s, 3H), 2.33 (dd, J=14.6. 7.23 Hz, 1H), 2.21 (dd, J=14.6, 6.8 Hz, 1H), 1.16 (s, 9H); $^{13}$C NMR (126 MHz, DMSO-d$_6$) δ 170.2, 168.1, 166.2, 148.0, 142.5, 138.1, 134.9, 133.0, 131.9, 129.3, 128.7, 127.7, 126.6, 126.1, 124.0, 102.2, 53.7, 50.1, 39.5, 38.8, 38.4, 28.4, 21.0.

Example 44—Synthesis of PKS21291

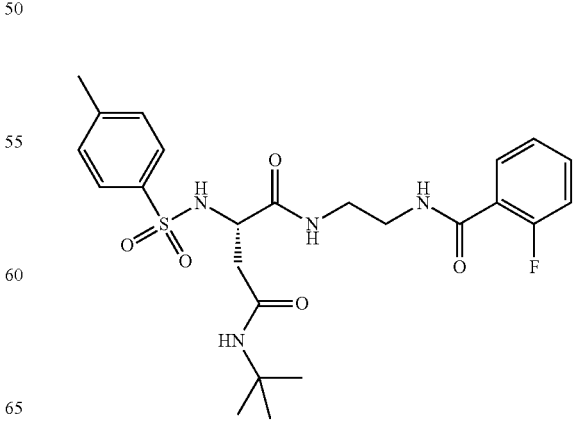

The title compound was synthesized by following the general procedure for HATU mediated coupling of 2-fluorobenzoic acid (4.6 mg, 33 μmol) and PKS21183 (15.0 mg, mol). After completion of the reaction, the mixture was purified by preparative LCMS to give product (13.9 mg, 91%) as a white solid. $^1$H NMR (500 MHz, DMSO-d$_6$) δ 8.22-8.13 (m, 1H), 7.95 (t, J=5.7 Hz, 1H), 7.78 (br, 1H), 7.68-7.60 (m, 3H), 7.57-7.47 (m, 1H), 7.38 (s, 1H), 7.35-7.23 (m, 4H), 4.03-3.92 (m, 1H), 3.24-3.08 (m, 2H), 3.08-2.92 (m, 2H), 2.35 (s, 3H), 2.31 (dd, J=14.6, 7.1 Hz, 1H), 2.19 (dd, J=14.6, 6.8 Hz, 1H), 1.15 (s, 9H); $^{13}$C NMR (126 MHz, DMSO-d$_6$) δ 170.1, 168.1, 163.7, 159.1 (d, J=249.0 Hz), 142.5, 138.1, 132.4 (d, J=8.8 Hz), 130.2, 129.2, 126.6, 124.4 (d, J=2.5 Hz), 123.9 (d, J=14.5 Hz), 116.1 (d, J=21.8 Hz), 53.7, 50.1, 39.4, 38.7, 38.2, 28.4, 20.9; $^{19}$F NMR (471 MHz, DMSO-d$_6$) δ −116.5 (m).

Example 45—Synthesis of PKS21295

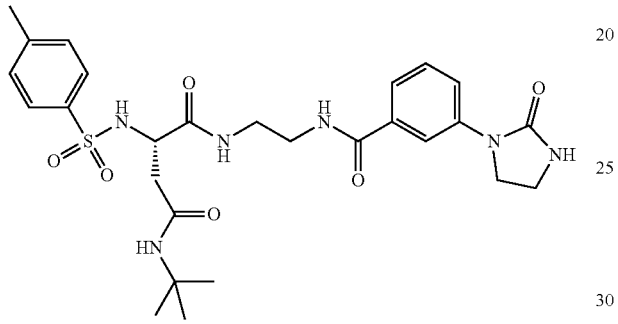

The title compound was synthesized by following the general procedure for HATU mediated coupling of 3-(2-oxoimidazolidin-1-yl)benzoic acid (6.80 mg, 33 μmol) and PKS21183 (15.0 mg, 30 μmol). After completion of the reaction, the mixture was purified by preparative LCMS to give product (14.1 mg, 82%) as a white solid. $^1$H NMR (500 MHz, DMSO-d$_6$) δ 8.29 (t, J=5.6 Hz, 1H), 7.99 (t, J=5.7 Hz, 1H), 7.86-7.80 (m, 2H), 7.79 (br, 1H), 7.64 (d, J=8.2 Hz, 2H), 7.45-7.39 (m, 2H), 7.37 (t, J=7.8 Hz, 1H), 7.29 (d, J=8.2 Hz, 2H), 7.03 (s, 1H), 3.99 (t, J=6.9 Hz, 1H), 3.91-3.84 (m, 2H), 3.45-3.39 (m, 2H), 3.20-3.12 (m, 2H), 3.08-2.92 (m, 2H), 2.38-2.28 (m, 1H), 2.33 (s, 3H), 2.20 (dd, J=14.5, 6.9 Hz, 1H), 1.16 (s, 9H). $^{13}$C NMR (126 MHz, DMSO-d$_6$) δ 170.2, 168.1, 166.4, 158.9, 142.5, 140.8, 138.1, 135.0, 129.2, 128.4, 126.6, 120.0, 119.7, 115.6, 53.7, 50.1, 44.5, 39.5, 38.8, 38.4, 36.5, 28.4, 20.9.

Example 46—Synthesis of PKS21315

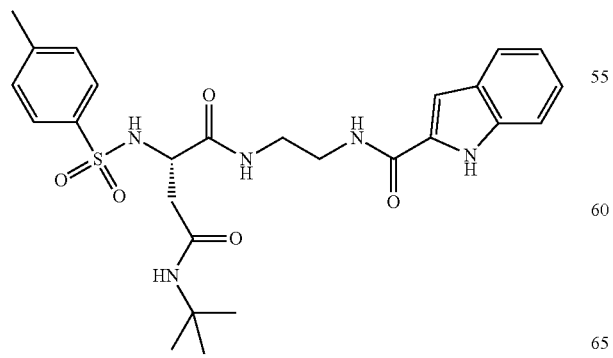

The title compound was synthesized by following the general procedure for HATU mediated coupling of 1H-indole-2-carboxylic acid (4.83 mg, 30.00 μmol) and PKS21183 (15.0 mg, 30 μmol). After completion of the reaction, the mixture was purified by preparative LCMS to give product (9.9 mg, 63%) as a white solid. $^1$H NMR (500 MHz, DMSO-d$_6$) δ 11.58 (d, J=2.2 Hz, 1H), 8.36 (t, J=5.7 Hz, 1H), 8.02 (t, J=5.8 Hz, 1H), 7.81 (br, 1H), 7.65 (d, J=8.0 Hz, 2H), 7.59 (d, J=7.9 Hz, 1H), 7.45-7.39 (m, 2H), 7.29 (d, J=8.0 Hz, 2H), 7.17 (t, J=7.6 Hz, 1H), 7.08 (d, J=1.9 Hz, 1H), 7.03 (t, J=7.4 Hz, 1H), 4.04-3.96 (m, 1H), 3.22-3.15 (m, 2H), 3.09-2.93 (m, 2H), 2.38-2.29 (m, 4H), 2.22 (dd, J=14.5, 6.8 Hz, 1H), 1.18 (s, 9H). $^{13}$C NMR (126 MHz, DMSO-d$_6$) δ 170.2, 168.1, 161.1, 142.5, 138.1, 136.4, 131.7, 129.2, 127.1, 126.6, 123.2, 121.4, 119.7, 112.3, 102.4, 53.8, 50.1, 39.5, 38.5, 38.2, 28.4, 21.0.

Example 47—Synthesis of PKS21242

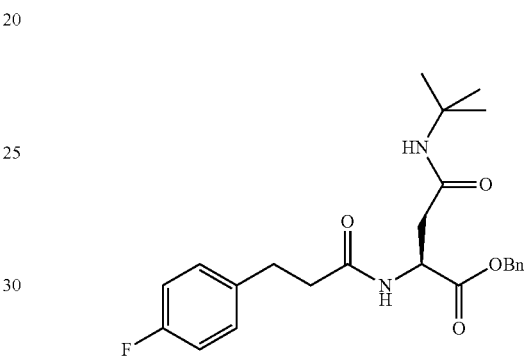

The title compound was synthesized by following the general procedure for HATU mediated coupling of 3-(4-fluorophenyl)propanoic acid (223.7 mg, 1.33 mmol) and N-tert-butyl-L-Aspargine benzyl ester (TFA salt; 521.9 mg, 1.33 mmol). After completion of the reaction, water was added. The white precipitate formed, was filtered, washed with water and dried in air to give product (515.0 mg, 90%) as a white solid. Product was pure (by NMR) and used in next step without further purification. $^1$H NMR (500 MHz, Chloroform-d) δ 7.37-7.28 (m, 5H), 7.18-7.09 (m, 2H), 6.98-6.90 (m, 2H), 6.88 (d, J=8.1 Hz, 1H), 5.28 (s, 1H), 5.20 (d, J=12.3 Hz, 1H), 5.14 (d, J=12.3 Hz, 1H), 4.84-4.76 (m, 1H), 2.92 (t, J=7.9 Hz, 2H), 2.80 (dd, J=15.8, 3.8 Hz, 1H), 2.56-2.44 (m, 3H), 1.27 (s, 9H).

Example 48—Synthesis of PKS21243

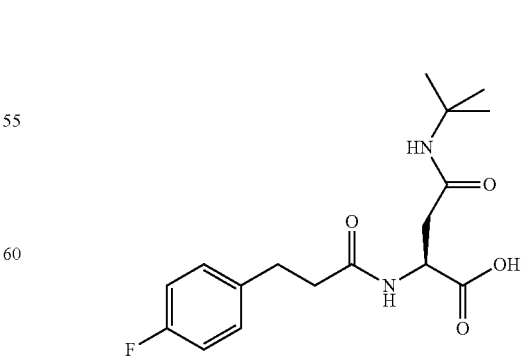

The title compound was synthesized by following the general procedure for O-debenzylation of PKS21242 (515.0 mg, 1.20 mmol). After completion of the reaction, the mixture was filtered through celite. Filtrate was evaporated and dried to give product (405.0 mg, quant.) as a white solid. Product was used in next step without further purification. ¹H NMR (500 MHz, DMSO-d₆) δ 12.50 (s, 1H), 8.04 (d, J=7.8 Hz, 1H), 7.42 (s, 1H), 7.27-7.16 (m, 2H), 7.10-7.01 (m, 2H), 4.52-4.41 (m, 1H), 2.78 (t, J=7.7 Hz, 2H), 2.49-2.44 (m, 1H), 2.42-2.34 (m, 3H), 1.22 (s, 9H).

Example 49—Synthesis of PKS21246

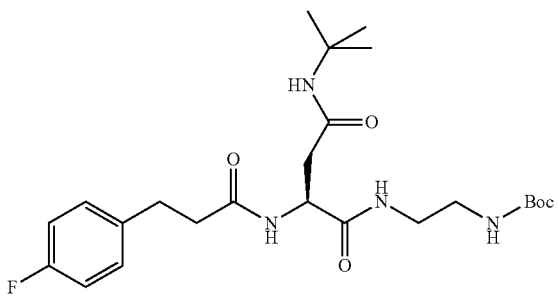 [SMILES: CC(C)(C)NC(=O)C[C@H](NC(=O)CCc1ccc(F)cc1)C(=O)NCCNC(=O)OC(C)(C)C]

The title compound was synthesized by following the general procedure of HATU mediated coupling of PKS21243 (310.0 mg, 0.916 mmol) and N-Boc-ethylenediamine (146.8 mg, 0.916 mmol). After completion of the reaction, water was added. The white precipitate formed, was filtered, washed with water and dried in air to give product (393.0 mg, 89%) as a white solid. Product was used in next step without further purification. ¹H NMR (500 MHz, DMSO-d₆) δ 7.94 (d, J=8.0 Hz, 1H), 7.80 (t, J=5.9 Hz, 1H), 7.35 (s, 1H), 7.27-7.18 (m, 2H), 7.11-7.02 (m, 2H), 6.75 (t, J=5.7 Hz, 1H), 4.51-4.39 (m, 1H), 3.13-2.90 (m, 4H), 2.78 (t, J=7.8 Hz, 2H), 2.43-2.36 (m, 3H), 2.29 (dd, J=14.7, 7.8 Hz, 1H), 1.37 (s, 9H), 1.21 (s, 9H).

Example 50—Synthesis of PKS21249

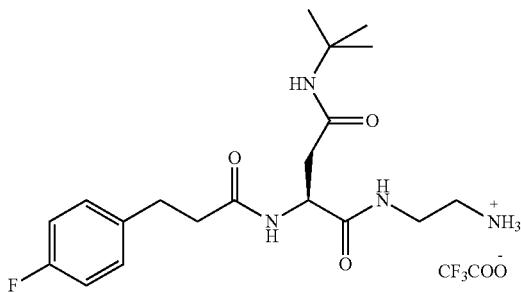

The title compound was synthesized by following the general procedure for Boc-deprotection of PKS21246 (390.0 mg, 0.812 mmol). Isolated crude was dried under vacuum and triturated with diethyl ether. Diethyl ether was decanted and white solid was dried to give product (400 mg, quant.). Product was used in next step without further purification. ¹H NMR (500 MHz, DMSO-d₆) δ 8.08-8.03 (m, 2H), 7.76 (br, 3H), 7.56 (s, 1H), 7.26-7.17 (m, 2H), 7.10-7.02 (m, 2H), 4.50-4.38 (m, 1H), 3.40-3.30 (m, 1H), 3.28-3.16 (m, 1H), 2.92-2.81 (m, 2H), 2.78 (t, J=7.9 Hz, 2H), 2.47-2.31 (m, 4H), 1.22 (s, 9H).

Example 51—Synthesis of PKS21254

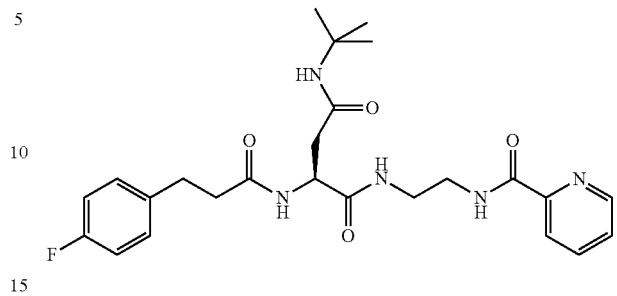

The title compound was synthesized by following the general procedure for HATU mediated coupling of picolinic acid (6.2 mg, 51 μmol) and PKS21249 (25.0 mg, 51 mol). After completion of the reaction, the mixture was purified by preparative LCMS to give product (19.5 mg, 79%) as an off-white solid. ¹H NMR (500 MHz, DMSO-d₆) δ 8.90 (t, J=6.1 Hz, 1H), 8.62 (d, J=4.5 Hz, 1H), 8.02 (d, J=7.8 Hz, 1H), 8.00-7.90 (m, 3H), 7.63-7.54 (m, 1H), 7.34 (s, 1H), 7.26-7.16 (m, 2H), 7.13-7.01 (m, 2H), 4.54-4.43 (m, 1H), 3.41-3.34 (m, 2H), 3.29-3.15 (m, 2H), 2.76 (t, J=7.9 Hz, 2H), 2.45-2.32 (m, 3H), 2.28 (dd, J=14.5, 8.0 Hz, 1H), 1.19 (s, 9H); ¹³C NMR (126 MHz, DMSO-d₆) δ 171.2, 171.0, 168.8, 164.2, 160.6 (d, J=240.0 Hz), 149.9, 148.3, 137.7, 137.4 (d, J=2.7 Hz), 129.9 (d, J=8.7 Hz), 126.5, 121.9, 114.9 (d, J=21.0 Hz), 50.1, 50.0, 38.8, 38.7, 38.6, 36.9, 30.1, 28.4. HRMS calc. for $C_{25}H_{32}FN_5O_4Na$ [M+Na]⁺: 508.2336. Found: 508.2324.

Example 52—Synthesis of PKS21255

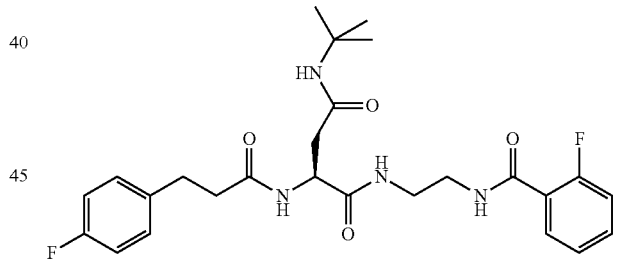

The title compound was synthesized by following the general procedure for HATU mediated coupling of 2-fluorobenzoic acid (7.1 mg, 51 μmol) and PKS21249 (25.0 mg, 51 μmol). After completion of the reaction, the mixture was purified by preparative LCMS to give product (20.8 mg, 82%) as a white solid. ¹H NMR (500 MHz, DMSO-d₆) δ 8.27 (t, J=5.8 Hz, 1H), 7.97 (d, J=8.1 Hz, 1H), 7.95-7.90 (m, 1H), 7.65 (t, J=7.6 Hz, 1H), 7.56-7.46 (m, 1H), 7.36 (s, 1H), 7.30-7.23 (m, 2H), 7.23-7.17 (m, 2H), 7.10-7.03 (m, 2H), 4.52-4.41 (m, 1H), 3.32-3.28 (m, 2H), 3.27-3.13 (m, 2H), 2.76 (t, J=7.9 Hz, 2H), 2.46-2.35 (m, 3H), 2.29 (dd, J=14.8, 7.8 Hz, 1H), 1.22-1.13 (m, 9H); ¹³C NMR (126 MHz, DMSO-d₆) δ 171.3, 171.1, 168.8, 163.9, 160.6 (d, J=240.3 Hz), 159.1 (d, J=249.3 Hz), 137.4, 132.4 (d, J=9.0 Hz), 130.2 (d, J=1.6 Hz), 129.9, 124.4 (d, J=2.7 Hz), 123.9 (d, J=14.4 Hz), 116.1 (d, J 23.4 Hz), 114.9 (d, J=21.4 Hz), 50.1, 50.0, 38.9, 38.6, 38.5, 36.9, 30.1, 28.4; ¹⁹F NMR (471 MHz, DMSO-d$_6$) δ −116.5 (m), −119.8 (m). HRMS calc. for C$_{26}$H$_{32}$F$_2$N$_4$O$_4$Na [M+Na]$^+$: 521.2289. Found: 521.2311.

Example 53—Synthesis of PKS21258

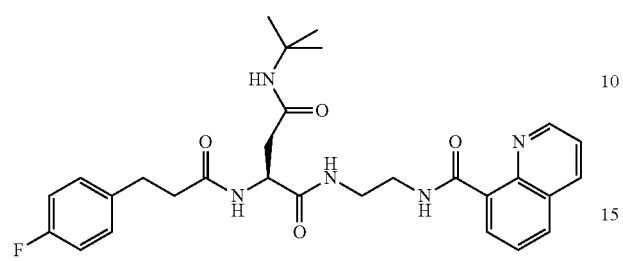

The title compound was synthesized by following the general procedure for HATU mediated coupling of quinoline-8-carboxylic acid (8.8 mg, 51 μmol) and PKS21249 (25.0 mg, 51 μmol). After completion of the reaction, the mixture was purified by preparative LCMS to give product (18.8 mg, 69%) as a white solid. $^1$H NMR (500 MHz, DMSO-d$_6$) δ 10.91 (t, J=5.7 Hz, 1H), 9.07 (dd, J=4.3, 2.1 Hz, 1H), 8.59-8.50 (m, 2H), 8.19 (dd, J=8.1, 2.1 Hz, 1H), 8.01 (t, J=6.0 Hz, 1H), 7.97 (d, J=8.1 Hz, 1H), 7.76-7.71 (m, 1H), 7.69-7.65 (m, 1H), 7.32 (s, 1H), 7.22-7.14 (m, 2H), 7.09-7.01 (m, 2H), 4.59-4.45 (m, 1H), 3.55-3.46 (m, 2H), 3.33-3.23 (m, 2H), 2.74 (t, J=8.0 Hz, 2H), 2.42 (dd, J=14.4, 5.2 Hz, 1H), 2.37 (t, J=7.7 Hz, 2H), 2.29 (dd, J=14.4, 8.3 Hz, 1H), 1.18 (s, 9H); $^{13}$C NMR (126 MHz, DMSO-d$_6$) δ 171.3, 171.0, 168.8, 165.4, 160.6 (d, J=241.1 Hz), 150.4, 144.7, 137.9, 137.4, 132.4, 132.1, 129.9 (d, J=8.2 Hz), 129.2, 128.2, 126.3, 121.5, 114.9 (d, J=20.1 Hz), 50.1, 50.0, 38.9, 38.8, 38.7, 36.9, 30.1, 28.4. $^{19}$F NMR (471 MHz, DMSO-d$_6$) δ −119.8 (m). HRMS calc. for C$_{29}$H$_{34}$FN$_5$O$_4$Na [M+Na]$^+$: 558.2493. Found: 558.2484.

Example 54—Synthesis of PKS21259

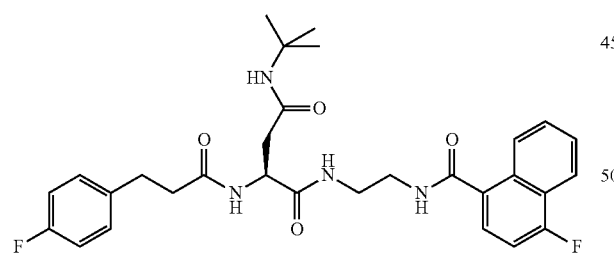

The title compound was synthesized by following the general procedure for HATU mediated coupling of 4-fluoronaphthalene-1-carboxylic acid (9.6 mg, 51 μmol) and PKS21249 (25.0 mg, 51 μmol). After completion of the reaction, the mixture was purified by preparative LCMS to give product (22.4 mg, 80%) as a white solid. $^1$H NMR (500 MHz, DMSO-d$_6$) δ 8.50 (t, J=5.7 Hz, 1H), 8.34-8.27 (m, 1H), 8.12-8.06 (m, 1H), 8.04-7.97 (m, 2H), 7.71-7.62 (m, 3H), 7.41-7.31 (m, 2H), 7.21-7.13 (m, 2H), 7.09-7.00 (m, 2H), 4.55-4.45 (m, 1H), 3.44-3.36 (m, 2H), 3.33-3.19 (m, 2H), 2.74 (t, J=7.9 Hz, 2H), 2.44 (dd, J=14.7, 6.1 Hz, 1H), 2.40-2.34 (m, 2H), 2.31 (dd, J=14.7, 7.8 Hz, 1H), 1.17 (s, 9H); $^{13}$C NMR (126 MHz, DMSO-d$_6$) δ 171.3, 171.1, 168.9, 168.0, 160.6 (d, J=241.5 Hz), 158.6 (d, J=252.5 Hz), 137.4, 131.5 (d, J=4.7 Hz), 131.2 (d, J=3.3 Hz), 129.9 (d, J=7.3 Hz), 127.9, 127.0, 126.0 (d, J=9.1 Hz), 125.8, 122.8 (d, J=16.3 Hz), 120.0 (d, J=5.5 Hz), 114.9 (d, J=20.5 Hz), 108.7 (d, J=19.9 Hz), 50.2, 50.0, 38.9, 38.7, 38.6, 36.9, 30.1, 28.4; $^{19}$F NMR (471 MHz, DMSO-d$_6$) δ −119.8 (m), −122.6 (m). HRMS calc. for C$_{30}$H$_{34}$F$_2$N$_4$O$_4$Na [M+Na]$^+$: 575.2446. Found: 575.2437.

Example 55—Synthesis of PKS21263

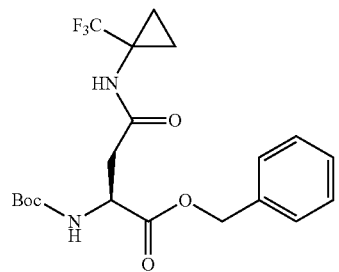 [SMILES: CC(C)(C)OC(=O)N[C@@H](CC(=O)NC1(C(F)(F)F)CC1)C(=O)OCc1ccccc1]

The title compound was synthesized by following the general procedure for HATU mediated coupling of Boc-Asp-OBn (64.7 mg, 0.20 mmol) and 1-(trifluoromethyl)cyclopropanamine (25.8 mg, 0.20 mmol). After completion of the reaction (2 hours), water was added and stirred at rt for 30 minutes. The white precipitate formed was filtered, washed with water and dried in air to give product (75 mg, 87%) as a white solid. $^1$H NMR (500 MHz, Chloroform-d) δ 7.40-7.28 (m, 5H), 6.19-6.07 (m, 1H), 5.79-5.61 (m, 1H), 5.19 (d, J=12.3 Hz, 1H), 5.15 (d, J=12.3 Hz, 1H), 4.65-4.46 (m, 1H), 2.91-2.81 (m, 1H), 2.72 (dd, J=15.5, 3.9 Hz, 1H), 1.42 (s, 9H), 1.32-1.25 (m, 2H), 1.07-1.00 (m, 2H).

Example 56—Synthesis of PKS21264

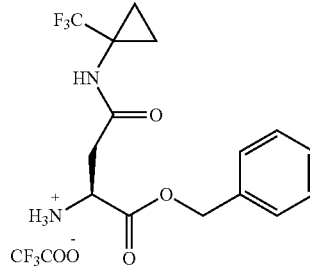

The title compound was synthesized by following the general procedure for Boc-deprotection of PKS21263 (70.0 mg, 0.163 mmol). After completion of the reaction, excess trifluoroacetic acid and dichloromethane were evaporated. Crude was dried under vacuum and triturated with hexane. Hexane was decanted and colorless gum was dried under vacuum to give product (72 mg, quant.). Product was used in next step without further purification. $^1$H NMR (500 MHz, DMSO-d$_6$) δ 9.00 (s, 1H), 8.39 (br, 3H), 7.42-7.32 (m, 5H), 5.23-5.13 (m, 2H), 4.45-4.30 (m, 1H), 2.80-2.74 (m, 2H), 1.29-1.17 (m, 2H), 1.01-0.86 (m, 2H).

Example 57—Synthesis of PKS21267

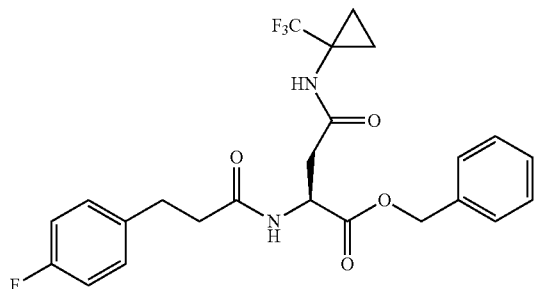

The title compound was synthesized by following the general procedure for HATU mediated coupling of 3-(4-fluorophenyl)propanoic acid (26.9 mg, 0.160 mmol) and PKS21264 (71.1 mg, 0.160 mmol). After completion of the reaction, water was added and the mixture was stirred at room temperature for 30 minutes. The white precipitate formed was filtered, washed with water and dried in air to give product (70 mg, 91%) as a white solid. $^1$H NMR (500 MHz, Chloroform-d) δ 7.41-7.27 (m, 5H), 7.17-7.08 (m, 2H), 6.99-6.87 (m, 2H), 6.70 (d, J=7.8 Hz, 1H), 6.12 (s, 1H), 5.21-5.08 (m, 2H), 4.96-4.75 (m, 1H), 2.95-2.82 (m, 3H), 2.69-2.60 (m, 1H), 2.57-2.42 (m, 2H), 1.33-1.21 (m, 2H), 1.05-0.91 (m, 2H).

Example 58—Synthesis of PKS21269

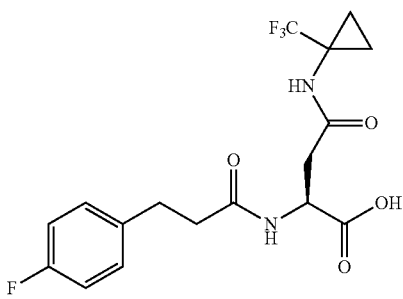 [SMILES: O=C(CCc1ccc(F)cc1)N[C@@H](CC(=O)NC1(C(F)(F)F)CC1)C(=O)O]

The title compound was synthesized by following the general procedure for O-debenzylation of PKS21267 (65.0 mg, 0.135 mmol). After completion of the reaction, the mixture was filtered through celite. Filtrate was evaporated and dried to give product (52.8 mg, quant.) as a white solid. $^1$H NMR (500 MHz, DMSO-d$_6$) δ 12.60 (br, 1H), 8.78-8.64 (m, 1H), 8.14-8.02 (m, 1H), 7.29-7.16 (m, 2H), 7.11-6.99 (m, 2H), 4.57-4.38 (m, 1H), 2.77 (t, J=7.8 Hz, 2H), 2.54 (dd, J=15.3, 5.9 Hz, 1H), 2.45-2.33 (m, 3H), 1.25-1.12 (m, 2H), 1.03-0.88 (m, 2H).

Example 59—Synthesis of PKS21273

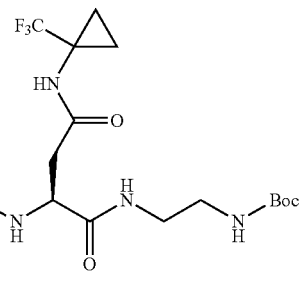

The title compound was synthesized by following the general procedure of HATU mediated coupling of PKS21269 (52.8 mg, 0.135 mmol) and N-Boc-ethylenediamine (23.8 mg, 0.149 mmol). After completion of the reaction, water was added and the mixture was stirred at room temperature for 30 minutes. The white precipitate formed was filtered, washed with water and dried in air to give product (70 mg, 97%) as a white solid. $^1$H NMR (500 MHz, DMSO-d$_6$) δ 8.59 (s, 1H), 8.01 (d, J=8.0 Hz, 1H), 7.83 (t, J=5.6 Hz, 1H), 7.29-7.20 (m, 2H), 7.13-7.04 (m, 2H), 6.78 (t, 1H), 4.59-4.45 (m, 1H), 3.15-2.90 (m, 4H), 2.79 (t, J=7.8 Hz, 2H), 2.56-2.48 (m, 1H), 2.45-2.36 (m, 2H), 2.32 (dd, J=15.2, 7.7 Hz, 1H), 1.39 (s, 9H), 1.24-1.16 (m, 2H), 1.02-0.93 (m, 2H).

Example 60—Synthesis of PKS21275

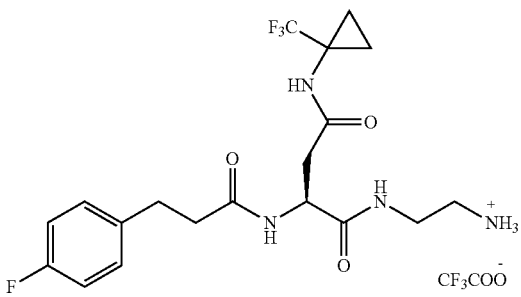

The title compound was synthesized by following the general procedure for Boc-deprotection of PKS21273 (65.0 mg, 0.122 mmol). After completion of the reaction (1.5 hours), excess trifluoroacetic acid and dichloromethane were evaporated. Crude was dried under vacuum and triturated with diethyl ether to give a white solid. Diethyl ether was decanted and white solid was dried under vacuum to give product (62.3 mg, 93%). The product was used in the next step without further purification. $^1$H NMR (500 MHz, DMSO-d$_6$) δ 8.70 (s, 1H), 8.10 (d, J=7.7 Hz, 1H), 8.02 (t, J=6.0 Hz, 1H), 7.70 (br, 3H), 7.27-7.16 (m, 2H), 7.14-7.01 (m, 2H), 4.55-4.42 (m, 1H), 3.36-3.27 (m, 1H), 3.27-3.18 (m, 1H), 2.88-2.80 (m, 2H), 2.78 (t, J=8.0 Hz, 2H), 2.57-2.51 (m, 1H), 2.44-2.32 (m, 3H), 1.24-1.14 (m, 2H), 1.01-0.89 (m, 2H).

Example 61—Synthesis of PKS21278

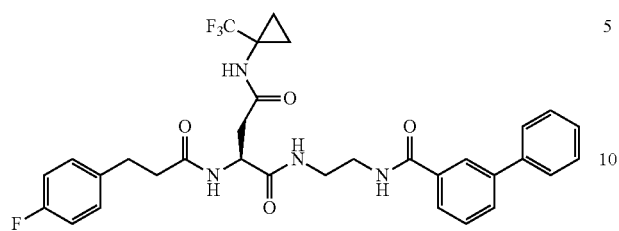

The title compound was synthesized by following the general procedure for HATU mediated coupling of 3-phenylbenzoic acid (5.5 mg, 28 μmol) and PKS21275 (13.7 mg, mol). The mixture was purified by preparative LCMS to give product (12.3 mg, 80%) as a white solid. $^1$H NMR (500 MHz, DMSO-$d_6$) δ 8.61 (s, 1H), 8.58 (t, J=5.6 Hz, 1H), 8.15-8.10 (m, 1H), 8.04 (d, J=8.1 Hz, 1H), 7.98 (t, J=5.7 Hz, 1H), 7.86-7.79 (m, 2H), 7.72 (d, J=7.6 Hz, 2H), 7.54 (t, J=7.7 Hz, 1H), 7.48 (t, J=7.6 Hz, 2H), 7.39 (t, J=7.4 Hz, 1H), 7.18 (dd, J=8.5, 5.6 Hz, 2H), 7.09-7.02 (m, 2H), 4.57-4.50 (m, 1H), 3.30-3.15 (m, 4H), 2.74 (t, J=7.9 Hz, 2H), 2.55-2.50 (m, 1H), 2.43-2.34 (m, 2H), 2.31 (dd, J=16.4, 8.8 Hz, 1H), 1.19-1.13 (m, 2H), 0.94 (d, J=6.3 Hz, 2H); $^{13}$C NMR (126 MHz, DMSO-$d_6$) δ 171.2, 170.9, 170.4, 166.4, 160.6 (d, J=241.5 Hz), 140.2, 139.5, 137.4, 135.1, 129.9 (d, J=8.5 Hz), 129.3, 129.0, 129.0, 127.8, 126.8, 126.4, 125.4 (q, J=275.9 Hz), 125.4, 114.9 (d, J=20.1 Hz), 49.8, 38.9, 38.7, 37.8, 36.9, 31.8 (q, J=36.8 Hz), 30.0, 11.0, 10.9; 19F NMR (471 MHz, DMSO-$d_6$) δ −74.3 (s), −119.8 (m). HRMS calc. for $C_{32}H_{32}F_4N_4O_4Na$ $[M+Na]^+$: 635.2257. Found: 635.2267.

Example 62—Synthesis of PKS21279

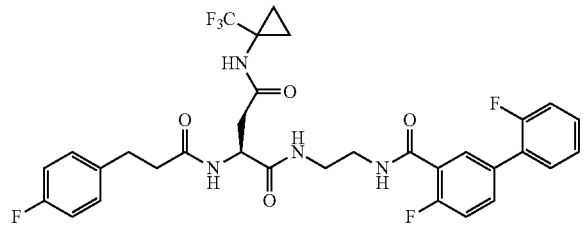 [SMILES: O=C(CCc1ccc(F)cc1)N[C@@H](CC(=O)NC1(C(F)(F)F)CC1)C(=O)NCCNC(=O)c1cc(-c2ccccc2F)ccc1F]

The title compound was synthesized by following the general procedure for HATU mediated coupling of 2-fluoro-5-(2-fluorophenyl)benzoic acid (6.4 mg, 28 μmol) and PKS21275 (13.7 mg, 25 μmol). The mixture was purified by preparative LCMS to give product (13.2 mg, 81%) as a white solid. $^1$H NMR (500 MHz, DMSO-$d_6$) δ 8.59 (s, 1H), 8.43-8.33 (m, 1H), 8.02 (d, J=8.1 Hz, 1H), 7.94 (t, J=5.7 Hz, 1H), 7.79 (dd, J=6.8, 2.4 Hz, 1H), 7.72-7.66 (m, 1H), 7.56 (td, J=7.9, 1.9 Hz, 1H), 7.48-7.36 (m, 2H), 7.35-7.27 (m, 2H), 7.18 (dd, J=8.5, 5.6 Hz, 2H), 7.08-7.01 (m, 2H), 4.56-4.46 (m, 1H), 3.47-3.26 (m, 2H), 3.26-3.11 (m, 2H), 2.73 (t, J=7.8 Hz, 2H), 2.55-2.50 (m, 1H), 2.41-2.25 (m, 3H), 1.19-1.10 (m, 2H), 0.96-0.88 (m, 2H); $^{13}$C NMR (126 MHz, DMSO-$d_6$) δ 171.2, 170.9, 170.3, 163.6, 160.6 (d, J=241.6 Hz), 159.8 (d, J=246.4 Hz), 158.8 (d, J=251.4 Hz), 137.4, 132.7 (d, J=6.0 Hz), 131.3, 130.8, 130.4, 130.0 (d, J=8.8 Hz), 129.9 (d, J=7.2 Hz), 126.6 (d, J=14.4 Hz), 125.4 (q, J=275.8 Hz), 125.3-124.9 (m), 124.2 (d, J=14.6 Hz), 116.5 (d, J=22.1 Hz), 116.2 (d, J=21.9 Hz), 114.9 (d, J=21.6 Hz), 49.8, 38.9, 38.5, 37.7, 36.8, 31.7 (q, J=37.1 Hz), 30.0, 11.0, 10.9; 19F NMR (471 MHz, DMSO-$d_6$) δ −74.4 (s), −117.8 (m), −119.8 (m), −120.8 (m). HRMS calc. for $C_{32}H_{30}F_6N_4O_4Na$ $[M+Na]^+$: 671.2069. Found: 671.2053.

Example 63—Synthesis of PKS21270

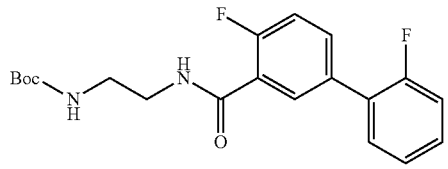 [SMILES: CC(C)(C)OC(=O)NCCNC(=O)c1cc(-c2ccccc2F)ccc1F]

The title compound was synthesized by following the general procedure for HATU mediated coupling of 2-fluoro-5-(2-fluorophenyl)benzoic acid (117.10 mg, 500 μmol) and N-boc-ethylenediamine (88.12 mg, 550 μmol). After completion of the reaction, water was added and the mixture was stirred at room temperature for 30 minutes. The white precipitate formed was filtered, washed with water, and dried in air to give product (160.0 mg, 85%) as a white solid. $^1$H NMR (500 MHz, Chloroform-d) δ 8.22 (d, J=7.3 Hz, 1H), 7.69-7.62 (m, 1H), 7.48-7.40 (m, 1H), 7.36-7.29 (m, 1H), 7.25-7.10 (m, 4H), 4.96 (br, 1H), 3.64-3.58 (m, 2H), 3.43-3.37 (m, 2H), 1.42 (s, 9H).

Example 64—Synthesis of PKS21274

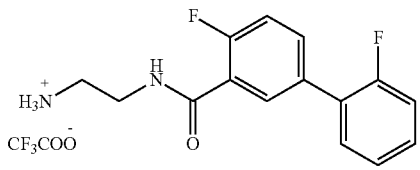 [SMILES: "CF3COO" ; NCCNC(=O)c1cc(-c2ccccc2F)ccc1F]

The title compound was synthesized by following the general procedure for Boc-deprotection of PKS21270 (150.0 mg, 399 μmol). After completion of the reaction, excess trifluoroacetic acid and dichloromethane were evaporated. Crude was dried under vacuum and triturated with diethyl ether to give a white solid. Diethyl ether was decanted and white solid was dried under vacuum to give product (155 mg, quant.). The product was used in the next step without further purification. $^1$H NMR (500 MHz, DMSO-$d_6$) δ 8.61-8.50 (m, 1H), 8.04-7.76 (m, 4H), 7.76-7.67 (m, 1H), 7.61-7.51 (m, 1H), 7.49-7.39 (m, 2H), 7.38-7.30 (m, 2H), 3.59-3.46 (m, 2H), 3.07-2.93 (m, 2H).

Example 65—Synthesis of PKS21277

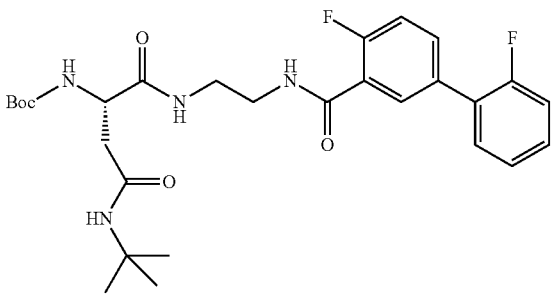 [SMILES: CC(C)(C)NC(=O)C[C@H](NC(=O)OC(C)(C)C)C(=O)NCCNC(=O)c1cc(-c2ccccc2F)ccc1F]

The title compound was synthesized by following the general procedure for HATU mediated coupling of (2S)-2-(tert-butoxycarbonylamino)-4-(tert-butylamino)-4-oxo-butanoic acid (28.8 mg, 100 µmol) and PKS21274 (39.0 mg, 100 µmol). After completion of the reaction, the mixture was purified by preparative LCMS to give product (43.0 mg, 79%) as a white solid. $^1$H NMR (500 MHz, DMSO-d$_6$) δ 8.44-8.33 (m, 1H), 7.98 (t, J=5.6 Hz, 1H), 7.83-7.75 (m, 1H), 7.74-7.67 (m, 1H), 7.60-7.52 (m, 1H), 7.48-7.42 (m, 1H), 7.42-7.29 (m, 4H), 6.74 (d, J=8.2 Hz, 1H), 4.24-4.13 (m, 1H), 3.40-3.24 (m, 3H), 3.24-3.15 (m, 1H), 2.38 (dd, J=14.3, 5.4 Hz, 1H), 2.30 (dd, J=14.3, 8.4 Hz, 1H), 1.34 (s, 9H), 1.19 (s, 9H). HRMS calc. for C$_{28}$H$_{36}$F$_2$N$_4$O$_5$Na[M+Na]$^+$: 569.2551. Found: 569.2564.

Example 66—Synthesis of PKS21284

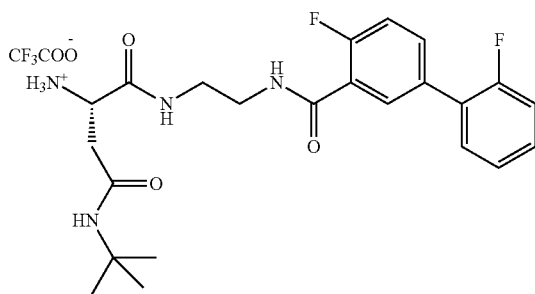 [SMILES: "CF3COO" ; CC(C)(C)NC(=O)C[C@H]([NH3+])C(=O)NCCNC(=O)c1cc(-c2ccccc2F)ccc1F]

The title compound was synthesized by following the general procedure for Boc-deprotection of PKS21277 (21.0 mg, 38 µmol). After completion of the reaction, excess trifluoroacetic acid and dichloromethane were evaporated. Crude was purified by preparative LCMS to give product (19.0 mg, 88%) as a colorless gum. $^1$H NMR (500 MHz, DMSO-d$_6$) δ 8.49 (t, J=5.2 Hz, 1H), 8.46-8.41 (m, 1H), 8.10 (d, J=4.8 Hz, 3H), 7.82-7.78 (m, 2H), 7.73-7.69 (m, 1H), 7.59-7.54 (m, 1H), 7.49-7.39 (m, 2H), 7.36-7.30 (m, 2H), 4.00-3.94 (m, 1H), 3.43-3.29 (m, 3H), 3.29-3.19 (m, 1H), 2.65 (dd, J=16.5, 5.1 Hz, 1H), 2.55 (dd, J 16.5, 7.8 Hz, 1H), 1.22 (s, 9H).

Example 67—Synthesis of PKS21293

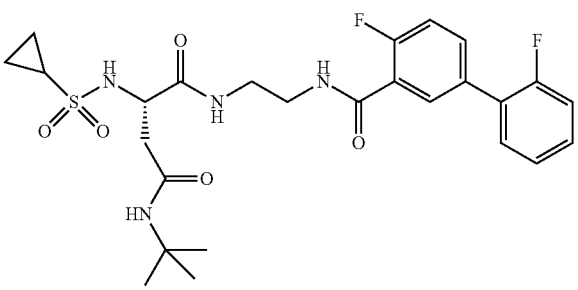 [SMILES: CC(C)(C)NC(=O)C[C@H](NS(=O)(=O)C1CC1)C(=O)NCCNC(=O)c1cc(-c2ccccc2F)ccc1F]

To a solution of PKS21284 (10.7 mg, 19 µmol) in dichloromethane (1.00 mL), triethylamine (5.77 mg, 57.00 µmol, 7.90 µL) was added at 0° C. The solution was warmed to room temperature (over 15 minutes) and cyclopropane-sulfonyl chloride (5.3 mg, 38 µmol) was added in one portion. The mixture was stirred at room temperature overnight. After completion of the reaction, dichloromethane was evaporated and crude was purified by preperative LCMS to give product (9.2 mg, 88%) as a white solid. $^1$H NMR (500 MHz, DMSO-d$_6$) δ 8.40-8.35 (m, 1H), 8.12 (t, J=5.6 Hz, 1H), 7.80-7.76 (m, 1H), 7.72-7.67 (m, 1H), 7.57 (td, J=7.9, 1.7 Hz, 1H), 7.49-7.37 (m, 3H), 7.36-7.29 (m, 3H), 4.14-4.03 (m, 1H), 3.42-3.25 (m, 3H), 3.25-3.16 (m, 1H), 2.49-2.42 (m, 2H), 2.37 (dd, J=14.8, 7.4 Hz, 1H), 1.19 (s, 9H), 0.89-0.78 (m, 4H). $^{13}$C NMR (126 MHz, DMSO-d$_6$) δ 171.2, 168.4, 163.5, 159.0 (d, J=247.3 Hz), 158.8 (d, J=251.1 Hz), 132.9-132.5 (m), 131.3 (d, J=2.6 Hz), 130.8, 130.3, 130.0 (d, J=7.4 Hz), 126.6 (d, J=12.8 Hz), 125.1 (d, J=2.9 Hz), 124.2 (d, J=14.6 Hz), 116.5 (d, J=22.9 Hz), 116.2 (d, J=22.1 Hz), 53.8, 50.1, 39.8, 39.0, 38.4, 30.2, 28.4, 5.0, 4.8. $^{19}$F NMR (471 MHz, DMSO-d$_6$) δ −117.8 (m), −120.8 (m).

Example 68—Synthesis of PKS21294

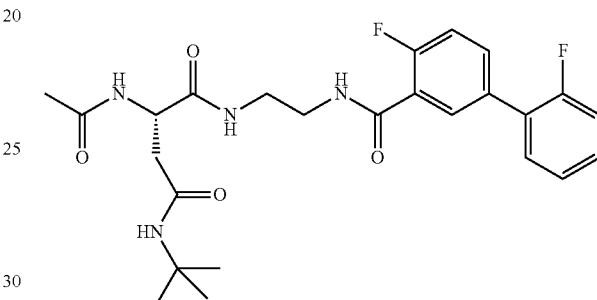

Hunig's base (8.7 mg, 67 µmol, 11.7 µL) and N,N-dimethylpyridin-4-amine (1.4 mg, 11 µmol) were added to a solution of PKS21284 (12.5 mg, 22 µmol) in dichloromethane (1.00 mL) at 0° C. The solution was stirred for 5 minutes, and acetic anhydride (2.7 mg, 26.8 µmol, 2.5 µL) was added. The reaction mixture was stirred at 0° C. for 1 hour. After completion of the reaction, dichloromethane was evaporated and crude was purified by preparative LCMS to give product (7.1 mg, 65%) as a white solid. $^1$H NMR (500 MHz, DMSO-d$_6$) δ 8.43-8.33 (m, 1H), 7.98 (t, J=5.7 Hz, 1H), 7.95 (d, J=8.1 Hz, 1H), 7.81-7.77 (m, 1H), 7.72-7.67 (m, 1H), 7.57 (td, J=7.9, 1.7 Hz, 1H), 7.48-7.42 (m, 1H), 7.39 (dd, J=10.2, 8.6 Hz, 1H), 7.36-7.30 (m, 3H), 4.50-4.39 (m, 1H), 3.41-3.28 (m, 3H), 3.28-3.12 (m, 2H), 2.42 (dd, J=14.5, 5.8 Hz, 1H), 2.29 (dd, J=14.5, 8.1 Hz, 1H), 1.80 (s, 3H), 1.18 (s, 9H); $^{13}$C NMR (126 MHz, DMSO-d$_6$) δ 171.4, 169.0, 168.9, 163.6, 159.0 (d, J=246.9 Hz), 158.8 (d, J=252.6 Hz), 132.8-132.5 (m), 131.4-131.2 (m), 130.8, 130.3, 130.0 (d, J=7.5 Hz), 126.6 (d, J=12.8 Hz), 125.0 (d, J=2.5 Hz), 124.2 (d, J=14.5 Hz), 116.5 (d, J=22.1 Hz), 116.2 (d, J=21.9 Hz), 50.2, 50.0, 39.0, 38.7, 38.5, 28.4, 22.6; $^{19}$F NMR (471 MHz, DMSO-d$_6$) δ −117.9 (m), −120.8 (m).

Example 69—Synthesis of PKS21276

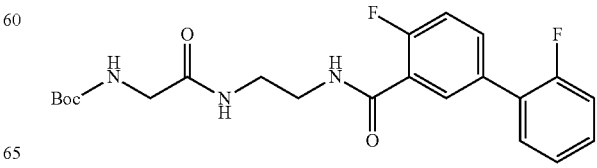

The title compound was synthesized by following the general procedure for HATU mediated coupling of Boc-glycine (19.3 mg, 110 µmol) and PKS21274 (39.0 mg, 100 µmol). After completion of the reaction, the mixture was purified by preparative LCMS to give product (38.0 mg, 88%) as a colorless solid. $^1$H NMR (500 MHz, Chloroform-d) δ 8.23-8.16 (m, 1H), 7.69-7.62 (m, 1H), 7.47-7.40 (m, 1H), 7.37-7.31 (m, 1H), 7.26-7.11 (m, 4H), 6.89 (t, J=5.7 Hz, 1H), 5.16 (br, 1H), 3.80 (d, J=4.2 Hz, 2H), 3.67-3.61 (m, 2H), 3.57-3.51 (m, 2H), 1.41 (s, 9H).

Example 70—Synthesis of PKS21285

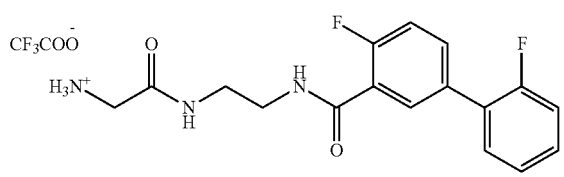 [SMILES: "CF3COO" ; [NH3+]CC(=O)NCCNC(=O)c1cc(-c2ccccc2F)ccc1F]

The title compound was synthesized by following the general procedure for Boc-deprotection of PKS21276 (32.0 mg, 74 µmol). After completion of the reaction, excess trifluoroacetic acid and dichloromethane were evaporated. Crude was dried under vacuum to give a product (33 mg, quant.). The product was used in next step without further purification. 10 $^1$H NMR (500 MHz, DMSO-d$_6$) δ 8.52-8.43 (m, 2H), 8.09-7.98 (m, 3H), 7.82-7.77 (m, 1H), 7.74-7.68 (m, 1H), 7.57 (td, J=7.9, 1.7 Hz, 1H), 7.48-7.38 (m, 2H), 7.37-7.30 (m, 2H), 3.56-3.49 (m, 2H), 3.41-3.34 (m, 2H), 3.34-3.28 (m, 2H).

Example 71—Synthesis of PKS21289

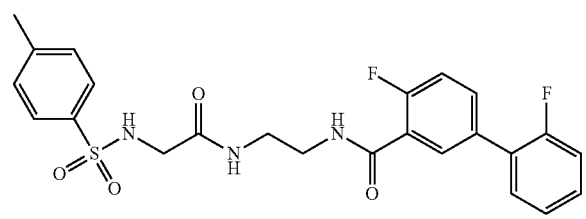 [SMILES: Cc1ccc(S(=O)(=O)NCC(=O)NCCNC(=O)c2cc(-c3ccccc3F)ccc2F)cc1]

The title compound was synthesized by following the general procedure for sulfonamide preparation of PKS21285 (16.00 mg, 35.77 µmol) with 4-methylbenzenesulfonyl chloride (13.6 mg, 72 µmol). After completion of the reaction, dichloromethane was evaporated and crude was purified by preparative LCMS to give product (14.8 mg, 85%) as a white solid. $^1$H NMR (500 MHz, DMSO-d$_6$) δ 8.43-8.34 (m, 1H), 8.02 (t, J=5.8 Hz, 1H), 7.86 (s, 1H), 7.80-7.74 (m, 1H), 7.73-7.69 (m, 1H), 7.67 (d, J=8.3 Hz, 2H), 7.57 (td, J=7.9, 1.9 Hz, 1H), 7.49-7.41 (m, 1H), 7.44-7.28 (m, 5H), 3.43-3.31 (m, 2H), 3.31-3.23 (m, 2H), 3.23-3.15 (m, 2H), 2.37 (s, 3H). $^{13}$C NMR (126 MHz, DMSO-d$_6$) δ 167.8, 163.5, 159.0 (d, J=246.9 Hz), 158.8 (d, J=251.2 Hz), 142.8, 137.1, 132.7 (d, J=8.7 Hz), 131.3, 130.8, 130.3, 130.0 (d, J=8.5 Hz), 129.5, 126.7, 126.6-126.5 (m), 125.1, 124.2 (d, J=14.6 Hz), 116.5 (d, J=22.4 Hz), 116.2 (d, J=22.1 Hz), 45.3, 39.0, 38.2, 21.0; $^{19}$F NMR (471 MHz, DMSO-d$_6$) δ –117.9 (m), –120.9 (m).

Example 72—Synthesis of PKS21280

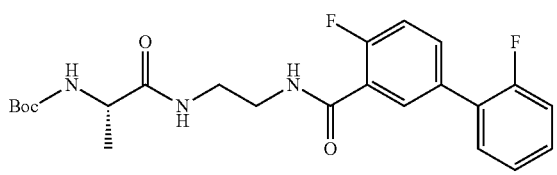 [SMILES: C[C@H](NC(=O)OC(C)(C)C)C(=O)NCCNC(=O)c1cc(-c2ccccc2F)ccc1F]

Triethylamine (75.8 mg, 749 µmol, 104 µL) was added to a solution of PKS21274 (39.0 mg, 100 µmol) in dichloromethane (3.00 mL) at 0° C. The mixture was stirred for 10 minutes and Boc-Ala-OSu (31.5 mg, 110 µmol) was added. The reaction mixture was allowed to warm to room temperature slowly. After completion of the reaction (2 hours), dichloromethane was evaporated and crude was purified by preparative LCMS to give product (36.3 mg, 81%) as a white solid. $^1$H NMR (500 MHz, DMSO-d6) δ 8.36 (t, J=5.5 Hz, 1H), 7.92 (t, J=5.5 Hz, 1H), 7.78 (dd, J=7.2, 2.4 Hz, 1H), 7.73-7.66 (m, 1H), 7.59-7.53 (m, 1H), 7.48-7.42 (m, 1H), 7.40 (dd, J=10.3, 8.5 Hz, 1H), 7.36-7.30 (m, 2H), 6.84 (d, J=7.4 Hz, 1H), 3.96-3.74 (m, 1H), 3.46-3.13 (m, 4H), 1.34 (s, 9H), 1.15 (d, J=7.2 Hz, 3H).

Example 73—Synthesis of PKS21286

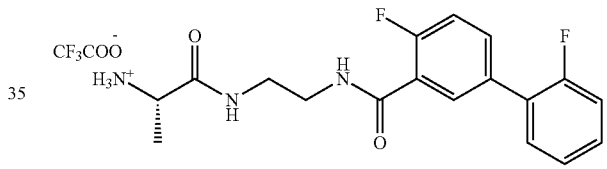

The title compound was synthesized by following the general procedure for Boc-deprotection of PKS21280 (30.0 mg, 67 µmol). After completion of the reaction, excess trifluoroacetic acid and dichloromethane were evaporated. Crude was dried under vacuum to give product (31.0 mg, quant.). The product was used in the next step without further purification. $^1$H NMR (500 MHz, DMSO-d$_6$) δ 8.50 (t, J=5.9 Hz, 1H), 8.45 (t, J=5.1 Hz, 1H), 8.20-7.99 (m, 3H), 7.78 (dd, J=6.8, 2.3 Hz, 1H), 7.74-7.67 (m, 1H), 7.60-7.52 (m, 1H), 7.49-7.38 (m, 2H), 7.37-7.29 (m, 2H), 3.84-3.71 (m, 1H), 3.46-3.30 (m, 3H), 3.30-3.14 (m, 1H), 1.34 (d, J=7.0 Hz, 3H).

Example 74—Synthesis of PKS21290

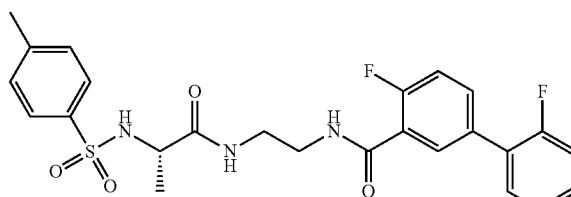

The title compound was synthesized by following the general procedure for sulfonamide preparation of PKS21286

(16.0 mg, 35 μmol) with 4-methylbenzenesulfonyl chloride (9.9 mg, 52 μmol). After completion of the reaction, dichloromethane was evaporated and the crude was purified by preparative LCMS to give product (12.4 mg, 71%) as a white solid. $^1$H NMR (500 MHz, DMSO-d$_6$) δ 8.36-8.30 (m, 1H), 7.99 (t, J=5.7 Hz, 1H), 7.89 (br, 1H), 7.78-7.75 (m, 1H), 7.72-7.68 (m, 1H), 7.65 (d, J=8.3 Hz, 2H), 7.56 (td, J=7.9, 1.9 Hz, 1H), 7.48-7.38 (m, 2H), 7.37-7.29 (m, 4H), 3.70-3.60 (m, 1H), 3.27-3.01 (m, 4H), 2.36 (s, 3H), 1.03 (d, J=7.1 Hz, 3H). $^{13}$C NMR (126 MHz, DMSO-d$_6$) δ 171.5, 163.4, 159.0 (d, J=245.7 Hz), 158.8 (d, J=252.8 Hz), 142.6, 138.1, 132.7 (d, J=7.8 Hz), 131.3, 130.8, 130.3, 130.0 (d, J=8.7 Hz), 129.4, 126.6, 126.6 (d, J=12.1 Hz), 125.1 (d, J=2.9 Hz), 124.2 (d, J=14.6 Hz), 116.5 (d, J=22.0 Hz), 116.2 (d, J=23.5 Hz), 52.0, 38.9, 38.1, 21.0, 18.8. $^{19}$F NMR (471 MHz, DMSO-d$_6$) δ −117.8 (m), −120.9 (m).

Example 75—Synthesis of PKS21281

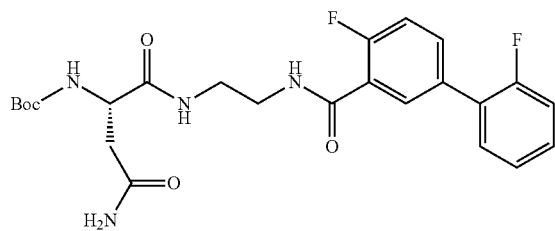 [SMILES: CC(C)(C)OC(=O)N[C@@H](CC(N)=O)C(=O)NCCNC(=O)c1cc(-c2ccccc2F)ccc1F]

The title compound was synthesized by following the general procedure for HATU mediated coupling of Boc-Asn-OH (23.2 mg, 100 μmol) and PKS21274 (39.0 mg, 100 mol). After completion of the reaction, the mixture was purified by preparative LCMS to give product (43.6 mg, 89%) as a white solid. $^1$H NMR (500 MHz, DMSO-d$_6$) δ 8.36 (t, J=5.6 Hz, 1H), 7.95 (t, J=5.6 Hz, 1H), 7.79 (dd, J=7.1, 2.5 Hz, 1H), 7.70 (ddt, J=8.7, 4.4, 2.0 Hz, 1H), 7.57 (td, J=7.9, 1.7 Hz, 1H), 7.49-7.41 (m, 1H), 7.40 (dd, J=10.3, 8.6 Hz, 1H), 7.38-7.28 (m, 2H), 7.28-7.21 (m, 1H), 6.87 (s, 1H), 6.81 (d, J=8.0 Hz, 1H), 4.18 (td, J=8.0, 5.3 Hz, 1H), 3.37-3.22 (m, 3H), 3.19 (dq, J=12.6, 6.3 Hz, 1H), 2.43 (dd, J=15.0, 5.3 Hz, 1H), 2.35 (dd, J=15.0, 8.1 Hz, 1H), 1.34 (s, 9H).

Example 76—Synthesis of PKS21283

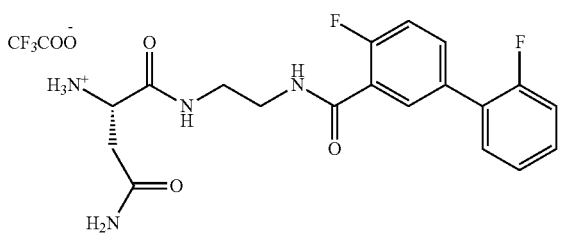 [SMILES: "CF3COO" ; NC(=O)C[C@H]([NH3+])C(=O)NCCNC(=O)c1cc(-c2ccccc2F)ccc1F]

The title compound was synthesized by following the general procedure for Boc-deprotection of PKS21281 (30.0 mg, 61 μmol). After completion of the reaction, excess trifluoroacetic acid and dichloromethane were evaporated. Crude was dried under vacuum and triturated with diethyl ether to give a white solid. Diethyl ether was decanted and the white solid was dried under vacuum to give product (30.8 mg, quant.). The product was used in the next step without further purification. $^1$H NMR (500 MHz, DMSO-d$_6$) δ 8.54 (t, J=5.3 Hz, 1H), 8.49-8.41 (m, 1H), 8.11 (d, J=5.2 Hz, 3H), 7.84-7.76 (m, 1H), 7.74-7.69 (m, 1H), 7.65 (br, 1H), 7.57 (td, J=7.9, 1.7 Hz, 1H), 7.48-7.38 (m, 2H), 7.37-7.28 (m, 2H), 7.23 (br, 1H), 4.05-3.95 (m, 1H), 3.43-3.29 (m, 3H), 3.29-3.20 (m, 1H), 2.70 (dd, J=16.8, 4.6 Hz, 1H), 2.58 (dd, J=16.8, 8.3 Hz, 1H).

Example 77—Synthesis of PKS21288

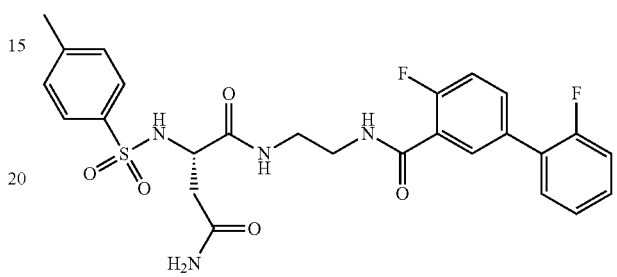

The title compound was synthesized by following the general procedure for sulfonamide preparation of PKS21283 (15.1 mg, 30 μmol) with 4-methylbenzenesulfonyl chloride (11.4 mg, 60 μmol). After completion of the reaction, dichloromethane was evaporated and crude was purified by preperative LCMS to give product (13.6 mg, 83%) as a white solid. $^1$H NMR (500 MHz, DMSO-d$_6$) δ 8.33-8.24 (m, 1H), 7.97 (t, J=5.8 Hz, 1H), 7.85 (br, 1H), 7.78 (dd, J=7.1, 2.4 Hz, 1H), 7.74-7.68 (m, 1H), 7.64 (d, J=8.3 Hz, 2H), 7.57 (td, J=7.9, 1.9 Hz, 1H), 7.48-7.38 (m, 2H), 7.36-7.28 (m, 4H), 7.27 (d, J=2.3 Hz, 1H), 6.84 (d, J=2.3 Hz, 1H), 4.04-3.95 (m, 1H), 3.25-3.09 (m, 2H), 3.09-2.92 (m, 2H), 2.39-2.30 (m, 4H), 2.21 (dd, J=15.1, 6.8 Hz, 1H); $^{13}$C NMR (126 MHz, DMSO-d$_6$) δ 170.7, 170.1, 163.4, 159.0 (d, J=246.9 Hz), 158.8 (d, J=251.2 Hz), 142.5, 138.1, 132.7 (d, J=8.3 Hz), 131.3, 130.8, 130.3, 130.0 (d, J=7.8 Hz), 129.2, 126.7, 126.6, 125.3-124.9 (m), 124.1 (d, J=14.1 Hz), 116.6 (d, J=23.4 Hz), 116.2 (d, J=22.1 Hz), 53.4, 38.8, 38.2, 38.2, 21.0; $^{19}$F NMR (471 MHz, DMSO-d$_6$) δ −117.8 (m), −120.9 (m).

Example 78—Determination of IC$_{50}$ Values Against Human Constitutive and Immuno-Proteasomes A 96-well-plate assays were used to determine the IC$_{50s}$ against the chymotryptic β5 activities of the proteasomes. Both human constitutive proteasome and immunoproteasome were purchased from Boston Biochem Inc. 1 μL of 100× compound in DMSO at designated concentrations were spotted at the bottom of the wells. DMSO was used as a control. Final concentrations of the inhibitors were from 100 μM to 0.098 μM. The hydrolysis of the substrate over time in each well was monitored at excitation 360 nm, emission 460 nm for 90 minutes. IC$_{50s}$ were estimated by fitting the velocities of hydrolysis against compound concentrations using PRISM. For IC$_{50s}$ against human proteasomes, the concentrations were 0.25 nM for the c-20S, 0.4 nM for the i-20S. Suc-LLVY-AMC was used for 35c at final concentration of 25 μM, and Ac-ANW-AMC for b5i at final concentration of 15 μM. SDS (0.02%) was used as activator, and 0.01% BSA was used in the reaction buffer.

Example 79—Determination of $EC_{50}$ Values Against Plasmodium Falciparum

Continuous in vitro cultures of Plasmodium falciparum: were maintained in human red blood cells (RBC) diluted to a hematocrit of 5% in RPMI 1640 medium with HEPES and Hypoxanthine and completed with 0.5% Albumax II (Invitrogen), 0.25% sodium bicarbonate, and 0.1 mg/ml gentamicin. Parasites were incubated at 37° C. in a gas mixture of 5% oxygen, 5% carbon dioxide, and 90% nitrogen.

Parasite sensitivity to novel compounds were determined using a SYBR Green (Invitrogen S1046) drug assay protocol. P. falciparum of various clinic stains were cultured with compounds at concentrations in a series of dilution in a clear, sterile 96-well plate for 72 hours. Subsequently, 150 l of the cultures were transferred to a black 96-well plate and placed in the freezer for red blood cell lysis. The plates were thawed and suspended in a Sybr Green Lysis buffer. GraphPad Prism was used to analyze the raw data collected through the super old plate reader in the back of the lab. Drug concentrations were converted to logarithms, normalized, and then curve fitted by non-linear regression to obtain $EC_{50}$ values. The results are shown in Tables 1 and 2.

TABLE 1

EC50s of Selected Compounds Against the Growth of Plasmodium falciparum in Red Blood Cells.

| ID | $EC_{50}$ (nM) (P.f.)[1] |
|---|---|
| PKS3080 | 23 |
| PKS3081 | 4520 |
| PKS21003 | >2770 |
| PKS21004 | 4.6 |
| PKS21018 | 364 |
| PKS21019 | 30 |
| PKS21025 | 320 |
| PKS21026 | 100 |
| PKS21221 | 0.55 |
| PKS21229 | 1 |
| PKS21224 | 11 |
| PKS21291 | 11 |
| PKS21292 | 2.9 |
| PKS21287 | 34 |
| TDI4258 | 29 |

[1]P.f.: 3D7, IC50s were determined as reported (Heinberg et al., "Direct Evidence for the Adaptive Role of Copy Number Variation on Antifolate Susceptibility in Plasmodium Falciparum," Mol. Microbiol. 88: 702-712 (2013), which is hereby incorporated by reference in its entirety).

TABLE 2

$EC_{50s}$ of PKS21004 and PKS21003 Against P. falciparum Strains.

| | | EC50s (nM) | |
|---|---|---|---|
| P. f. Strain | Phenotype | PKS21004 | PKS21003 |
| 3D7 | SUL - R | 0.0046 | >2.77 |
| HB3 | PYR - R | 0.010 | >2.77 |
| D6 | Pan - S | 0.004 | >2.77 |
| Sb1-a6 | ATOV - R | 0.0048 | >2.77 |
| Dd2 | MDR | 0.0048 | >2.77 |
| V1S | MDR | 0.0017 | >2.77 |
| IPC 3663 | ART - S | 0.006 | >2.77 |
| IPC 5188 | ART - S | 0.0015 | >2.77 |
| IPC 4884 | ART - R | 0.0052 | >2.77 |
| IPC 5202 | ART - R | 0.0046 | NT |
| IPC 4912 | ART - R | 0.0058 | NT |

ART: artemisinin; ATOV: Atovaquone; MDR: multi-drug resistant; PYR: pyrimethamine; R: resistant; S: sensitive; SUL: sulfadoxine.

Example 80—Cell Viability Assay

Multiple myeloma cell lines MM. 1S (200,000 cells/mL) and RPMI 8226 (200,000 cells/mL), B lymphoma cell line Karpas 106P (800,000 cells/mL), and liver cancer cell line HepG2 (12,000 cells/mL) were used to determine the cytotoxicity of compounds. Cells were cultured at 37° C. in a humidified air/5% $CO_2$ atmosphere in medium supplemented with 10% fetal bovine serum, except for the medium for Karpas-1106P cells which contained 20% fetal bovine serum, and 100 units/ml penicillin/100 µg/ml streptomycin in RPMI 1640 medium. 12,000 cells/well. Cells plated in a 96-well plate were treated with compounds at the indicated concentrations for 72 hours at 37° C. in a tissue culture incubator with 5% $CO_2$. Viable cells were counted using Cell-titer/Glo™ assay kit. EC50s were calculated using PRISM (Graphpad). The results are shown in Table 3.

TABLE 3

Inhibition of Intracellular Proteasomal Activities and Cytotoxicity of PKS21221.

| IC50 (µM) | | | EC50 (µM) | | | |
|---|---|---|---|---|---|---|
| Karpas | | | | | | |
| Karpas β5i | β5 | HepG β5c | MM1.S | 8226 | Karpas | HepG2 |
| 0.172 | 0.118 | 2.0 | 0.095 | 0.075 | 0.84 | 3.0 |

β5i activity was assayed with (Ac-ANW)2-R110;
β5 and β5c activity was assayed with suc-LLVY-luciferin.
Data were given as mean ± SEM.

Example 81—Protocol for Anti-Malarial Assay

Plasmodium falciparum: parasites were cultured in human red cells. Drug assays were run in 96 well plates at a total volume of 200 µl. Assays were set up at a starting parasitemia (percent of infected red cells) of 0.5%. Test compounds were plated at concentrations of 2778 nM to 0.4 nM. The test plates were grown under standard low oxygen conditions at 37° C. for 72 hours. At that time the plates were prepared for growth determination, first the plates were frozen and thawed to lyse the red blood cells, 150 l of the lysed thawed culture was transferred to a black 96 well plate, and mixed in a lysis buffer with SYBR green DNA dye. The fluorescence of each well was recorded in a plate reader with excitation wavelength 490 nm and emission wavelength 530 nm and normalized relative to DMSO control. The EC50s were determined using Prism software.

Figure 3:
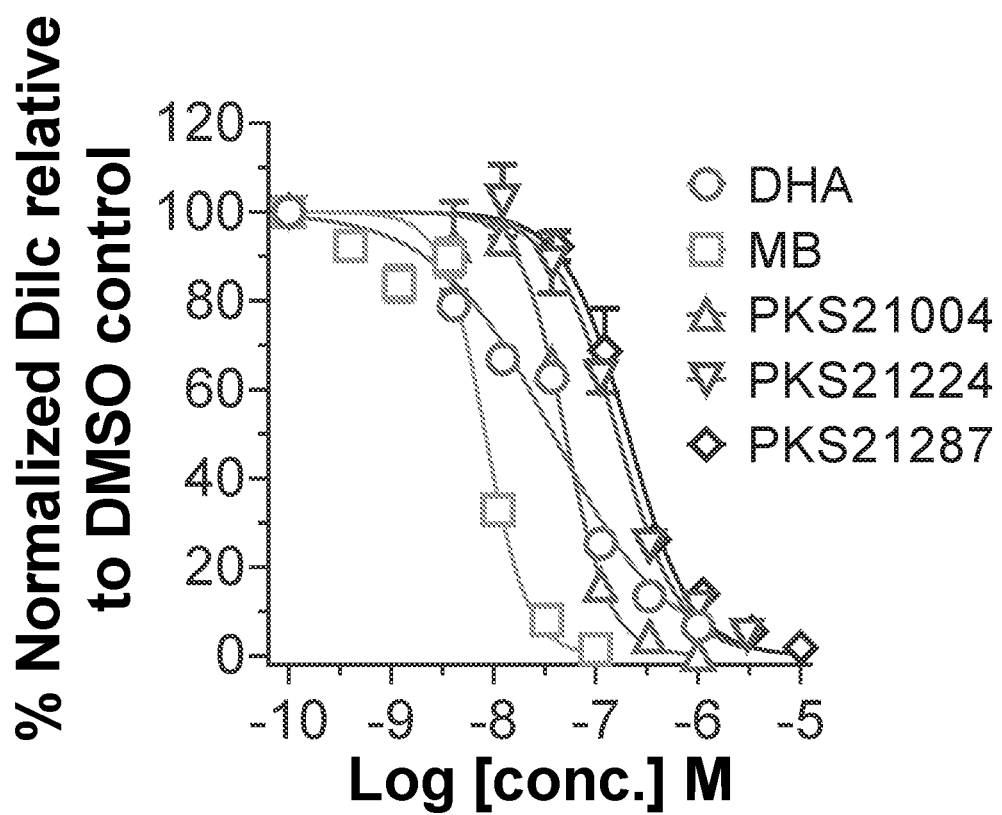
FIG. 3 is a graph showing antiplasmodial activity for compounds PKS21004, PKS21287, and PKS21224 against *Plasmodium falciparum*: at gametocyte stage. Dihydroartemisinin and methylene blue were used as positive controls.

Asexual replication of NF54 peg4-tdTomato parasites was eliminated by treating with 50 mM GlcNAc and 20 U/mL Heparin for 3 days. NF54 peg4-tdTomato parasites then were maintained using standard culture techniques. Gametocytes were induced synchronously according to Fivelman et al., "Improved Synchronous Production of Plasmodium Falciparum Gametocytes in Vitro," Mol, Biochem. Parasitol. 154(1):119-123 (2007), which is hereby incorporated by reference in its entirety. Asexual replication was eliminated by treating with 50 mM GlcNAc for 3 days. Gametocyte killing assays were setup on days 5 and 10 in triplicate 96-well format at 1% hematocrit and 2% gametocytemia. Compounds were setup in triplicate and serially diluted 3-fold. In addition, 6 solvent controls (DMSO) were distributed evenly across the plate. Following a 72 hour incubation, Stage III-IV (Day 5-7) and Stage IV-V (Day 10-12), (start the incubation in the afternoon on Day 5 and Day 10, take out plate for assay on Day8 and Day13 afternoon) cultures were stained with 16 nM Hoechst 33342 and 50 nM DilC1(5) for 30 min at 37 C. Using a Cytek DxP12 flow cytometer, gametocytemia was determined by gating for DNA+, hemozoin-high cells and gametocyte viability was inferred based on mitochondrial membrane potential-dependent accumulation of DilC1(5) for 2000-3000 gametocytes (Tanaka et al., "Potent Plasmodium Falciparum Gametocytocidal Activity of Diaminonaphthoquinones, Lead Antimalarial Chemotypes Identified in an Antimalarial Compound Screen," Antimicrob. Agents Chemother. 2015, 59:1389 (2015), which is hereby incorporated by reference in its entirety). Mean DilC1(5) signal was normalized to solvent control and the overall minimum and used to calculate the EC50 (FIG. 3 and Table 4).

TABLE 4

EC50s of Compounds Against Pf Gametocytes.

| Compound ID | $EC_{50}$ |
|---|---|
| PKS21004 | 50 nM |
| PKS21224 | 162 nM |
| PKS21287 | 206 nM |

Figure 4A:
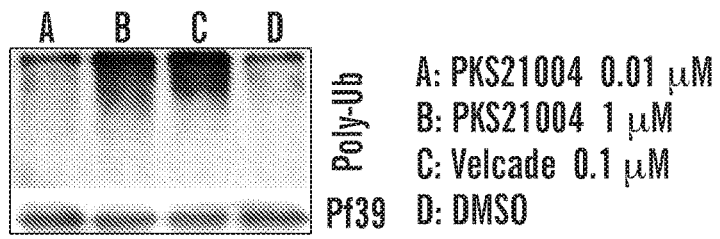
FIGS. 4A-4C show that PKS21004 leads to accumulation of poly-ubiquitinated proteins in *P. falciparum* cells (FIG. 4A); PKS21004 and PKS21287 block labeling of β5 active subunits of Pf20S by proteasome activity probe MV151 (FIG. 4B); and PKS21004 inhibits *P. berghei* growth in liver HepG2 cells after 6- (square and line) and 14-hours (circle and line) incubation and PKS21004 also prevents invasion of liver cells by *P. berghei* after removing PKS21004 followed a 2-hour pretreatment (triangle and line) (FIG. 4C).
Figure 4B:
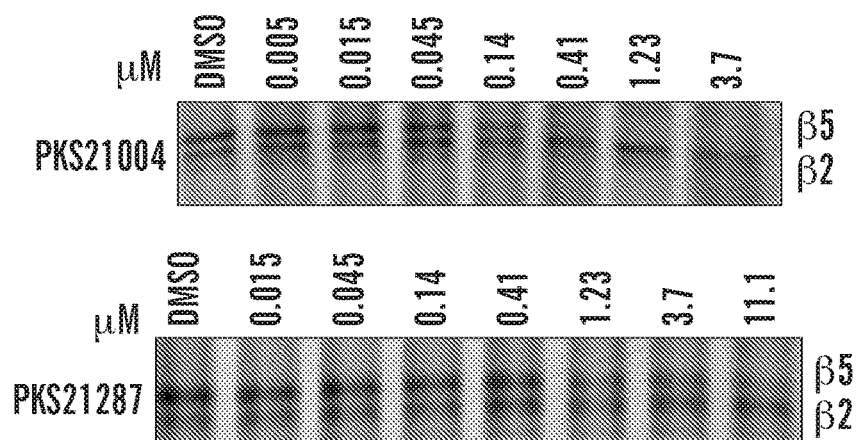
Figure 4C:
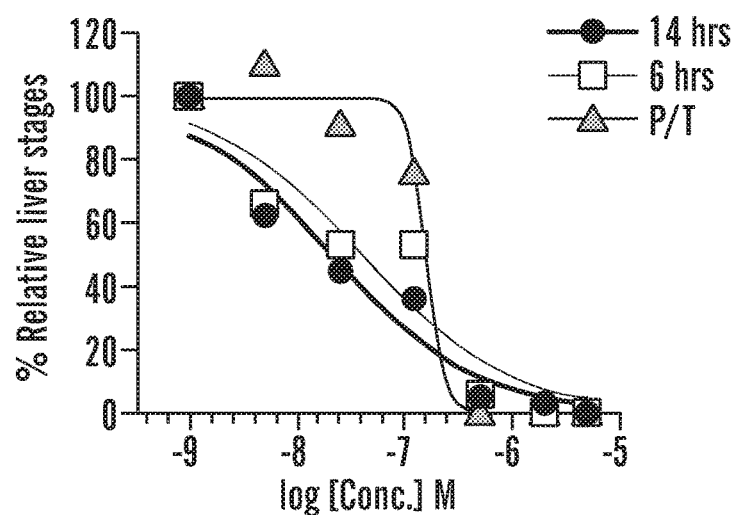

FIG. 4A shows accumulation of poly-ub proteins in *P. falciparum* schizonts 4 hours post treatment with inhibitors at indicated concentrations (BTZ: bortezomib). FIG. 4B shows that AsnEDAs specifically inhibit 35 active subunit of Pf20S. Pf lysates were incubated with inhibitors at indicated concentrations for 1 hour prior to incubation with MV151 (2 µM) for an additional hour. SDS pages were scanned on a Typhoon fluorescent scanner. Top: PKS21004 inhibited the labeling of Pf20S J35, whereas PKS21003 did not. BTZ was used as a positive control. Middle and bottom: PKS21004 and PKS21287 dose-dependently inhibited the labeling of the Pf20S β5. FIG. 4C shows dose-dependent killing of *P. berghei* on sporozoite stage by PKS21004 (P/T: sporozoites pre-treated with PKS21004 for 30 minutes on ice, and added to HepG2 cells in 10× media volume and the media was replaced after 4 hours (triangle). PKS21004 & sporozoites incubated with HepG2 and media was replaced after 6 hours (square) and 14 hours (circle). EC50s were 157 nM, 41 nM, and 21 nM, respectively.

Example 82—Results and Discussion

To regulate immune responses through proteasome inhibition with less mechanism-based toxicity to immune cells and little or none to other cells, it would be useful to inhibit i-20S selectively, sparing c-20S. Consistent with this notion, and unlike disruption of genes encoding c-20S subunits, disruption of genes encoding β1i, β2i, and β5i results in mice that are healthy, fertile, and immunocompetent (Kincaid et al, "Mice Completely Lacking Immunoproteasomes Show Major Changes in Antigen Presentation," *Nat. Immunol.* 13:129-135 (2012), which is hereby incorporated by reference in its entirety). Indeed, relatively selective inhibition of β5i over β5c with the compound ONX-0914 has been efficacious in several mouse models of autoimmune disease (Kalim et al., "Immunoproteasome Subunit LMP7 Deficiency and Inhibition Suppresses Th1 and Th17 but Enhances Regulatory T Cell Differentiation," *J. Immunol.* 189:4182-4193 (2012); Basler et al., "Inhibition of the Immunoproteasome Ameliorates Experimental Autoimmune Encephalomyelitis," *EMBO Mol Med* 6:226-238 (2014); Basler et al., "Prevention of Experimental Colitis by a Selective Inhibitor of the Immunoproteasome," *J. Immunol.* 185:634-641 (2010); Muchamuel et al., "A Selective Inhibitor of the Immunoproteasome Subunit LMP7 Blocks Cytokine Production and Attenuates Progression of Experimental Arthritis," *Nat. Med.* 15:781-787 (2009); Ichikawa et al., "Beneficial Effect of Novel Proteasome Inhibitors in Murine Lupus via Dual Inhibition of Type I Interferon and Autoantibody-Secreting Cells," *Arthritis Rheum,* 64:493-503 (2012), which are hereby incorporated by reference in their entirety). However, ONX-0914 belongs to the peptide epoxyketone class of inhibitors whose irreversible mechanism involves recruiting the hydroxyl and amino groups of the active site $Thr^{1N}$ into formation of a morpholine adduct with the epoxyketone warhead (Groll et al., "Crystal Structure of Epoxomicin: 20S Proteasome Reveals a Molecular Basis for Selectivity of α',β'-Epoxyketone Proteasome Inhibitors," *J. Am. Chem. Soc.* 122:1237-1238 (2000), which is hereby incorporated by reference in its entirety). Long-term use of an irreversible inhibitor presents a risk of toxicity from the gradual, cumulative inhibition of c-20S and unknown targets. Therefore, it would be desirable to develop inhibitors that are both more highly selective for i-20S and reversible. An additional benefit might accrue from a noncompetitive mode of action, so that progressive accumulation of substrate does not lessen the degree of inhibition. The present application reports the serendipitous discovery of a novel class of noncovalent compounds that non-competitively and selectively inhibit chymotryptic β5i over β5c.

A novel class of the N,C-capped dipeptides that selectively inhibit the *Mycobacterium tuberculosis* proteasome over human c-20S was recently reported (Lin et al., "Inhibitors Selective for Mycobacterial Versus Human Proteasomes," *Nature* 461(7264):621-626 (2009), which is hereby incorporated by reference in its entirety). It was later found that this class of inhibitors also selectively inhibits i-20S over c-20S (Fan et al., "Oxathiazolones Selectively Inhibit the Human Immunoproteasome over the Constitutive Proteasome," *ACS Med. Chem. Lett.* 5:405-410 (2014), which is hereby incorporated by reference in its entirety), reflecting that the mycobacterial and human c-20S proteasomes share an enlarged S1 pocket and preferred oligopeptide substrates (Lin et al., "Distinct Specificities of *Mycobacterium Tuberculosis* and Mammalian Proteasomes for N-Acetyl Tripeptide Substrates," *J. Biol. Chem.* 283:34423-34431 (2008); Blackburn et al., "Characterization of a New Series of Non-Covalent Proteasome Inhibitors with Exquisite Potency and Selectivity for the 20S β5-Subunit," *Biochem. J.* 430: 461-476 (2010), which are hereby incorporated by reference in their entirety). A novel class of N,C-capped dipeptidomimetics was developed by incorporating β-amino acid into the N,C-capped dipeptides with marked selectivity for i-20S over c-20S (Singh et al., "Immunoproteasome β5i-Selective Dipeptidomimetic Inhibitors," *Chem. Med. Chem.* 11(19): 2127-2131 (2016), which is hereby incorporated by reference in its entirety). Thus, some of the features found in the mycobacterial 20S inhibitors were leveraged for the rational design of i-20S selective inhibitors. The amide bonds in select N,C-capped dipeptides were systematically replaced with bioisosteres. Reversing the amide bond at the C-cap and replacing the amino acid with an aromatic carboxyl acid resulted in a novel chemotype: Asn-ethylenediamine (AsnEDA). The first compound of this class, PKS3080, yielded modest IC50s of 0.37 and 1.22 µM against human β5i and 05c, respectively. Replacement of the 1-naphthoyl with 2-naphthoyl (producing PKS21025) improved potency against β5i by 3-fold with increased selectivity to 26-fold.

Next, the N-cap, C-cap, ethylene, and Asn side chain substitutions were varied. Replacement of the N-cap with [1,1'-biphenyl]-4-carboxamide (PKS21003) and [1,1'-biphenyl]-3-carboxamide (PKS21004) drastically impacted activity. PKS21003 had no detectable activity against either β5i or β5c (IC50>100 μM for both), whereas PKS21004 was a potent inhibitor of both β5i and β5c, with IC50s of 0.058 and 0.326 μM, respectively. Inhibition of the β5 subunits was specific, as no inhibition was observed of β1 or β2 activities in either i-20S or c-20S (Table 5).

TABLE 5

IC50s of compounds against human immunoproteasome β5i and constitutive proteasome β5c subunits.

| ID | Structures | IC50 (μM) Hu i-20S (Ac-ANW-AMC) | IC50 (μM) Hu c-20S (Suc-LLVY-AMC) |
|---|---|---|---|
| PKS3080 | PKS3080 | 0.37 | 1.22 |
| PKS21003 | PKS21003 | >100 | >100 |
| PKS21004 | PKS21004 | 0.058 | 0.326 |

TABLE 5-continued

IC50s of compounds against human immunoproteasome β5i and constitutive proteasome β5c subunits.

| ID | Structures | IC50 (μM) | |
| --- | --- | --- | --- |
| | | Hu i-20S (Ac-ANW-AMC) | Hu c-20S (Suc-LLVY-AMC) |
| PKS21018 | PKS21018 | 2.35 | 14.6 |
| PKS21019 | PKS21019 | 0.276 | 3.46 |
| PKS21025 | PKS21025 | 0.284 | 3.60 |
| PKS21026 | PKS21026 | 0.11 | 1.16 |

TABLE 5-continued

IC50s of compounds against human immunoproteasome β5i and constitutive proteasome β5c subunits.

| ID | Structures | IC50 (μM) | |
| --- | --- | --- | --- |
| | | Hu i-20S (Ac-ANW-AMC) | Hu c-20S (Suc-LLVY-AMC) |
| PKS21028 | PKS21028 | 2.06 | 7.25 |
| PKS21030 | PKS21030 | 0.39 | 0.068 |
| PKS21186 | PKS21186 | 0.125 | 2.76 |
| PKS21187 | PKS21187 | 0.016 | 0.36 |

TABLE 5-continued
IC50s of compounds against human immunoproteasome β5i and constitutive proteasome β5c subunits.
| ID | Structures | IC50 (μM) Hu i-20S (Ac-ANW-AMC) | Hu c-20S (Suc-LLVY-AMC) |
|---|---|---|---|
| PKS21195 | 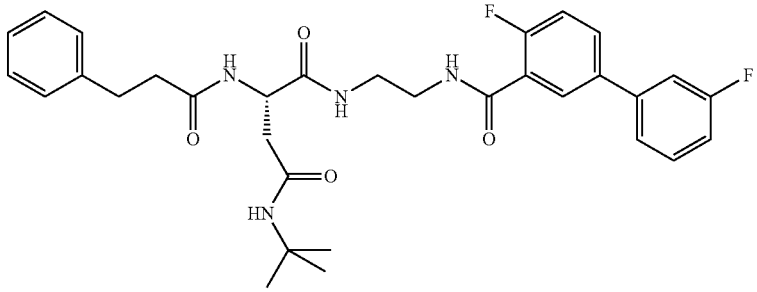 PKS21195 | 0.059 | 1.94 |
| PKS21196 | 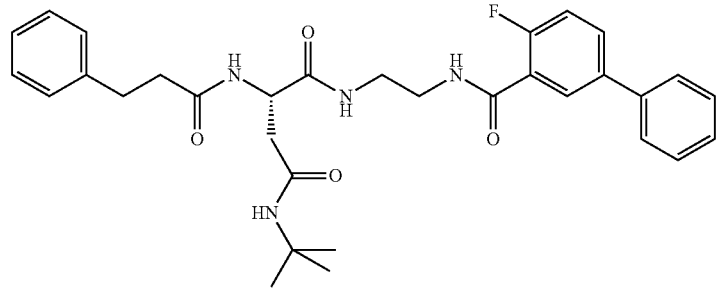 PKS21196 | 0.044 | 0.818 |
| PKS21208 | 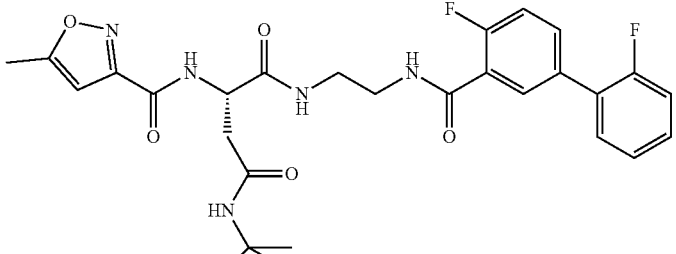 PKS21208 | 0.027 | 1.04 |
| PKS21221 | 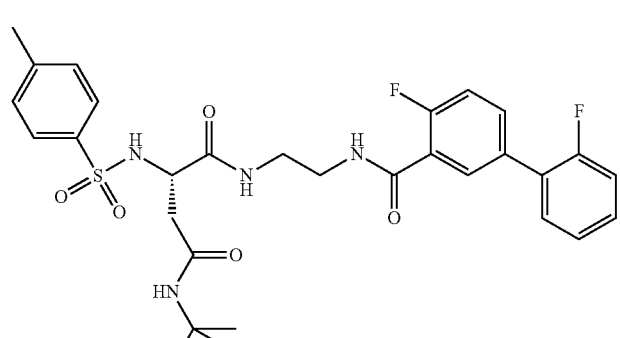 PKS21221 | 0.0041 | 0.106 |

TABLE 5-continued
IC50s of compounds against human immunoproteasome β5i and constitutive proteasome β5c subunits.
| ID | Structures | IC50 (μM) Hu i-20S (Ac-ANW-AMC) | Hu c-20S (Suc-LLVY-AMC) |
|---|---|---|---|
| PKS21224 | 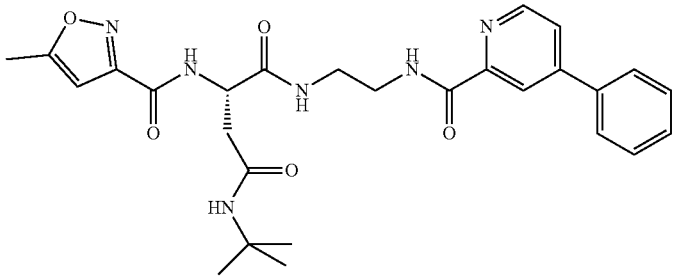 PKS21224 | 0.746 | 33.74 |
| PKS21225 | 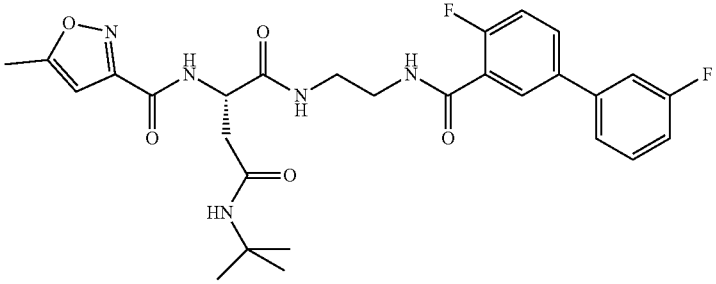 PKS21225 | 0.269 | 11.76 |
| PKS21228 | 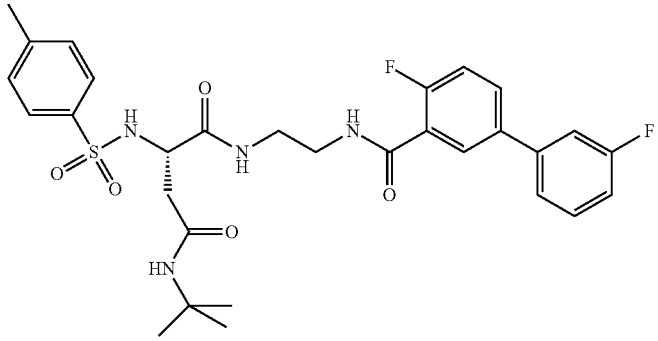 PKS21228 | 0.012 | 0.42 |
| PKS21229 | 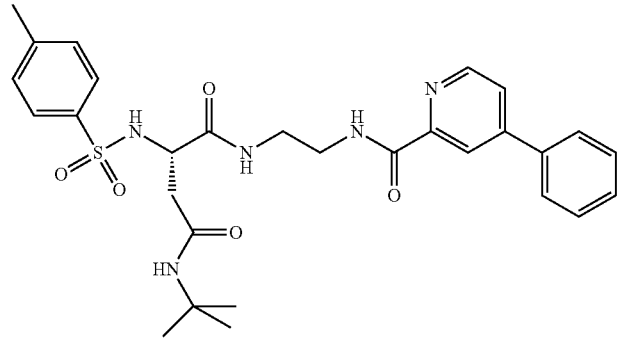 PKS21229 | 0.019 | 0.51 |

TABLE 5-continued
IC50s of compounds against human immunoproteasome β5i and constitutive proteasome β5c subunits.
| ID | Structures | IC50 (μM) | |
| --- | --- | --- | --- |
| | | Hu i-20S (Ac-ANW-AMC) | Hu c-20S (Suc-LLVY-AMC) |
| PKS21250 | 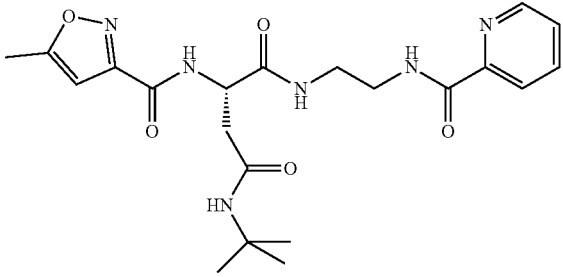 PKS21250 | 65.6 | >100 |
| PKS21251 | 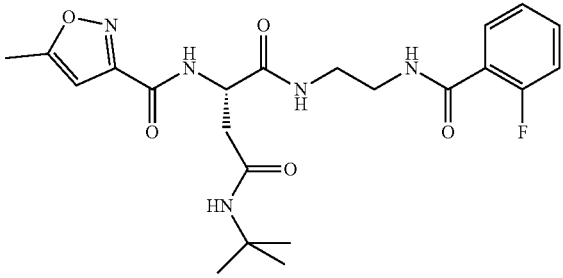 PKS21251 | 6.34 | 39 |
| PKS21254 | 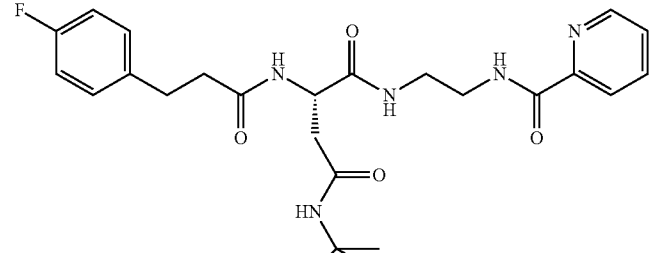 PKS21254 | 7.77 | 57.4 |
| PKS21255 | 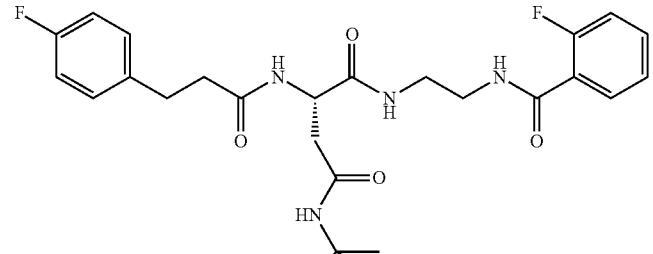 PKS21255 | 0.74 | 3.64 |

TABLE 5-continued
IC50s of compounds against human immunoproteasome β5i and constitutive proteasome β5c subunits.
| ID | Structures | IC50 (μM) Hu i-20S (Ac-ANW-AMC) | IC50 (μM) Hu c-20S (Suc-LLVY-AMC) |
|---|---|---|---|
| PKS21258 | 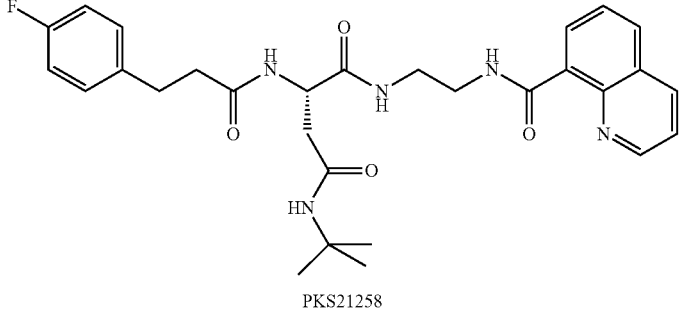 | 2.41 | 22.66 |
| PKS21259 | 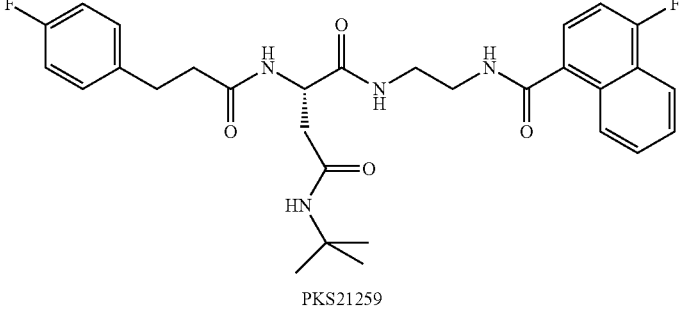 | 0.158 | 2.24 |
| PKS21276 | 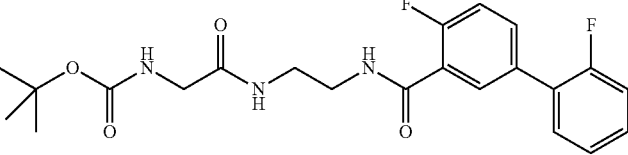 | 24.25 | >100 |
| PKS21277 | 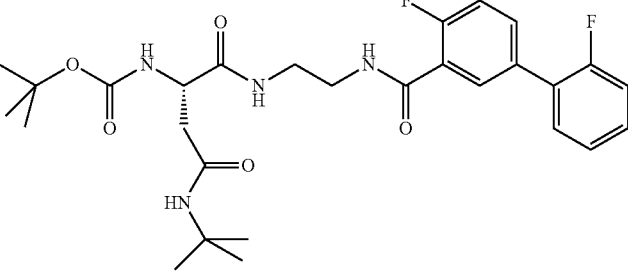 | 0.112 | 3.65 |
| PKS21280 | 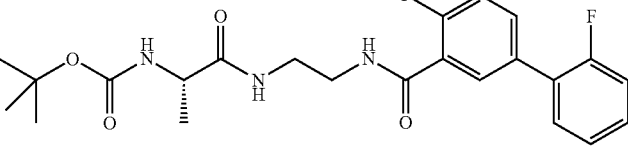 | 33.23 | >100 |

TABLE 5-continued
IC50s of compounds against human immunoproteasome β5i and constitutive proteasome β5c subunits.
| ID | Structures | IC50 (μM) Hu i-20S (Ac-ANW-AMC) | IC50 (μM) Hu c-20S (Suc-LLVY-AMC) |
|---|---|---|---|
| PKS21281 | 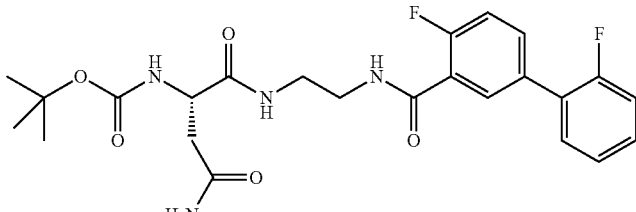 PKS21281 | >100 | >100 |
| PKS21278 | 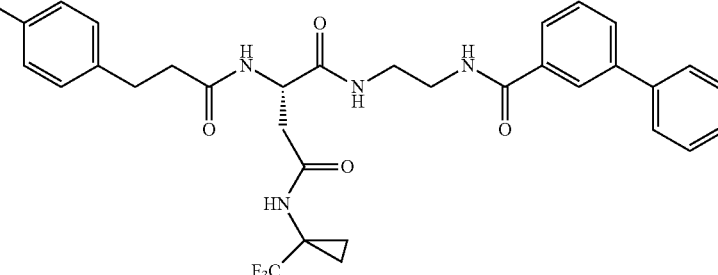 PKS21278 | 0.080 | 0.165 |
| PKS21279 | 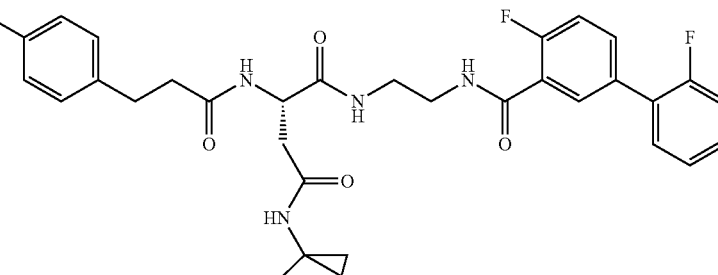 PKS21279 | 0.037 | 0.114 |
| PKS21282 | 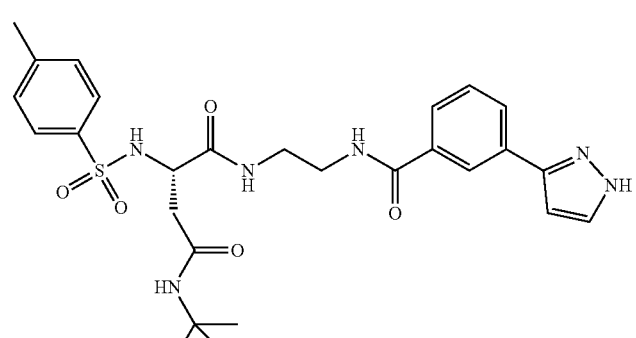 PKS21282 | 0.069 | 1.29 |

TABLE 5-continued
IC50s of compounds against human immunoproteasome β5i and constitutive proteasome β5c subunits.
| ID | Structures | IC50 (μM) Hu i-20S (Ac-ANW-AMC) | Hu c-20S (Suc-LLVY-AMC) |
|---|---|---|---|
| PKS21284 | 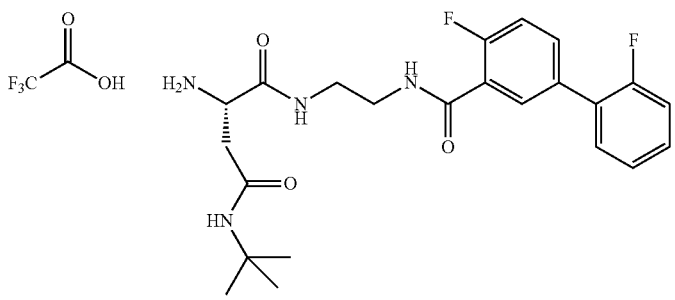 PKS21284 | 0.626 | 3.09 |
| PKS21287 | 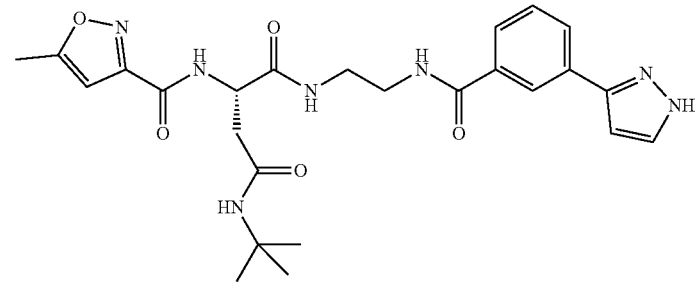 PKS21287 | 1.15 | 21.06 |
| PKS21288 | 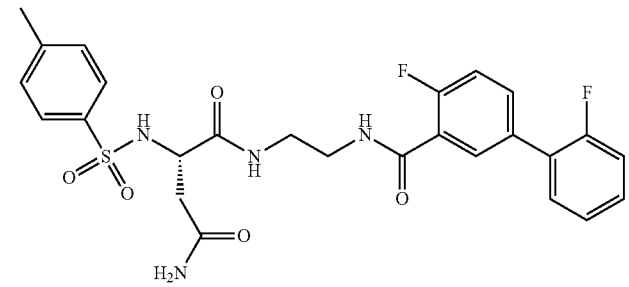 PKS21288 | 4.14 | >100 |
| PKS21289 | 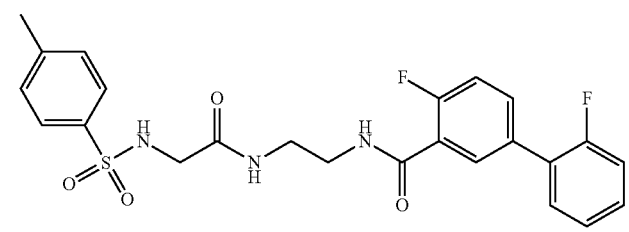 PKS21289 | 40.3 | 60.8 |

TABLE 5-continued
IC50s of compounds against human immunoproteasome β5i and constitutive proteasome β5c subunits.
| ID | Structures | IC50 (μM) | |
|---|---|---|---|
| | | Hu i-20S (Ac-ANW-AMC) | Hu c-20S (Suc-LLVY-AMC) |
| PKS21290 | 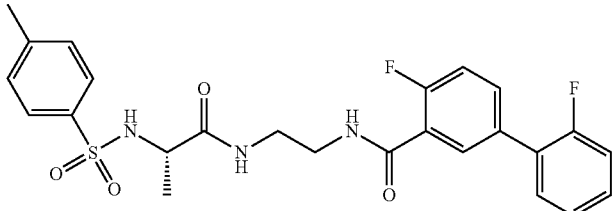 PKS21290 | >100 | >100 |
| PKS21291 | 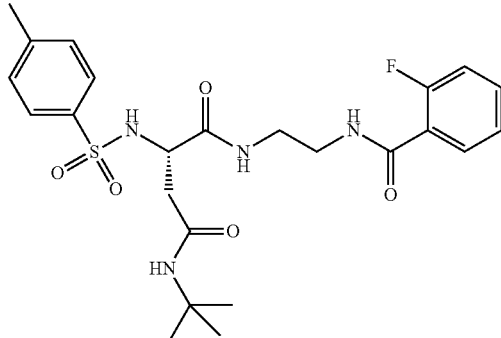 PKS21291 | 0.055 | 0.52 |
| PKS21292 | 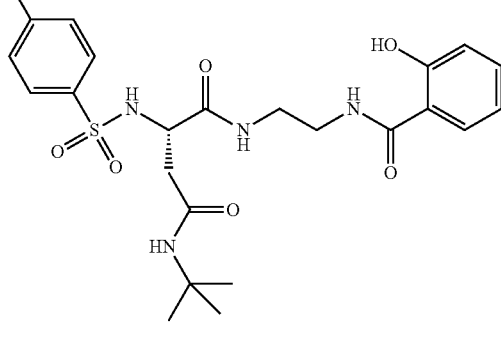 PKS21292 | 0.015 | 0.187 |
| PKS21293 | 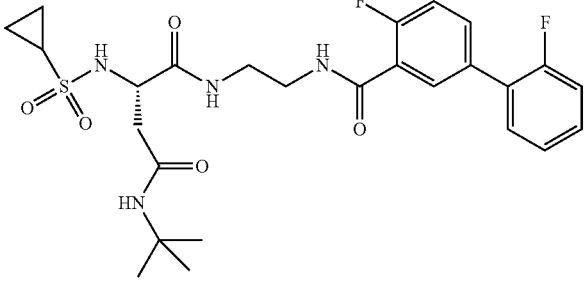 PKS21293 | 0.015 | 0.96 |

TABLE 5-continued

IC50s of compounds against human immunoproteasome β5i and constitutive proteasome β5c subunits.

| ID | Structures | IC50 (μM) | |
|---|---|---|---|
| | | Hu i-20S (Ac-ANW-AMC) | Hu c-20S (Suc-LLVY-AMC) |
| PKS21294 | PKS21294 | 0.62 | 13.3 |
| PKS21295 | PKS21295 | 0.129 | 2.39 |
| PKS21315 | PKS21315 | 0.174 | N/A |

A washout experiment was used to confirm the reversibility of this class of proteasome inhibitors, as expected from their non-covalent chemistry. Dialysis of a preincubated mixture of c-20S and PKS21004 fully restored of β5c activity (FIG. 1A). Kinetic analysis indicated that PKS21004 is a noncompetitive inhibitor of β5i and β5c with respect with their substrates, respectively. With increasing concentration of PKS21004, $V_{max}$ decreased and $K_M$ remained constant in the case of β5c inhibition, and $V_{max}$ and $K_M$ both decreased in the case of β5i inhibition (FIGS. 1B-E), indicating that inhibition of β5i and β5c by PKS21004 are of mixed type noncompetitive with $α_{c-20S} ≈ 0.57$ and $α_{i-20S} ≈ 0.28$, indicating that PKS21004 binds more tightly to the β5c and β5i with substrate bound than without substrate, respectively. Decreasing $V_{max}/K_M$ with increasing PKS21004 concentration also suggests that PKS21004 is not an uncompetitive inhibitor of either 20S (Copeland R. A., *Evaluation of Enzyme Inhibitors in Drug Discovery: A Guide for Medicinal Chemists and Pharmacologists,* 2d Ed., John Wiley & Sons, Inc., Hoboken, N.J., pp. 1-538 (2013), which is hereby incorporated by reference in its entirety).

The foregoing features of these AsnEDA encouraged a further round of SAR studies (Table 5) based on varying the carboxylic acid at the ethylenediamine, the N-cap at the Asn, and the side chain of the Asn, based on PKS21004. All compounds listed in the Table 5 were synthesized as described in Examples 6-77. All final compounds were confirmed by NMR and HRMS. IC50s of all compounds against β5i and β5c (Table 5), β1i, β2i, β1c and β2c were determined following a reported method (Lin et al., "N,C-Capped Dipeptides With Selectivity for Mycobacterial Proteasome Over Human Proteasomes: Role of S3 and S1 Binding Pockets," *J Am Chem Soc*. 135:9968-9971 (2013), which is hereby incorporated by reference in its entirety). All compounds were specific for the β5 subunit; no inhibition of β1i, β1c, β2i or β2c was observed, no inhibition <33 μM. Comparing the ethylenediamine with a methyl-ethylenediamine (PKS21018) and a 1,3-propyldiamine (PKS21019) indicated that the ethylenediamine gave the greatest potency for β5i and selectivity over β5c. The [1,1'-biphenyl]-3-carboxamide of PKS21004 was then modified with the following substituents: 4'-fluoro (PKS21026), 4'-cyano (PKS21028), 4-fluoro (PKS21196), 4,3'-difluoro (PKS21195) and 4,2'-difluoro (PKS21187). The 4'-substitutions decreased potency, while 4- and 4,3'-substitutions did not. Best, 4,2'-difluoro-(PKS21187) improved potency against β5i to IC50 0.015 μM and improved selectivity to ~20-fold over inhibition of β5c.

Next, an Asp-$^t$Bu substitution on PKS21277, an intermediate in the synthesis of PKS21187, was investigated. PKS21277 was modestly potent against β5i with 36-fold selectivity over β5c. Replacing the Asp-$^t$Bu with Gly (PKS21276), Ala (PKS21280), or Asn (PKS21281) abolished the inhibitory activities against both β5i and 05c, suggesting that Asp-$^t$Bu is critical for optimal binding to β5. Phenylpropionate was then replaced with tosyl on the N-cap of the Asn of PKS21187, yielding PKS21221. IC50s were determined to be 2.4 nM against β5i and 70 nM against β5c, representing 30-fold selectivity. Again, replacing the Asp-$^t$Bu of PKS21221 with Gly (PKS21289), Ala (PKS21290) or Asn (PKS21288) eliminated inhibitory activity against both β5i and β5c.

Figure 5:
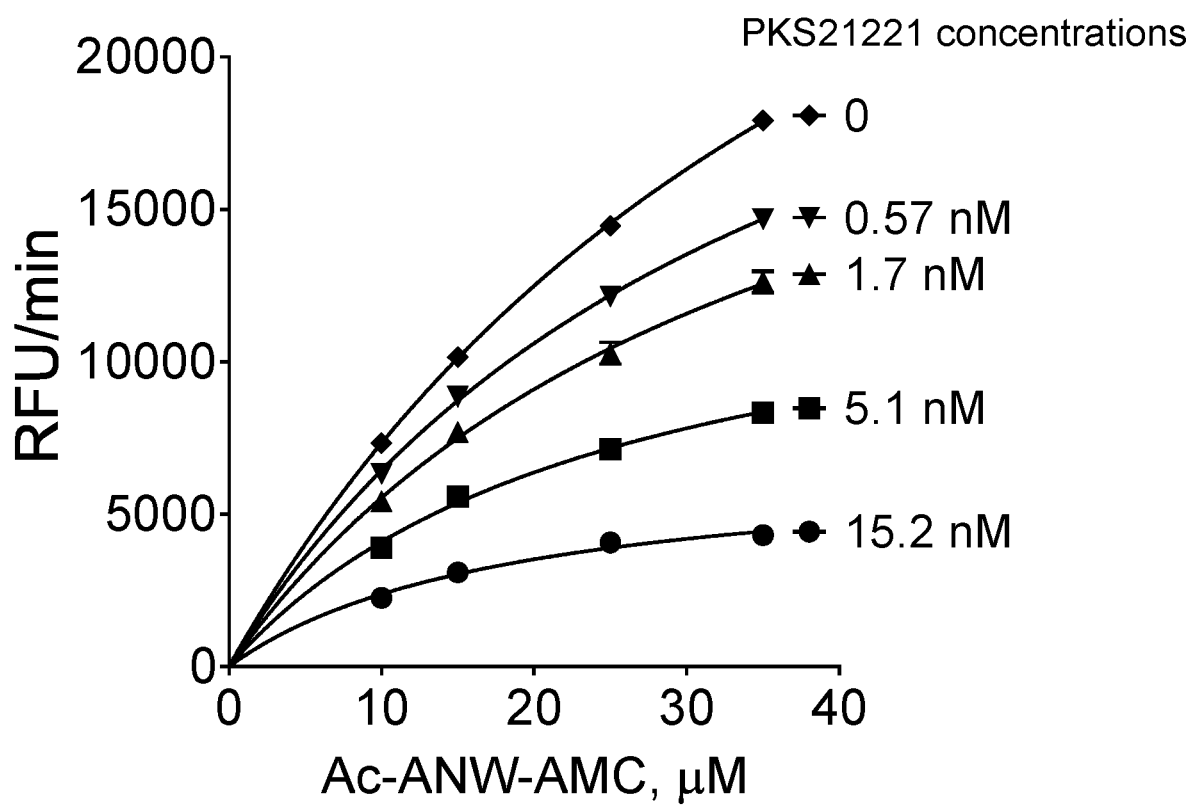
FIG. 5 is a graph showing that PKS21221 noncompetitively inhibits immunoproteasome beta5i activity.

To corroborate that the noncompetitive modality of inhibition was shared among this class of compounds, PKS21221 was tested against β5i and confirmed the noncompetitive mechanism and c was determined to be 0.26 (FIG. 5), in agreement with that of PKS21004.

Figure 2A:
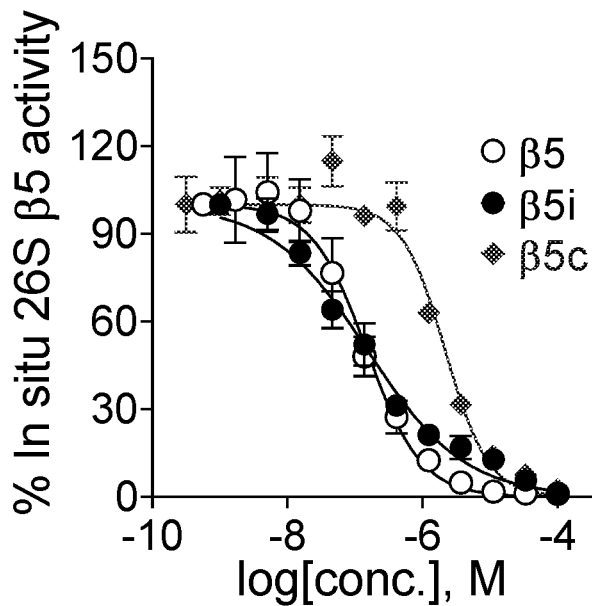
FIGS. 2A-2B are graphs showing proteasome inhibition by PKS21221 inside the cells and its cytotoxicity against transformed cell lines.
Figure 2B:
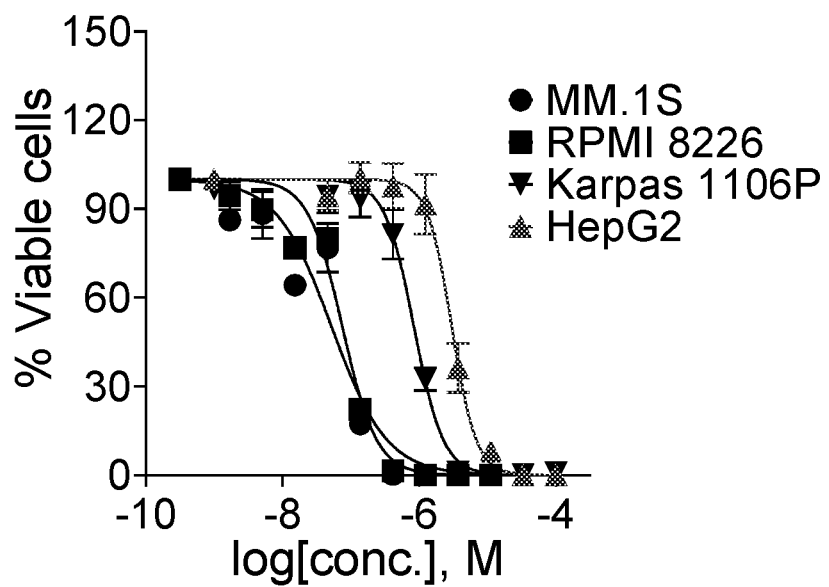

To determine if the class of inhibitors was cell penetrable, the B-cell lymphoma line Karpas 1106P (Singh et al., "Immunoproteasome β5i-Selective Dipeptidomimetic Inhibitors," *Chem. Med. Chem*. 11(19):2127-2131 (2016), which is hereby incorporated by reference in its entirety) (expressing a high proportion of i-20S over c-20S) was treated with PKS21221 before incubation with either (Ac-ANW)$_2$—R110 (a specific substrate of β5i) or suc-LLVY-luciferin (a substrate of β5). IC50 values with both substrates were identical and indicated cell-penetrating ability. Similarly, PKS21221 inhibited β5c activity in HepG2 hepatoma cells with an IC50 of 2.0 μM. No β5i activity was detected in HepG2 cells using (Ac-ANW)$_2$—R110 as substrate (FIG. 2A). Correlating to varying PKS21221's intracellular proteasome inhibition in immune and regular cell lines, cytotoxicity of PKS21221 against multiple myeloma cell lines MM1.S and 8226 (FIG. 2B and Table 3).

In summary, a novel chemotype of proteasome inhibitors that non-covalently and noncompetitively inhibit the chymotryptic 05 subunits of the proteasomes was identified. AsnEDA analogues as the selective inhibitors of the β5i over the β5c were developed. This is the first reported example of potent, noncovalent, noncompetitive, and selective β5i inhibitors. Unlike the competitive inhibitors whose intracellular activity is often diminished over time when substrates buildup, noncompetitive inhibitors, on the other hand, retain the inhibitory activity, and in this case of the β5i inhibition, the buildup of substrate actually enhances the binding of the inhibitor, which may broaden the therapeutic window for treatment of autoimmune and inflammatory disorders. The versatility of the AsnEDA chemotype for proteasome inhibitors will be further demonstrated in a companion paper describing the development of selective inhibitors for the *Plasmodium falciparum*: proteasome over human host proteasomes.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A compound of Formula (I):

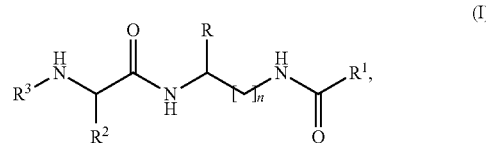

wherein

R is H or $C_{1-6}$ alkyl;

$R^1$ is selected from the group consisting of monocyclic and bicyclic aryl, biphenyl, monocyclic and bicyclic heteroaryl, wherein monocyclic and bicyclic aryl, biphenyl, monocyclic and bicyclic heteroaryl can be optionally substituted from 1 to 3 times with a substituent selected independently at each occurrence thereof from the group consisting of halogen, cyano, —OH, aryl, heteroaryl, non-aromatic heterocycle, and non-aromatic heterocycle substituted with =O;

$R^2$ is independently selected at each occurrence thereof from the group consisting of $C_{1-2}$ alkyl, alkenyl, monocyclic and bicyclic aryl, monocyclic and bicyclic heteroaryl, monocyclic and bicyclic heterocyclyl, and —(CH$_2$)$_m$C(O)NHR$^4$, wherein alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

$R^3$ is selected from the group consisting of H, —SO$_p$R$^5$, —C(O)(CH$_2$)$_k$Ar, —SO$_2$Ar, —SO$_2$C$_{3-8}$ cycloalkyl, —C(O)(CH$_2$)$_k$Het, and —C(O)C$_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;

$R^4$ is selected from the group consisting of H, $C_{1-6}$ alkyl, and $C_{3-8}$ cycloalkyl, wherein $C_{3-8}$ cycloalkyl can be optionally substituted with —CF$_3$;

$R^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO₂, —CF₃, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;

m is 1 or 2;

n is 1, 2, or 3; and p is 1 or 2;

or an oxide thereof, a pharmaceutically acceptable salt thereof, a solvate thereof, or a prodrug thereof.

2. The compound according to claim 1, which has the Formula (Ia):

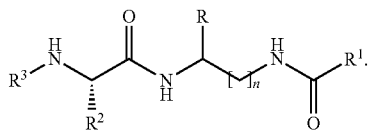

(Ia)

3. The compound according to claim 2, which has the Formula (Ib):

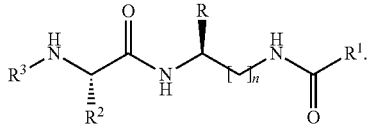

(Ib)

4. The compound according to claim 2, which has the Formula (Ic):

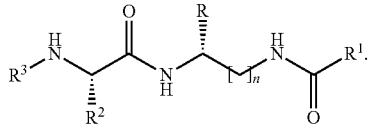

(Ic)

5. The compound according to claim 1, wherein alkenyl is C$_{2-6}$ alkenyl.

6. The compound according to claim 1, wherein R¹ is

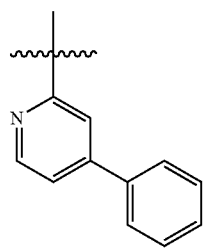

7. The compound according to claim 1, wherein R¹ is selected from the group consisting of

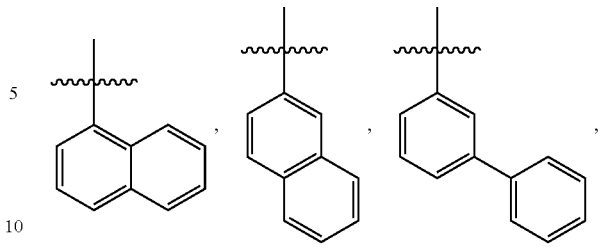

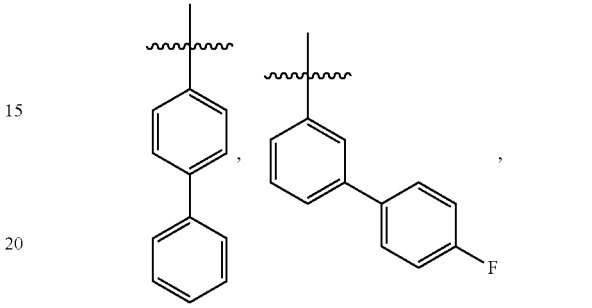

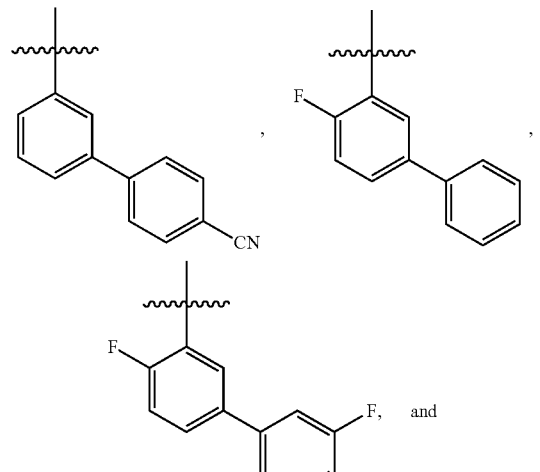

8. The compound according to claim 1, wherein R² is selected from the group consisting of CH₃,

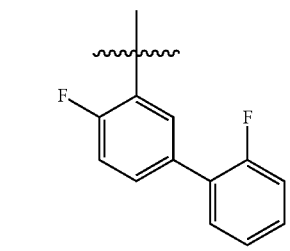

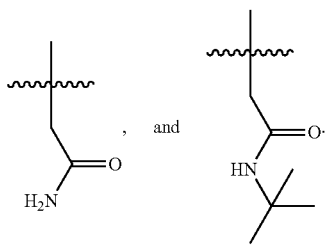

9. The compound according to claim 1, wherein R³ is selected from the group consisting of H,
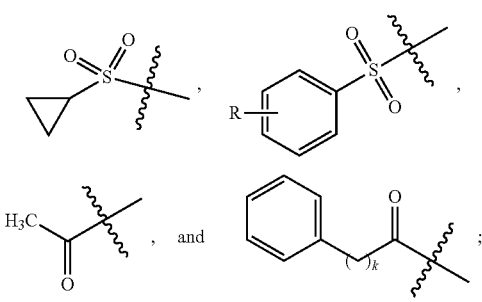
and
R is C$_{1-6}$ alkyl.
10. The compound according to claim 1, wherein the compound of Formula (I) is
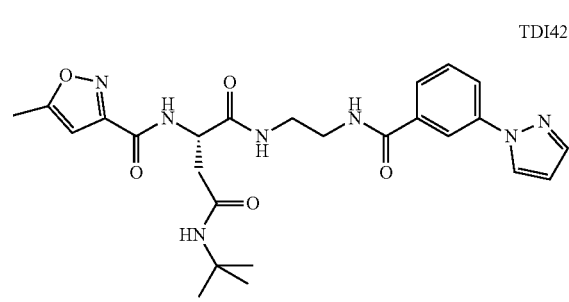
TDI4258
11. The compound according to claim 1, wherein the compound of Formula (I) is selected from the group consisting of:
PKS3080
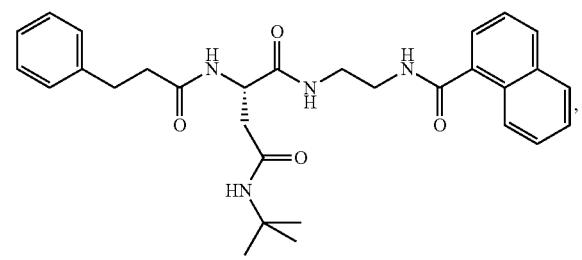
PKS21003
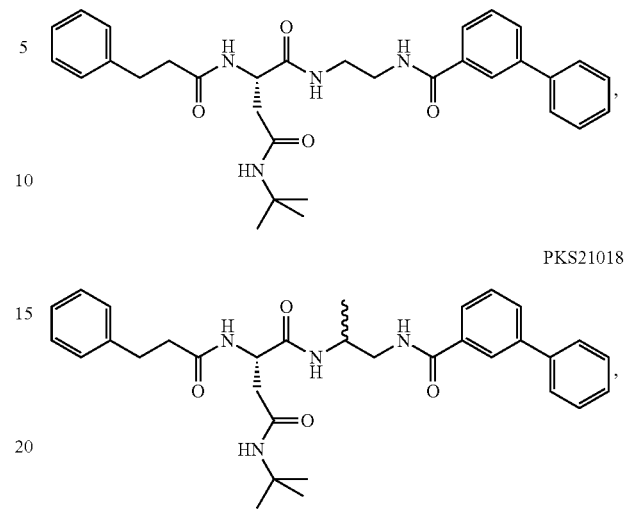
-continued
PKS21004
PKS21018
PKS21019
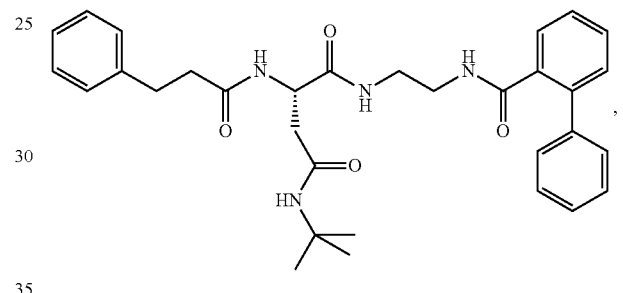
PKS21025
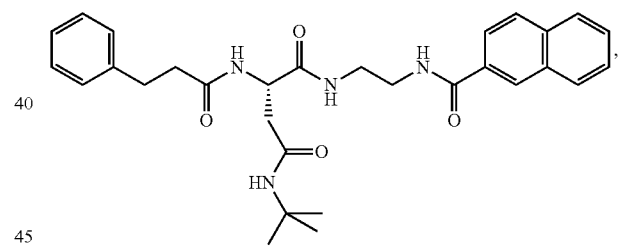
PKS21026
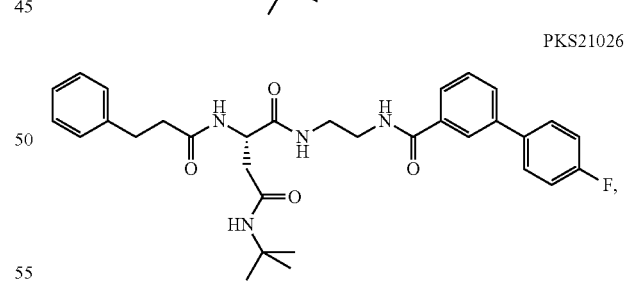
PKS21028
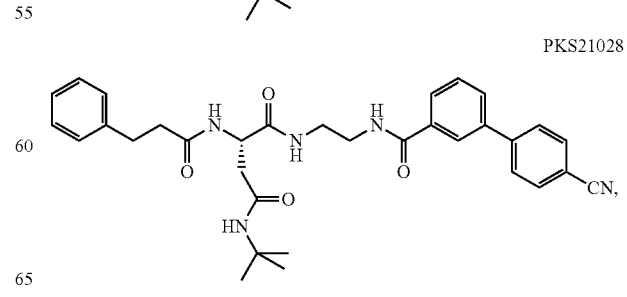

PKS21030
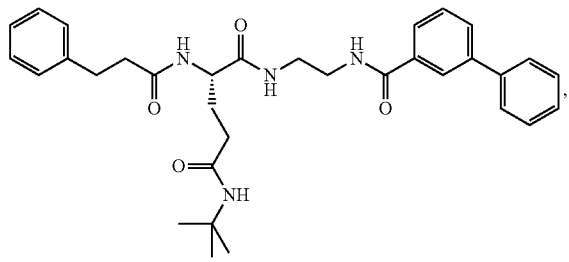
PKS21186
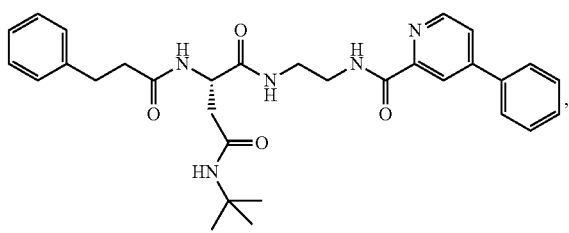
PKS21187
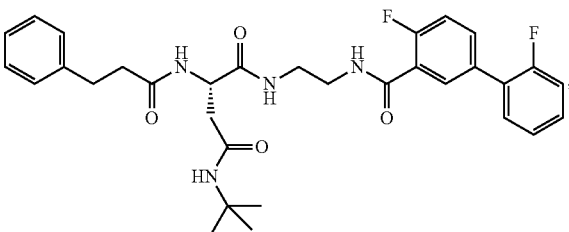
PKS21195
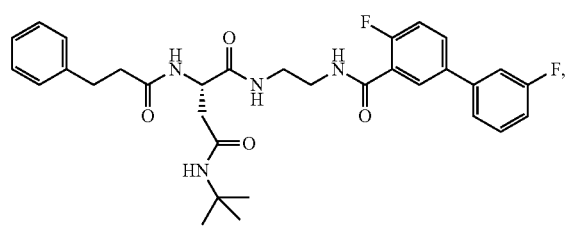
PKS21196
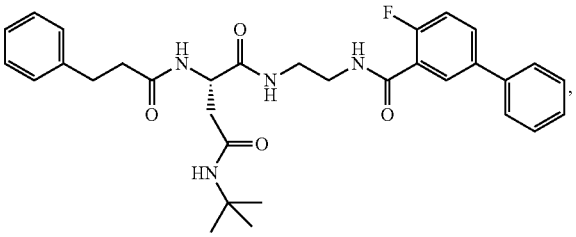
PKS21208
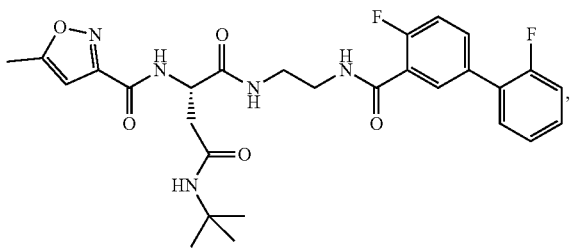
PKS21221
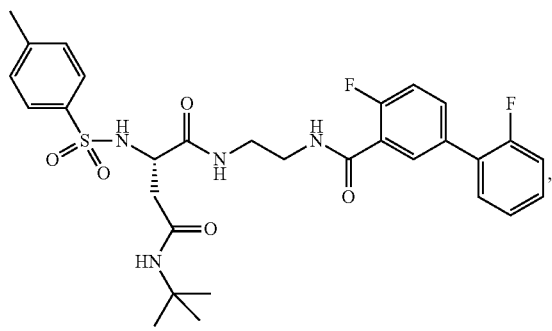
PKS21224
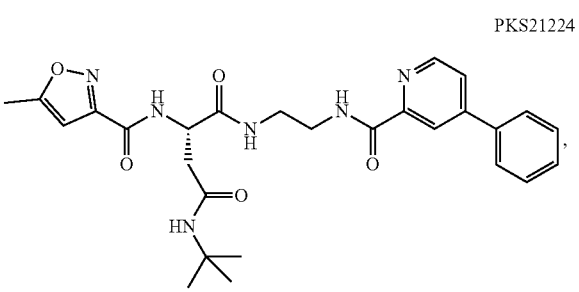
PKS21225
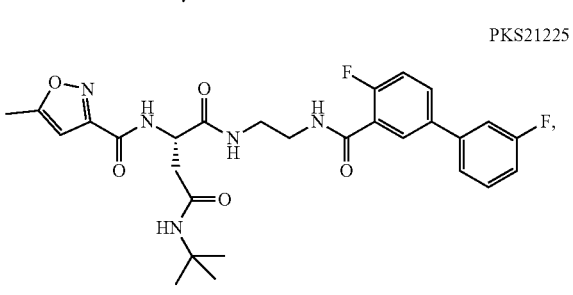
PKS21228
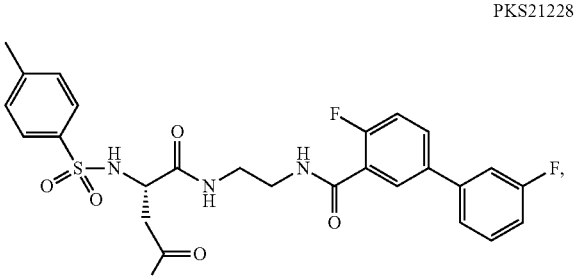
PKS21229
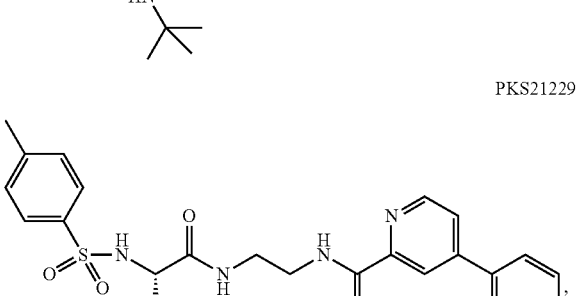

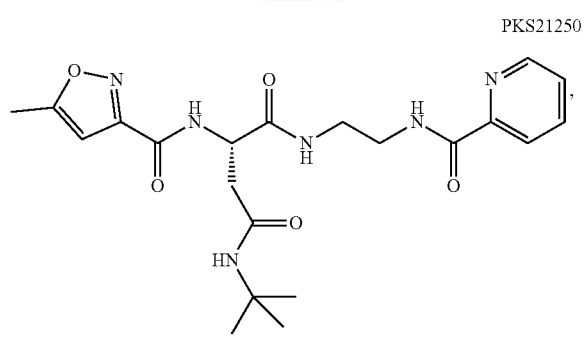
PKS21250
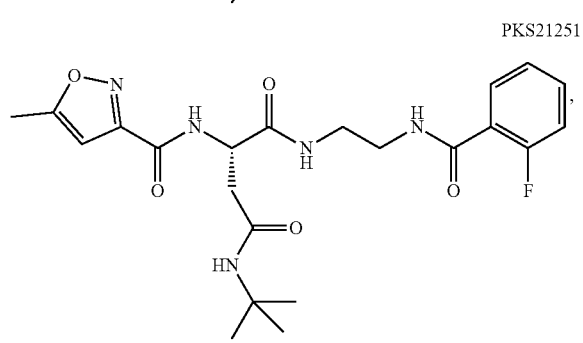
PKS21251
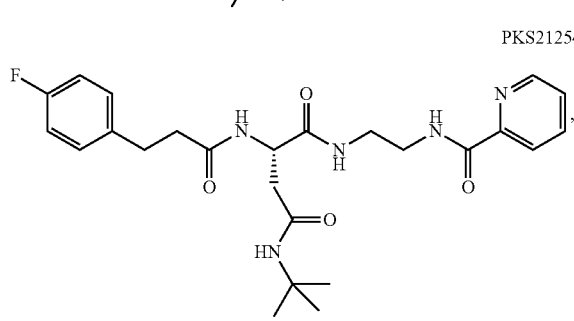
PKS21254
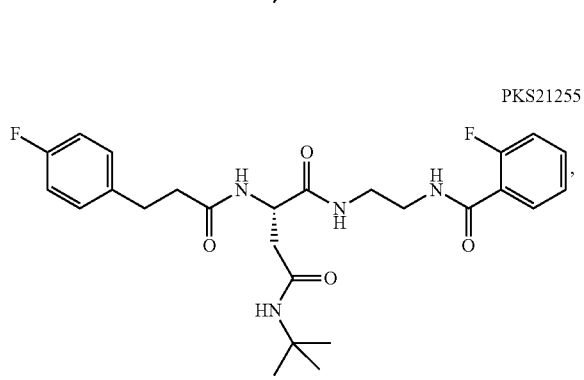
PKS21255
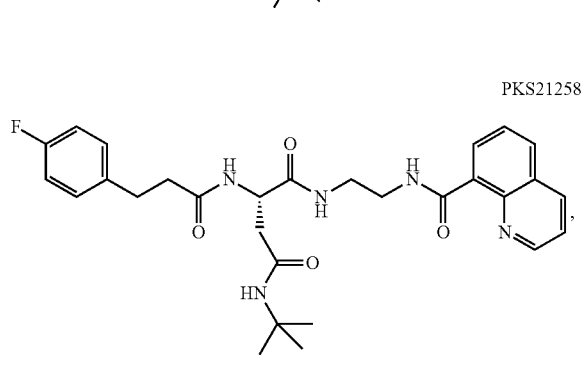
PKS21258
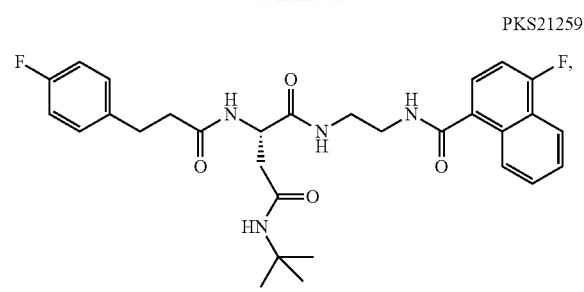
PKS21259
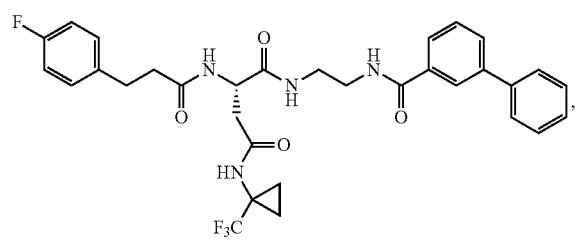
PKS21278
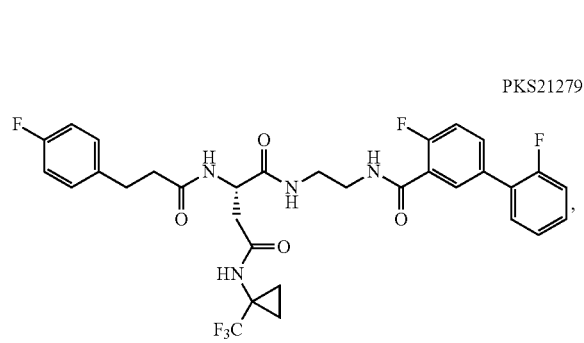
PKS21279
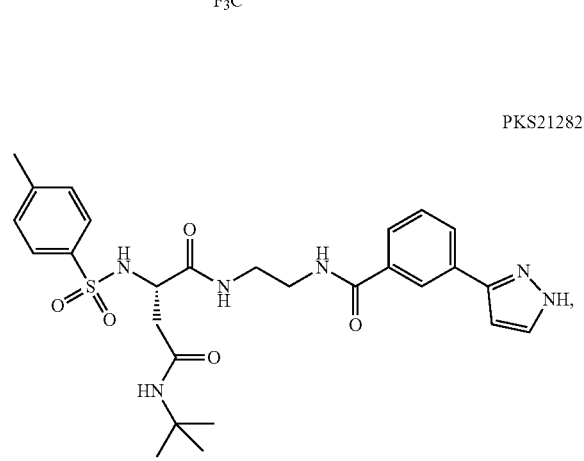
PKS21282
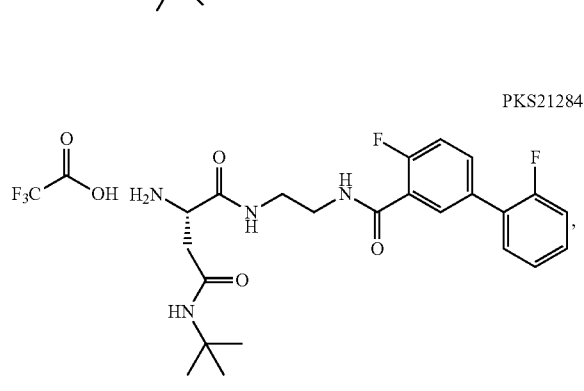
PKS21284

PKS21287
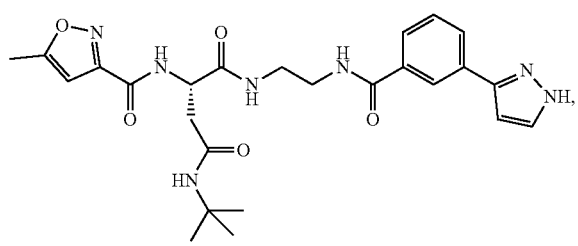
PKS21293
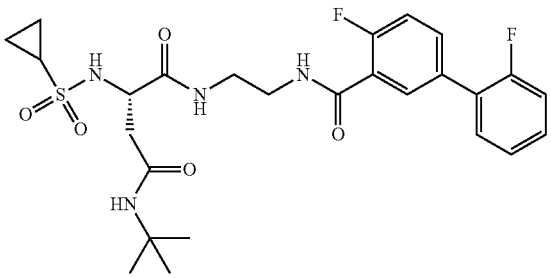
PKS21288
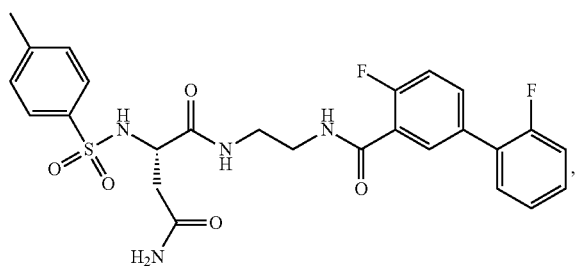
PKS21294
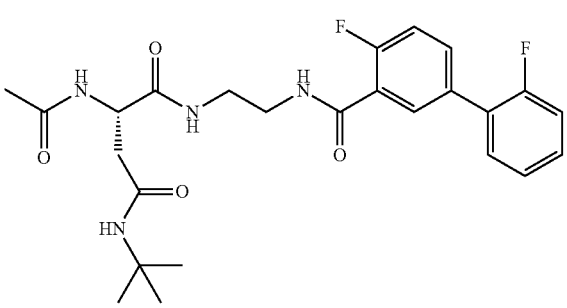
PKS21290
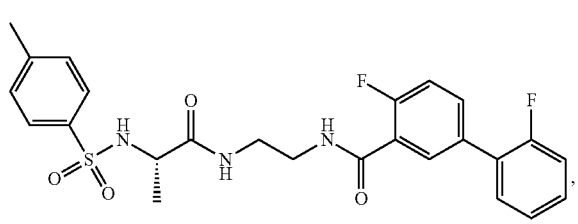
PKS21295
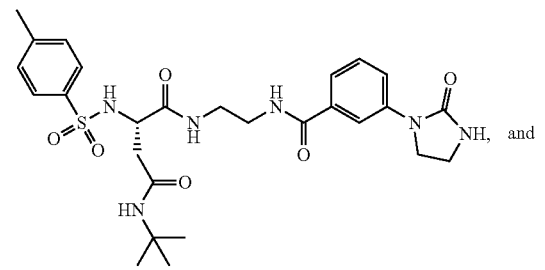
PKS21291
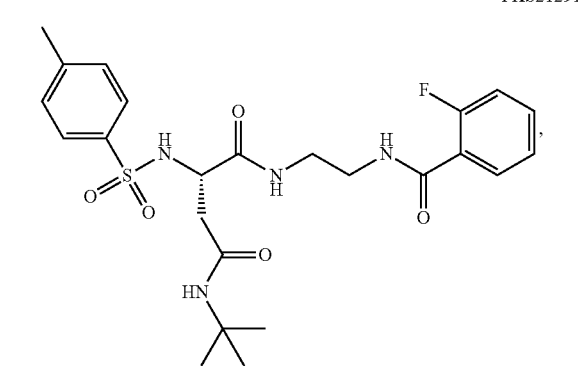
PKS21315
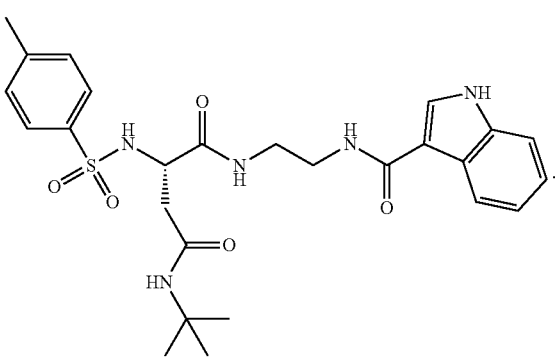
PKS21292
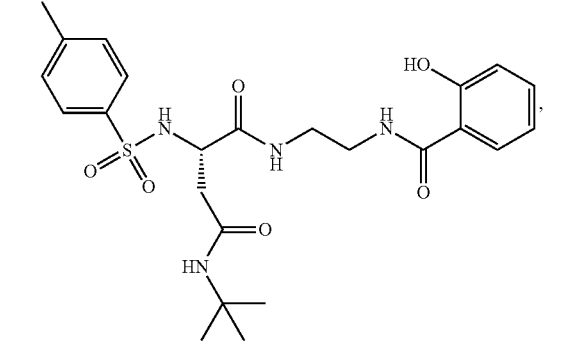
12. A method of treating cancer, autoimmune disorders, or inflammatory disorders in a subject or for providing immunosuppression, said method comprising:
administering to the subject in need thereof a compound of the Formula (I):

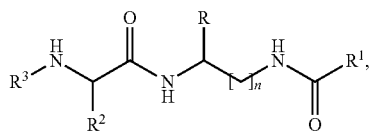

wherein
R is H or $C_{1-6}$ alkyl;
R$^1$ is selected from the group consisting of monocyclic and bicyclic aryl, biphenyl, monocyclic and bicyclic heteroaryl, wherein monocyclic and bicyclic aryl, biphenyl, monocyclic and bicyclic heteroaryl can be optionally substituted from 1 to 3 times with a substituent selected independently at each occurrence thereof from the group consisting of halogen, cyano, —OH, aryl, heteroaryl, non-aromatic heterocycle, and non-aromatic heterocycle substituted with =O;
R$^2$ is independently selected at each occurrence thereof from the group consisting of $C_{1-2}$ alkyl, alkenyl, monocyclic and bicyclic aryl, monocyclic and bicyclic heteroaryl, monocyclic and bicyclic heterocyclyl, and —(CH$_2$)$_m$C(O)NHR$^4$, wherein alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;
R$^3$ is selected from the group consisting of H, —SO$_p$R$^5$, —C(O)(CH$_2$)$_k$Ar, —SO$_2$Ar, —SO$_2$C$_{3-8}$ cycloalkyl, —C(O)(CH$_2$)$_k$Het, —C(O)C$_{1-6}$ alkyl, and —C(O) OC$_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;
R$^4$ is selected from the group consisting of H, $C_{1-6}$ alkyl, and $C_{3-8}$ cycloalkyl, wherein $C_{3-8}$ cycloalkyl can be optionally substituted with —CF$_3$;
R$^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;
k is 0 or 2;
m is 1 or 2;
n is 1, 2, or 3; and
p is 1 or 2;
or an oxide thereof, a pharmaceutically acceptable salt thereof, a solvate thereof, or a prodrug thereof,
wherein the autoimmune disorder is selected from the group consisting of arthritis, colitis, multiple sclerosis, lupus, systemic sclerosis, and sjögren syndrome;
the cancer is selected from the group consisting of multiple myeloma, lymphoma, and other hematological cancers; the inflammatory disorder is Crohn's disease or ulcerative colitis; and
the immunosuppression is provided for transplanted organs or tissues or is used to prevent transplant rejection and graft-verse-host disease.

13. The method according to claim 12, wherein the said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

14. A pharmaceutical composition comprising a therapeutically effective amount of the compound according to claim 1 and a pharmaceutically acceptable carrier.

15. A method of inhibiting chymotryptic β5i in a cell or a tissue, said method comprising:
providing a compound of Formula (I):

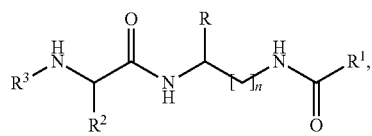

wherein
R is H or $C_{1-6}$ alkyl;
R$^1$ is selected from the group consisting of monocyclic and bicyclic aryl, biphenyl, monocyclic and bicyclic heteroaryl, wherein monocyclic and bicyclic aryl, biphenyl, monocyclic and bicyclic heteroaryl can be optionally substituted from 1 to 3 times with a substituent selected independently at each occurrence thereof from the group consisting of halogen, cyano, —OH, aryl, heteroaryl, non-aromatic heterocycle, and non-aromatic heterocycle substituted with =O;
R$^2$ is independently selected at each occurrence thereof from the group consisting of $C_{1-2}$ alkyl, alkenyl, monocyclic and bicyclic aryl, monocyclic and bicyclic heteroaryl, monocyclic and bicyclic heterocyclyl, and —(CH$_2$)$_m$C(O)NHR$^4$, wherein alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;
R$^3$ is selected from the group consisting of H, —SO$_p$R$^5$, —C(O)(CH$_2$)$_k$Ar, —SO$_2$Ar, —SO$_2$C$_{3-8}$ cycloalkyl, —C(O)(CH$_2$)$_k$Het, —C(O)C$_{1-6}$ alkyl, and —C(O) OC$_{1-6}$ alkyl, wherein aryl (Ar) and heteroaryl (Het) can be optionally substituted from 1 to 3 times with a substituent selected independently at each occurrence thereof from halogen or $C_{1-6}$ alkyl;
R$^4$ is selected from the group consisting of H, $C_{1-6}$ alkyl, and $C_{3-8}$ cycloalkyl, wherein $C_{3-8}$ cycloalkyl can be optionally substituted with —CF$_3$;
R$^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;

m is 1 or 2;

n is 1, 2, or 3;

p is 1 or 2; and contacting a cell or tissue with the compound under conditions effective to inhibit chymotryptic β5i.

16. A method of treating infectious disease in a subject, said method comprising:

administering to the subject in need thereof a compound of the Formula (I):

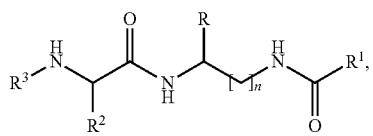

(I)

wherein

R is H or C$_{1-6}$ alkyl;

R$^1$ is selected from the group consisting of monocyclic and bicyclic aryl, biphenyl, monocyclic and bicyclic heteroaryl, wherein monocyclic and bicyclic aryl, biphenyl, monocyclic and bicyclic heteroaryl can be optionally substituted from 1 to 3 times with a substituent selected independently at each occurrence thereof from the group consisting of halogen, cyano, —OH, aryl, heteroaryl, non-aromatic heterocycle, and non-aromatic heterocycle substituted with =O;

R$^2$ is independently selected at each occurrence thereof from the group consisting of C$_{1-2}$ alkyl, alkenyl, monocyclic and bicyclic aryl, monocyclic and bicyclic heteroaryl, monocyclic and bicyclic heterocyclyl, and —(CH$_2$)$_m$C(O)NHR$^4$, wherein alkenyl, monocyclic and bicyclic aryl, monocyclic and bicyclic heteroaryl, monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

R$^3$ is selected from the group consisting of H, —SO$_p$R$^5$, —C(O)(CH$_2$)$_k$Ar, —SO$_2$Ar, SO$_2$C$_{3-8}$ cycloalkyl, —C(O)(CH$_2$)$_k$Het, —C(O)C$_{1-6}$ alkyl, and —C(O)OC$_{1-6}$ alkyl, wherein aryl (Ar) and heteroaryl (Het) can be optionally substituted from 1 to 3 times with a substituent selected independently at each occurrence thereof from halogen or C$_{1-6}$ alkyl;

R$^4$ is selected from the group consisting of H, C$_{1-6}$ alkyl, and C$_{3-8}$ cycloalkyl, wherein C$_{3-8}$ cycloalkyl can be optionally substituted with —CF$_3$;

R$^5$ is selected from the group consisting of alkyl, alkenyl, monocyclic and bicyclic aryl, monocyclic and bicyclic heteroaryl, and monocyclic and bicyclic heterocyclyl, wherein alkyl, alkenyl, monocyclic and bicyclic aryl, monocyclic and bicyclic heteroaryl, and monocyclic and bicyclic heterocyclyl can be optionally substituted from 1 to 3 times with a substituent selected independently at each occurrence thereof from the group consisting of halogen, cyano, —OH, —NO$_2$, —CF$_3$, —OC$_{1-6}$ alkyl, alkyl, alkenyl, monocyclic and bicyclic aryl, monocyclic and bicyclic heteroaryl, and monocyclic and bicyclic heterocyclyl;

k is 0 or 2;

m is 1 or 2;

n is 1, 2, or 3; and p is 1 or 2;

or an oxide thereof, a pharmaceutically acceptable salt thereof, a solvate thereof, or a prodrug thereof.

17. The method according to claim 16, wherein the infectious disease is caused by bacterial, viral, parasitic, and fungal infectious agents.

18. The method of claim 12, wherein the compound of Formula (I) has the Formula (Ia):

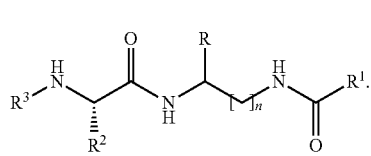

(Ia)

19. The method of claim 12, wherein the compound of Formula (I) has the Formula (Ib):

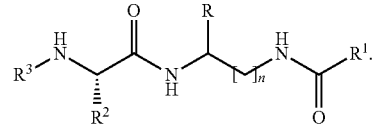

(Ib)

20. The method of claim 12, wherein the compound of Formula (I) has the Formula (Ic):

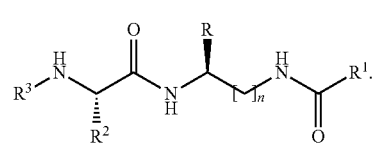

(Ic)

21. The method of claim 12, wherein 10 is

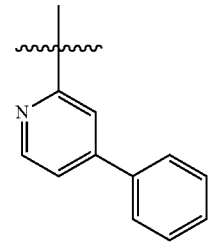

22. The method of claim 12, wherein R$^1$ is selected from the group consisting of

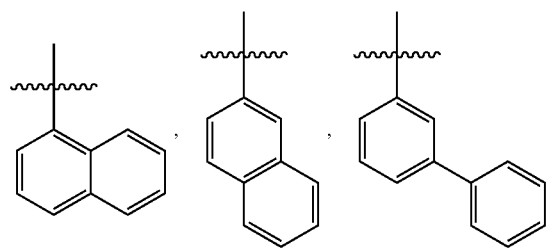
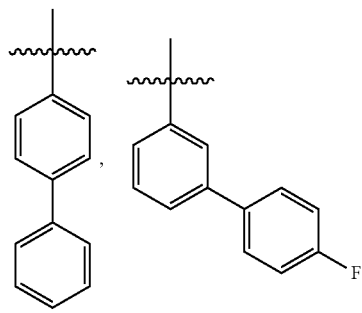
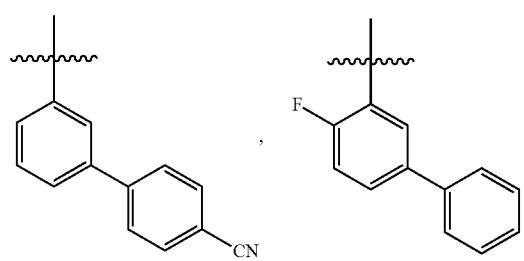
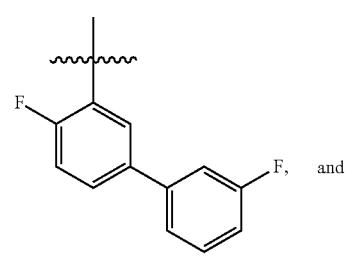
23. The method of claim 12, wherein R² is selected from the group consisting of CH₃,
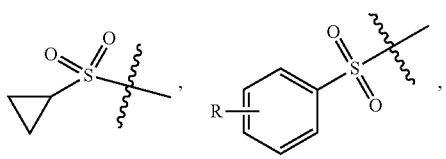, and 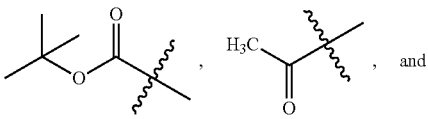
24. The method of claim 12, wherein R³ is selected from the group consisting of H,
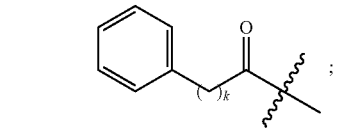
and
R is $C_{1-6}$ alkyl.
25. The method of claim 12, wherein the compound of Formula (I) is
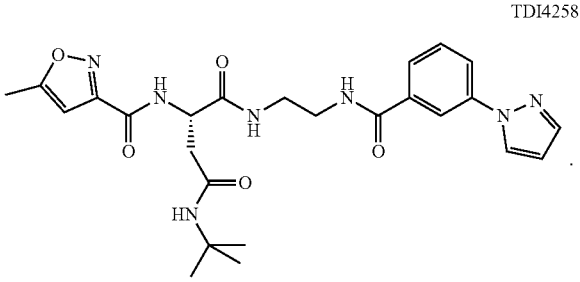 [SMILES: Cc1cc(C(=O)N[C@@H](CC(=O)NC(C)(C)C)C(=O)NCCNC(=O)c2cccc(-n3cccn3)c2)no1]
.
26. The method of claim 12, wherein the compound of Formula (I) is selected from the group consisting of:

117 118
PKS3080
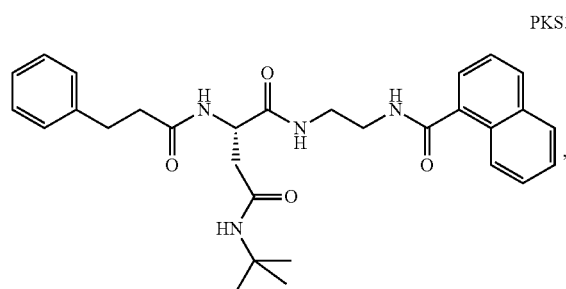
PKS21003
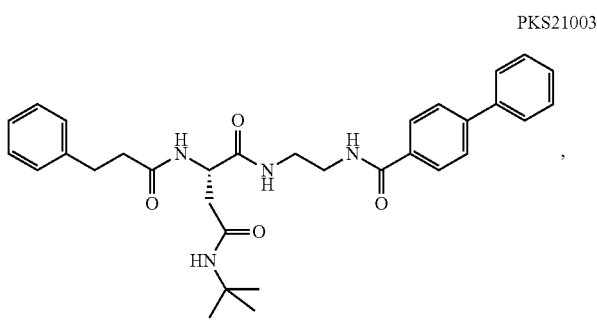
PKS21004
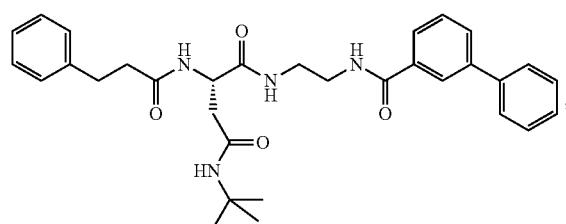
PKS21018
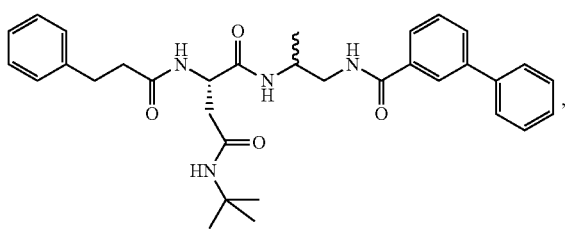
PKS21019
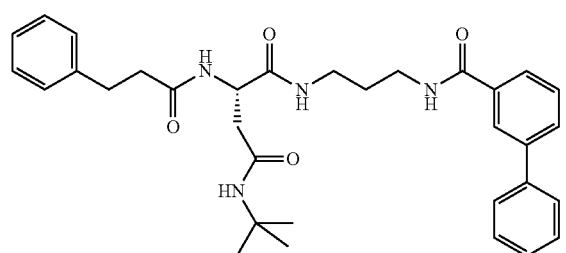
PKS21025
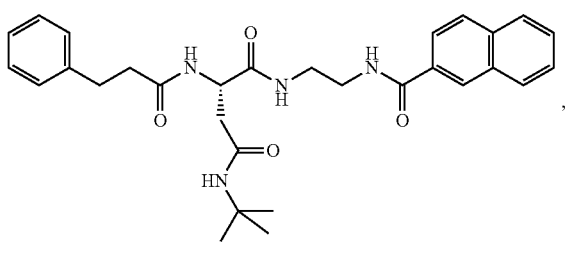
PKS21026
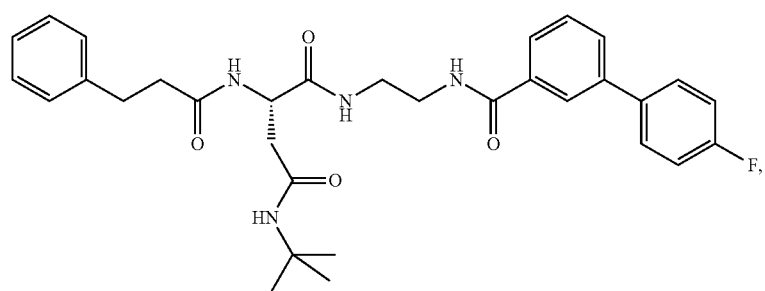
PKS21028
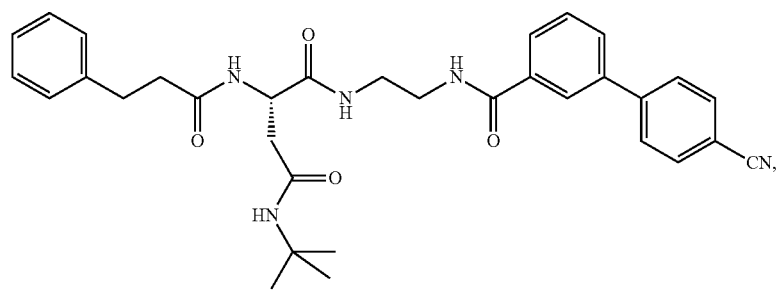

-continued
PKS21030
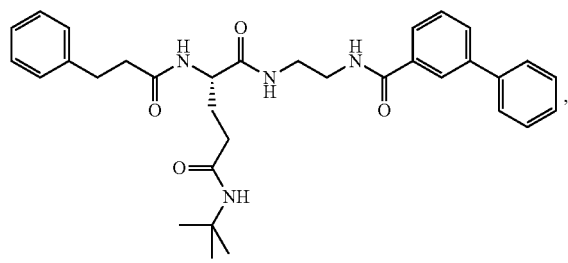
PKS21186
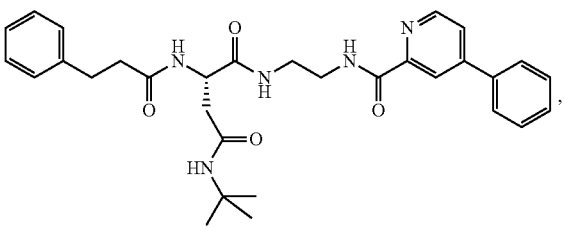
PKS21187
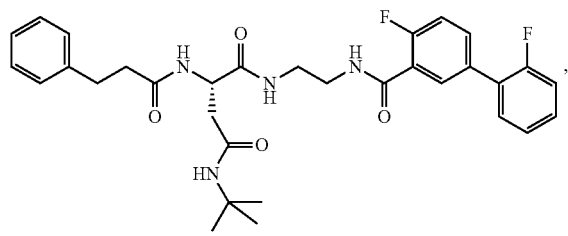
PKS21195
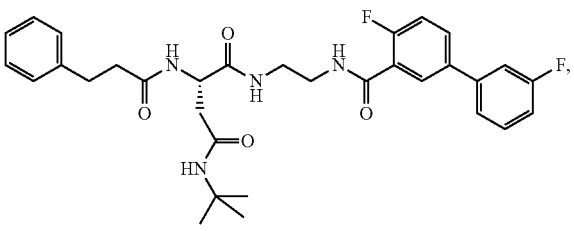
PKS21196
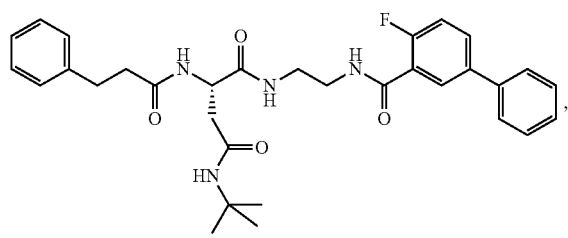
PKS21208
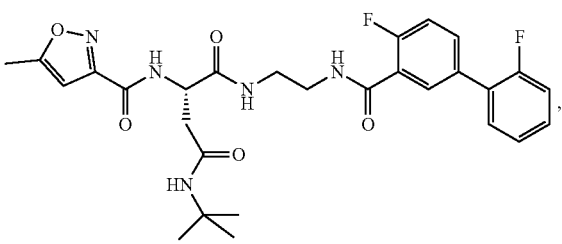
PKS21221
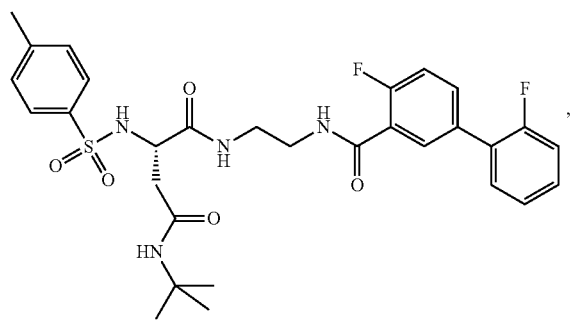
PKS21224
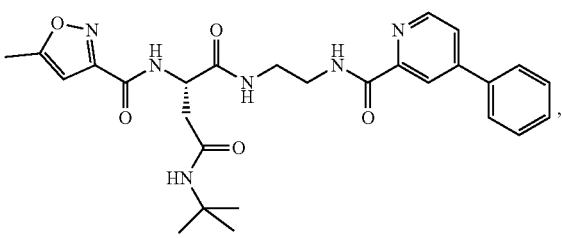
PKS21225
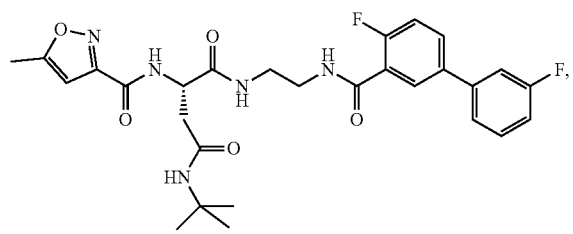
PKS21228
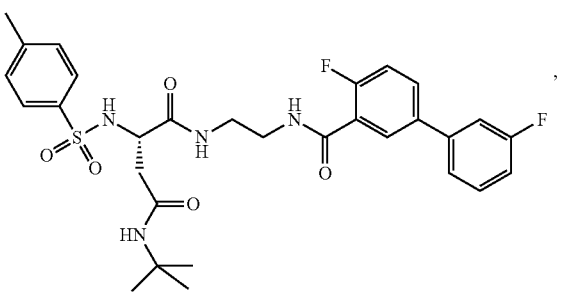

-continued
PKS21229
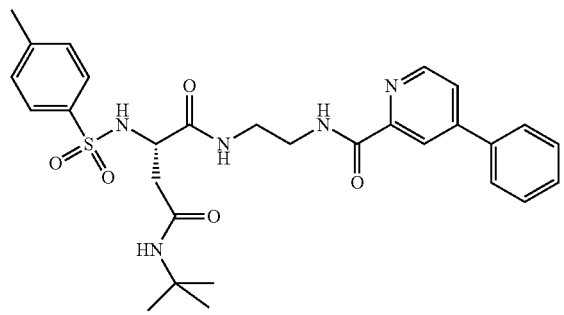
PKS21250
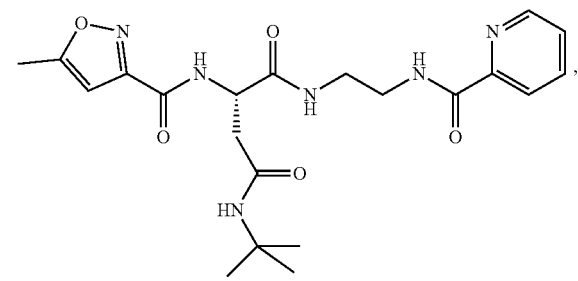
PKS21251
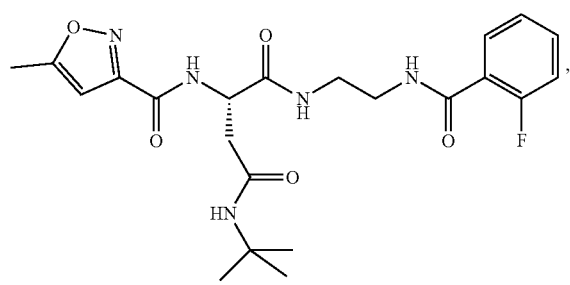
PKS21254
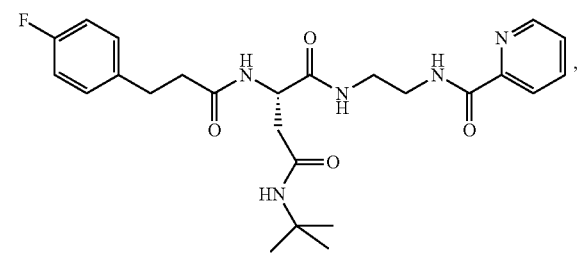
PKS21255
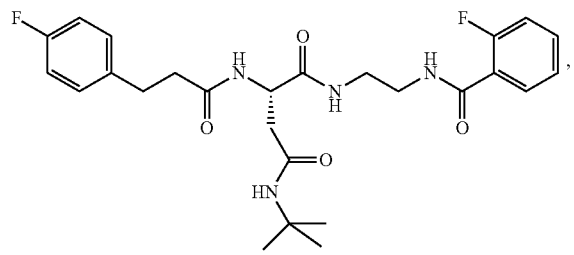
PKS21258
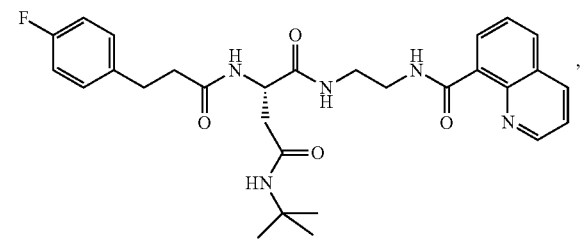
PKS21259
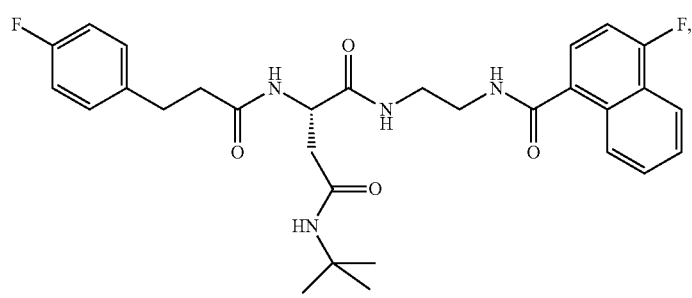
PKS21277
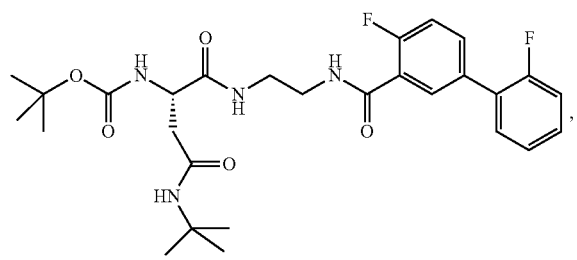
PKS21280
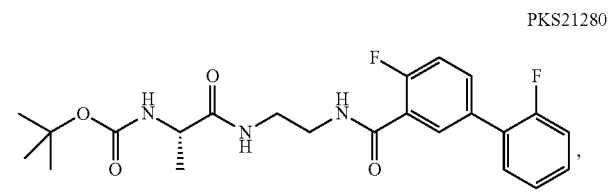

-continued
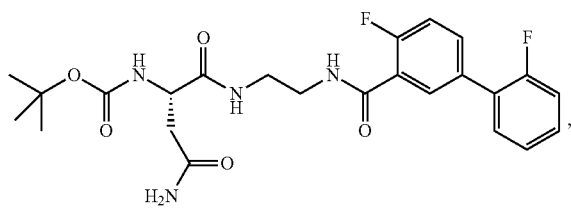
PKS21281
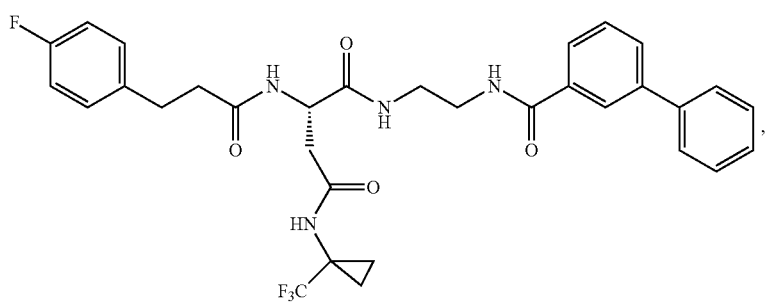
PKS21278
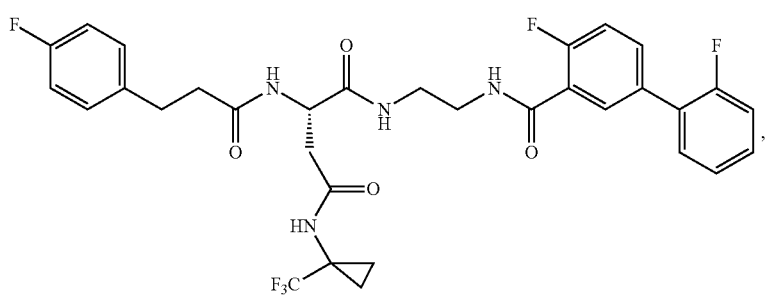
PKS21279
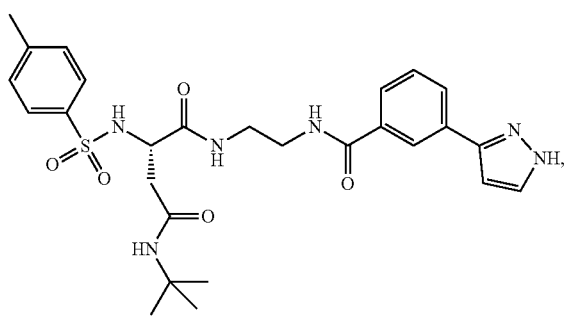
PKS21282
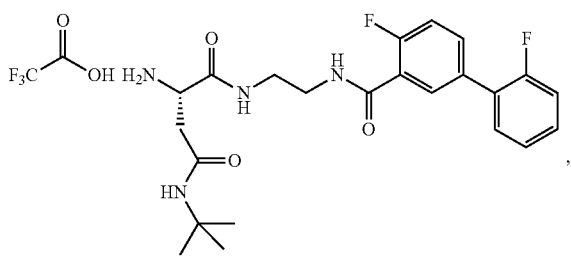
PKS21284
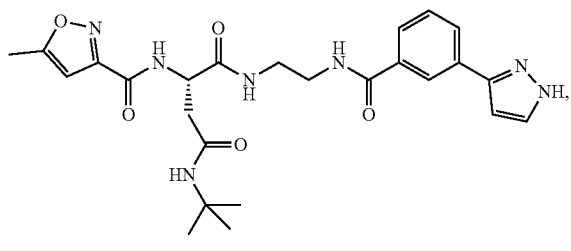
PKS21287
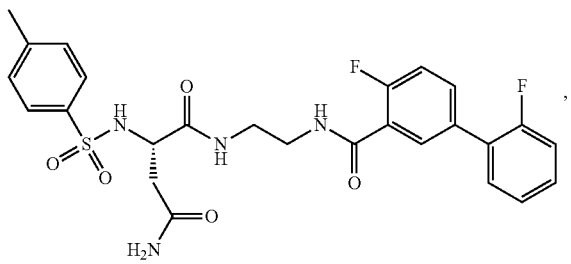
PKS21288

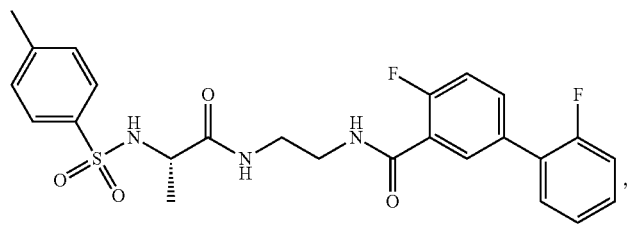
PKS21290
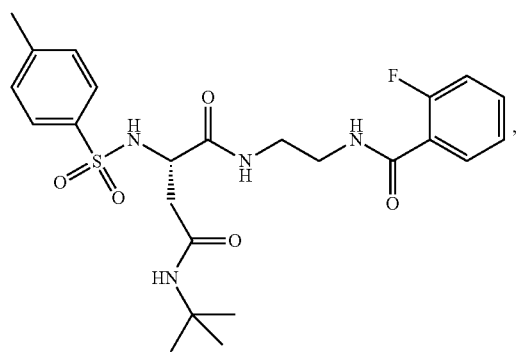
PKS21291
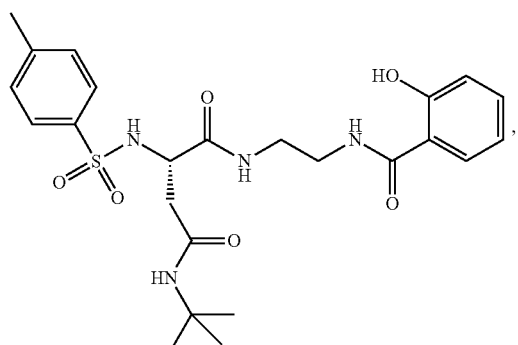
PKS21292
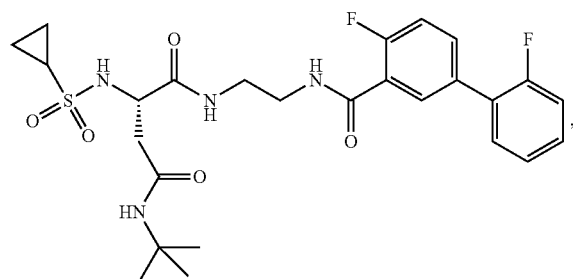
PKS21293
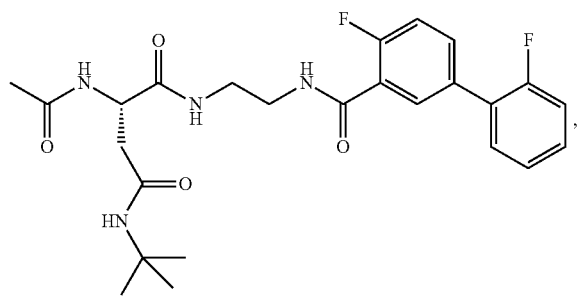
PKS21294
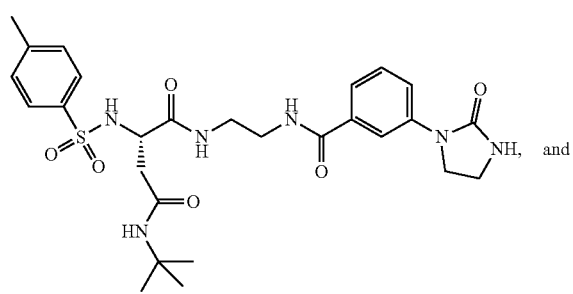
PKS21295, and
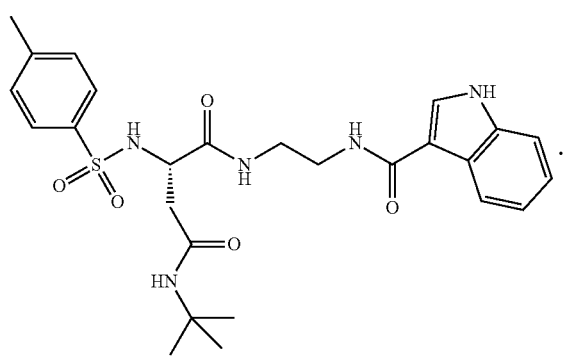
PKS21315.
27. The method of claim 15, wherein the compound of Formula (I) has the Formula (Ia):
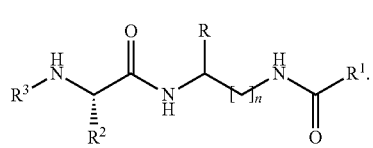
(Ia)
28. The method of claim 15, wherein the compound of Formula (I) has the Formula (Ib):
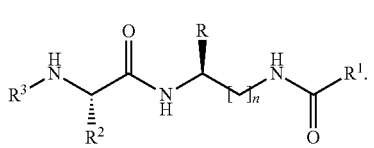
(Ib)

29. The method of claim 15, wherein the compound of Formula (I) has the Formula (Ic):

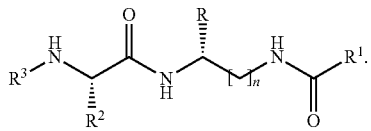

30. The method of claim 15, wherein R¹ is

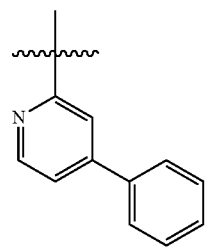

31. The method of claim 15, wherein R¹ is selected from the group consisting of

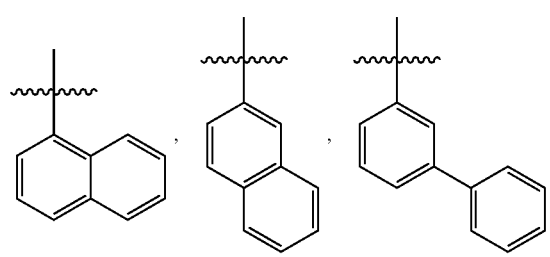

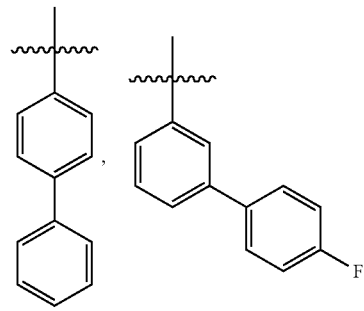

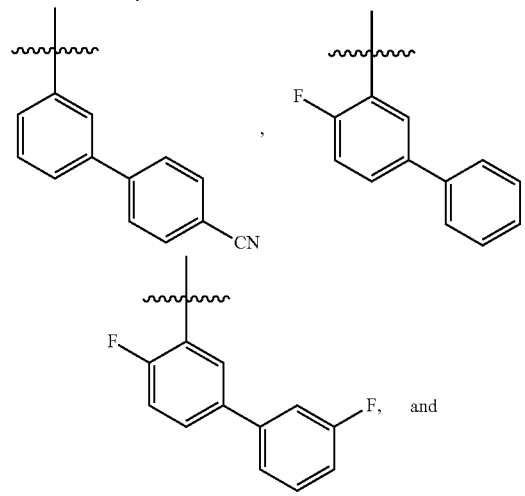

32. The method of claim 15, wherein R² is selected from the group consisting of CH₃,

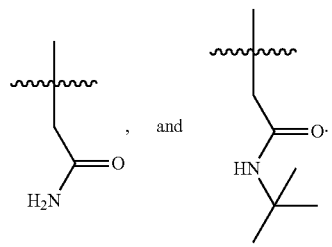

33. The method of claim 15, wherein R³ is selected from the group consisting of H,

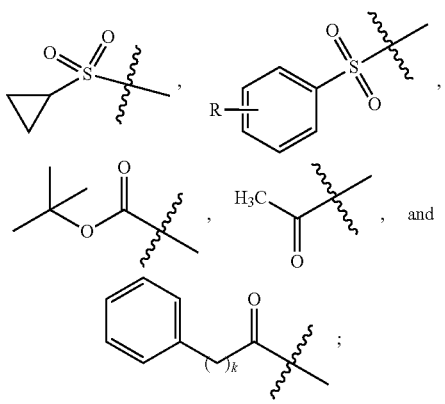

and
R is $C_{1-6}$ alkyl.

34. The method of claim 15, wherein the compound of Formula (I) is

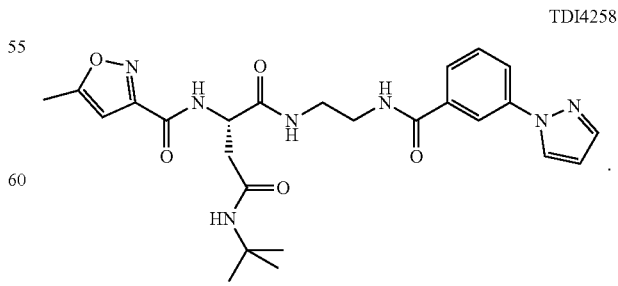

35. The method of claim 15, wherein the compound of Formula (I) is selected from the group consisting of:

| 129 | 130 |
|---|---|
| 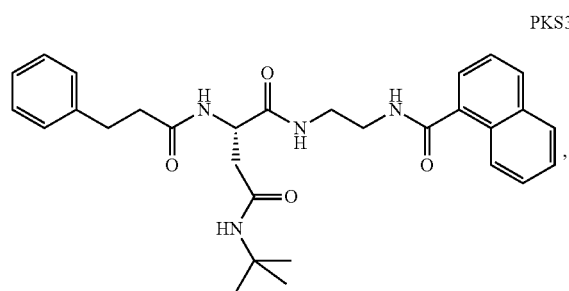 PKS3080 | 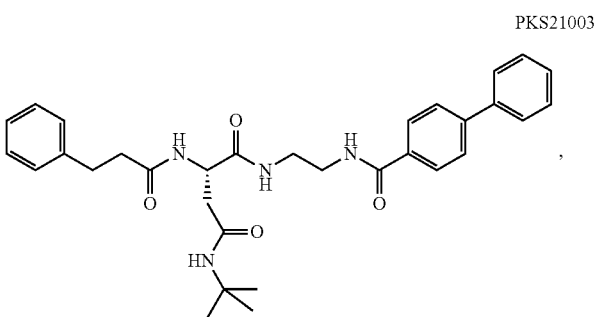 PKS21003 |
| 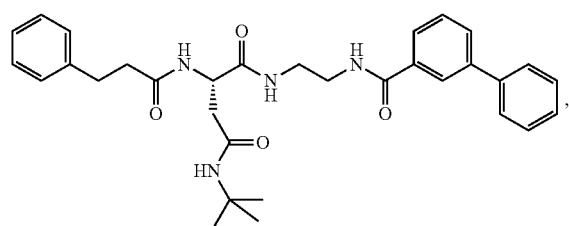 PKS21004 | 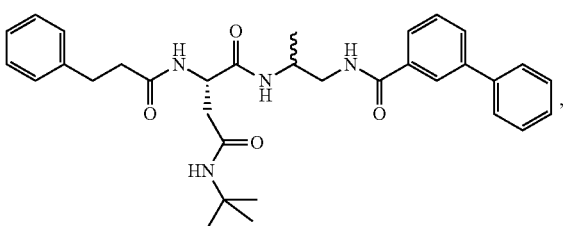 PKS21018 |
| 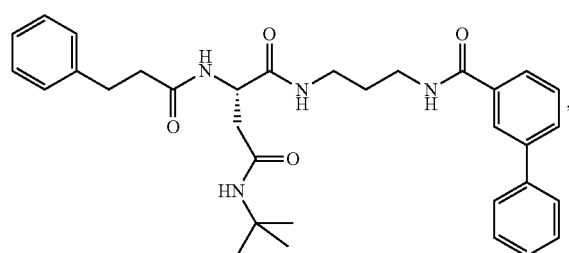 PKS21019 | 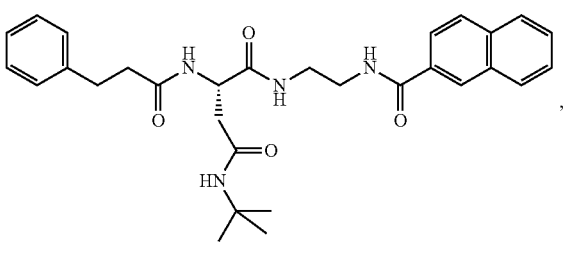 PKS21025 |
| 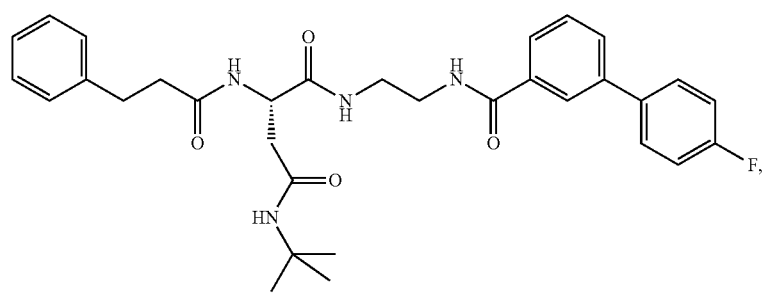 PKS21026 | |
| 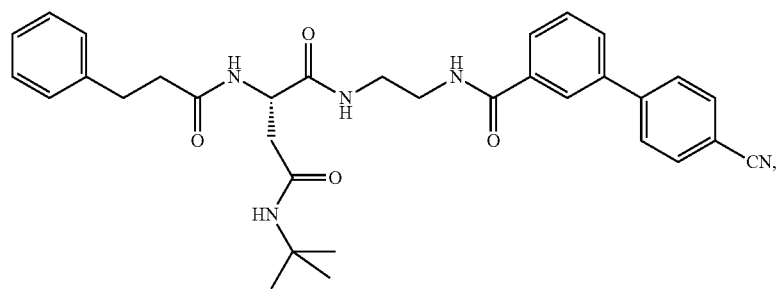 PKS21028 | |

-continued
PKS21030
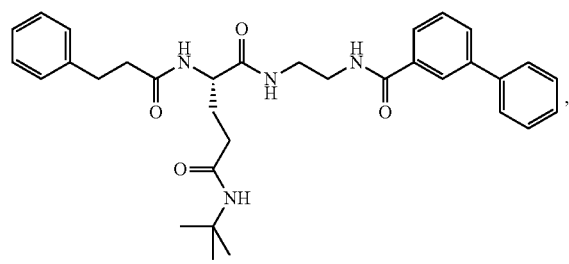
PKS21186
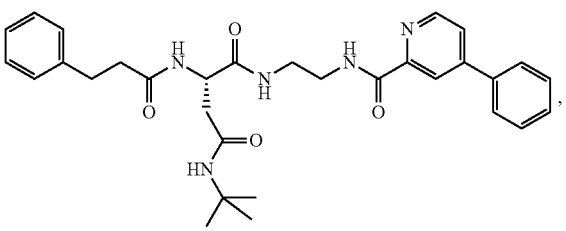
PKS21187
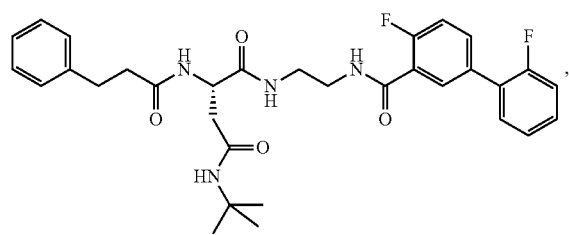
PKS21195
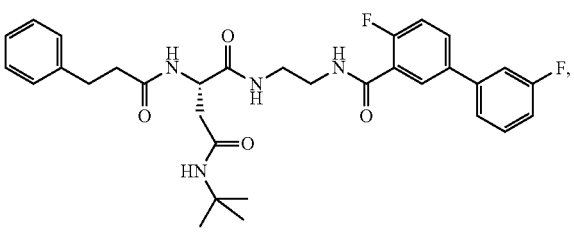
PKS21196
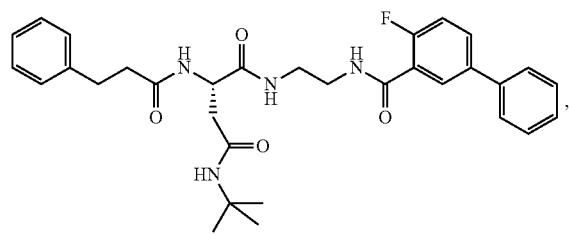
PKS21208
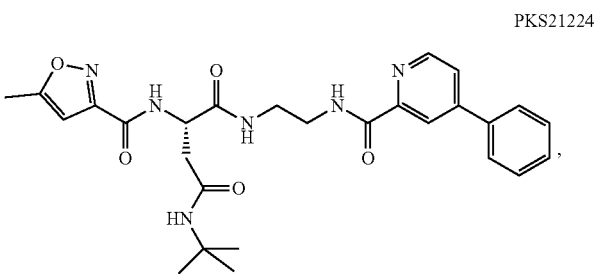
PKS21221
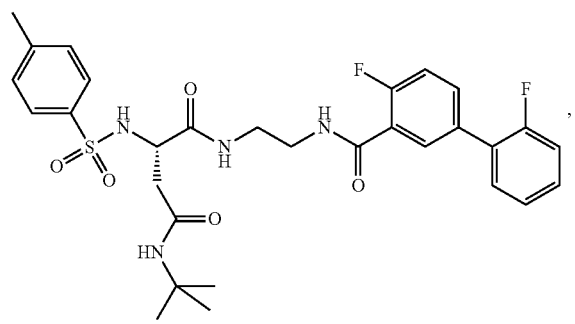
PKS21224
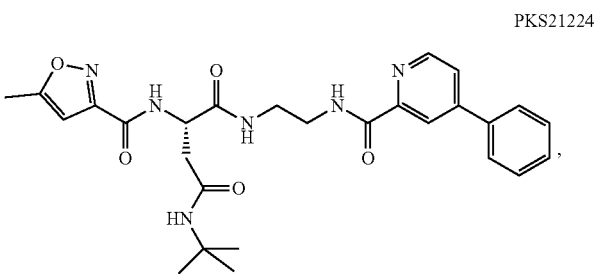
PKS21225
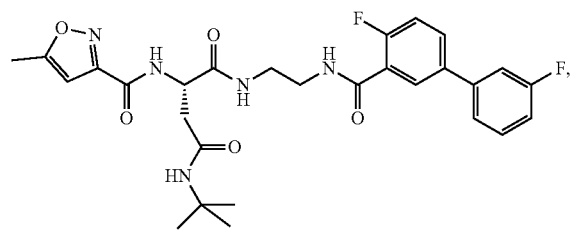
PKS21228
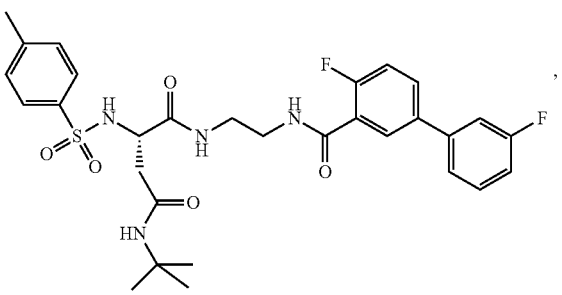

-continued
PKS21229
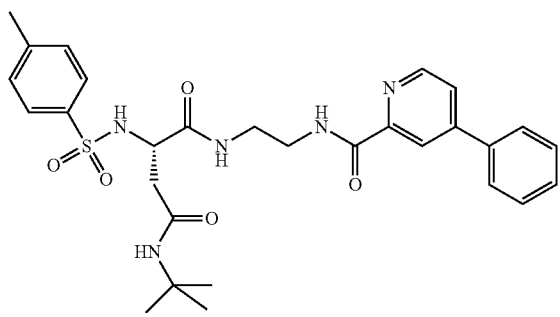
PKS21250
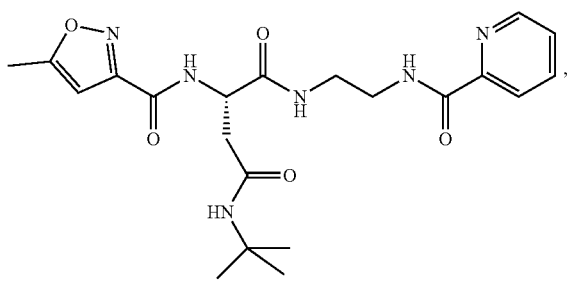
PKS21251
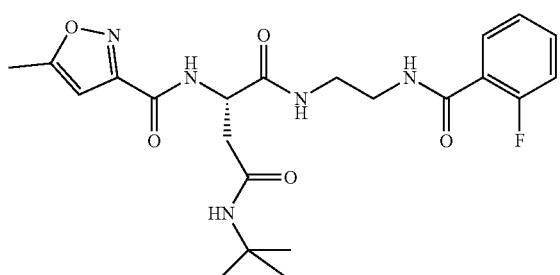
PKS21254
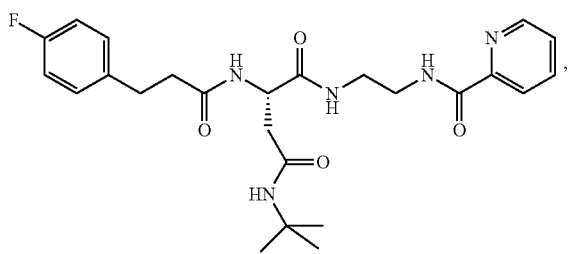
PKS21255
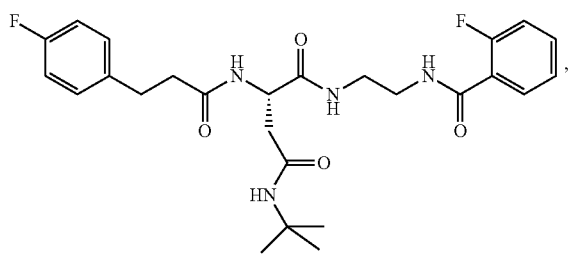
PKS21258
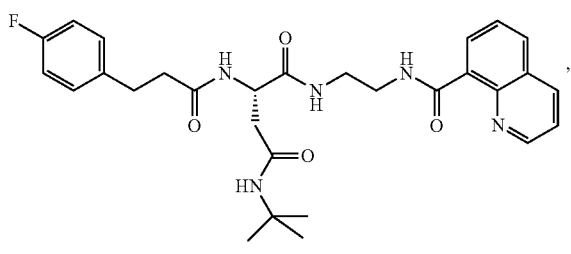
PKS21259
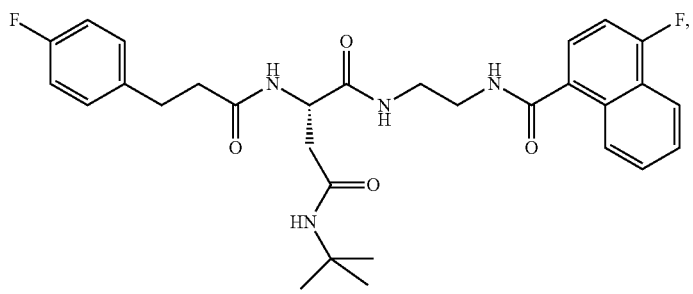
PKS21277
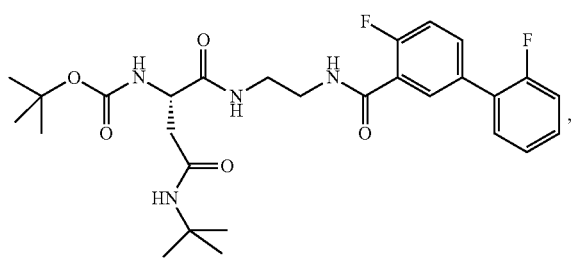
PKS21280
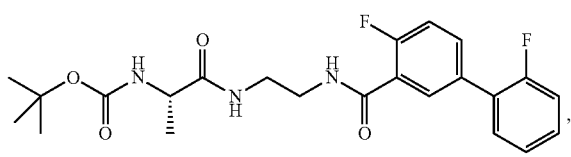

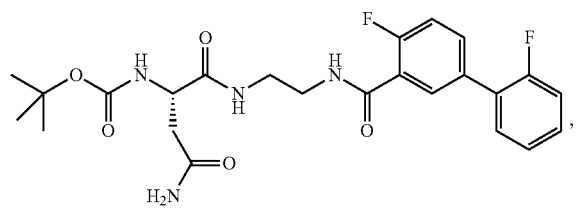
PKS21281
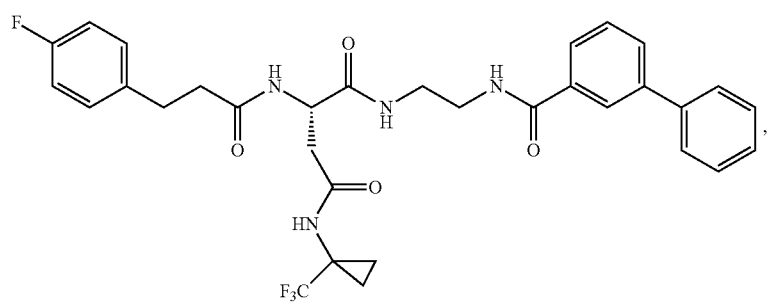
PKS21278
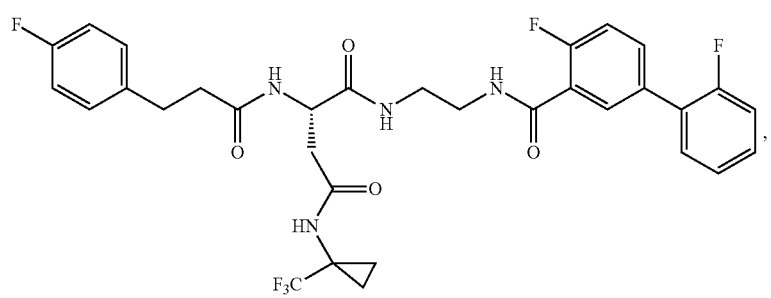
PKS21279
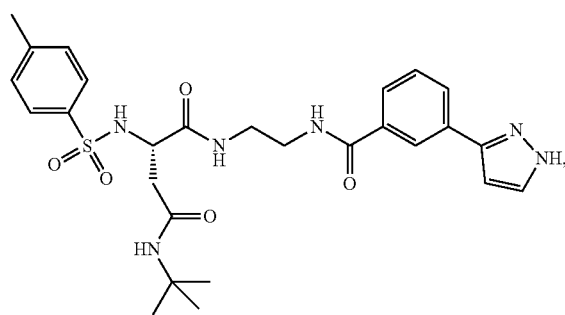
PKS21282
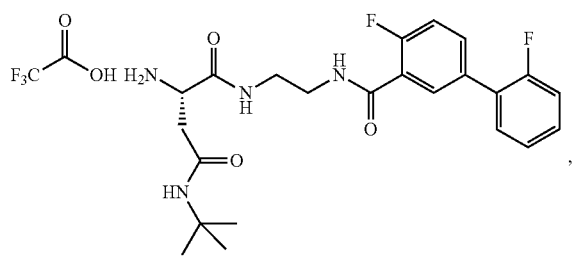
PKS21284
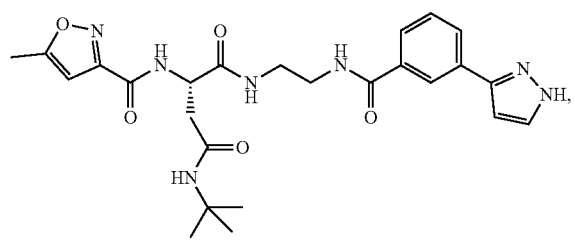
PKS21287
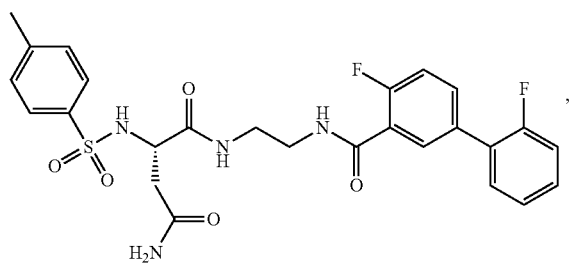
PKS21288

-continued
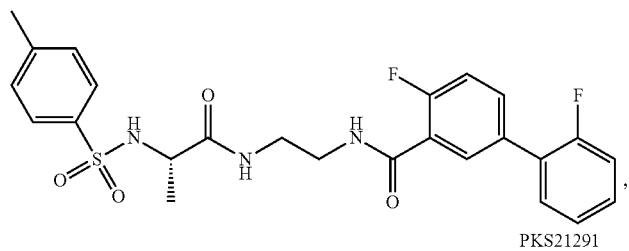
PKS21290
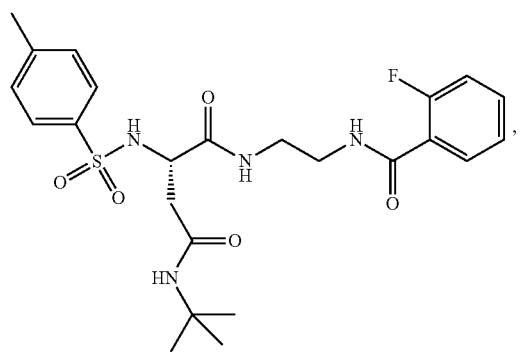
PKS21291
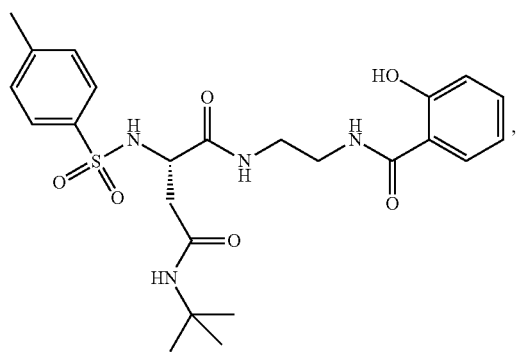
PKS21292
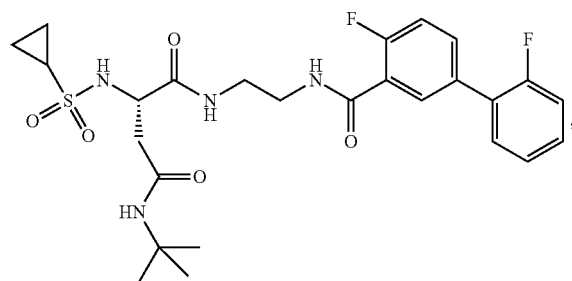
PKS21293
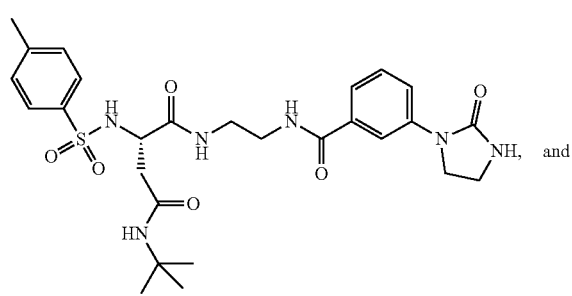
PKS21294
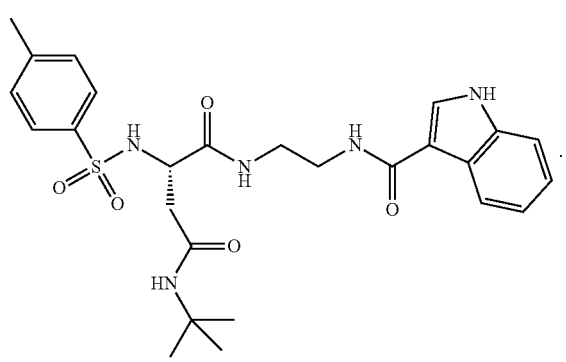
PKS21295
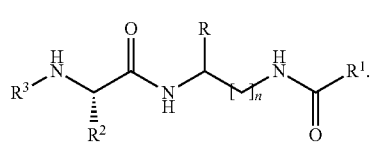
PKS21315, and
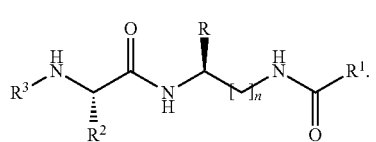
.
36. The method of claim 16, wherein the compound of Formula (I) has the Formula (Ia):
$$\text{(Ia)}$$
37. The method of claim 16, wherein the compound of Formula (I) has the Formula (Ib):
$$\text{(Ib)}$$

38. The method of claim 16, wherein the compound of Formula (I) has the Formula (Ic):

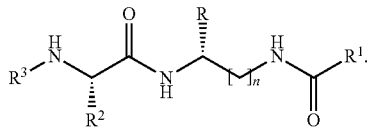
(Ic)

39. The method of claim 16, wherein $R^1$ is

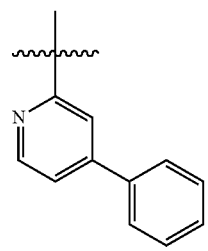

40. The method of claim 16, wherein $R^1$ is selected from the group consisting of

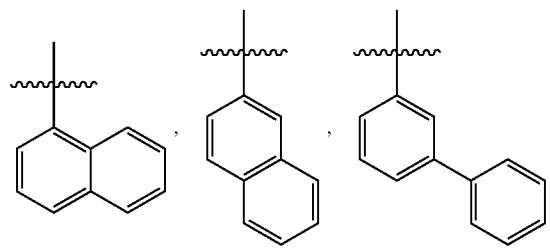

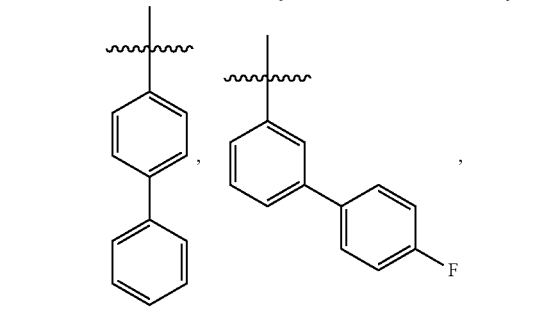

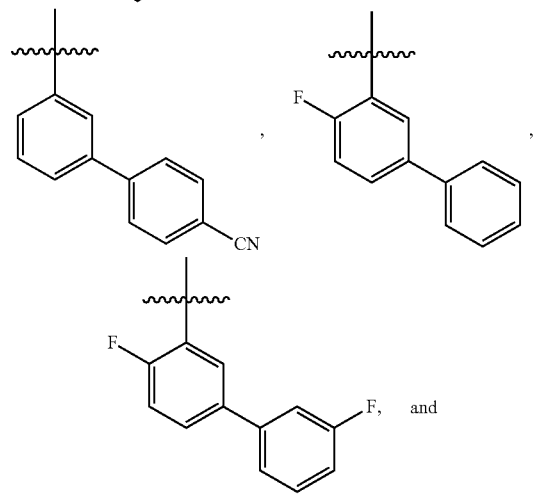

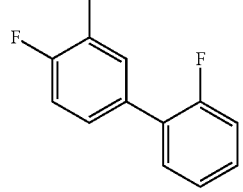

41. The method of claim 16, wherein $R^2$ is selected from the group consisting of $CH_3$,

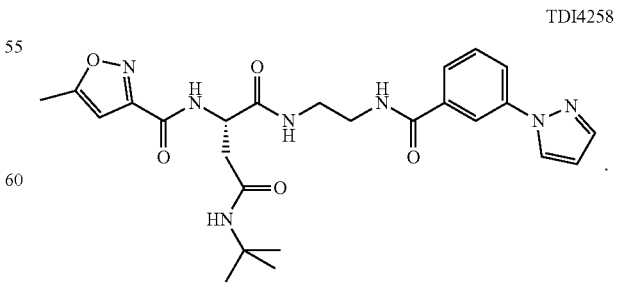

42. The method of claim 16, wherein $R^3$ is selected from the group consisting of H, and
R is $C_{1-6}$ alkyl.

43. The method of claim 16, wherein the compound of Formula (I) is

TDI4258

44. The method of claim 16, wherein the compound of Formula (I) is selected from the group consisting of:

141                                         142
PKS3080
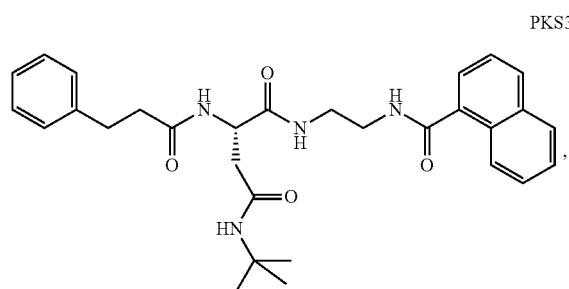
PKS21003
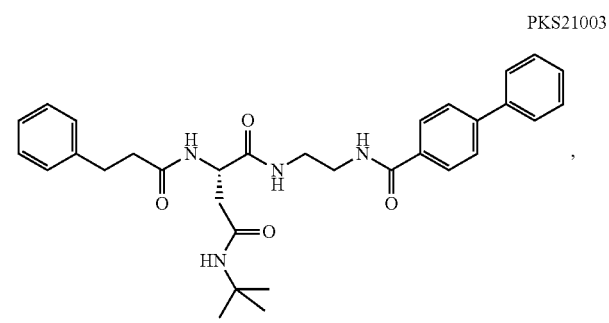
PKS21004
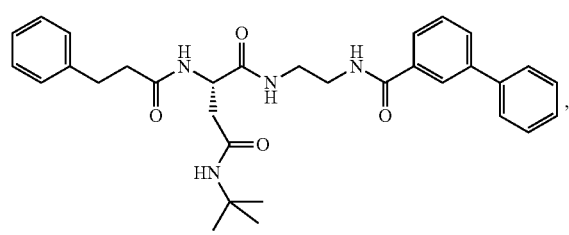
PKS21018
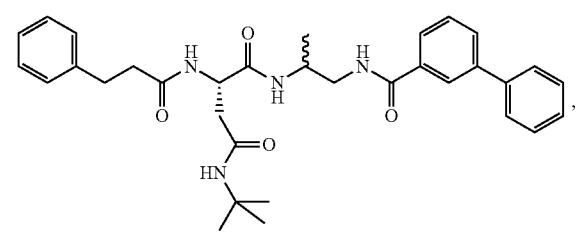
PKS21019
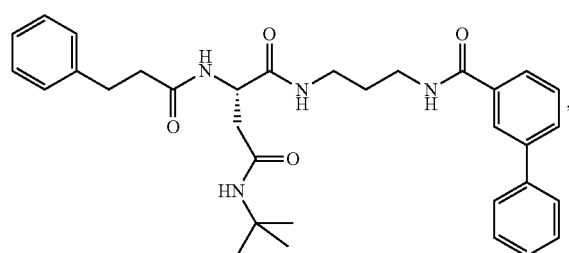
PKS21025
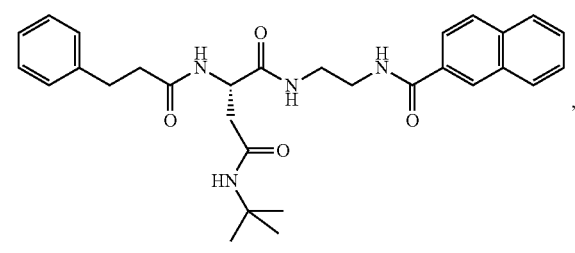
PKS21026
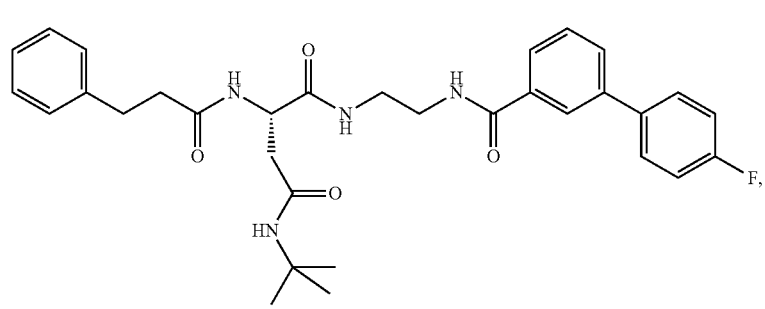
PKS21028
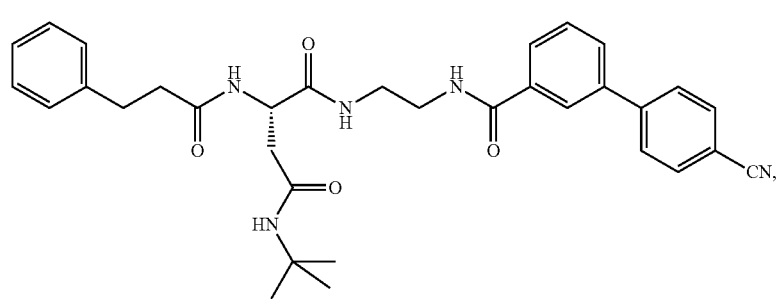

-continued
PKS21030
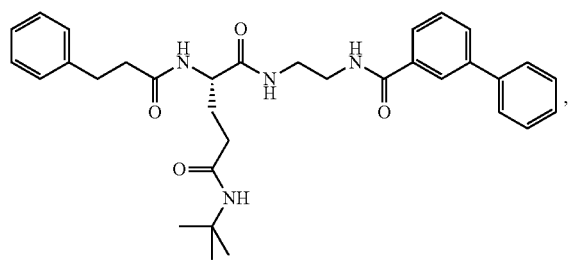
PKS21186
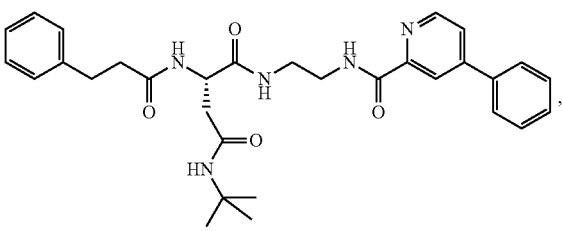
PKS21187
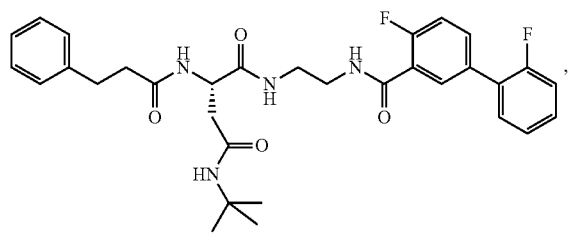
PKS21195
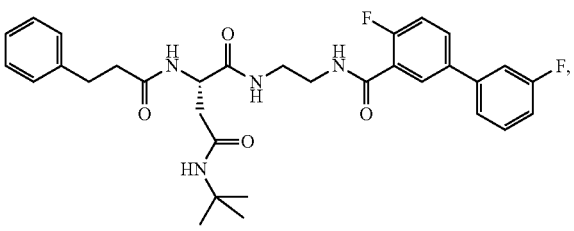
PKS21196
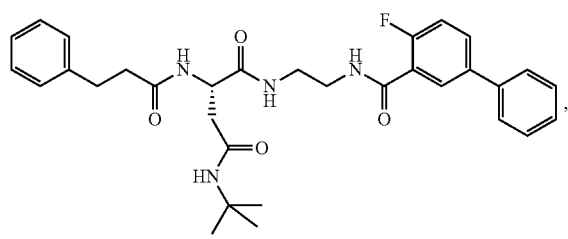
PKS21208
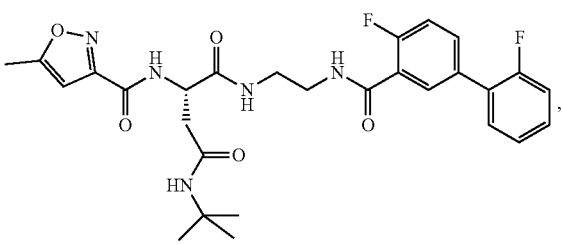
PKS21221
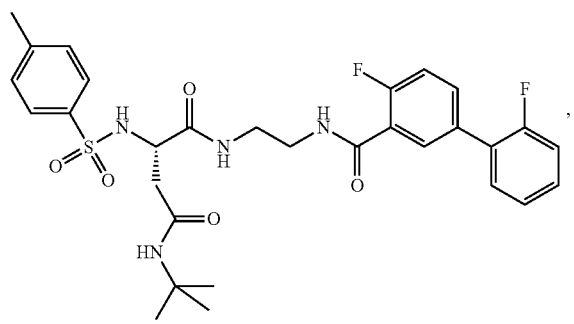
PKS21224
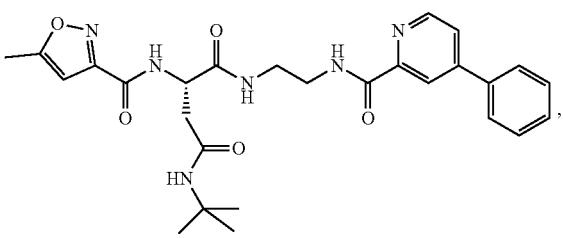
PKS21225
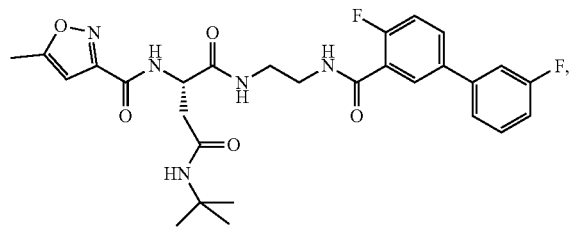
PKS21228
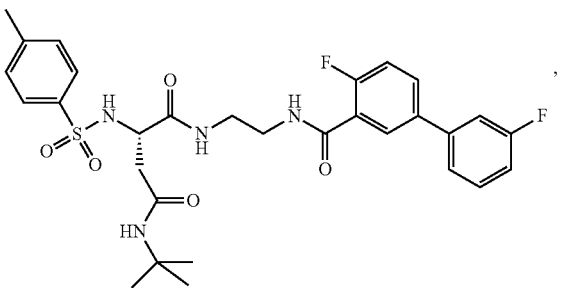

-continued
PKS21229
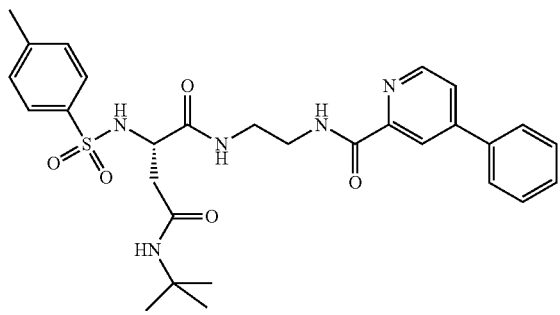
PKS21250
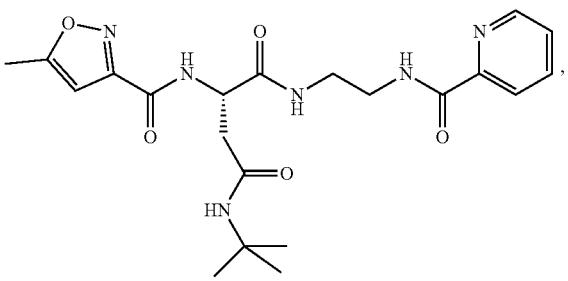
PKS21251
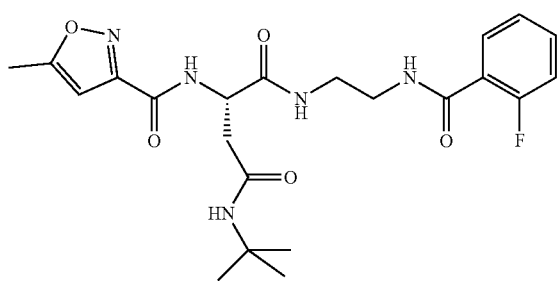
PKS21254
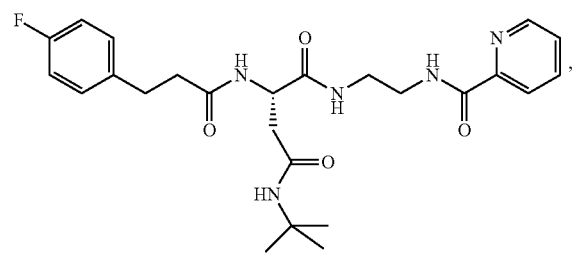
PKS21255
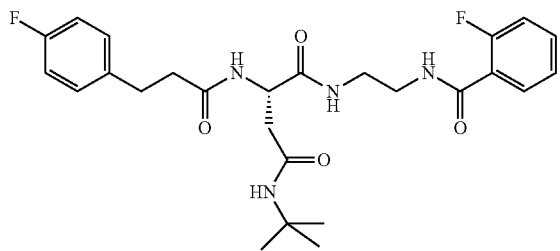
PKS21258
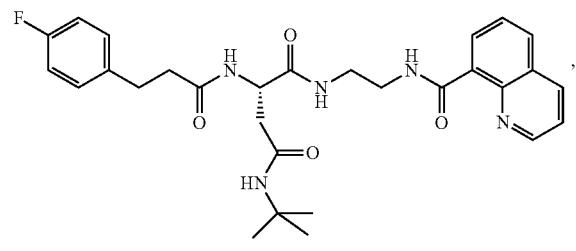
PKS21259
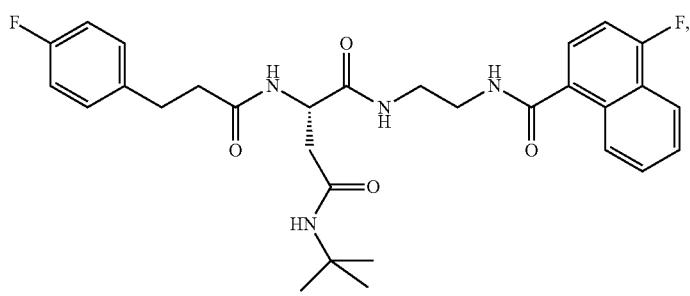
PKS21277
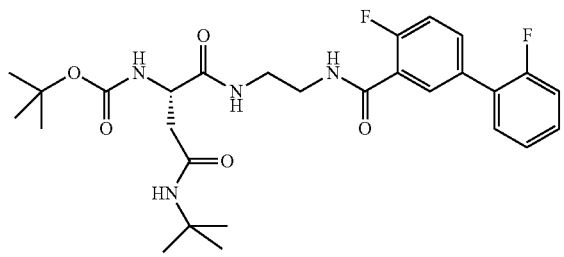
PKS21280
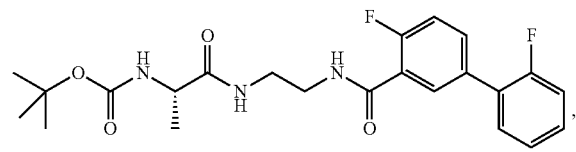

-continued
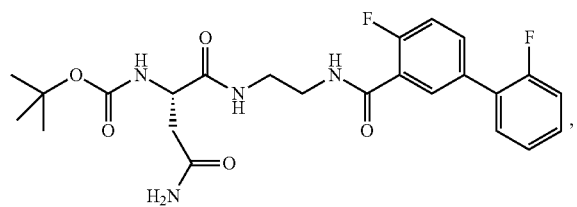
PKS21281
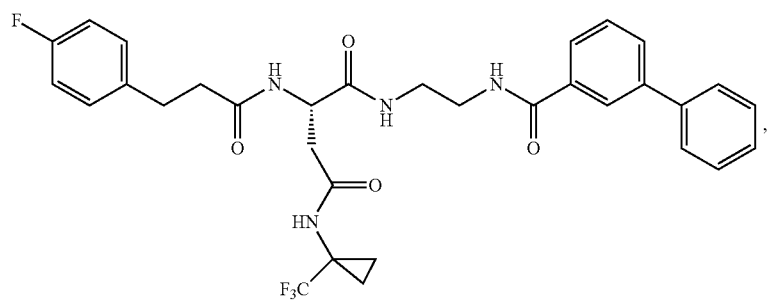
PKS21278
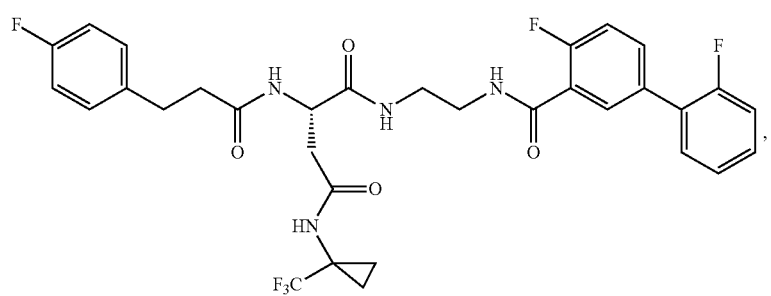
PKS21279
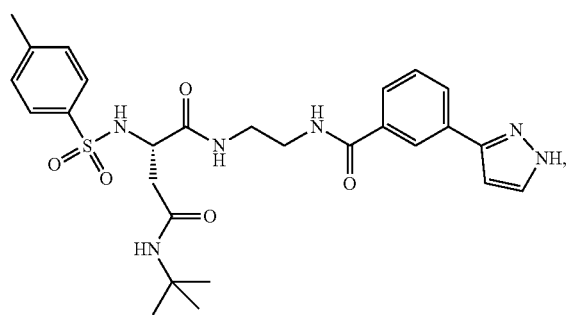
PKS21282
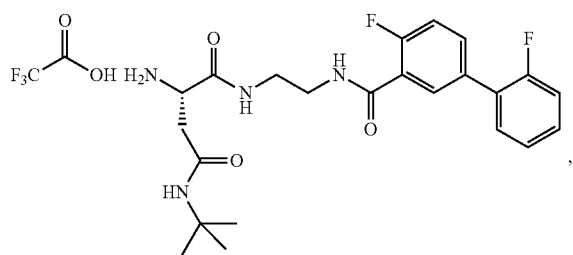
PKS21284
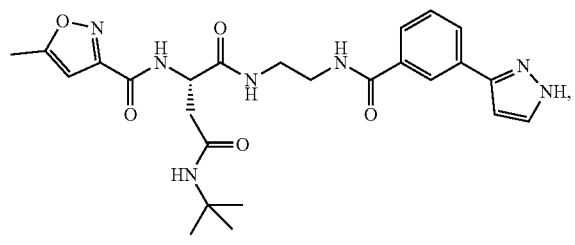
PKS21287
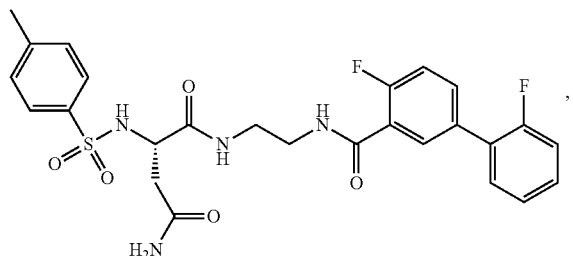
PKS21288

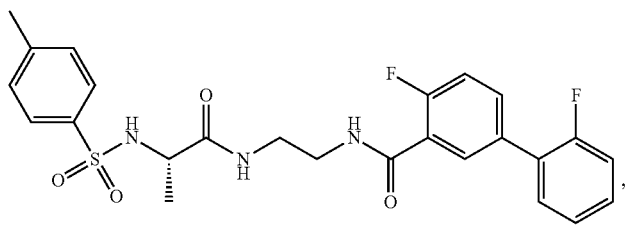

PKS21290

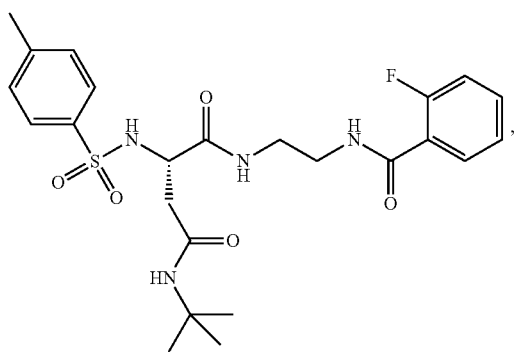

PKS21291

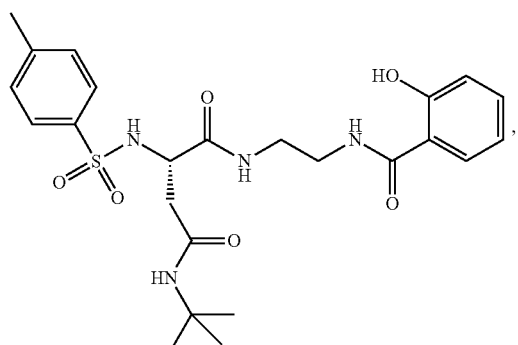

PKS21292

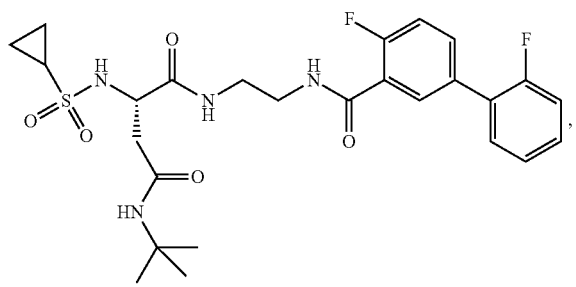

PKS21293

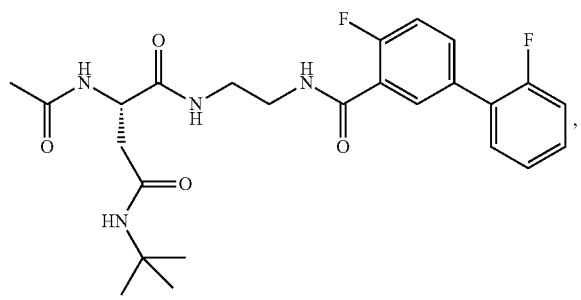

PKS21294

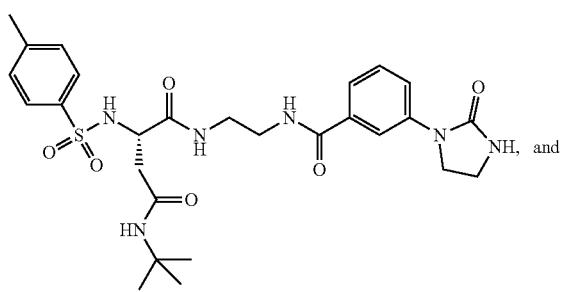

PKS21295, and

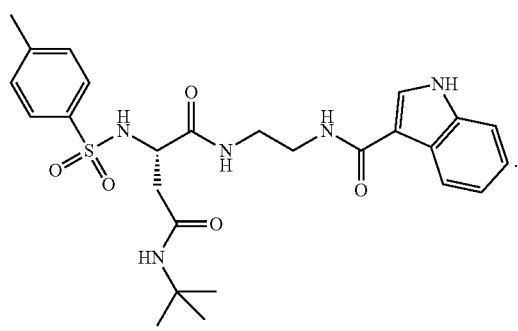

PKS21315.

45. The method according to claim 16, wherein the said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

46. The method according to claim 16, wherein the infectious disease is caused by bacterial, viral, parasitic, and fungal infectious agents.

47. The method according to claim 16, wherein the infectious disease is caused by a bacteria selected from the group consisting of *Escherichia coli, Salmonella, Shigella, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis*, Rickettsial pathogens, *Nocardia*, and *Actinomycetes*.

48. The method according to claim 16, wherein the infectious disease is caused by a fungal infectious agent selected from the group consisting of *Cryptococcus neoformans, Blastomyces dermatitidis, Histoplasma capsulatum, Coccidioides immitis, Paracoccicioides brasiliensis, Can-*

*dida albicans, Aspergillus fumigautus, Phycomycetes (Rhizopus), Sporothrix schenckii, Chromomycosis,* and *Maduromycosis.*

49. The method according to claim 16, wherein the infectious disease is caused by a viral infectious agent selected from the group consisting of human immunodeficiency virus, human T-cell lymphocytotrophic virus, hepatitis viruses, Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

* * * * *

UNITED STATES PATENT AND TRADEMARK OFFICE
CERTIFICATE OF CORRECTION

PATENT NO.       : 11,066,397 B2                           Page 1 of 1
APPLICATION NO.  : 15/768628
DATED            : July 20, 2021
INVENTOR(S)      : Gang Lin et al.

It is certified that error appears in the above-identified patent and that said Letters Patent is hereby corrected as shown below:

In the Claims

At Claim 11, Column 104, delete the following chemical formula:

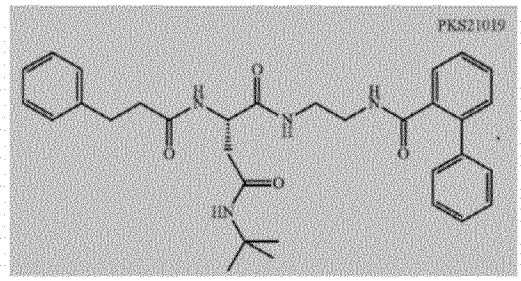

and insert the following chemical formula in its place:

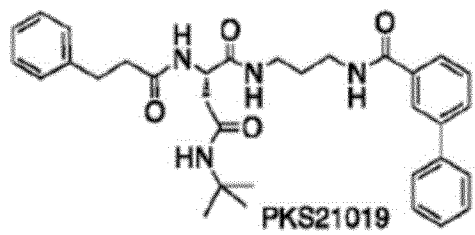

At Claim 11, Column 110, Line 1-15, insert commas after the structure of the compound PKS21293, Column 110, Line 16-30, insert comma after the structure of the compound PKS21294.

At Claim 12, Column 111, Line 22, delete "$C_{1-2}$alkyl" and insert --$C_{1-2}$ alkyl-- in its place.

At Claim 16, Column 113, Line 52, delete "$SO_2C_{3-8}$ cycloalkyl" and insert -- —$SO_2C_{3-8}$ cycloalkyl-- in its place.

At Claim 21, Column 114, Line 52, delete "10" and insert --$R^1$-- in its place.

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*